US011447451B2

(12) United States Patent
Guzaev et al.

(10) Patent No.: US 11,447,451 B2
(45) **Date of Patent: *Sep. 20, 2022**

(54) SOLID SUPPORTS AND PHOSPHORAMIDITE BUILDING BLOCKS FOR OLIGONUCLEOTIDE CONJUGATES

(71) Applicant: AM Chemicals LLC, Oceanside, CA (US)

(72) Inventors: Andrei Pavel Guzaev, Escondido, CA (US); Vladimir Y. VVedenskiy, San Diego, CA (US); Khirud Gogoi, San Marcos, CA (US)

(73) Assignee: AM Chemicals LLC, Oceanside, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/878,491

(22) Filed: May 19, 2020

(65) Prior Publication Data

US 2020/0277260 A1 Sep. 3, 2020

Related U.S. Application Data

(63) Continuation of application No. 15/650,773, filed on Jul. 14, 2017, now Pat. No. 10,781,175.

(60) Provisional application No. 62/363,023, filed on Jul. 15, 2016.

(51) Int. Cl.

| | |
|---|---|
| ***C07D 211/22*** | (2006.01) |
| ***C07F 9/59*** | (2006.01) |
| ***C07F 9/6561*** | (2006.01) |
| ***C07F 9/6558*** | (2006.01) |
| ***C07F 9/568*** | (2006.01) |
| ***C07F 9/24*** | (2006.01) |
| ***C07D 205/04*** | (2006.01) |
| ***C07D 401/12*** | (2006.01) |
| ***C07D 409/06*** | (2006.01) |
| ***C07D 491/18*** | (2006.01) |
| ***C07D 493/10*** | (2006.01) |
| ***C07D 495/04*** | (2006.01) |
| ***C07H 1/00*** | (2006.01) |
| ***C07H 15/26*** | (2006.01) |
| ***C07H 21/00*** | (2006.01) |
| ***C07J 43/00*** | (2006.01) |

(52) U.S. Cl.

CPC .......... *C07D 211/22* (2013.01); *C07D 205/04* (2013.01); *C07D 401/12* (2013.01); *C07D 409/06* (2013.01); *C07D 491/18* (2013.01); *C07D 493/10* (2013.01); *C07D 495/04* (2013.01); *C07F 9/2458* (2013.01); *C07F 9/568* (2013.01); *C07F 9/59* (2013.01); *C07F 9/6561* (2013.01); *C07F 9/65583* (2013.01); *C07F 9/65586* (2013.01); *C07H 1/00* (2013.01); *C07H 15/26* (2013.01); *C07H 21/00* (2013.01); *C07J 43/003* (2013.01); *Y02P 20/55* (2015.11)

(58) Field of Classification Search

CPC ... C07D 211/22; C07D 205/04; C07D 401/12

See application file for complete search history.

(56) References Cited

U.S. PATENT DOCUMENTS

| | | | | |
|---|---|---|---|---|
| 3,336,730 | A | 8/1967 | Mcbride et al. | |
| 4,415,732 | A | 11/1983 | Caruthers et al. | |
| 4,458,066 | A | 7/1984 | Caruthers et al. | |
| 4,500,707 | A | 2/1985 | Caruthers et al. | |
| 4,668,777 | A | 5/1987 | Caruthers et al. | |
| 5,132,418 | A | 7/1992 | Caruthers et al. | |
| 5,141,813 | A | 8/1992 | Nelson | |
| 5,420,330 | A | 5/1995 | Brush | |
| 5,464,746 | A | 11/1995 | Fino | |
| 5,585,481 | A | 12/1996 | Arnold, Jr. et al. | |
| 5,656,744 | A | 8/1997 | Arnold, Jr. et al. | |
| 5,696,251 | A | 12/1997 | Arnold, Jr. et al. | |
| 5,698,391 | A | 12/1997 | Cook et al. | |
| 5,886,177 | A | 3/1999 | Cook et al. | |
| 5,997,861 | A | 12/1999 | Virtanen et al. | |
| 6,005,093 | A | 12/1999 | Wood et al. | |
| 6,008,398 | A | 12/1999 | Gentles et al. | |
| 6,011,020 | A | 1/2000 | Gold et al. | |
| 6,013,783 | A | 1/2000 | Kaiser et al. | |
| 6,031,091 | A | 2/2000 | Arnold, Jr. et al. | |
| 6,031,117 | A | 2/2000 | Kaiser et al. | |
| 6,130,323 | A * | 10/2000 | Su ......................... | C07F 9/2416 536/22.1 |
| 6,326,487 | B1 | 12/2001 | Peyman et al. | |
| 7,026,114 | B1 | 4/2006 | Barone et al. | |
| 7,241,770 | B2 | 7/2007 | Mentzel et al. | |

(Continued)

FOREIGN PATENT DOCUMENTS

| | | | |
|---|---|---|---|
| EP | 1431297 | A1 | 6/2004 |
| EP | 967217 | A2 | 12/2005 |

(Continued)

OTHER PUBLICATIONS

U.S. Appl. No. 15/650,773 , "Final Office Action", dated Nov. 8, 2019, 13 pages.

(Continued)

*Primary Examiner* — Pancham Bakshi

(74) *Attorney, Agent, or Firm* — Kilpatrick Townsend & Stockton, LLP; Jennifer Blackburn

(57) ABSTRACT

Novel non-nucleoside solid supports and phosphoramidite building blocks for preparation of synthetic oligonucleotides containing at least one non-nucleosidic moiety conjugated to a ligand of practical interest and synthetic processes for making the same are disclosed. Furthermore, oligomeric compounds are prepared using said solid supports and phosphoramidite building blocks, preferably followed by removal of protecting groups to provide oligonucleotides conjugated to ligands of interest.

20 Claims, 6 Drawing Sheets

Specification includes a Sequence Listing.

(56) References Cited

U.S. PATENT DOCUMENTS

| | | | |
|---|---|---|---|
| 7,314,711 B2 | 1/2008 | Richter et al. | |
| 7,427,678 B2 | 9/2008 | Pieken et al. | |
| 7,491,805 B2 | 2/2009 | Vargeese et al. | |
| 7,705,136 B2 | 4/2010 | Golova et al. | |
| 7,723,528 B2 | 5/2010 | Guzaev | |
| 7,741,467 B2 | 6/2010 | Will | |
| 7,745,608 B2 | 6/2010 | Manoharan et al. | |
| 8,017,762 B2 | 9/2011 | Manoharan et al. | |
| 8,292,209 B2 | 10/2012 | Saito et al. | |
| 8,394,948 B2 | 3/2013 | Nelson et al. | |
| 8,945,515 B2 | 2/2015 | Blanchard et al. | |
| 9,156,865 B2 | 10/2015 | Segev | |
| 9,267,171 B2 | 2/2016 | Feng et al. | |
| 9,290,531 B2 | 3/2016 | Huebner et al. | |
| 10,781,175 B2 * | 9/2020 | Guzaev | C07D 205/04 |
| 10,808,246 B2 * | 10/2020 | Manoharan | C12N 15/111 |
| 2006/0178509 A1 | 8/2006 | Reddy | |
| 2006/0194213 A1 | 8/2006 | Golova et al. | |
| 2013/0066063 A1 | 3/2013 | Berry et al. | |
| 2014/0142253 A1 | 5/2014 | Srivastava et al. | |
| 2016/0017325 A1 | 1/2016 | Ullmann et al. | |
| 2016/0039850 A1 | 2/2016 | Segev | |
| 2016/0083414 A1 | 3/2016 | Guzaev et al. | |
| 2018/0016232 A1 | 1/2018 | Guzaev et al. | |

FOREIGN PATENT DOCUMENTS

| | | | |
|---|---|---|---|
| EP | 1431298 | A1 | 3/2006 |
| EP | 1333101 | A1 | 3/2007 |
| EP | 1308452 | A2 | 3/2008 |
| EP | 1538154 | A1 | 12/2008 |
| WO | 9012020 | A1 | 10/1990 |
| WO | 9117169 | A1 | 11/1991 |
| WO | 9320094 | A1 | 10/1993 |
| WO | 9404550 | A1 | 3/1994 |
| WO | 9406815 | A1 | 3/1994 |
| WO | 9419364 | A2 | 9/1994 |
| WO | 9424120 | A1 | 10/1994 |
| WO | 9429329 | A1 | 12/1994 |
| WO | 9501987 | A1 | 1/1995 |
| WO | 1995000329 | A1 | 1/1995 |
| WO | 9503296 | A1 | 2/1995 |
| WO | 9518820 | A1 | 7/1995 |
| WO | 9532739 | A1 | 12/1995 |
| WO | 9620289 | A1 | 7/1996 |
| WO | 9622297 | A1 | 7/1996 |
| WO | 9628438 | A1 | 9/1996 |
| WO | 9631523 | A1 | 10/1996 |
| WO | 9632841 | A1 | 10/1996 |
| WO | 9728168 | A1 | 8/1997 |
| WO | 9743298 | A1 | 11/1997 |
| WO | 9743451 | A1 | 11/1997 |
| WO | 9853316 | A1 | 11/1998 |
| WO | 2000027860 | A2 | 5/2000 |
| WO | 2001042505 | A2 | 6/2001 |
| WO | 2001044220 | A2 | 6/2001 |
| WO | 2001084234 | A1 | 11/2001 |
| WO | 2002044398 | A2 | 6/2002 |
| WO | 2002094185 | A2 | 11/2002 |
| WO | 2002099141 | A1 | 12/2002 |
| WO | 2003004602 | A2 | 1/2003 |
| WO | 2003019145 | A1 | 3/2003 |
| WO | 2003052132 | A2 | 6/2003 |
| WO | 2003052133 | A2 | 6/2003 |
| WO | 2003074510 | A1 | 9/2003 |
| WO | 2003104249 | A1 | 12/2003 |
| WO | 2004019002 | A2 | 3/2004 |
| WO | 2004022703 | A2 | 3/2004 |
| WO | 2005007666 | A1 | 1/2005 |
| WO | 2005043127 | A2 | 5/2005 |
| WO | 2005083073 | A1 | 9/2005 |
| WO | 2005103247 | A2 | 11/2005 |
| WO | 2006088490 | A2 | 8/2006 |
| WO | 2006125447 | A2 | 11/2006 |
| WO | 2007098336 | A2 | 8/2007 |
| WO | 2007106907 | A2 | 9/2007 |
| WO | 2008014979 | A2 | 2/2008 |
| WO | 2008049972 | A1 | 5/2008 |
| WO | 2008073959 | A2 | 6/2008 |
| WO | 2008129548 | A2 | 10/2008 |
| WO | 2008141799 | A1 | 11/2008 |
| WO | 2008147824 | A2 | 12/2008 |
| WO | 2008157696 | A2 | 12/2008 |
| WO | 2009007397 | A1 | 1/2009 |
| WO | 2009073809 | A2 | 6/2009 |
| WO | 2009074076 | A1 | 6/2009 |
| WO | 2009082606 | A2 | 7/2009 |
| WO | 2009126933 | A2 | 10/2009 |
| WO | 2010001902 | A1 | 1/2010 |
| WO | 2010039548 | A2 | 4/2010 |
| WO | 2010071852 | A1 | 6/2010 |
| WO | 2010129672 | A1 | 11/2010 |
| WO | 2010147673 | A2 | 12/2010 |
| WO | 2010151714 | A2 | 12/2010 |
| WO | 2011060379 | A2 | 5/2011 |
| WO | 2011087707 | A1 | 7/2011 |
| WO | 2011105610 | A1 | 9/2011 |
| WO | 2011100131 | A2 | 10/2011 |
| WO | 2011126937 | A1 | 10/2011 |
| WO | 2011133876 | A2 | 10/2011 |
| WO | 2012018729 | A1 | 2/2012 |
| WO | 2012029434 | A1 | 3/2012 |
| WO | 2012085064 | A1 | 6/2012 |
| WO | 2012085069 | A2 | 6/2012 |
| WO | 2012119846 | A1 | 9/2012 |
| WO | 2013036748 | A1 | 3/2013 |
| WO | 2014147095 | A1 | 9/2014 |
| WO | 2014157565 | A1 | 10/2014 |
| WO | 2014178082 | A1 | 11/2014 |
| WO | 2014179620 | A2 | 11/2014 |
| WO | 2014179626 | A2 | 11/2014 |
| WO | 2015006740 | A2 | 1/2015 |
| WO | 2015012912 | A2 | 1/2015 |
| WO | 2015042447 | A1 | 3/2015 |
| WO | 2015064718 | A1 | 5/2015 |
| WO | 2015091953 | A1 | 6/2015 |
| WO | 2015091958 | A1 | 6/2015 |
| WO | 2015109136 | A2 | 7/2015 |
| WO | 2015113776 | A1 | 8/2015 |
| WO | 2015132577 | A1 | 9/2015 |
| WO | 2015168589 | A2 | 11/2015 |
| WO | 2015168618 | A2 | 11/2015 |
| WO | 2015168635 | A2 | 11/2015 |
| WO | 2018013999 | A1 | 1/2018 |

OTHER PUBLICATIONS

U.S. Appl. No. 15/650,773 , "Non-Final Office Action", dated Jun. 17, 2019, 18 pages.

U.S. Appl. No. 15/650,773 , "Notice of Allowance", dated Feb. 19, 2020, 9 pages.

Bossa et al., "Carbamic Acid and Carbamate Formation in NH:CO ices—UV Irradiation Versus Thermal Processes", Astronomy & Astrophysics, vol. 492, No. 3, Nov. 6, 2008, pp. 719-724.

EP17828586.2 , "Extended European Search Report", dated Mar. 10, 2020, 11 pages.

Guzaev et al., "2-Benzamidoethyl Group—A Novel Type of Phosphate Protecting Group for Oligonucleotide Synthesis", Journal of the American Chemical Society, vol. 123 No., Feb. 7, 2001, 11 pages.

Guzaev et al., "A Novel Phosphate Protection for Oligonucleotide Synthesis: the 2-[(1-Naphthyl)carbamoyloxy]ethyl (NCE) Group", Tetrahedron Lett, vol. 41, 2000, pp. 5623-5626.

Guzaev et al., "Attachment of Nucleosides and Other Linkers to Solid-Phase Supports for Oligonucleotide Synthesis.", Current Protocols in Nucleic Acid Chemistry Ed. Beaucage, S. L, vol. 52, John Wiley & Sons: 2013, 2013, 23 pages.

Guzaev et al., "Novel Non-Nucleosidic Building Blocks for the Preparation of Multilabeled Oligonucleotides", Bioconjugate Chern., vol. 7, No. 2, Mar. 28, 1996, pp. 240-248.

PCT International Application No. PCT/US2017/042259 , "International Preliminary Report on Patentability", Jan. 24, 2019, 7 pages.

(56) References Cited

OTHER PUBLICATIONS

PCT International Application No. PCT/US2017/042259 , "International Search Report and Written Opinion", dated Dec. 5, 2017, 10 pages.
PCT International Application No. PCT/US2017/042259 , "Invitation to Pay Add'l Fees and Partial Search Report", dated Oct. 3, 2017, 2 pages.
Petrie et al., "An improved CPG support for the synthesis of 3'-amine-tailed oligonucleotides", Bioconjugate Chemistry, vol. 3, 1992, pp. 85-87.
Reddy et al., "Fast cleavage and deprotection of oligonucleatides", Tetrahedron Lett., vol. 35, 1994, pp. 4311-4314.
Reed et al., "Acridine- and cholesterol-derivatized solid supports for improved synthesis of 3'-modified oligonucleotides", Bioconjugate Chemistry, vol. 2, 1991, pp. 217-225.
Reusch , "Rearrangements Induced by Cationic or Electron Deficient Sites", Availale online at : https://www2.chemistry.msu.edu/faculty/reusch/virttxtjml/rearrang.htm, May 5, 2013, pp. 1-17.
Thaden et al., "Automated synthesis of oligodeoxyribonucleosidemethylphosphonates having [N-(3-aminoprop-1-yl-)-N-(2-hydroxyethyl-)-2-aminoethyl] phosphate or methylphosphonic acid at the 3'-end using a modified controlled pore glass support.", Bioconjugate Chemistry, vol. 4, 1993, pp. 395-401.
Vu et al., "Use of phthaloyl protecting group for the automated synthesis of 3'-[(hydroxypropyl)amino] and 3'-[(hydroxypropyltriglycyl] oligonucleotide conjugates", Bioconjugate Chemistry, vol. 6, 1995, pp. 599-607.
IL264221, "Office Action", dated Jan. 10, 2021, 4 pages.
IL264221, "Office Action", dated Dec. 30, 2021, 6 pages.

* cited by examiner

7a: n = 2, $R^1$ = DMT;
8a: n = 2, $R^1$ = TMT;
9a: n = 1, $R^1$ = DMT;
10a: n = 1, $R^1$ = TMT;

23: n = 2, $R^1$ = DMT;
24: n = 2, $R^1$ = TMT;
25: n = 1, $R^1$ = DMT;
26: n = 1, $R^1$ = TMT;

27: n = 2, $R^1$ = DMT;
28: n = 2, $R^1$ = TMT;
29: n = 1, $R^1$ = DMT;
30: n = 1, $R^1$ = TMT;

31: n = 2, $R^1$ = DMT;
32: n = 2, $R^1$ = TMT;
33: n = 1, $R^1$ = DMT;
34: n = 1, $R^1$ = TMT;

35: n = 2, $R^1$ = DMT;
36: n = 2, $R^1$ = TMT;
37: n = 1, $R^1$ = DMT;
38: n = 1, $R^1$ = TMT;

39: n = 2, $R^1$ = DMT;
40: n = 2, $R^1$ = TMT;
41: n = 1, $R^1$ = DMT;
42: n = 1, $R^1$ = TMT;

23: n = 2, $R^1$ = DMT;
24: n = 2, $R^1$ = TMT;
25: n = 1, $R^1$ = DMT;
26: n = 1, $R^1$ = TMT;

43k: n = 2, $R^1$ = DMT;
44k: n = 2, $R^1$ = TMT;
45k: n = 1, $R^1$ = DMT;
46k: n = 1, $R^1$ = TMT;

47k: n = 2, $R^1$ = DMT;
48k: n = 2, $R^1$ = TMT;
49k: n = 1, $R^1$ = DMT;
50k: n = 1, $R^1$ = TMT;

51k: n = 2, $R^1$ = DMT;
52k: n = 2, $R^1$ = TMT;
53k: n = 1, $R^1$ = DMT;
54k: n = 1, $R^1$ = TMT;

55: n = 2, $R^1$ = DMT;
56: n = 2, $R^1$ = TMT;
57: n = 1, $R^1$ = DMT;
58: n = 1, $R^1$ = TMT;

7c, 8c

59: R1 = DMT, 60: R1 = TMT

61: R1 = DMT, 62: R1 = TMT

63: R1 = DMT, 64: R1 = TMT

65: R1 = DMT, 66: R1 = TMT

67: R1 = DMT, 68: R1 = TMT

4

69

70

71

73

74

26 75 75 75 76 77 77

SOLID SUPPORTS AND PHOSPHORAMIDITE BUILDING BLOCKS FOR OLIGONUCLEOTIDE CONJUGATES

CROSS-REFERENCE TO RELATED APPLICATIONS

This application is a continuation of and claims priority to U.S. patent application Ser. No. 15/650,773, filed on Jul. 14, 2017, which claims priority to U.S. Provisional Patent Application No. 62/363,023, filed on Jul. 15, 2016. The contents of the aforementioned disclosures are hereby incorporated by reference in their entirety and for all purposes.

REFERENCE TO A "SEQUENCE LISTING," A TABLE, OR A COMPUTER PROGRAM LISTING APPENDIX SUBMITTED ON A COMPACT DISK

The instant application contains a Sequence Listing which has been submitted via EFS-Web and is hereby incorporated by reference in its entirety. Said ACSII copy, created on Aug. 25, 2017, is named 095111-000310US-1055706 SL.txt and is 491 kilo bytes in size.

FIELD OF THE INVENTION

The disclosure herein relates to compounds, compositions and methods of use for the synthesis of oligonucleotides modified by building blocks of non-nucleosidic structure. For example, the disclosure relates to non-nucleosidic phosphoramidite building blocks and solid supports for synthesis of modified oligonucleotides, compositions comprising such non-nucleosidic phosphoramidite building blocks, solid supports, and methods of using such building blocks and supports in the synthesis of modified oligonucleotides.

SUMMARY OF THE RELATED ART

A number of innovations have been introduced to the art of oligonucleotide synthesis. Amongst these innovations have been the development of excellent orthogonal protecting groups, activators, reagents, and synthetic conditions. The oligonucleotides themselves have been subject to a variety of modifications and improvements. Amongst these are chemistries that deliver properties that are not present in naturally occurring oligonucleotides i.e. reduced negative charge, hydrophobicity, ability to emit fluorescence, protein and receptor binding properties, etc. These novel chemistries generally involve modification building blocks of non-nucleosidic nature that become constituent parts of the oligonucleotide.

There are several structural motifs known in the art for the construction of non-nucleosidic reagents for making derivatized synthetic oligonucleotides.

A number of non-nucleosidic phosphoramidite reagents and solid supports disclosed have been derived from 1,2-diols featuring a side chain for the attachment of ligands via linkers of variable length. In these structures, the primary hydroxy group is used for the placement of a 4,4'-dimethoxytrityl (DMT) group, while an amidite or a succinate moiety is placed at the secondary hydroxy group.

Two approaches to attach a side chain bearing a ligand are known in the art. In one approach, the primary hydroxy group of glycerol is alkylated by a side chain bearing a functional group for further extension with a ligand. A variety of phosphoramidite building blocks and solid supports have been disclosed for the attachment of amino groups (WO 2008/129548, US 20160039850, U.S. Pat. Nos. 8,292,209, 9,156,865), carbonyl groups (WO 2007/106907), tocopherol (WO 2008/014979), cholesterol (WO 2015/091958, WO 2010/129672, WO 2008/014979, WO 94/04550, U.S. Pat. No. 6,326,487, WO 2010/151714), other hydrophobic modifiers (WO 2014/147095, US20160017325, WO 2006/125447, U.S. Pat. No. 5,420,330) biotin (WO 2015/091958, WO 2010/151714, WO 91/17169, U.S. Pat. No. 6,326,487), fluorescent labels (WO/2005-JP7666, EP 1538154, WO 2004/022703, WO 2003/052132, WO 2003/052133, WO 96/28438, WO 96/20289, WO 94/24120, WO 91/17169, U.S. Pat. No. 6,005,093), crosslinking moieties (WO 2000/027860), ligands for Diels-Alder-type conjugation (WO 2013/036748, US20130066063), and other ligands (WO 2011/126937, 2006/125447, WO 9622297, U.S. Pat. Nos. 6,011,020, 6,008,398).

Those skilled in the art know that reagents derived from vicinal diols share one common disadvantage. Upon attachment of the reagent to the terminus of a synthetic oligonucleotide, one of the vicinal hydroxy functions becomes connected to said oligonucleotide via a phosphotriester moiety. When the oligonucleotide synthesis starts from said non-nucleosidic solid support, the other hydroxy function is connected to the solid phase material via an ester group. During the final deprotection of the oligonucleotides (under strong basic conditions), said ester function is cleaved simultaneously and competitively with 2-cyanoethyl protecting group of the phosphate.

The hydroxy group released by the cleavage of the ester may attack the phosphotriester moiety, which results in the loss of the non-nucleosidic moiety together with the phosphate group from the oligonucleotide. In other words, the solid supports of this kind work, to an extent, as universal solid supports of low efficiency. Examples of universal solid supports of similar structures and their use in oligonucleotide chemistry have been disclosed, for instance, in WO 95/01987 and in Reddy, M. P., Hanna, N. B., and Farooqui, F. Fast cleavage and deprotection of oligonucleotides. *Tetrahedron Lett.* 1994, 35, 4311-4314.

When phosphoramidite building blocks of this group are attached at the 5'-terminus of oligonucleotides, the purity of the deprotected products depends on whether the 5'-terminal DMT group was present in the oligonucleotides when the basic deprotection was carried out. The deprotection of the 5'-DMT-protected oligonucleotides results in less complex reaction mixtures. In contrast, oligonucleotides having the free pseudo-5'-hydroxy group suffer, to an extent, from the loss of the non-nucleosidic moiety in a manner similar to that described above.

Alternatively, an amino group of 3-amino-1,2-propanediol (aminoglycerol) may serve as a point of attachment of a ligand by acylation with an appropriate carboxylic acid. A number of phosphoramidite building blocks and solid supports constructed in this manner have been disclosed, for example, bearing protected amino groups (WO 2005/103247, WO 2015/113776, U.S. Pat. Nos. 6,031,091, 5,141,813), tertiary amino groups (WO 97/28168, WO 95/18820, U.S. Pat. Nos. 6,008,398, 5,698,391, 5,886,177), protected aminooxy groups (WO 2002/094185, U.S. Pat. No. 7,491,805), protected carboxylate functions (WO 95/18820, U.S. Pat. Nos. 5,886,177, 5,698,391), protected mercapto groups (WO 2003/074510), esters of phenylboronic acid (U.S. Pat. Nos. 6,031,117, 6,013,783), hydrophobic motifs (WO 2015/091958), intercalators and fluorescent labels (WO 2010/001902, WO 2009/007397, WO 95/18820, U.S. Pat. Nos.

5,886,177, 5,698,391), chelating moieties (EP 1308452), N-acetyl-D-galactosamine residues (WO 2015/006740), and unnatural nucleic bases (WO 2011/133876).

In the course of the final deprotection, oligonucleotides assembled using phosphoramidites and/or solid supports derived from N-acylaminoglycerol suffer from lower yields due to major side reactions (Petrie, C. R., Reed, M. W., Adams, A. D., and Meyer, R. B. Jr. An improved CPG support for the synthesis of 3'-amine-tailed oligonucleotides. *Bioconjug. Chem.* 1992, 3, 85-87; Reed, M. W., Adams, A. D., Nelson, J. S., and Meyer, R. B. Jr. 1991. Acridine- and cholesterol-derivatized solid supports for improved synthesis of 3'-modified oligonucleotides. *Bioconjug. Chem.* 1991, 2, 217-225; Thaden, J. and Miller, P. S. Automated synthesis of oligodeoxyribonucleosidemethylphosphonates having [N-(3-aminoprop-1-yl-)-N-(2-hydroxyethyl-)-2-aminoethyl] phosphate or methylphosphonic acid at the 3'-end using a modified controlled pore glass support. *Bioconjug. Chem.* 1993, 4, 395-401; Vu, H., Joyce, N., Rieger, M., Walker, D., Goldknopf, I., Hill, T. S., Jayaraman, K., and Mulvey, D. Use of phthaloyl protecting group for the automated synthesis of 3'-[(hydroxypropyl)amino] and 3'-[(hydroxypropyltriglycyl] oligonucleotide conjugates. *Bioconjug. Chem.* 1995, 6, 599-607).

First, the loss of the linker together with the adjacent phosphate may occur in a manner similar to that disclosed for reagents derived from glycerol. With the appropriate protection of one of the hydroxy groups and the amino function, this side reaction may become the main process that is used in commercial Universal Solid Supports disclosed in WO 2008/049972 and WO 2002/044398.

The second major side reaction is typical for N-acylated aminoethanols and results in the intramolecular nucleophilic attack by the oxygen of the amido group on the carbon attached to the oxygen of the P—O fragment as disclosed in (Guzaev, A. P. and Manoharan, M. 2-Benzamidoethyl Group—a Novel Type of Phosphate Protecting Group for Oligodeoxynucleotide Synthesis. *J. Am. Chem. Soc.* 2001, 123, 783-793; Guzaev, A. P. and Manoharan, M. A Novel Phosphate Protection for Oligonucleotide Synthesis: the 2-[(1-Naphthyl)carbamoyloxy]ethyl (NCE) Group. *Tetrahedron Lett.* 2000, 41, 5623-5626). The process results in the loss of the linker with the formation of oligonucleotides bearing 3'-terminal phosphate group. Once the non-nucleosidic linker is attached, said side reaction may occur at all steps: in the course of the chain assembly of oligonucleotides and during the final deprotection.

The disadvantages of non-nucleosidic building blocks and solid supports derived from 1,2-diol systems were partially addressed in reagents derived from 1,3-diols. One family of reagents has been derived either from glycerol or from 2-(ω-functionalyzed alkyl)-1,3-propanediol wherein one of the primary hydroxy groups bore the DMT protection while the other served for the attachment of a phosphoramidite moiety.

In the glycerol family, the secondary hydroxy group was either protected or bore a side chain terminated by modifiers of interest. Reagents have been disclosed in the art bearing nucleic bases (WO 2008/147824, WO 2003/004602), protected residues of monosaccharides (U.S. Pat. No. 9,290,531), or protected hydroxy groups (WO 2012/119846, WO 2011/060379).

Derived from 2-(ω-functionalyzed alkyl)-1,3-propanediol backbone, phosphoramidite building blocks and solid supports have been disclosed featuring protected amino groups (WO 98/53316, WO 97/28168, U.S. Pat. Nos. 7,314,711, 6,031,091, 6,008,398, 5,696,251, 5,656,744, 5,585,481), lipoic acid (US Patent Appl. 2014/0142253), acridin (U.S. Pat. No. 6,326,487), fluorescein (WO 2015/109136, WO 2015/091958, WO 2015/091953, WO 2011/087707, WO 95/32739), fluorescence quenchers (WO 2003/019145), and biotin (WO 2012/085064, WO 2012/085069, U.S. Pat. No. 6,326,487).

The main disadvantage of the disclosed reagents is that 1-O,3-O-unsymmetrically substituted 2-derivatized 1,3-propanediols, unless stereochemically resolved, exist as mixtures of enantiomers and hence embed the unwanted stereoheterogeneity in modified oligonucleotides.

Yet another group of reagents derived from 2-substituted 1,3-diols featured the core structures of serinol (2-amino-1,3-propanediol) and threoninol (2-amino-1,3-butanediol) wherein the primary hydroxy groups bore the DMT protection while the other, either primary (serinol) or secondary (threoninol) hydroxy group served for the attachment of a phosphoramidite moiety. The primary amino group was either protected or was acylated to bear a side chain terminated by modifiers of interest. Both serinol and threoninol, the starting materials for manufacturing of these reagents, are produced from the respective natural amino acids and hence are expensive.

In addition, as disclosed in a web-site of the Assignee of U.S. Pat. Nos. 8,394,948 and 8,945,515, oligonucleotides incorporating these building blocks suffer from a side reaction unless stored at −20° C. (http://www.glenresearch.com/ProductFiles/Product.php?item=10-1996). Similar to all oligonucleotides prepared using reagents incorporating a fragment of N-acyl aminoethanol, oligonucleotides derivatized with serinol and threoninol-based reagents may suffer from the loss of the linker accompanied by the release of the terminally phosphorylated oligonucleotides as disclosed above for aminoglycerol. Although substantially more expensive, threoninol reagents display two advantages over serinol counterparts: the ease of synthetic preparation due to the distinctly different hydroxy groups in the starting material and, when chirally pure threoninol is used, stereohomogeneity of oligonucleotide products.

Derived from serinol backbone, phosphoramidite building blocks and solid supports have been disclosed featuring protected amino groups (WO 2015/113776, WO 2015/006740, WO 2014/178082, WO 97/28168, WO 96/32841, WO 96/31523, WO 96/22297, U.S. Pat. Nos. 8,394,948, 6,008,398, 5,997,861), reactive double (U.S. Pat. No. 7,705,136) and triple bonds (WO 2015/012912), cholesterol (WO 94/04550) and other hydrophobic residues (WO 2008/141799), intercalators (WO 2006/088490), fluorescein and biotin (U.S. Pat. No. 8,394,948), and negative charges formed by carboxylic (WO 2008/141799) and boronic acids (U.S. Pat. No. 6,031,117).

Derived from threoninol backbone, phosphoramidite building blocks and solid supports have been disclosed featuring protected amino groups (WO 2015/006740), photocrosslinkers (WO 2015/064718, WO 2014/157565), hydrophobic residues (WO 2011/105610), intercalators (WO 2012/029434, WO 2011/105610, WO 2010/147673, WO 2010/071852, WO 2005/083073), and fluorescein (U.S. Pat. No. 7,026,114) and other fluorescent labels (WO 2009/007397).

Yet another group of reagents derived from 1,3-diols feature the core structures of 2-(aminomethyl)-1,3-propanediol and 2-(ω-functionalized alkyl)-1,3-propanediol wherein the primary hydroxy groups bore the DMT protection while the other, secondary, hydroxy group served for the attachment of a phosphoramidite moiety. One of the disadvantages of these reagents is that, unless stereochemically resolved, they embed the unwanted stereo-heterogeneity in modified oligonucleotides.

In 2-(aminomethyl)-1,3-propanediol, the primary amino group was acylated to bear a side chain terminated by a trifluoroacetyl-protected primary amino group (WO 94/19364). Similar to all oligonucleotides prepared using reagents incorporating a fragment of N-acyl aminoethanol, oligonucleotides derivatized with 2-(aminomethyl)-1,3-propanediol-based reagents may suffer from the loss of the linker accompanied by the release of the terminally phosphorylated oligonucleotides as disclosed above for aminoglycerol.

Derived from the backbone of 2-(w-functionalized alkyl)-1,3-propanediol, phosphoramidite building blocks and solid supports have been disclosed featuring protected amino groups (WO 2001/084234, U.S. Pat. No. 7,427,678), a DMT-protected hydroxy group (WO 2008/073959), constrained alkynes (WO 2013/036748), 2-nitrophenyl residue (WO 2010/151714, WO 2008/157696, EP 1333101), folic acid (WO 2012/018729), and residues of carbazoles, dibenzofurans, 3-Ph-adamantane, quinolone, and acridine capable of soliciting immune response (WO 95/03296 WO 95/0329, WO 94/29329, WO 93/20094, U.S. Pat. No. 5,464,746).

A number of phosphoramidite building blocks and solid supports disclosed in the art have been derived from cyclic structures. One structural motif widely appreciated by skilled artisans is that of 2'-deoxy-β-D-ribose present in natural nucleosides. Similar to nucleosidic building blocks, the primary 5'-hydroxy groups bore the DMT protection, while the secondary 3'-hydroxy group served for the attachment of a phosphoramidite moiety or the succinate linker. The side chain to bear modifiers of interest was attached either by glycosidation via a 1'-O position or directly via the C-1' carbon. The preparation of both types of reagents requires a multi-step synthesis and is labor-intensive, which precluded said reagents from commercial success.

Derived from the backbone of 1'-O-(ω-functionalized alkyl)-2'-deoxy-β-D-ribose, phosphoramidite building blocks and solid supports have been disclosed featuring intercalators (WO 2004/019002), hydrophobic groups (WO 2014/147095), positively-charged groups (WO 2015/132577), crosslinkers (WO 90/12020, U.S. Pat. No. 9,267,171), allyl (WO 2009/074076) and 2-nitrobenzyl (WO 94/06815) groups.

Derived from the backbone of 1',2'-dideoxy-1'-(ω-functionalized alkyl)-β-D-ribose, phosphoramidite building blocks and solid supports have been disclosed featuring intercalators anthracene, phenanthrene, pyrene, tetracene, and pentacene (WO 97/43298), stilbene (WO 2001/044220 WO 2001/044220 WO 2004/019002, WO 97/43298), and fluorescein (EP 967217).

Yet another group of reagents derived from 1,3-diols feature the core structure of 1,1-bis(hydroxymethyl)-4-aminocyclohexane wherein the primary hydroxy groups bore the DMT protection while the other hydroxy group served for the attachment of a phosphoramidite moiety or the succinate linker. The primary amino group was acylated to bear a side chain terminated by a trifluoroacetyl-protected primary amino group (WO 97/43451), fluorescein (EP 1431298, EP 716899916V. 1431297, WO 97/43451, U.S. Pat. No. 7,741,467), and biotin (WO 97/43451). The preparation of said reagents requires a multi-step synthesis and is labor-intensive. Another disadvantage thereof is that, unless stereochemically resolved, the unwanted stereo-heterogeneity is embedded in the modified oligonucleotides.

Yet another group of reagents of the type of cyclic 1,3-diols has been derived from the core structure of hydroxyprolinol wherein the primary hydroxy groups bore the DMT protection while the other hydroxy group served for the attachment of a phosphoramidite moiety or the succinate linker. The secondary amino group was acylated to bear a side chain terminated by a protected primary amino group (WO 2015/006740, WO 2011/087707, WO 2003/104249), protected polyamines (WO 2009/126933), alkyne (WO 2010/039548, WO 2011/100131), azobenzene WO 2011/087707, WO 2005/043127, WO 2002/099141, WO 2001/042505) fluorescein (WO 2007/098336), folic acid (WO 2009/082606), various mono- and oligosaccharides (WO 2015/168589, WO 2015/168618, WO 2015/168635, WO 2015/042447, WO 2015/006740, WO 2014/179626, WO 2014/179620, WO 2014/179620, WO 2009/073809), various compounds bound via a disulfide linkage (WO 2009/126933, U.S. Pat. Nos. 8,017,762, 7,745,608).

SUMMARY OF THE INVENTION

Those skilled in the art will appreciate the utility of oligonucleotides derivatized with non-nucleosidic modifiers. Said compounds combine the natural ability of oligonucleotides to form duplexes with complementary DNA or RNA with useful physical and chemical properties added by modifiers. Such properties include, but are not limited to, protein binding, binding to specific receptors, soliciting immune response, intercalation, fluorescence and its quenching, chemiluminescence, hydrophobicity, specific reactivity to compounds of interest, catalytic activity, and charge alteration.

Several processes for the solid phase synthesis of oligonucleotide compounds are known to those skilled in the art and may be employed with the present invention. Said processes are disclosed, for example, in U.S. Pat. No. 4,458,066 (issued Jul. 3, 1984), U.S. Pat. No. 4,500,707 (issued Feb. 19, 1985), and U.S. Pat. No. 5,132,418 (issued Nov. 27, 1990).

A process for the preparation of phosphoramidite building blocks is disclosed in U.S. Pat. No. 4,415,732 (issued Nov. 15, 1983). Certain nucleoside phosphoramidite compounds are disclosed in U.S. Pat. No. 4,668,777 (issued May 26, 1987).

In accordance with certain aspects of the present invention, there are provided novel compounds which may serve as phosphoramidite building blocks and solid supports for preparation of oligomeric compounds, analogs of natural and chemically modified oligonucleotides, wherein a non-nucleosidic moiety bearing a ligand of practical interest is either linked to the 3'-or the 5'-terminal nucleoside via a phosphate or a phosphorothioate residue or introduced in the middle of the chain of an oligonucleotide.

In accordance with another aspect of the present invention, there are provided novel oligomeric compounds, phosphotriester analogs of natural oligonucleotides with improved physico-chemical properties, wherein a carbohydrate moiety is linked to the internucleosidic phosphate residue.

In accordance with a further aspect and embodiment of the present invention, there are provided methods for synthetic preparation of said oligomeric compounds.

Other aspects and embodiments of the present invention will be apparent to those skilled in the art.

These objects are satisfied by the present invention which provides novel non-nucleoside phosphoramidite building blocks and solid supports useful in preparation of oligomeric compounds and methods for making such oligomeric compounds.

Abbreviations

Ac: Acetyl;
Bz: benzoyl;
CPG: Controlled Pore Glass;
Dabcyl: 4-(dimethylamino)azobenzene-4'-carbonyl;
Dabsyl: 4-(dimethylamino)azobenzene-4'-sulfonyl;
DCM: dichloromethane;
DMF: N,N-dimethylformamide;
DMT: bis(4-methoxyphenyl)phenylmethyl (4,4'-dimethoxytrityl);
EDC-HCl: N-(3-dimethylaminopropyl)-N'-ethylcarbodiimide hydrochloride;
Fmoc: (9-fluorenyl)methyloxycarbonyl;
TBTU: 2-(1H-benzotriazol-1-yl)-1,1,3,3-tetramethyluronium tetrafluoroborate;
HOBT: N-hydroxybenzotriazole;
ib: isobutyryl;
MeCN: acetonitrile;
MPPS: Macroporous Polystyrene;
TEA: triethylamine;
NMI: N-methylimidazol;
ES MS: mass-spectrometry with electron-spray ionization;
HPLC: high-performance liquid chromatography;
Py: pyridine;
TMT: tris(4-methoxyphenyl)methyl (4,4',4"-trimethoxytrityl).

DETAILED DESCRIPTION OF THE PREFERRED EMBODIMENTS

Figure 1:
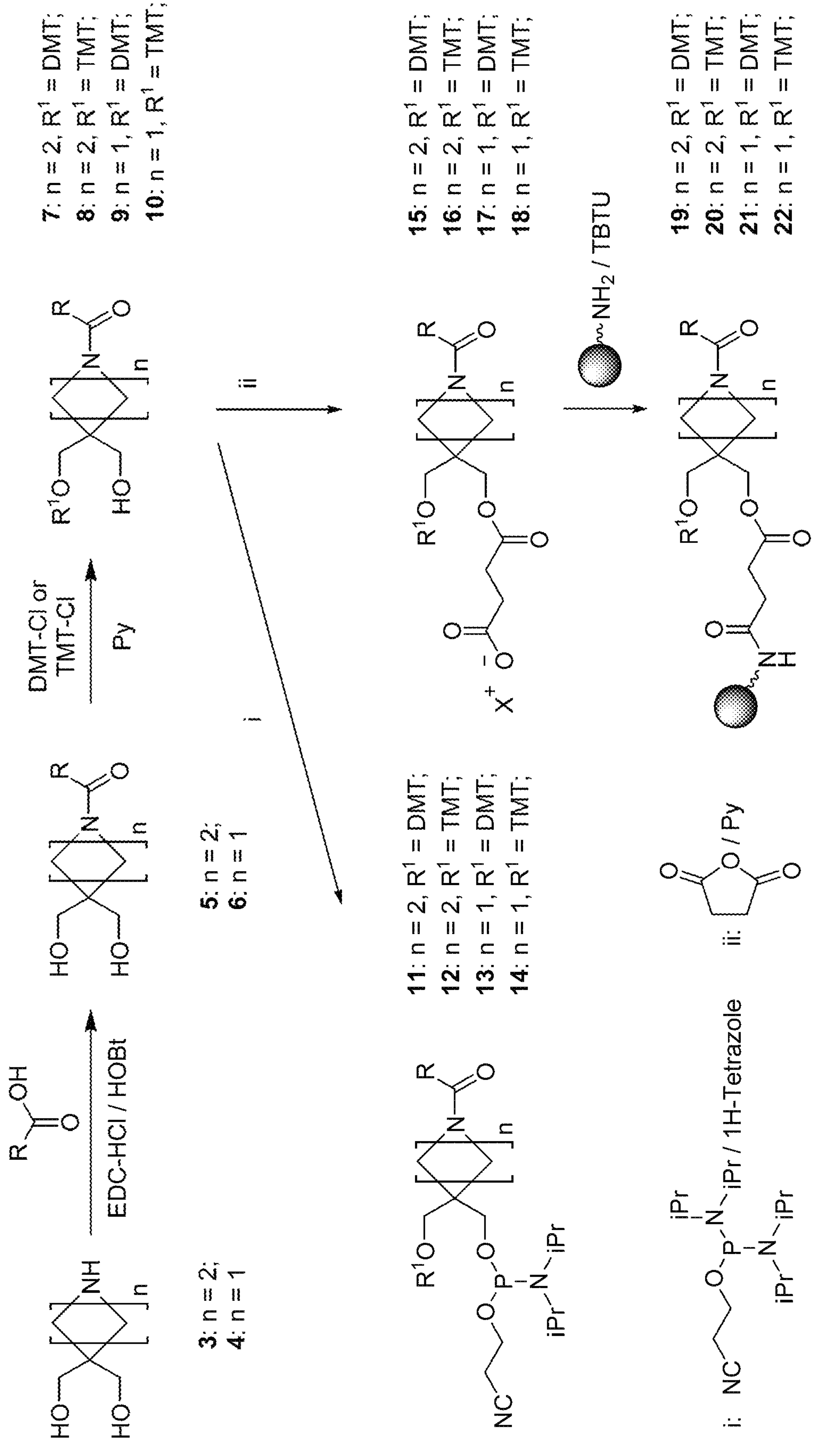
FIG. 1 shows structures and a synthetic scheme for the preparation of phosphoramidite building blocks 11a-k-14a-k and solid supports 19a-k-22a-k.

The present invention provides chemical preparations of oligonucleotides, chemical entities useful in such preparation, and processes for such preparation. More specifically, the invention provides novel non-nucleosidic phosphoramidite building blocks and solid supports for incorporation of a variety of useful ligands to natural oligonucleotides and their phosphorothioate analogs in the course of synthesis on solid phase. The phosphoramidite building blocks and solid supports according to the invention are highly efficient. These compounds are inexpensive to manufacture. They are stable in the solid state or in solution over an extensive period of time. The attachment thereof to oligonucleotides does not create any new chiral centers and hence does not complicate the isolation of the ligand-modified oligonucleotides. Said oligonucleotides do not suffer from any unwanted side reactions. The patents and publications cited in this specification are well-known to those skilled in the art and are hereby incorporated by reference in their entirety.

Upon examination of the data disclosed in the prior art, skilled artisans will appreciate the fact that, in order to eliminate side reactions in modified oligonucleotides, an optimal structure for preparation of such oligonucleotides should be derived from 1,3-propanediol or a longer $\alpha,\omega$-alkanediol and that a functional group to serve as an attachment point for ligands of interest should be at least 4 carbons away from any of the hydroxy groups. Further, to avoid the formation of new chiral centers in such modified oligonucleotides, the optimal linker should not possess any chiral or pro-chiral centers. Phosphoramidite building blocks and solid supports derived from such linkers are described herein in accordance with the present invention.

Thus, in a first aspect, the invention provides novel compounds which may serve as building blocks for the preparation of oligomeric compounds, analogs of natural oligonucleotides, wherein an artificial moiety is attached at the 5'- or at the 3'-termini, or in the middle of the chain, or in any combination thereof according to Formula I:

Formula I

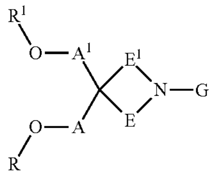

wherein:

Each A and $A^1$ is, independently, a linking moiety $—[(CH_2)_aM(CH_2)_b]_c—$ wherein:
- Each a, b, and c is, independently, an integer from 0 to 6;
- M is a chemical bond, oxygen atom, sulfur atom, $NQ^1$, $—N(Q^1)C(═O)N(Q^2)$-, $—C(═O)N(Q^1)$-, or $—N(Q^1)C(═O)—$ wherein:
  - Each $Q^1$ and $Q^2$ is independently hydrogen atom, methyl group, ethyl group, propyl group, isopropyl group, acetyl group, trifluoroacetyl group, phenoxyacetyl group, benzoyl group, or 9-fluorenylmethyloxycarbonyl group;

Each E and $E^1$ is, independently, a linking moiety $—[(CH_2)_dM^1(CH_2)_e]_f—$ wherein:
- Each d, e, and f is, independently, an integer from 0 to 3;
- $M^1$ is a chemical bond, oxygen atom, sulfur atom, $NQ^3$, $—N(Q^3)C(═O)N(Q^4)$-, $—C(═O)N(Q^3)$-, or $—N(Q^3)C(═O)—$ wherein:
  - Each $Q^3$ and $Q^4$ is independently hydrogen atom, methyl group, ethyl group, propyl group, isopropyl group, acetyl group, trifluoroacetyl group, phenoxyacetyl group, benzoyl group, or 9-fluorenylmethyloxycarbonyl group;

G is selected from hydrogen, a substituted or unsubstituted aliphatic group, a substituted or unsubstituted cycloaliphatic group, a substituted or unsubstituted aromatic group, a substituted or unsubstituted heteroaromatic group, a substituted or unsubstituted heterocyclic group, a nitrogen protecting group, $—CH_2$-L, —C(=O)-L, —C(=O)—OL, —C(=O)—NHL, —S(=O)-L, —S(=O)—NHL, —$SO_2$-L, and —$SO_2$—NHL, wherein:

L is selected from hydrogen, an optionally protected hydroxy group, an optionally protected amino group, or a linking moiety —$[[(CH_2)_gX^1(CH_2)_h]$—$X^2$—$[(CH_2)_iX^3(CH_2)_j]]_k$-J, wherein:

Each g, h, i, j, and k is, independently, an integer from 0 to 6;

Each $X^1$, $X^2$, and $X^3$ is, independently, an atom of oxygen, $CH_2$ group, an atom of sulfur, —C(=O)—, —SS—, —S(=O)—, $SO_2$, $NQ^5$, —C(=O)N($Q^5$)-, —OC(=O)N($Q^5$)-, —N($Q^5$)C(=O)—, —N($Q^5$)C(=O)O—, —N($Q^5$)C(=O)N($Q^6$)-, 1,4-phenylidene, or 1H-1,2,3-triazole-1,4-diyl wherein:

Each $Q^5$ and $Q^6$ is, independently, hydrogen atom, methyl group, ethyl group, propyl group, isopropyl group, acetyl group, trifluoroacetyl group, phenoxyacetyl group, benzoyl group, or 9-fluorenylmethyloxycarbonyl group;

J is selected from a hydrogen atom, an optionally protected hydroxyl group, an optionally protected primary amino group, an optionally protected alkylamino group, a dialkylamino group, a trialkylammonium group, an azido group, an ethynyl group —C≡CH, a hydroxy group alkylated with α-tocopherol, a hydroxy group alkylated with optionally protected N-acetyl-D-galactosamine, a primary amino group acylated with a ligand selected from optionally protected fluorescein-5-carboxylic acid, optionally protected fluorescein-6-carboxylic acid, N,N,N',N'-tetramethylrhodamine-5-carboxylic acid, N,N,N',N'-tetramethylrhodamine-6-carboxylic acid, ω-((1,3-dioxo-1,3,3a,4,7,7a-hexahydro-2H-4,7-epoxyisoindol-2-yl)oxy)alkanoic acid, ω-((1,3-dioxo-1,3,3a,4,7,7a-hexahydro-2H-4,7-methanoisoindol-2-yl)oxy)alkanoic acid, optionally protected biotin, 4'-(dimethylamino)-azobenzene-4-carboxylic acid, 4-pyrenylbutyryc acid, triethyl ethylenediaminetetraacetic acid, bicyclo[2.2.1]hept-5-ene-2-carboxylic acid, 2-(bicyclo[2.2.1]hept-5-en-2-yl)acetic acid, 2-((6,6-difluorocyclooct-4-yn-1-yl)oxy)acetic acid, 4-((2,2-difluorocyclooct-3-yn-1-yl)methyl)benzoic acid, 11,12-didehydro-γ-oxo-dibenz[b,f]azocine-5(6H)-butanoic acid, 3-(cyclooctatetraene)propionic acid, lipoic acid, a primary or a secondary amino group sulfonylated with 4'-(dimethylamino)-azobenzene-4-sulfonic acid, a primary or a secondary amino group carbamoylated with cholesterylcarbonic acid, a primary or a secondary amino group alkylated with 6-chloro-2-methoxyacridine, an optionally protected carboxy group, a carboxy group forming an amide with 1-amino-ω-[(1,3-dioxo-3a,4,7,7a-tetrahydro-2H-4,7-methanoisoindol-2-yl)oxy]alkane, a carboxy group forming an amide with 1-amino-ω-[(1,3-dioxo-3a,4,7,7a-tetrahydro-2H-4,7-epoxyisoindol-2-yl)oxy]alkane, or a carboxy group forming an amide with 11,12-didehydro-5,6-dihydrodibenz[b,f]azocine;

One of R and $R^1$ is selected from hydrogen or a protecting group of trityl type selected from (4-methoxyphenyl)diphenylmethyl, bis-(4-methoxyphenyl)phenylmethyl, tris-(methoxyphenyl)methyl, 9-phenylxanthen-9-yl, or 9-(p-methoxyphenyl)xanthen-9-yl; The other of R and $R^1$ is selected from hydrogen, a protecting group, PA, or $L^1$, wherein:

PA is a phosphoramidite moiety:

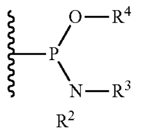

wherein:

Each $R^2$ and $R^3$ is, independently, C1 to C6 alkyl, or $R^2$ and $R^3$ together with the nitrogen atom they are attached to form a cycle wherein $R^2$+$R^3$=$(CH_2)_mY(CH_2)_n$ wherein Y is an atom of oxygen or $CH_2$ group;

Each m and n is, independently, an integer from 2 to about 5;

$R^4$ is a phosphite and phosphate protecting group selected from methyl, allyl, 2-cyanoethyl, 4-cyano-2-butenyl, 2-cyano-1,1-dimethylethyl, 2-(trimethylsilyl)ethyl, 2-(S-acetylthio)ethyl, 2-(S-pivaloylthio)ethyl, 2-(4-nitrophenyl)ethyl, 2,2,2-trichloroethyl, 2,2,2-trichloro-1,1-dimethylethyl, 1,1,1,3,3,3-hexafluoro-2-propyl, fluorenyl-9-methyl, 2-chlorophenyl, 4-chlorophenyl, or 2,4-dichlorophenyl;

$L^1$ is a linking moiety —C(=O)—$[[(CH_2)_pZ^1(CH_2)_q]_r$—$Z^2$—$[(CH_2)_sZ^3(CH_2)_t]_u]_v$—W, wherein:

Each p, q, r, s, t, u, and v is, independently, an integer from 0 to 6;

Each $Z^1$, $Z^2$, and $Z^3$ is selected, independently, from a chemical bond, an atom of oxygen, an atom of sulfur, —C(=O)—, —SS—, —S(=O)—, $SO_2$, $NQ^7$, —C(=O)N($Q^7$)-, —OC(=O)N($Q^7$)-, —N($Q^7$)C(=O)—, —N($Q^7$)C(=O)O—, or —N($Q^7$)C(=O)N($Q^8$)-, wherein:

Each $Q^7$ and $Q^8$ is independently an atom of hydrogen, methyl group, ethyl group, propyl group, isopropyl group, acetyl group, trifluoroacetyl group, phenoxyacetyl group, benzoyl group, or 9-fluorenylmethyloxycarbonyl group;

W is a hydroxy group, a negatively charged atom of oxygen $O^-$, or a solid phase material selected from a controlled pore glass, magnetic controlled pore glass, silica-containing particles, polymers of styrene, copolymers of styrene and divinylbenzene, controlled pore glass grafted with polymers of styrene, controlled pore glass grafted with copolymers of styrene and divinylbenzene, copolymers of styrene and divinylbenzene grafted with polyethyleneglycol, copolymers of dimethylacrylamide and N,N-bisacryloylethylenediamine, flat glass surface, or soluble support media;

In certain embodiments of the present invention, one of R and $R^1$ of Formula I is selected from tris-(4-methoxyphenyl)methyl protecting group, bis-(4-methoxyphenyl)phenylmethyl protecting group, 9-phenylxanthen-9-yl protecting group, or 9-(4-methoxyphenyl)xanthen-9-yl protecting group and the other of R and $R^1$ is selected from a residue of succinic acid optionally further attached to a solid phase material W via the second carboxylic function or a residue of diglycolic acid optionally further attached to a solid phase material W via the second carboxylic function.

In certain embodiments of the present invention, one of R and $R^1$ is selected from tris-(4-methoxyphenyl)methyl protecting group, bis-(4-methoxyphenyl)phenylmethyl protecting group, 9-phenylxanthen-9-yl protecting group, or 9-(4- methoxyphenyl)xanthen-9-yl protecting group and the other of R and $R^1$ is a phosphoramidite moiety PA.

In certain embodiments of the present invention, each $R^2$ and $R^3$ is isopropyl group or $R^2$ and $R^3$ together with the nitrogen they are attached to form a cycle so that $R^2+R^3$=—$(CH_2)_4$—, $R^2+R^3$=—$(CH_2)_5$—, or $R^2+R^3$=—$(CH_2)$ 2-O—$(CH_2)_2$—.

In certain embodiments of the present invention, each A and $A^1$ of Formula I is independently selected from —$CH_2$— or —$(CH_2)_2$—.

In certain embodiments of the present invention, each E and $E^1$ of Formula I is independently selected from —$CH_2$—, —$OCH_2$—, —$(CH_2)_2$—, or —$O(CH_2)_2$—.

In certain embodiments of the present invention, G of Formula I is selected from an atom of hydrogen, an alkyl group, a trifluoroacetyl group, (9H-fluoren-9-yl)methoxycarbonyl (Fmoc) group, 6-(trifluoroacetylamino)hexanoyl, 6-heptynoyl, 6-azidohexanoyl, 6-aminohexanoyl protected at the amino group with (9H-fluoren-9-yl)methoxycarbonyl (Fmoc) group, [4-(1-pyrenyl)butyryl-1], ω-[[(3,4,6-tri-O-acetyl-2-acetamido-2-deoxy-β-D-galactopyranosyl)]oxy]alkanoyl, ω-hydroxyalkanoic acid further alkylated at the hydroxy group with α-tocopherol, 6-[[4-(1-pyrenyl)butyryl-1]amino]hexanoyl, 6-[(6-heptynoyl-1)amino]hexanoyl, 6-aminohexanoyl further acylated at the amino group with 4-(dimethylamino)azobenzene-4'-carboxylic acid, 6-aminohexanoyl further sulfonylated at the amino group with 4-(dimethylamino)azobenzene-4'-sulfonic acid, 6-aminohexanoyl further acylated at the amino group with a protected 6-carboxyfluorescein, 6-aminohexanoyl further acylated at the amino group with a protected 5-carboxyfluorescein, 6-aminohexanoyl further acylated at the amino group with 5-carboxy-N,N, N'N'-tetramethylrhodamine, 6-aminohexanoyl further acylated at the amino group with 6-carboxy-N,N,N'N'-tetramethylrhodamine, 6-aminohexanoyl further acylated at the amino group with ω-((1,3-dioxo-1,3,3a,4,7,7a-hexahydro-2H-4,7-epoxyisoindol-2-yl)oxy)alkanoic acid, 6-aminohexanoyl further acylated at the amino group with ω-((1,3-dioxo-1,3,3a,4,7,7a-hexahydro-2H-4,7-methanoisoindol-2-yl)oxy)alkanoic acid, 6-aminohexanoyl further acylated at the amino group with bicyclo[2.2.1]hept-5-ene-2-carboxylic acid, 6-aminohexanoyl further acylated at the amino group with 2-(bicyclo[2.2.1]hept-5-en-2-yl)acetic acid, 6-aminohexanoyl further acylated at the amino group with ω-(bicyclo[2.2.1]hept-5-en-2-yl)alkanoic acid, 6-aminohexanoyl further acylated at the amino group with 8-[[(3,4,6-tri-O-acetyl-2-acetamido-2-deoxy-(β-D-galactopyranosyl)]oxy]-3,6-dioxooctanoic acid, 6-aminohexanoyl further acylated at the amino group with ω-[[(3,4,6-tri-O-acetyl-2-acetamido-2-deoxy-β-D-galactopyranosyl)]oxy]alkanoic acid, 6-aminohexanoyl further acylated at the amino group with lipoic acid, 6-aminohexanoyl further acylated at the amino group with 2-((6,6-difluorocyclooct-4-yn-1-yl)oxy)acetic acid, 6-aminohexanoyl further acylated at the amino group with 4-((2,2-difluorocyclooct-3-yn-1-yl)methyl)benzoic acid, 6-aminohexanoyl further acylated at the amino group with 11,12-didehydro-γ-oxo-dibenz[b,f]azocine-5(6H)-butanoic acid, 6-aminohexanoyl further acylated at the amino group with 3-(cyclooctatetraene)propionic acid, 6-aminohexanoyl further carbamoylated at the amino group with cholesterylcarbonic acid, 6-aminohexanoyl further acylated at the amino group with optionally protected D-biotin, 6-[(6-chloro-2-methoxyacridin-9-yl)amino]hexanoyl, a residue of diglycolic acid optionally protected at the second carboxylic group, a residue of diglycolic acid further forming an amide with 1-amino-ω-[(1,3-dioxo-3a,4,7,7a-tetrahydro-2H-4,7-methanoisoindol-2-yl)oxy]alkane, a residue of diglycolic acid further forming an amide with 1-amino-ω-[(1,3-dioxo-3a,4,7,7a-tetrahydro-2H-4,7-epoxyisoindol-2-yl)oxy]alkane, a residue of diglycolic acid further forming an amide with 11,12-didehydro-5,6-dihydrodibenz[b,f]azocine, a residue of diglycolic further acid forming an amide with 11,12-didehydro-5,6-dihydrodibenz[b,f]azocine, a residue of diglycolic acid further forming an amide with 1,13-diamino-4,7,10-trioxatridecane, optionally protected at the second amino group, or a residue of diglycolic acid wherein the second carboxy group further forms an amide with 1,13-diamino-4,7,10-trioxatridecane further acylated at the second amino group with optionally protected D-biotin.

In certain embodiments of the present invention, one of R and $R^1$ of Formula I is 4,4'-dimethoxytrityl group, and the other is a residue of succinic acid optionally attached to a solid phase material, each A and $A^1$ is —$CH_2$—, each E and $E^1$ is —$(CH_2)_2$—, and G is selected from an atom of hydrogen, an alkyl group, a trifluoroacetyl group, (9H-fluoren-9-yl)methoxycarbonyl (Fmoc) group, 6-(trifluoroacetylamino)hexanoyl, 6-heptynoyl, 6-azidohexanoyl, 6-aminohexanoyl protected at the amino group with (9H-fluoren-9-yl)methoxycarbonyl (Fmoc) group, [4-(1-pyrenyl)butyryl-1], ω-[[(3,4,6-tri-O-acetyl-2-acetamido-2-deoxy-β-D-galactopyranosyl)]oxy]alkanoyl, ω-hydroxyalkanoic acid further alkylated at the hydroxy group with α-tocopherol, 6-[[4-(1-pyrenyl)butyryl-1]amino]hexanoyl, 6-[(6-heptynoyl-1)amino]hexanoyl, 6-aminohexanoyl further acylated at the amino group with 4-(dimethylamino)azobenzene-4'-carboxylic acid, 6-aminohexanoyl further sulfonylated at the amino group with 4-(dimethylamino)azobenzene-4'-sulfonic acid, 6-aminohexanoyl further acylated at the amino group with a protected 6-carboxyfluorescein, 6-aminohexanoyl further acylated at the amino group with a protected 5-carboxyfluorescein, 6-aminohexanoyl further acylated at the amino group with 5-carboxy-N,N, N'N'-tetramethylrhodamine, 6-aminohexanoyl further acylated at the amino group with 6-carboxy-N,N,N'N'-tetramethylrhodamine, 6-aminohexanoyl further acylated at the amino group with ω-((1,3-dioxo-1,3,3a,4,7,7a-hexahydro-2H-4,7-epoxyisoindol-2-yl)oxy)alkanoic acid, 6-aminohexanoyl further acylated at the amino group with ω-((1,3-dioxo-1,3,3a,4,7,7a-hexahydro-2H-4,7-methanoisoindol-2-yl)oxy)alkanoic acid, 6-aminohexanoyl further acylated at the amino group with bicyclo[2.2.1]hept-5-ene-2-carboxylic acid, 6-aminohexanoyl further acylated at the amino group with 2-(bicyclo[2.2.1]hept-5-en-2-yl)acetic acid, 6-aminohexanoyl further acylated at the amino group with ω-(bicyclo[2.2.1]hept-5-en-2-yl)alkanoic acid, 6-aminohexanoyl further acylated at the amino group with 8-[[(3,4,6-tri-O-acetyl-2-acetamido-2-deoxy-β-D-galactopyranosyl)]oxy]-3,6-dioxooctanoic acid, 6-aminohexanoyl further acylated at the amino group with ω-[[(3,4,6-tri-O-acetyl-2-acetamido-2-deoxy-β-D-galactopyranosyl)]oxy]alkanoic acid, 6-aminohexanoyl further acylated at the amino group with lipoic acid, 6-aminohexanoyl further acylated at the amino group with 2-((6,6-difluorocyclooct-4-yn-1-yl)oxy)acetic acid, 6-aminohexanoyl further acylated at the amino group with 4-((2,2-difluorocyclooct-3-yn-1-yl)methyl)benzoic acid, 6-aminohexanoyl further acylated at the amino group with 11,12-didehydro-γ-oxo-dibenz[b,f]azocine-5(6H)-butanoic acid, 6-aminohexanoyl further acylated at the amino group with 3-(cyclooctatetraene)propionic acid, 6-aminohexanoyl further carbamoylated at the amino group with cholesterylcarbonic acid, 6-aminohexanoyl further acylated at the amino group with optionally protected D-biotin, 6-[(6-chloro-2-methoxyacridin-9-yl)amino]hexanoyl, a residue of diglycolic acid optionally protected at the second carboxylic group, a residue of diglycolic acid further forming an amide with 1-amino-ω-[(1,3-dioxo-3a,4,7,7a-tetrahydro-2H-4,7-methanoisoindol-2-yl)oxy]alkane, a residue of diglycolic acid further forming an amide with 1-amino-ω-[(1,3-dioxo-3a,4,7,7a-tetrahydro-2H-4,7-epoxyisoindol-2-yl)oxy]alkane, a residue of diglycolic acid further forming an amide with 11,12-didehydro-5,6-dihydrodibenz[b,f]azocine, a residue of diglycolic further acid forming an amide with 11,12-didehydro-5,6-dihydrodibenz[b,f]azocine, a residue of diglycolic acid further forming an amide with 1,13-diamino-4,7,10-trioxatridecane, optionally protected at the second amino group, or a residue of diglycolic acid wherein the second carboxy group further forms an amide with 1,13-diamino-4,7,10-trioxatridecane further acylated at the second amino group with optionally protected D-biotin.

In other embodiments of the present invention, one of R and $R^1$ of Formula I is 4,4'-dimethoxytrityl group, and the other is a residue of succinic acid optionally attached to a solid phase material, each A, $A^1$, E, and $E^1$ is —$CH_2$—, and G is selected from an atom of hydrogen, an alkyl group, a trifluoroacetyl group, (9H-fluoren-9-yl)methoxycarbonyl (Fmoc) group, 6-(trifluoroacetylamino)hexanoyl, 6-heptynoyl, 6-azidohexanoyl, 6-aminohexanoyl protected at the amino group with (9H-fluoren-9-yl)methoxycarbonyl (Fmoc) group, [4-(1-pyrenyl)butyryl-1], co-[[(3,4,6-tri-O-acetyl-2-acetamido-2-deoxy-β-D-galactopyranosyl)]oxy]alkanoyl, co-hydroxyalkanoic acid further alkylated at the hydroxy group with α-tocopherol, 6-[[4-(1-pyrenyl)butyryl-1]amino]hexanoyl, 6-[(6-heptynoyl-1)amino]hexanoyl, 6-aminohexanoyl further acylated at the amino group with 4-(dimethylamino)azobenzene-4'-carboxylic acid, 6-aminohexanoyl further sulfonylated at the amino group with 4-(dimethylamino)azobenzene-4'-sulfonic acid, 6-aminohexanoyl further acylated at the amino group with a protected 6-carboxyfluorescein, 6-aminohexanoyl further acylated at the amino group with a protected 5-carboxyfluorescein, 6-aminohexanoyl further acylated at the amino group with 5-carboxy-N,N,N'N'-tetramethylrhodamine, 6-aminohexanoyl further acylated at the amino group with 6-carboxy-N,N,N'N'-tetramethylrhodamine, 6-aminohexanoyl further acylated at the amino group with ω-((1,3-dioxo-1,3,3a,4,7,7a-hexahydro-2H-4,7-epoxyisoindol-2-yl)oxy)alkanoic acid, 6-aminohexanoyl further acylated at the amino group with ω-((1,3-dioxo-1,3,3a,4,7,7a-hexahydro-2H-4,7-methanoisoindol-2-yl)oxy)alkanoic acid, 6-aminohexanoyl further acylated at the amino group with bicyclo[2.2.1]hept-5-ene-2-carboxylic acid, 6-aminohexanoyl further acylated at the amino group with 2-(bicyclo[2.2.1]hept-5-en-2-yl)acetic acid, 6-aminohexanoyl further acylated at the amino group with ω-(bicyclo[2.2.1]hept-5-en-2-yl)alkanoic acid, 6-aminohexanoyl further acylated at the amino group with 8-[[(3,4,6-tri-O-acetyl-2-acetamido-2-deoxy-β-D-galactopyranosyl)]oxy]-3,6-dioxooctanoic acid, 6-aminohexanoyl further acylated at the amino group with ω-[[(3,4,6-tri-O-acetyl-2-acetamido-2-deoxy-β-D-galactopyranosyl)]oxy]alkanoic acid, 6-aminohexanoyl further acylated at the amino group with lipoic acid, 6-aminohexanoyl further acylated at the amino group with 2-((6,6-difluorocyclooct-4-yn-1-yl)oxy)acetic acid, 6-aminohexanoyl further acylated at the amino group with 4-((2,2-difluorocyclooct-3-yn-1-yl)methyl)benzoic acid, 6-aminohexanoyl further acylated at the amino group with 11,12-didehydro-γ-oxo-dibenz[b,f]azocine-5(6H)-butanoic acid, 6-aminohexanoyl further acylated at the amino group with 3-(cyclooctatetraene)propionic acid, 6-aminohexanoyl further carbamoylated at the amino group with cholesteryl-carbonic acid, 6-aminohexanoyl further acylated at the amino group with optionally protected D-biotin, 6-[(6-chloro-2-methoxyacridin-9-yl)amino]hexanoyl, a residue of diglycolic acid optionally protected at the second carboxylic group, a residue of diglycolic acid further forming an amide with 1-amino-ω-[(1,3-dioxo-3a,4,7,7a-tetrahydro-2H-4,7-methanoisoindol-2-yl)oxy]alkane, a residue of diglycolic acid further forming an amide with 1-amino-ω-[(1,3-dioxo-3a,4,7,7a-tetrahydro-2H-4,7-epoxyisoindol-2-yl)oxy]alkane, a residue of diglycolic acid further forming an amide with 11,12-didehydro-5,6-dihydrodibenz[b,f]azocine, a residue of diglycolic further acid forming an amide with 11,12-didehydro-5,6-dihydrodibenz[b,f]azocine, a residue of diglycolic acid further forming an amide with 1,13-diamino-4,7,10-trioxatridecane, optionally protected at the second amino group, or a residue of diglycolic acid wherein the second carboxy group further forms an amide with 1,13-diamino-4,7,10-trioxatridecane further acylated at the second amino group with optionally protected D-biotin.

In yet another embodiment of the present invention, one of R and $R^1$ of Formula I is 4,4',4"-trimethoxytrityl group, and the other is a residue of succinic acid optionally attached to a solid phase material, each A and $A^1$ is —$CH_2$—, each E and $E^1$ is —$(CH_2)_2$—, and G is selected from an atom of hydrogen, an alkyl group, a trifluoroacetyl group, (9H-fluoren-9-yl)methoxycarbonyl (Fmoc) group, 6-(trifluoroacetylamino)hexanoyl, 6-heptynoyl, 6-azidohexanoyl, 6-aminohexanoyl protected at the amino group with (9H-fluoren-9-yl)methoxycarbonyl (Fmoc) group, [4-(1-pyrenyl)butyryl-1], ω-[[(3,4,6-tri-O-acetyl-2-acetamido-2-deoxy-β-D-galactopyranosyl)]oxy]alkanoyl, ω-hydroxyalkanoic acid further alkylated at the hydroxy group with α-tocopherol, 6-[[4-(1-pyrenyl)butyryl-1]amino]hexanoyl, 6-[(6-heptynoyl-1)amino]hexanoyl, 6-aminohexanoyl further acylated at the amino group with 4-(dimethylamino)azobenzene-4'-carboxylic acid, 6-aminohexanoyl further sulfonylated at the amino group with 4-(dimethylamino)azobenzene-4'-sulfonic acid, 6-aminohexanoyl further acylated at the amino group with a protected 6-carboxyfluorescein, 6-aminohexanoyl further acylated at the amino group with a protected 5-carboxyfluorescein, 6-aminohexanoyl further acylated at the amino group with 5-carboxy-N,N,N'N'-tetramethylrhodamine, 6-aminohexanoyl further acylated at the amino group with 6-carboxy-N,N,N'N'-tetramethylrhodamine, 6-aminohexanoyl further acylated at the amino group with ω-((1,3-dioxo-1,3,3a,4,7,7a-hexahydro-2H-4,7-epoxyisoindol-2-yl)oxy)alkanoic acid, 6-aminohexanoyl further acylated at the amino group with ω-((1,3-dioxo-1,3,3a,4,7,7a-hexahydro-2H-4,7-methanoisoindol-2-yl)oxy)alkanoic acid, 6-aminohexanoyl further acylated at the amino group with bicyclo[2.2.1]hept-5-ene-2-carboxylic acid, 6-aminohexanoyl further acylated at the amino group with 2-(bicyclo[2.2.1]hept-5-en-2-yl)acetic acid, 6-aminohexanoyl further acylated at the amino group with ω-(bicyclo[2.2.1]hept-5-en-2-yl)alkanoic acid, 6-aminohexanoyl further acylated at the amino group with 8-[[(3,4,6-tri-O-acetyl-2-acetamido-2-deoxy-β-D-galactopyranosyl)]oxy]-3,6-dioxooctanoic acid, 6-aminohexanoyl further acylated at the amino group with ω-[[(3,4,6-tri-O-acetyl-2-acetamido-2-deoxy-β-D-galactopyranosyl)]oxy]alkanoic acid, 6-aminohexanoyl further acylated at the amino group with lipoic acid, 6-aminohexanoyl further acylated at the amino group with 2-((6,6-difluorocyclooct-4-yn-1-yl)oxy)acetic acid, 6-aminohexanoyl further acylated at the amino group with 4-((2,2-difluorocyclooct-3-yn-1-yl)methyl)benzoic acid, 6-aminohexanoyl further acylated at the amino group with 11,12-didehydro-γ-oxo-dibenz[b,f]azocine-5(6H)-butanoic acid, 6-aminohexanoyl further acylated at the amino group with 3-(cyclooctatetraene)propionic acid, 6-aminohexanoyl further carbamoylated at the amino group with cholesteryl-carbonic acid, 6-aminohexanoyl further acylated at the amino group with optionally protected D-biotin, 6-[(6-chloro-2-methoxyacridin-9-yl)amino]hexanoyl, a residue of diglycolic acid optionally protected at the second carboxylic group, a residue of diglycolic acid further forming an amide with 1-amino-ω-[(1,3-dioxo-3a,4,7,7a-tetrahydro-2H-4,7-methanoisoindol-2-yl)oxy]alkane, a residue of diglycolic acid further forming an amide with 1-amino-ω-[(1,3-dioxo-3a,4,7,7a-tetrahydro-2H-4,7-epoxyisoindol-2-yl)oxy]alkane, a residue of diglycolic acid further forming an amide with 11,12-didehydro-5,6-dihydrodibenz[b,f]azocine, a residue of diglycolic further acid forming an amide with 11,12-didehydro-5,6-dihydrodibenz[b,f]azocine, a residue of diglycolic acid further forming an amide with 1,13-diamino-4,7,10-trioxatridecane, optionally protected at the second amino group, or a residue of diglycolic acid wherein the second carboxy group further forms an amide with 1,13-diamino-4,7,10-trioxatridecane further acylated at the second amino group with optionally protected D-biotin.

In yet another embodiment of the present invention, one of R and $R^1$ of Formula I is 4,4,4"-trimethoxytrityl group, and the other is a residue of succinic acid optionally attached to a solid phase material, each A, $A^1$, E, and $E^1$ is —$CH_2$—, and G is selected from an atom of hydrogen, an alkyl group, a trifluoroacetyl group, (9H-fluoren-9-yl)methoxycarbonyl (Fmoc) group, 6-(trifluoroacetylamino)hexanoyl, 6-heptynoyl, 6-azidohexanoyl, 6-aminohexanoyl protected at the amino group with (9H-fluoren-9-yl)methoxycarbonyl (Fmoc) group, [4-(1-pyrenyl)butyryl-1], ω-[[(3,4,6-tri-O-acetyl-2-acetamido-2-deoxy-β-D-galactopyranosyl)]oxy]alkanoyl, ω-hydroxyalkanoic acid further alkylated at the hydroxy group with α-tocopherol, 6-[[4-(1-pyrenyl)butyryl-1]amino]hexanoyl, 6-[(6-heptynoyl-1)amino]hexanoyl, 6-aminohexanoyl further acylated at the amino group with 4-(dimethylamino)azobenzene-4'-carboxylic acid, 6-aminohexanoyl further sulfonylated at the amino group with 4-(dimethylamino)azobenzene-4'-sulfonic acid, 6-aminohexanoyl further acylated at the amino group with a protected 6-carboxyfluorescein, 6-aminohexanoyl further acylated at the amino group with a protected 5-carboxyfluorescein, 6-aminohexanoyl further acylated at the amino group with 5-carboxy-N,N,N'N'-tetramethylrhodamine, 6-aminohexanoyl further acylated at the amino group with 6-carboxy-N,N,N'N'-tetramethylrhodamine, 6-aminohexanoyl further acylated at the amino group with ω-((1,3-dioxo-1,3,3a,4,7,7a-hexahydro-2H-4,7-epoxyisoindol-2-yl)oxy)alkanoic acid, 6-aminohexanoyl further acylated at the amino group with ω-((1,3-dioxo-1,3,3a,4,7,7a-hexahydro-2H-4,7-methanoisoindol-2-yl)oxy)alkanoic acid, 6-aminohexanoyl further acylated at the amino group with bicyclo[2.2.1]hept-5-ene-2-carboxylic acid, 6-aminohexanoyl further acylated at the amino group with 2-(bicyclo[2.2.1]hept-5-en-2-yl)acetic acid, 6-aminohexanoyl further acylated at the amino group with ω-(bicyclo[2.2.1]hept-5-en-2-yl)alkanoic acid, 6-aminohexanoyl further acylated at the amino group with 8-[[(3,4,6-tri-O-acetyl-2-acetamido-2-deoxy-(β-D-galactopyranosyl)]oxy]-3,6-dioxooctanoic acid, 6-aminohexanoyl further acylated at the amino group with ω-[[(3,4,6-tri-O-acetyl-2-acetamido-2-deoxy-β-D-galactopyranosyl)]oxy]alkanoic acid, 6-aminohexanoyl further acylated at the amino group with lipoic acid, 6-aminohexanoyl further acylated at the amino group with 2-((6,6-difluorocyclooct-4-yn-1-yl)oxy)acetic acid, 6-aminohexanoyl further acylated at the amino group with 4-((2,2-difluorocyclooct-3-yn-1-yl)methyl)benzoic acid, 6-aminohexanoyl further acylated at the amino group with 11,12-didehydro-γ-oxo-dibenz[b,f]azocine-5(6H)-butanoic acid, 6-aminohexanoyl further acylated at the amino group with 3-(cyclooctatetraene)propionic acid, 6-aminohexanoyl further carbamoylated at the amino group with cholesteryl-carbonic acid, 6-aminohexanoyl further acylated at the amino group with optionally protected D-biotin, 6-[(6-chloro-2-methoxyacridin-9-yl)amino]hexanoyl, a residue of diglycolic acid optionally protected at the second carboxylic group, a residue of diglycolic acid further forming an amide with 1-amino-ω-[(1,3-dioxo-3a,4,7,7a-tetrahydro-2H-4,7-methanoisoindol-2-yl)oxy]alkane, a residue of diglycolic acid further forming an amide with 1-amino-ω-[(1,3-dioxo-3a,4,7,7a-tetrahydro-2H-4,7-epoxyisoindol-2-yl)oxy]alkane, a residue of diglycolic acid further forming an amide with 11,12-didehydro-5,6-dihydrodibenz[b,f]azocine, a residue of diglycolic further acid forming an amide with 11,12-didehydro-5,6-dihydrodibenz[b,f]azocine, a residue of diglycolic acid further forming an amide with 1,13-diamino-4,7,10-trioxatridecane, optionally protected at the second amino group, or a residue of diglycolic acid wherein the second carboxy group further forms an amide with 1,13-diamino-4,7,10-trioxatridecane further acylated at the second amino group with optionally protected D-biotin.

In yet another embodiment of the present invention, one of R and $R^1$ of Formula I is 4,4'-dimethoxytrityl group, and the other is PA wherein each $R^2$ and $R^3$ is isopropyl group and $R^4$ is 2-cyanoetyl group, each A and $A^1$ is —$CH_2$—, each E and $E^1$ is —$(CH_2)_2$—, and G is selected from an atom of hydrogen, an alkyl group, a trifluoroacetyl group, (9H-fluoren-9-yl)methoxycarbonyl (Fmoc) group, 6-(trifluoroacetylamino)hexanoyl, 6-heptynoyl, 6-azidohexanoyl, 6-aminohexanoyl protected at the amino group with (9H-fluoren-9-yl)methoxycarbonyl (Fmoc) group, [4-(1-pyrenyl)butyryl-1], ω-[[(3,4,6-tri-O-acetyl-2-acetamido-2-deoxy-β-D-galactopyranosyl)]oxy]alkanoyl, ω-hydroxyalkanoic acid further alkylated at the hydroxy group with α-tocopherol, 6-[[4-(1-pyrenyl)butyryl-1]amino]hexanoyl, 6-[(6-heptynoyl-1)amino]hexanoyl, 6-aminohexanoyl further acylated at the amino group with 4-(dimethylamino)azobenzene-4'-carboxylic acid, 6-aminohexanoyl further sulfonylated at the amino group with 4-(dimethylamino)azobenzene-4'-sulfonic acid, 6-aminohexanoyl further acylated at the amino group with a protected 6-carboxyfluorescein, 6-aminohexanoyl further acylated at the amino group with a protected 5-carboxyfluorescein, 6-aminohexanoyl further acylated at the amino group with 5-carboxy-N,N,N'N'-tetramethylrhodamine, 6-aminohexanoyl further acylated at the amino group with 6-carboxy-N,N,N'N'-tetramethylrhodamine, 6-aminohexanoyl further acylated at the amino group with ω-((1,3-dioxo-1,3,3a,4,7,7a-hexahydro-2H-4,7-epoxyisoindol-2-yl)oxy)alkanoic acid, 6-aminohexanoyl further acylated at the amino group with ω-((1,3-dioxo-1,3,3a,4,7,7a-hexahydro-2H-4,7-methanoisoindol-2-yl)oxy)alkanoic acid, 6-aminohexanoyl further acylated at the amino group with bicyclo[2.2.1]hept-5-ene-2-carboxylic acid, 6-aminohexanoyl further acylated at the amino group with 2-(bicyclo[2.2.1]hept-5-en-2-yl)acetic acid, 6-aminohexanoyl further acylated at the amino group with ω-(bicyclo[2.2.1]hept-5-en-2-yl)alkanoic acid, 6-aminohexanoyl further acylated at the amino group with 8-[[(3,4,6-tri-O-acetyl-2-acetamido-2-deoxy-β-D-galactopyranosyl)]oxy]-3,6-dioxooctanoic acid, 6-aminohexanoyl further acylated at the amino group with ω-[[(3,4,6-tri-O-acetyl-2-acetamido-2-deoxy-β-D-galactopyranosyl)]oxy]alkanoic acid, 6-aminohexanoyl further acylated at the amino group with lipoic acid, 6-aminohexanoyl further acylated at the amino group with 2-((6,6-difluorocyclooct-4-yn-1-yl)oxy)acetic acid, 6-aminohexanoyl further acylated at the amino group with 4-((2,2-difluorocyclooct-3-yn-1-yl)methyl)benzoic acid, 6-aminohexanoyl further acylated at the amino group with 11,12-didehydro-γ-oxo-dibenz[b,f]azocine-5(6H)-butanoic acid, 6-aminohexanoyl further acylated at the amino group with 3-(cyclooctatetraene)propionic acid, 6-aminohexanoyl further carbamoylated at the amino group with cholesteryl-carbonic acid, 6-aminohexanoyl further acylated at the amino group with optionally protected D-biotin, 6-[(6-chloro-2-methoxyacridin-9-yl)amino]hexanoyl, a residue of diglycolic acid optionally protected at the second carboxylic group, a residue of diglycolic acid further forming an amide with 1-amino-ω-[(1,3-dioxo-3a,4,7,7a-tetrahydro-2H-4,7-methanoisoindol-2-yl)oxy]alkane, a residue of diglycolic acid further forming an amide with 1-amino-ω-[(1,3-dioxo-3a,4,7,7a-tetrahydro-2H-4,7-epoxyisoindol-2-yl)oxy]alkane, a residue of diglycolic acid further forming an amide with 11,12-didehydro-5,6-dihydrodibenz[b,f]azocine, a residue of diglycolic further acid forming an amide with 11,12-didehydro-5,6-dihydrodibenz[b,f]azocine, a residue of diglycolic acid further forming an amide with 1,13-diamino-4,7,10-trioxatridecane, optionally protected at the second amino group, or a residue of diglycolic acid wherein the second carboxy group further forms an amide with 1,13-diamino-4,7,10-trioxatridecane further acylated at the second amino group with optionally protected D-biotin.

In yet another embodiment of the present invention, $R^1$ of Formula I is 4,4'-dimethoxytrityl group, $R^2$ is PA wherein each $R^2$ and $R^3$ is isopropyl group and $R^4$ is 2-cyanoetyl group, each A, $A^1$, E, and $E^1$ is —$CH_2$—, and G is selected from an atom of hydrogen, an alkyl group, a trifluoroacetyl group, (9H-fluoren-9-yl)methoxycarbonyl (Fmoc) group, 6-(trifluoroacetylamino)hexanoyl, 6-heptynoyl, 6-azido-hexanoyl, 6-aminohexanoyl protected at the amino group with (9H-fluoren-9-yl)methoxycarbonyl (Fmoc) group, [4-(1-pyrenyl)butyryl-1], co-[[(3,4,6-tri-O-acetyl-2-acetamido-2-deoxy-β-D-galactopyranosyl)]oxy]alkanoyl, o-hydroxyalkanoic acid further alkylated at the hydroxy group with α-tocopherol, 6-[[4-(1-pyrenyl)butyryl-1]amino]hexanoyl, 6-[(6-heptynoyl-1)amino]hexanoyl, 6-aminohexanoyl further acylated at the amino group with 4-(dimethylamino)azobenzene-4'-carboxylic acid, 6-aminohexanoyl further sulfonylated at the amino group with 4-(dimethylamino)azobenzene-4'-sulfonic acid, 6-aminohexanoyl further acylated at the amino group with a protected 6-carboxyfluorescein, 6-aminohexanoyl further acylated at the amino group with a protected 5-carboxyfluorescein, 6-aminohexanoyl further acylated at the amino group with 5-carboxy-N,N,N'N'-tetramethylrhodamine, 6-aminohexanoyl further acylated at the amino group with 6-carboxy-N,N,N'N'-tetramethylrhodamine, 6-aminohexanoyl further acylated at the amino group with ω-((1,3-dioxo-1,3,3a,4,7,7a-hexahydro-2H-4,7-epoxyisoindol-2-yl)oxy)alkanoic acid, 6-aminohexanoyl further acylated at the amino group with ω-((1,3-dioxo-1,3,3a,4,7,7a-hexahydro-2H-4,7-methanoisoindol-2-yl)oxy)alkanoic acid, 6-aminohexanoyl further acylated at the amino group with bicyclo[2.2.1]hept-5-ene-2-carboxylic acid, 6-aminohexanoyl further acylated at the amino group with 2-(bicyclo[2.2.1]hept-5-en-2-yl)acetic acid, 6-aminohexanoyl further acylated at the amino group with ω-(bicyclo[2.2.1]hept-5-en-2-yl)alkanoic acid, 6-aminohexanoyl further acylated at the amino group with 8-[[(3,4,6-tri-O-acetyl-2-acetamido-2-deoxy-β-D-galactopyranosyl)]oxy]-3,6-dioxooctanoic acid, 6-aminohexanoyl further acylated at the amino group with ω-[[(3,4,6-tri-O-acetyl-2-acetamido-2-deoxy-β-D-galactopyranosyl)]oxy]alkanoic acid, 6-aminohexanoyl further acylated at the amino group with lipoic acid, 6-aminohexanoyl further acylated at the amino group with 2-((6,6-difluorocyclooct-4-yn-1-yl)oxy)acetic acid, 6-aminohexanoyl further acylated at the amino group with 4-((2,2-difluorocyclooct-3-yn-1-yl)methyl)benzoic acid, 6-aminohexanoyl further acylated at the amino group with 11,12-didehydro-γ-oxo-dibenz[b,f]azocine-5(6H)-butanoic acid, 6-aminohexanoyl further acylated at the amino group with 3-(cyclooctatetraene)propionic acid, 6-aminohexanoyl further carbamoylated at the amino group with cholesteryl-carbonic acid, 6-aminohexanoyl further acylated at the amino group with optionally protected D-biotin, 6-[(6-chloro-2-methoxyacridin-9-yl)amino]hexanoyl, a residue of diglycolic acid optionally protected at the second carboxylic group, a residue of diglycolic acid further forming an amide with 1-amino-ω-[(1,3-dioxo-3a,4,7,7a-tetrahydro-2H-4,7-methanoisoindol-2-yl)oxy]alkane, a residue of diglycolic acid further forming an amide with 1-amino-ω-[(1,3-dioxo-3a,4,7,7a-tetrahydro-2H-4,7-epoxyisoindol-2-yl)oxy]alkane, a residue of diglycolic acid further forming an amide with 11,12-didehydro-5,6-dihydrodibenz[b,f]azocine, a residue of diglycolic further acid forming an amide with 11,12-didehydro-5,6-dihydrodibenz[b,f]azocine, a residue of diglycolic acid further forming an amide with 1,13-diamino-4,7,10-trioxatridecane, optionally protected at the second amino group, or a residue of diglycolic acid wherein the second carboxy group further forms an amide with 1,13-diamino-4,7,10-trioxatridecane further acylated at the second amino group with optionally protected D-biotin.

In yet another embodiment of the present invention, one of R and $R^1$ of Formula I is 4,4',4"-trimethoxytrityl group, and the other is PA wherein each $R^2$ and $R^3$ is isopropyl group and $R^4$ is 2-cyanoetyl group, each A and $A^1$ is —$CH_2$—, each E and $E^1$ is —$(CH_2)_2$—, and G is selected from an atom of hydrogen, an alkyl group, a trifluoroacetyl group, (9H-fluoren-9-yl)methoxycarbonyl (Fmoc) group, 6-(trifluoroacetylamino)hexanoyl, 6-heptynoyl, 6-azido-hexanoyl, 6-aminohexanoyl protected at the amino group with (9H-fluoren-9-yl)methoxycarbonyl (Fmoc) group, [4-(1-pyrenyl)butyryl-1], wo-[[(3,4,6-tri-O-acetyl-2-acetamido-2-deoxy-β-D-galactopyranosyl)]oxy]alkanoyl, ω-hydroxyalkanoic acid further alkylated at the hydroxy group with α-tocopherol, 6-[[4-(1-pyrenyl)butyryl-1]amino]hexanoyl, 6-[(6-heptynoyl-1)amino]hexanoyl, 6-aminohexanoyl further acylated at the amino group with 4-(dimethylamino)azobenzene-4'-carboxylic acid, 6-aminohexanoyl further sulfonylated at the amino group with 4-(dimethylamino)azobenzene-4'-sulfonic acid, 6-aminohexanoyl further acylated at the amino group with a protected 6-carboxyfluorescein, 6-aminohexanoyl further acylated at the amino group with a protected 5-carboxyfluorescein, 6-aminohexanoyl further acylated at the amino group with 5-carboxy-N,N,N'N'-tetramethylrhodamine, 6-aminohexanoyl further acylated at the amino group with 6-carboxy-N,N,N'N'-tetramethylrhodamine, 6-aminohexanoyl further acylated at the amino group with ω-((1,3-dioxo-1,3,3a,4,7,7a-hexahydro-2H-4,7-epoxyisoindol-2-yl)oxy)alkanoic acid, 6-aminohexanoyl further acylated at the amino group with ω-((1,3-dioxo-1,3,3a,4,7,7a-hexahydro-2H-4,7-methanoisoindol-2-yl)oxy)alkanoic acid, 6-aminohexanoyl further acylated at the amino group with bicyclo[2.2.1]hept-5-ene-2-carboxylic acid, 6-aminohexanoyl further acylated at the amino group with 2-(bicyclo[2.2.1]hept-5-en-2-yl)acetic acid, 6-aminohexanoyl further acylated at the amino group with ω-(bicyclo[2.2.1]hept-5-en-2-yl)alkanoic acid, 6-aminohexanoyl further acylated at the amino group with 8-[[(3,4,6-tri-O-acetyl-2-acetamido-2-deoxy-(β-D-galactopyranosyl)]oxy]-3,6-dioxooctanoic acid, 6-aminohexanoyl further acylated at the amino group with ω-[[(3,4,6-tri-O-acetyl-2-acetamido-2-deoxy-β-D-galactopyranosyl)]oxy]alkanoic acid, 6-aminohexanoyl further acylated at the amino group with lipoic acid, 6-aminohexanoyl further acylated at the amino group with 2-((6,6-difluorocyclooct-4-yn-1-yl)oxy)acetic acid, 6-aminohexanoyl further acylated at the amino group with 4-((2,2-difluorocyclooct-3-yn-1-yl)methyl)benzoic acid, 6-aminohexanoyl further acylated at the amino group with 11,12-didehydro-γ-oxo-dibenz[b,f]azocine-5(6H)-butanoic acid, 6-aminohexanoyl further acylated at the amino group with 3-(cyclooctatetraene)propionic acid, 6-aminohexanoyl further carbamoylated at the amino group with cholesterylcarbonic acid, 6-aminohexanoyl further acylated at the amino group with optionally protected D-biotin, 6-[(6-chloro-2-methoxyacridin-9-yl)amino]hexanoyl, a residue of diglycolic acid optionally protected at the second carboxylic group, a residue of diglycolic acid further forming an amide with 1-amino-ω-[(1,3-dioxo-3a,4,7,7a-tetrahydro-2H-4,7-methanoisoindol-2-yl)oxy]alkane, a residue of diglycolic acid further forming an amide with 1-amino-ω-[(1,3-dioxo-3a,4,7,7a-tetrahydro-2H-4,7-epoxyisoindol-2-yl)oxy]alkane, a residue of diglycolic acid further forming an amide with 11,12-didehydro-5,6-dihydrodibenz[b,f]azocine, a residue of diglycolic further acid forming an amide with 11,12-didehydro-5,6-dihydrodibenz[b,f]azocine, a residue of diglycolic acid further forming an amide with 1,13-diamino-4,7,10-trioxatridecane, optionally protected at the second amino group, or a residue of diglycolic acid wherein the second carboxy group further forms an amide with 1,13-diamino-4,7,10-trioxatridecane further acylated at the second amino group with optionally protected D-biotin.

In yet another embodiment of the present invention, one of R and $R^1$ of Formula I is 4,4',4"-trimethoxytrityl group, and the other is PA wherein each $R^2$ and $R^3$ is isopropyl group and $R^4$ is 2-cyanoetyl group, each A, $A^1$, E and $E^1$ is $—CH_2—$, and G is selected from an atom of hydrogen, an alkyl group, a trifluoroacetyl group, (9H-fluoren-9-yl) methoxycarbonyl (Fmoc) group, 6-(trifluoroacetylamino) hexanoyl, 6-heptynoyl, 6-azidohexanoyl, 6-aminohexanoyl protected at the amino group with (9H-fluoren-9-yl) methoxycarbonyl (Fmoc) group, [4-(1-pyrenyl)butyryl-1], ω-[[(3,4,6-tri-O-acetyl-2-acetamido-2-deoxy-β-D-galactopyranosyl)]oxy]alkanoyl, ω-hydroxyalkanoic acid further alkylated at the hydroxy group with α-tocopherol, 6-[[4-(1-pyrenyl)butyryl-1]amino]hexanoyl, 6-[(6-heptynoyl-1) amino]hexanoyl, 6-aminohexanoyl further acylated at the amino group with 4-(dimethylamino)azobenzene-4'-carboxylic acid, 6-aminohexanoyl further sulfonylated at the amino group with 4-(dimethylamino)azobenzene-4'-sulfonic acid, 6-aminohexanoyl further acylated at the amino group with a protected 6-carboxyfluorescein, 6-aminohexanoyl further acylated at the amino group with a protected 5-carboxyfluorescein, 6-aminohexanoyl further acylated at the amino group with 5-carboxy-N,N,N'N'-tetramethylrhodamine, 6-aminohexanoyl further acylated at the amino group with 6-carboxy-N,N,N'N'-tetramethylrhodamine, 6-aminohexanoyl further acylated at the amino group with ω-((1,3-dioxo-1,3,3a,4,7,7a-hexahydro-2H-4,7-epoxyisoindol-2-yl) oxy)alkanoic acid, 6-aminohexanoyl further acylated at the amino group with ω-((1,3-dioxo-1,3,3a,4,7,7a-hexahydro-2H-4,7-methanoisoindol-2-yl)oxy)alkanoic acid, 6-aminohexanoyl further acylated at the amino group with bicyclo [2.2.1]hept-5-ene-2-carboxylic acid, 6-aminohexanoyl further acylated at the amino group with 2-(bicyclo[2.2.1] hept-5-en-2-yl)acetic acid, 6-aminohexanoyl further acylated at the amino group with ω-(bicyclo[2.2.1]hept-5-en-2-yl)alkanoic acid, 6-aminohexanoyl further acylated at the amino group with 8-[[(3,4,6-tri-O-acetyl-2-acetamido-2-deoxy-β-D-galactopyranosyl)]oxy]-3,6-dioxooctanoic acid, 6-aminohexanoyl further acylated at the amino group with ω-[[(3,4,6-tri-O-acetyl-2-acetamido-2-deoxy-β-D-galactopyranosyl)]oxy]alkanoic acid, 6-aminohexanoyl further acylated at the amino group with lipoic acid, 6-aminohexanoyl further acylated at the amino group with 2-((6,6-difluorocyclooct-4-yn-1-yl)oxy)acetic acid, 6-aminohexanoyl further acylated at the amino group with 4-((2,2-difluorocyclooct-3-yn-1-yl)methyl)benzoic acid, 6-aminohexanoyl further acylated at the amino group with 11,12-didehydro-γ-oxo-dibenz[b,f]azocine-5(6H)-butanoic acid, 6-aminohexanoyl further acylated at the amino group with 3-(cyclooctatetraene)propionic acid, 6-aminohexanoyl further carbamoylated at the amino group with cholesterylcarbonic acid, 6-aminohexanoyl further acylated at the amino group with optionally protected D-biotin, 6-[(6-chloro-2-methoxyacridin-9-yl)amino]hexanoyl, a residue of diglycolic acid optionally protected at the second carboxylic group, a residue of diglycolic acid further forming an amide with 1-amino-ω-[(1,3-dioxo-3a,4,7,7a-tetrahydro-2H-4,7-methanoisoindol-2-yl)oxy]alkane, a residue of diglycolic acid further forming an amide with 1-amino-ω-[(1,3-dioxo-3a,4,7,7a-tetrahydro-2H-4,7-epoxyisoindol-2-yl)oxy]alkane, a residue of diglycolic acid further forming an amide with 11,12-didehydro-5,6-dihydrodibenz[b,f]azocine, a residue of diglycolic further acid forming an amide with 11,12-didehydro-5,6-dihydrodibenz[b,f]azocine, a residue of diglycolic acid further forming an amide with 1,13-diamino-4,7,10-trioxatridecane, optionally protected at the second amino group, or a residue of diglycolic acid wherein the second carboxy group further forms an amide with 1,13-diamino-4,7,10-trioxatridecane further acylated at the second amino group with optionally protected D-biotin.

In certain embodiments of the present invention, W is selected from controlled pore glass, a copolymer of styrene and divinylbenzene, controlled pore glass grafted with a polymer of styrene, controlled pore glass grafted with a copolymer of styrene and divinylbenzene, or flat glass surface.

In a second aspect, the present invention provides novel oligomeric compounds, analogs of natural oligonucleotides, having the structure according to Formula II:

Formula II

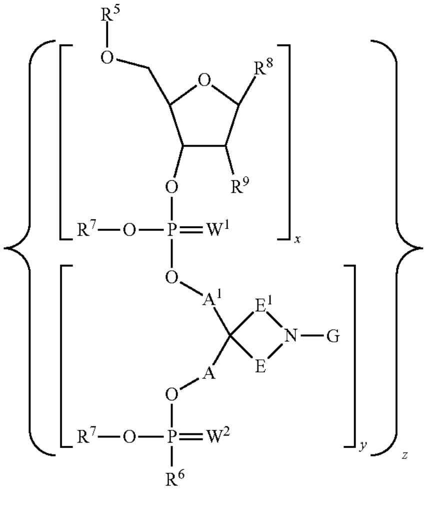

wherein:

with the proviso that only one of $R^5$, $R^6$, and $R^{10}$ is simultaneously a linker connected to a solid support, $R^5$ is hydrogen atom, a protecting group selected from (4-methoxyphenyl)diphenylmethyl, bis-(4-methoxyphenyl)phenylmethyl, tris-(methoxyphenyl)methyl, 9-phenylxanthen-9-yl, or 9-(p-methoxyphenyl)xanthen-9-yl, a point of attachment to solid phase material, or a linker of universal family;

$R^6$ is hydrogen atom, a protecting group selected from (4-methoxyphenyl)diphenylmethyl, bis-(4-methoxyphenyl)phenylmethyl, tris-(methoxyphenyl)methyl, 9-phenylxanthen-9-yl, or 9-(p-methoxyphenyl)xanthen-9-yl, a point of attachment to solid phase material, a linker of universal family, a non-nucleosidic moiety of Formula III or a nucleosidic moiety of Formula IV:

FORMULA III

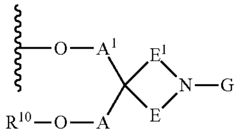

FORMULA IV

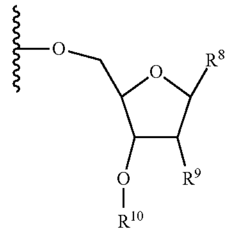

wherein:

$R^{10}$ is, independently, hydrogen atom, a protecting group selected from (4-methoxyphenyl)diphenylmethyl, bis-(4-methoxyphenyl)phenylmethyl, tris-(4-methoxyphenyl)methyl, 9-phenylxanthen-9-yl, or 9-(4-methoxyphenyl)xanthen-9-yl, or a point of attachment to solid phase material;

Each $R^7$ is, independently, a negative charge compensated by a cation or a phosphate protecting group selected from methyl, allyl, 2-cyanoethyl, 4-cyano-2-butenyl, 2-cyano-1,1-dimethylethyl, 2-(trimethylsilyl)ethyl, 2-(S-acetylthio)ethyl, 2-(S-pivaloylthio)ethyl, 2-(4-nitrophenyl)ethyl, 2,2,2-trichloroethyl, 2,2,2-trichloro-1,1-dimethylethyl, 1,1,1,3,3,3-hexafluoro-2-propyl, fluorenyl-9-methyl, 2-chlorophenyl, 4-chlorophenyl, or 2,4-dichlorophenyl;

Each $R^8$ is independently an optionally protected nucleic base selected from adenine, cytosine, guanine, thymine, uracil, 2-aminoadenine, N6-methyladenine, 7-deazaadenine, 7-deaza-8-azaadenine, 8-aminoadenine, 5-methylcytosine, N4-ethylcytosine, 7-deazaguanine, 7-deaza-8-azaguanine, 8-aminoguanine, 7-deazaxanthyne, hypoxanthine;

Each $R^9$ is, independently, hydrogen atom, fluorine atom, hydroxy group, substituted hydroxy group $OR^{11}$, or substituted amino group $NR^{12}R^{13}$ wherein:

Each $R^{11}$ is, independently, a $C_1$ to $C_6$ alkyl, 2-alkoxyethyl group, trialkysilyl group, or N-methylcarboxamidomethyl group;

Each $R^{12}$ and $R^{13}$ is, independently, hydrogen atom, methyl group, ethyl group, propyl group, isopropyl group, acetyl group, trifluoroacetyl group, phenoxyacetyl group, benzoyl group, or 9-fluorenylmethyloxycarbonyl group;

Each $W^1$ and $W^2$ is, independently, oxygen or sulfur; and

Each x, y, and z is, independently, an integer from 0 to about 100 (in some illustrative embodiments, x, y, and z are independently 0-50; in other embodiments x, y, and z are independently 0-20; in further embodiments x, y, and z are independently 0-10, or any other suitable range).

Each A and $A^1$ is, independently, a linking moiety $—[(CH_2)_aM(CH_2)_b]_c—$ wherein:

Each a, b, and c is, independently, an integer from 0 to 6;

M is a covalent bond, oxygen atom, sulfur atom, $NQ^1$, $—N(Q^1)C(=O)N(Q^2)$-, $—C(=O)N(Q^1)$-, or $—N(Q^1)C(=O)—$ wherein:

Each $Q^1$ and $Q^2$ is independently hydrogen atom, methyl group, ethyl group, propyl group, isopropyl group, acetyl group, trifluoroacetyl group, phenoxyacetyl group, benzoyl group, or 9-fluorenylmethyloxycarbonyl group;

Each E and $E^1$ is, independently, a linking moiety $—[(CH_2)_dM^1(CH_2)_e]_f—$ wherein:

Each d, e, and f is, independently, an integer from 0 to 6;

$M^1$ is a covalent bond, oxygen atom, sulfur atom, $NQ^3$, $—N(Q^3)C(=O)N(Q^4)$-, $—C(=O)N(Q^3)$-, or $—N(Q^3)C(=O)—$ wherein:

Each $Q^3$ and $Q^4$ is independently hydrogen atom, methyl group, ethyl group, propyl group, isopropyl group, acetyl group, trifluoroacetyl group, phenoxyacetyl group, benzoyl group, or 9-fluorenylmethyloxycarbonyl group;

G is selected from hydrogen, a substituted or unsubstituted aliphatic group, a substituted or unsubstituted cycloaliphatic group, a substituted or unsubstituted aromatic group, a substituted or unsubstituted heteroaromatic group, a substituted or unsubstituted heterocyclic group, a nitrogen protecting group, $—CH_2$-L, $—C(=O)$-L, $—C(=O)—OL$, $—C(=O)—NHL$, $—S(=O)$-L, $—S(=O)—NHL$, $—SO_2$-L, and $—SO_2—NHL$, wherein:

L is selected from hydrogen, an optionally protected hydroxy group, an optionally protected amino group, or a linking moiety $—[[(CH_2)_gX^1(CH_2)_h]—X^2—[(CH_2)_iX^3(CH_2)_j]]_k$-J, wherein:

Each g, h, i, j, and k is, independently, an integer from 0 to 6;

Each $X^1$, $X^2$, and $X^3$ is, independently, an atom of oxygen, $CH_2$ group, an atom of sulfur, $—C(=O)—$, $—SS—$, $—S(=O)—$, $SO_2$, $NQ^5$, $—C(=O)N(Q^5)$-, $—OC(=O)N(Q^5)$-, $—N(Q^5)C(=O)—$, $—N(Q^5)C(=O)O—$, $—N(Q^5)C(=O)N(Q^6)$-, 1,4-phenylidene, or 1H-1,2,3-triazole-1,4-diyl wherein:

Each $Q^5$ and $Q^6$ is, independently, hydrogen atom, methyl group, ethyl group, propyl group, isopropyl group, acetyl group, trifluoroacetyl group, phenoxyacetyl group, benzoyl group, or 9-fluorenylmethyloxycarbonyl group;

J is selected from a hydrogen atom, an optionally protected hydroxyl group, an optionally protected primary amino group, an optionally protected alkylamino group, a dialkylamino group, a trialkylammonium group, an azido group, an ethynyl group $—C\equiv CH$, a hydroxy group alkylated with α-tocopherol, a hydroxy group alkylated with optionally protected N-acetyl-D-galactosamine, a primary amino group acylated with a ligand selected from optionally protected fluorescein-5-carboxylic acid, optionally protected fluorescein-6-carboxylic acid, N,N,N',N'-tetramethylrhodamine-5-carboxylic acid, N,N,N',N'-tetramethylrhodamine-6-carboxylic acid, ω-((1,3-dioxo-1,3,3a,4,7,7a-hexahydro-2H-4,7-epoxyisoindol-2-yl)oxy)alkanoic acid, ω-((1,3-dioxo-1,3,3a,4,7,7a-hexahydro-2H-4,7-methanoisoindol-2-yl)oxy)alkanoic acid, optionally protected biotin, 4'-(dimethylamino)-azobenzene-4-carboxylic acid, 4-pyrenylbutyryc acid, triethyl ethylenediaminetetraacetic acid, bicyclo[2.2.1]hept-5-ene-2-carboxylic acid, 2-(bicyclo[2.2.1]hept-5-en-2-yl)acetic acid, 2-((6,6-difluorocyclooct-4-yn-1-yl)oxy)acetic acid, 4-((2,2-difluorocyclooct-3-yn-1-yl)methyl)benzoic acid, 11,12-didehydro-γ-oxo-dibenz[b,f]azocine-5(6H)-butanoic acid, 3-(cyclooctatetraene)propionic acid, lipoic acid, a primary or a secondary amino group sulfonylated with 4'-(dimethylamino)-azobenzene-4-sulfonic acid, a primary or a secondary amino group carbamoylated with cholesterylcarbonic acid, a primary or a secondary amino group alkylated with 6-chloro-2-methoxyacridine, an optionally protected carboxy group, a carboxy group forming an amide with 1-amino-ω-[(1,3-dioxo-3a,4,7,7a-tetrahydro-2H-4,7-methanoisoindol-2-yl)oxy]alkane, a carboxy group forming an amide with 1-amino-ω-[(1,3-dioxo-3a,4,7,7a-tetrahydro-2H-4,7-epoxyisoindol-2-yl)oxy]alkane, a carboxy group forming an amide with 11,12-didehydro-5,6-dihydrodibenz[b,f]azocine;

In a third aspect, the present invention provides methods for synthetic preparation of said oligonucleotide conjugates according to Formula II wherein $R^6$ is the compound of Formula III:

- providing a solid support of Formula I wherein one of R and $R^1$ is hydrogen and the other of R and $R^1$ is L;
- reacting said solid support of Formula I with a compound of Formula I wherein one of R and $R^1$ is a hydroxy protecting group and the other of R and $R^1$ is PA or with a protected nucleoside phosphoramidite building blocks as required by the sequence of a target oligonucleotide conjugate;
- further reacting said functionalized solid support with a capping agent and optionally treating said functionalized solid support with an oxidizing agent or with a sulfurizing agent.

In certain embodiments, said method further comprises: (a) deblocking said hydroxy protecting group to give a reactive hydroxy group; (b) treating said reactive hydroxy group with an additional phosphoramidite building block bearing a further protected hydroxy group to produce an extended compound; (c) reacting the extended compound with a capping reagent; (d) optionally contacting the product of step (b) with an oxidizing or sulfurizing agent; and optionally repeating steps (a)-(d) one or more times to form an oligonucleotide conjugate.

In a fourth aspect, the present invention provides methods for synthetic preparation of said oligonucleotide conjugates according to Formula II wherein $R^6$ is the compound of Formula IV:

- providing a compound of Formula I wherein one of R and $R^1$ is a hydroxy protecting group and the other of R and $R^1$ is PA;
- reacting said compound of Formula I or a protected nucleoside phosphoramidite building block, as required by the sequence of a target oligonucleotide conjugate, with a solid support of Formula V wherein one of $R^{14}$ and $R^{15}$ is hydrogen and the other of $R^{14}$ and $R^{15}$ is an attachment to a solid phase material;

FORMULA V

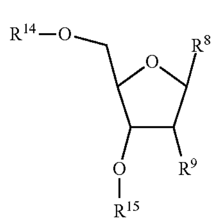

- further reacting said functionalized solid support with a capping agent and optionally treating said functionalized solid support with an oxidizing agent or with a sulfurizing agent.

In certain embodiments, said method further comprises: (a) deblocking said hydroxy protecting group to give a reactive hydroxy group; (b) treating said reactive hydroxy group with an additional phosphoramidite building block bearing a further protected hydroxy group to produce an extended compound; (c) reacting the extended compound with a capping reagent; (d) optionally contacting the product of step (b) with an oxidizing or sulfurizing agent; and optionally repeating steps (a)-(d) one or more times to form an oligonucleotide conjugate.

Certain starting materials used in the present invention are protected nucleoside phosphoramidites readily available from commercial sources (Glen Research, Sterling, Va., ChemGenes, Inc., Waltham, Mass.; Rasayan, Inc., Encinitas, Calif.). 3,3-Bis(hydroxymethyl)azetidine hydrochloride, p/n AZB30083 can be purchased from A2Z Chemicals (Irvine, Calif.).

Commercial compound 1 was first reacted with aqueous formaldehyde in the presence of a catalytic amount of $K_2CO_3$ to form a product of aldol addition 2, which was, without isolation, reduced to a diol 2. To remove the Boc protection, the latter was treated with an anhydrous

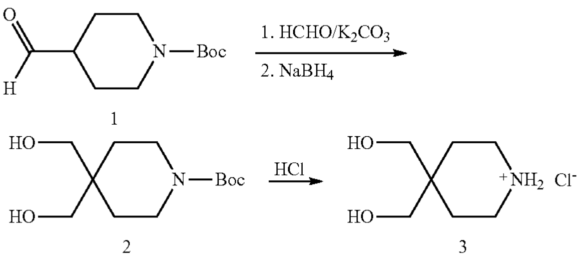

1

2

3 solution of hydrogen chloride in dioxane to give a hydrochloride of 4,4-bis(hydroxymethyl)piperidine 3.

N-acylated 4,4-bis(hydroxymethyl)piperidines 5a-5k and 3,3-bis(hydroxymethyl)azetidines 6a-6k (FIG. 1; see Table 1 for the structures of radicals R) were next obtained by the selective acylation of compounds 3 and 4, respectively, at the amino group with the respective carboxylic acids activated with HOBT and EDC-HCl.

The obtained compounds 5a-5k and 6a-6k were selectively protected at one of the hydroxy groups by treating with either DMT-Cl or TMT-Cl in pyridine to give compounds 7a-7k, 8a-8k, 9a-9k, and 10a-10k. These were directly converted to phosphoramidite building blocks 11a-

11k, 12a-12k, 13a-13k, and 14a-14k by the action of 2-cyanoethyl N,N,N'N'-tetraisopropylphosphorodiamidite in the presence of 1H-tetrazole and, by treating with succinic anhydride in pyridine, to hemisuccinate esters 15a-15k, 16a-16k, 17a-17k, and 18a-18k. The hemisuccinate esters were, upon activation with TBTU, attached to solid phase materials, aminopropyl-derivatized CPG and aminomethylated MPPS to give solid supports 19a-19k, 20a-20k, 21a-21k, and 22a-22k for the 3'-derivatization of synthetic oligonucleotides.

Figure 2:
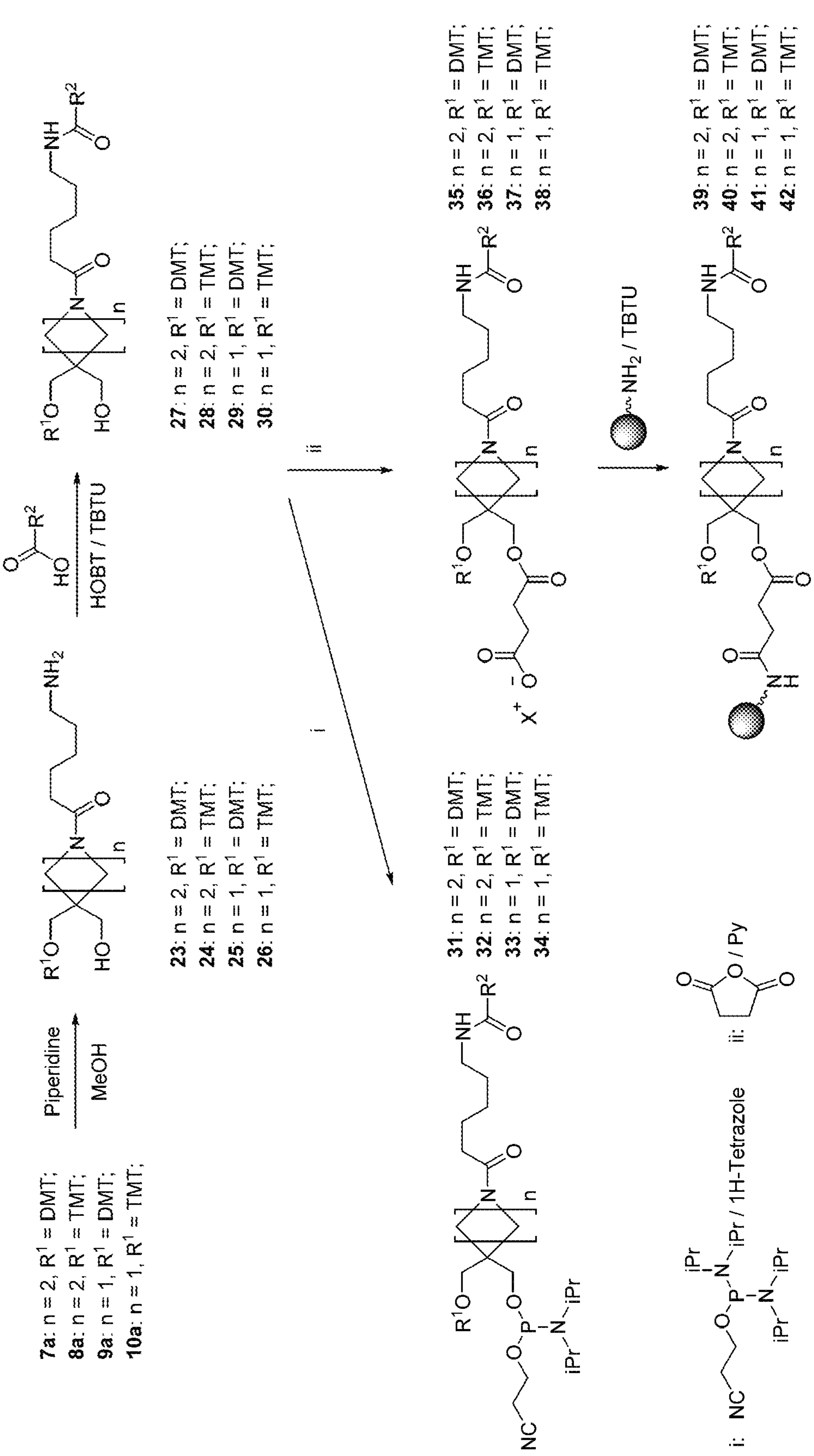
FIG. 2 shows structures and a synthetic scheme for the preparation of phosphoramidite building blocks 31a-j-34a-j, and 31k,m,n-34k,m,n, and 31p-34p and solid supports 39a-j-42a-j and 39k,m,n,p-42k,m,n,p.

In order to obtain phosphoramidite building blocks and solid supports with an extended side chain, Fmoc protecting group in compounds 7a, 8a, 9a, and 10a was removed first by treatment with piperidine in methanol to give compounds 23, 24, 25, and 26 followed by the selective acylation of the latter compounds at their amino group with the respective carboxylic acids upon activation of the latter with HOBT and EDC-HCl (FIG. 2; see Table 1 for the structures of radicals $R^2$). The compounds 27a-27p, 28a-28p, 29a-29p, and 30a-30p thus obtained were converted to the respective phosphoramidite building blocks 31a-31p, 32a-32p, 33a-33p, and 34a-34p by the action of 2-cyanoethyl N,N,N'N'-tetraisopropylphosphorodiamidite in the presence of 1H-tetrazole and, by treating with succinic anhydride in pyridine, to hemisuccinate esters 35a-35p, 36a-36p, 37a-37p, and 38a-38p. The hemisuccinate esters were, upon activation with TBTU, attached to solid phase materials, aminopropyl-derivatized CPG and aminomethylated MPPS to give solid supports 39a-39p, 40a-40p, 41a-41p, and 42a-42p for the 3'-derivatization of synthetic oligonucleotides.

Figure 3:
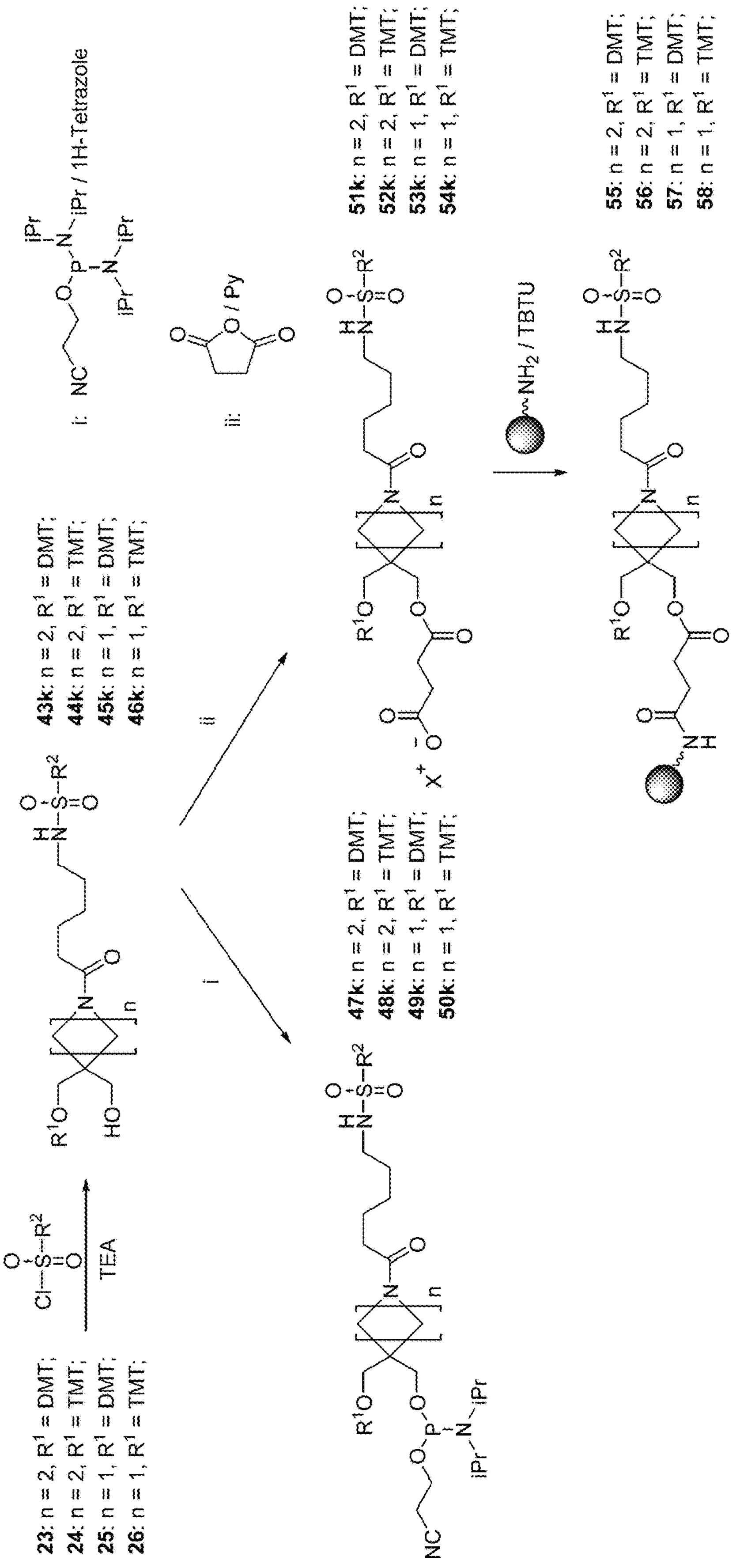
FIG. 3 shows structures and a synthetic scheme for the preparation of phosphoramidite building blocks 47k-50k and solid supports 55k-58k.

To obtain phosphoramidite building blocks and solid supports derivatized with Dabsyl group at the side chain, compounds 19-22 were first sulfonylated at the amino function by treating with Dabsyl chloride in the presence of TEA (FIG. 3; see Table 1 for the structures of radicals $R^2$). The compounds 43k, 44k, 45k, and 46k thus obtained were converted to the respective phosphoramidite building blocks 47k, 48k, 49k, and 50k by the action of 2-cyanoethyl N,N,N'N'-tetraisopropylphosphorodiamidite in the presence of 1H-tetrazole and, by treating with succinic anhydride in pyridine, to hemisuccinate esters 51k, 52k, 53k, and 54k. The hemisuccinate esters were, upon activation with TBTU, attached to solid phase materials, aminopropyl-derivatized CPG and aminomethylated MPPS to give solid supports 55k, 56k, 57k, and 58k for the 3'-derivatization of synthetic oligonucleotides.

Figure 4:
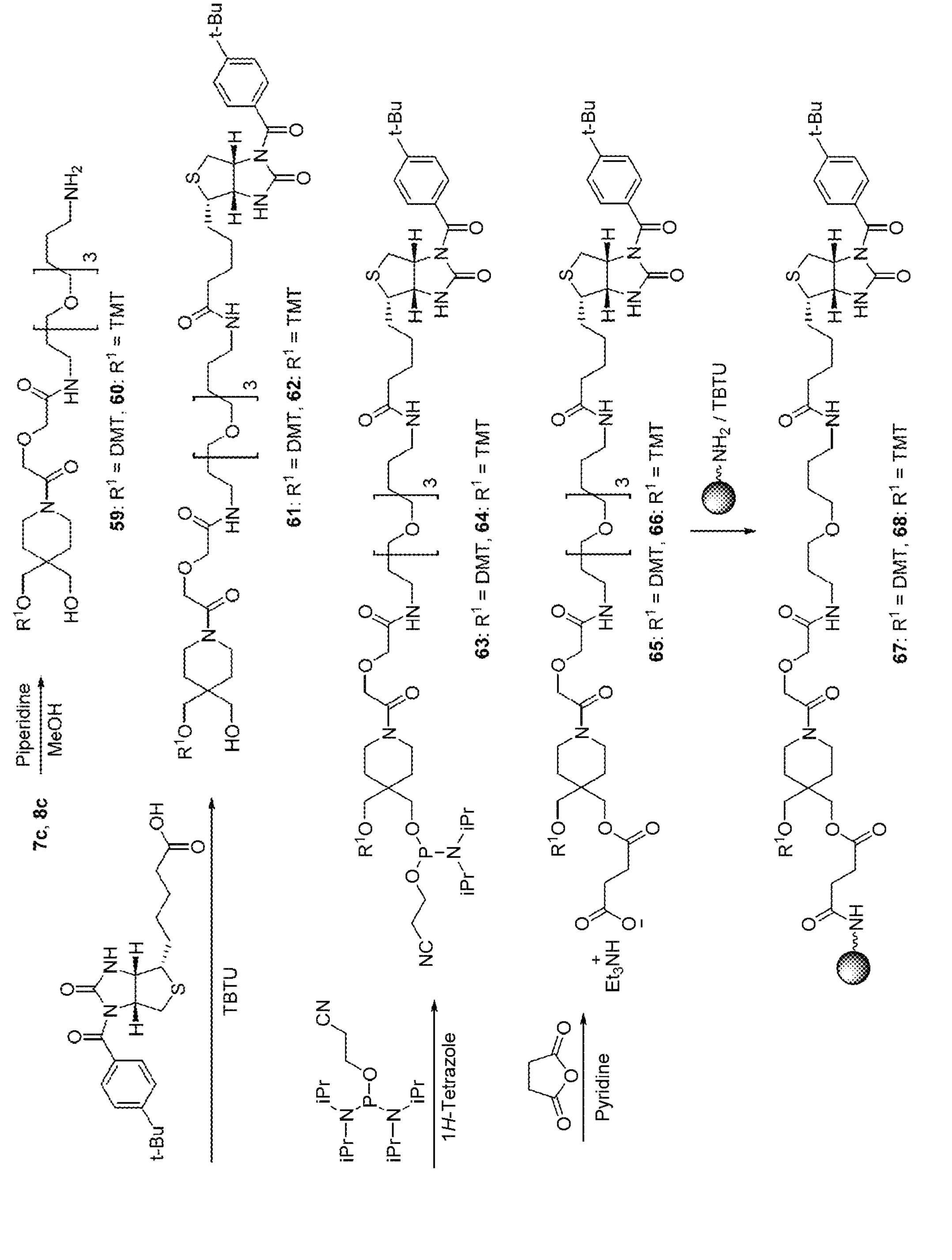
FIG. 4 shows structures and a synthetic scheme for the preparation of phosphoramidite building blocks 63, 64 and solid supports 67, 68.

To afford synthetic tools for introduction of D-biotin into synthetic oligonucleotides, phosphoramidite building blocks 63 and 64 and solid supports 67, 68 were synthesized (FIG. 4). Compounds 7c and 8c were treated with piperidine in methanol, which removed the Fmoc protection. The released amino group of compounds 59 and 60 was acylated with N-protected D-biotin using TBTU as a coupling reagent to give compounds 61 and 62. These were converted to phosphoramidite building blocks 63 and 64 by the action of 2-cyanoethyl N,N,N'N'-tetraisopropylphosphorodiamidite in the presence of 1H-tetrazole and to the respective hemisuccinates 65 and 66 by treating with succinic anhydride in pyridine. The hemisuccinate esters 65 and 66 were, upon activation with TBTU, attached to solid phase materials, aminopropyl-derivatized CPG and aminomethylated MPPS to give solid supports 67 and 68 for the 3'-derivatization of synthetic oligonucleotides with biotin.

Figure 5:
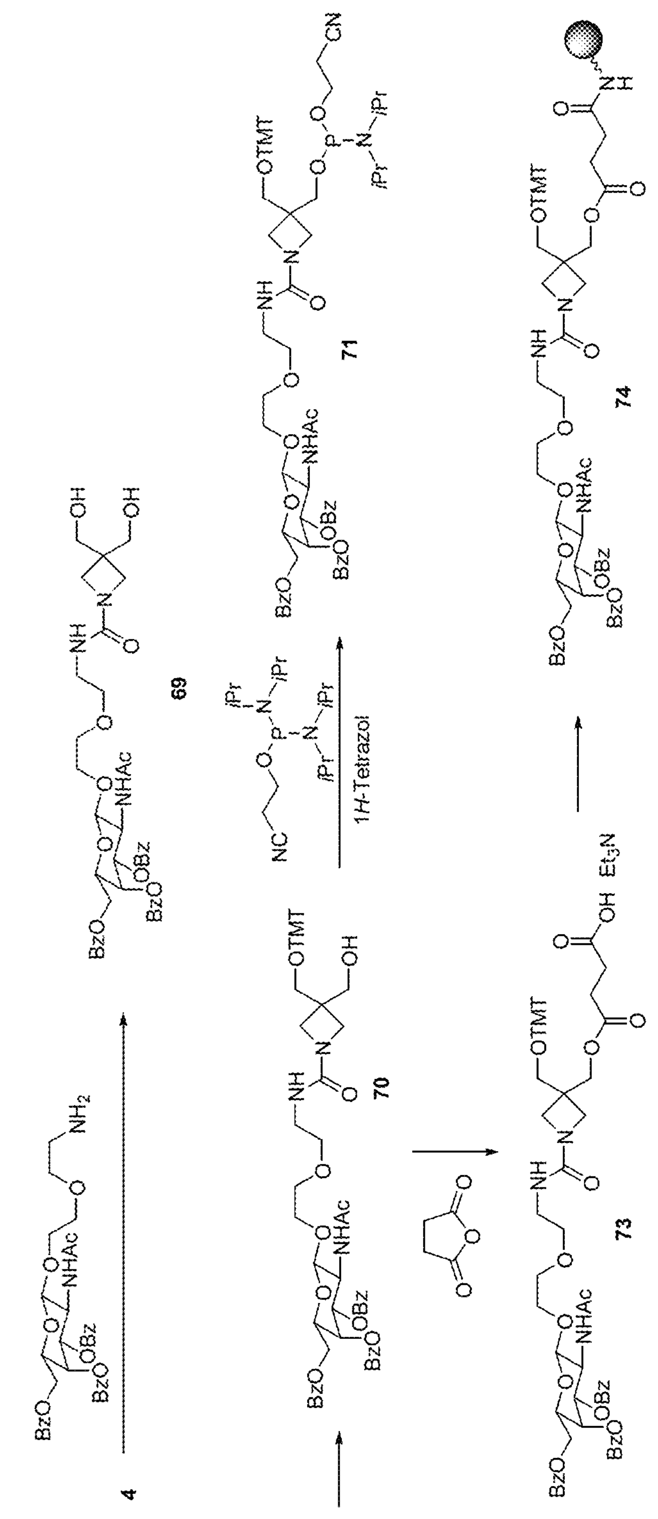
FIG. 5 shows structures and a synthetic scheme for the preparation of phosphoramidite building block 71 and solid support 74.
Figure 6:
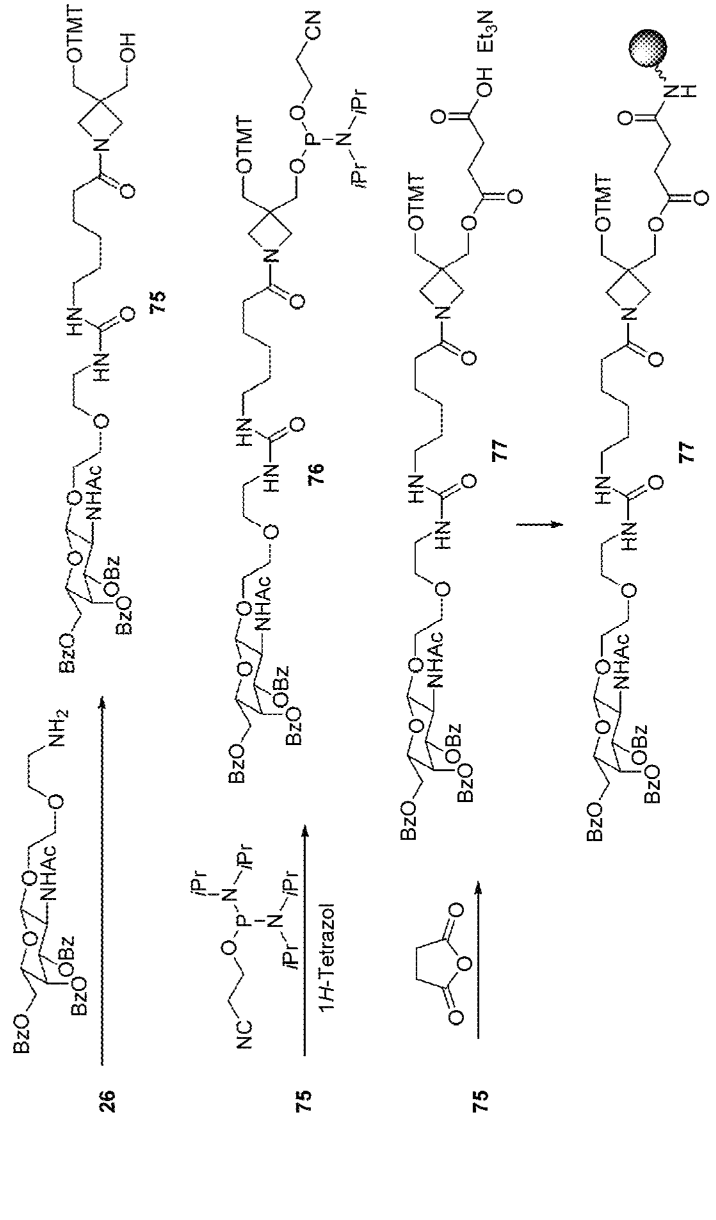
FIG. 6 shows structures and a synthetic scheme for the preparation of phosphoramidite building block 76 and solid support 78.

The utility of a ureido linkage for construction of non-nucleosidic phosphoramidites and solid supports was demonstrated by synthesis of N-acetyl-D-galactosamine-derivatized phosphoramidite building blocks 71 and 76 and solid supports 74 and 78 as disclosed in FIG. 5 and FIG. 6.

TABLE 1

Structures of Radicals R and $R^2$ in Compounds 5-58.

| Compound # | R | $R^2$ |
| --- | --- | --- |
| 5a-22a | 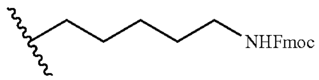 | — |
| 5b-22b | 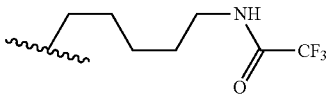 [SMILES: *CCCCCNC(=O)C(F)(F)F] | — |
| 5c-22c | 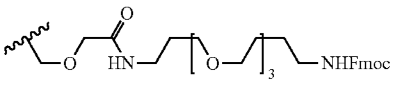 | — |
| 5d-22d | 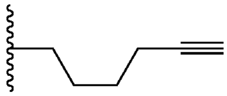 [SMILES: *CCCCC#C] | — |
| 5e-22e | 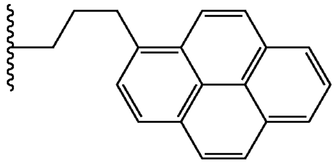 [SMILES: *CCCc1ccc2ccc3cccc4ccc1c2c34] | — |

TABLE 1-continued
| Structures of Radicals R and $R^2$ in Compounds 5-58. | | |
|---|---|---|
| Compound # | R | $R^2$ |
| 5f-22f | 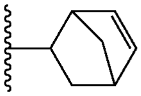 [SMILES: *C1CC2C=CC1C2] | — |
| 5g-22g | 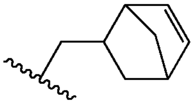 [SMILES: *CC1CC2C=CC1C2] | — |
| 5h-22h | 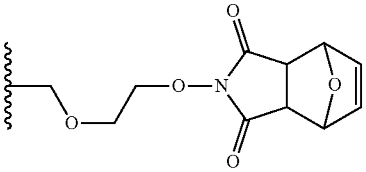 [SMILES: *COCCON1C(=O)C2C3C=CC(O3)C2C1=O] | — |
| 5i-22i | 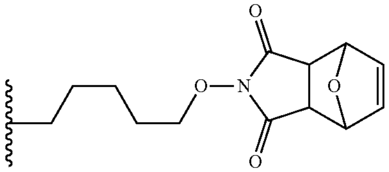 [SMILES: *CCCCCON1C(=O)C2C3C=CC(O3)C2C1=O] | — |
| 5j-22j | 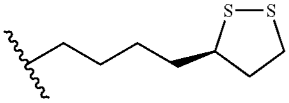 [SMILES: *CCCC[C@@H]1CCSS1] | — |
| 5k-22k | 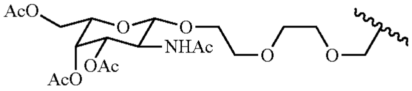 [SMILES: *COCCOCCOC1OC(COC(C)=O)C(OC(C)=O)C(OC(C)=O)C1NC(C)=O] | — |
| 27a-42a | — | 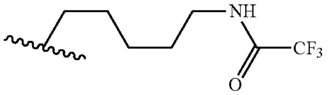 [SMILES: *CCCCCNC(=O)C(F)(F)F] |
| 27b-42b | — | 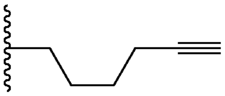 [SMILES: *CCCCC#C] |
| 27c-42c | — | 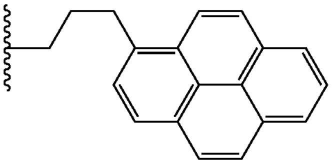 [SMILES: *CCCc1ccc2ccc3cccc4ccc1c2c34] |
| 27d-42d | — | 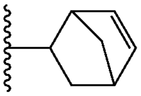 [SMILES: *C1CC2C=CC1C2] |
| 27e-42e | — | 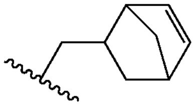 |

TABLE 1-continued
| Structures of Radicals R and $R^2$ in Compounds 5-58. | | |
|---|---|---|
| Compound # | R | $R^2$ |
| 27f-42f | — | 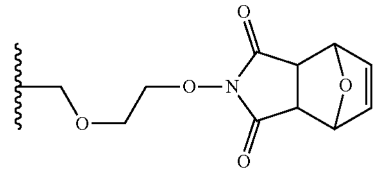 [SMILES: *COCCON1C(=O)C2C3C=CC(O3)C2C1=O] |
| 27g-42g | — | 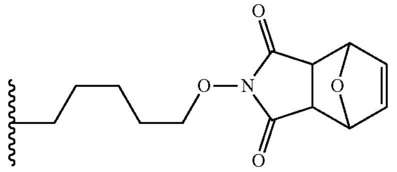 [SMILES: *CCCCCON1C(=O)C2C3C=CC(O3)C2C1=O] |
| 27h-42h | — | 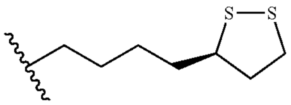 [SMILES: *CCCC[C@@H]1CCSS1] |
| 27i-42i | — | 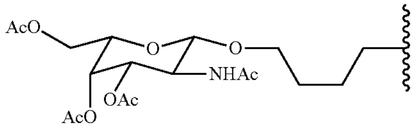 [SMILES: *CCCCOC1OC(COC(C)=O)C(OC(C)=O)C(OC(C)=O)C1NC(C)=O] |
| 27j-42j | — | 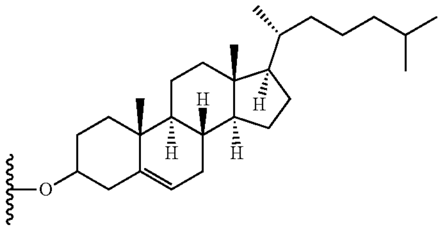 |
| 27k-42k<br>43k-58k | — | 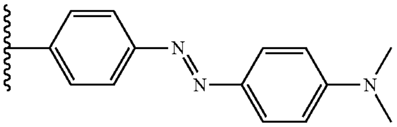 [SMILES: *c1ccc(/N=N/c2ccc(N(C)C)cc2)cc1] |
| 27m-42m | — | 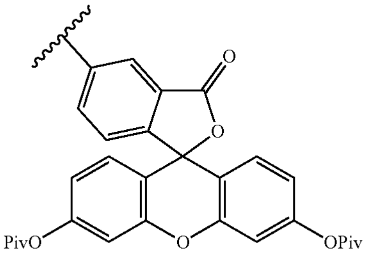 |
| 27n-42n | — | 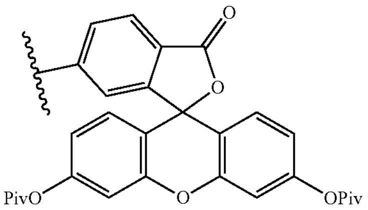 |

TABLE 1-continued

Structures of Radicals R and $R^2$ in Compounds 5-58.

| Compound # | R | $R^2$ |
|---|---|---|
| 27p-42p | — | 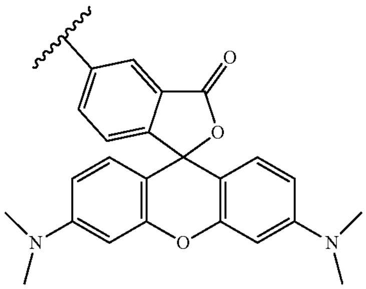 |

The non-nucleosidic phosphoramidite building blocks and solid supports synthesized as disclosed above were tested in preparation of oligonucleotide conjugates derivatized at the 5'- or the 3'-termini, respectively. The following oligonucleotides wherein X stands for a non-nucleosidic moiety were synthesized:

5'-X-(Tp)$_{11}$T-3'; _(SEQ ID NO: 1);

5'-(Tp)$_{15}$-X-3'; _(SEQ ID NO: 2);

5'-X-d(TAG TGC TAG ATG CCT)-3'; _(SEQ ID NO: 3);

5'-d(TAG TGC TAG ATG CCT)-X-3'; _(SEQ ID NO: 3);

5'-X-d(CCA CTA CCT GAG CAC CCA GTT)-3'; _(SEQ ID NO: 4);

5'-d(CCA CTA CCT GAG CAC CCA GTT)-X-3'; _(SEQ ID NO: 4);

5'-X-d(CTG GGT GCT CAG GTA GTG GTT)-3'; _(SEQ ID NO: 5);

5'-d(CTG GGT GCT CAG GTA GTG GTT)-X-3'; _(SEQ ID NO: 5);

5'-X-d(CTG GGT GCT CAG GTA GTG GTT)-3' phosphorothioate; _(SEQ ID NO: 5);

5'-d(CTG GGT GCT CAG GTA GTG GTT)-X-3' phosphorothioate. _(SEQ ID NO: 5).

The final cleavage and deprotection of nucleic bases was carried out by treating the solid support-bound, 5'-DMT or 5'-TMT-protected oligonucleotides under the following conditions widely accepted in the industry:

1. Conc. aqueous ammonium hydroxide for 8 h at 65° C.
2. Treatment with a mixture of diethylamine and acetonitrile (5:1) for 3 min followed by acetonitrile wash and final deprotection with conc. aqueous ammonium hydroxide for 8 h at 65° C.
3. A mixture of conc. aqueous ammonium hydroxide with 40% aqueous methylamine (1:1) for 15 min at 65° C.
4. Treatment with a mixture of diethylamine and acetonitrile (5:1) for 3 min followed by acetonitrile wash and final deprotection with a solution of ethylenediamine in toluene (1:1) for 2 h at room temperature, acetonitrile wash, and eltion of the product with water.
5. 50 mM $K_2CO_3$ in methanol at room temperature.

Crude reaction mixtures were analyzed by reverse-phase HPLC and by ES MS to demonstrate that the non-nucleosidic moieties were stable under all tested conditions except for 50 mM $K_2CO_3$ in methanol.

Accordingly, the efficient preparation of analogs of oligonucleotides modified with ligands of practical interest and their phosphorothioate analogs using the novel non-nucleosidic solid supports and phosphoramidite building blocks described herein has been demonstrated. Said solid supports and phosphoramidite building blocks can be readily synthesized by artisans possessing ordinary skills. Conveniently, oligonucleotide analogs synthesized using said solid supports and phosphoramidite building blocks are stable under the most common basic deprotection conditions and do not possess any additional stereoheterogeneity.

EXAMPLES

The following examples are intended to further illustrate certain preferred embodiments of the invention and are not intended to be limiting in their nature.

General Information

Protected 2'-deoxynucleoside 2-cyanoethyl phosphoramidites, protected ribonucleoside 2-cyanoethyl phosphoramidites, 5'-O-DMT-thymidine CPG500, and all ancillary reagents for oligonucleotide synthesis were purchased from Glen Research (Sterling, Va.). Sulfurizing reagent, N'-(3-thioxo-3H-1,2,4-dithiazol-5-yl)-N,N-dimethylmethanimidamide was prepared as disclosed in U.S. Pat. No. 7,723,582. Anhydrous MeCN was purchased from Honeywell Burdick & Jackson (Muskegon, Mich.). All other chemicals were purchased from TCI America (Portland, Oreg.).

Example 1

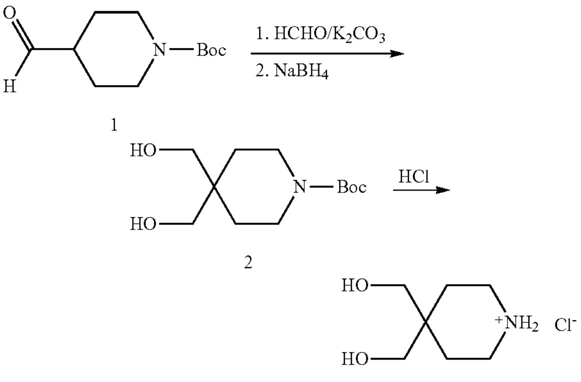

1

2

3

4,4-Bis(hydroxymethyl)piperidine hydrochloride 3

Dipotassium carbonate (32.2 g, 0.233 mol) was added to a stirred mixture of compound 1 (AK Scientific, 99.5 g, 0.466 mol), water (250 mL), methanol (350 mL), and formaldehyde (37.85 g of 37%, 0.466 mol) at 0° C. and was then kept for 18 h at 0° C. The solvent was evaporated to about 30% of the initial volume, and the mixture was extracted with ethyl acetate (5×100 mL). The organic phase was washed with water, brine, dried over $Na_2CO_3$, and evaporated to dryness. The crude material was dissolved in methanol (400 mL), and $NaBH_4$ (39.51 g, 2.24 eq) was added at 0° C. over 30 min. The reaction mixture was stirred for 30 min at 0° C. and overnight at room temperature. The mixture was quenched with concentrated $NH_4Cl$ solution and evaporated to about 25% of the initial volume. This was extracted with ethyl acetate (6×100 mL) and washed with brine. The extract was dried over $Na_2SO_4$ and evaporated. The solid obtained was re-crystallized from ethyl acetate/hexanes (1:3) to give 70.25 g (61.4%) of pure diol 2.

Cold HCl in dioxane (4.25N, 100 mL) was added to compound 2 (26.14 g, 0.107 mol) dissolved in DCM (50 mL) over 15 min at 0° C. The mixture was kept at room temperature for 24 h and evaporated. The residue was stirred with anhydrous ether, and the solid formed was filtered off, washed with ether, and dried in vacuo to give compound 3 (19.03 g, 98.2%) as a white hygroscopic solid.

Example 2

3

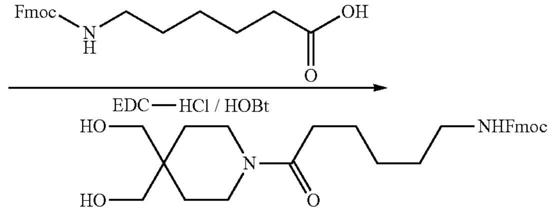

5a (9H-fluoren-9-yl)methyl (6-(4,4-bis(hydroxymethyl) piperidin-1-yl)-6-oxohexyl)carbamate 5a A solution of N-Fmoc-6-aminohexanoic acid (Chem Impex International, Inc., 3.533 g, 10 mmol), N-hydroxybenzotriazole (HOBt, 1.837 g, 12 mmol) and EDC-HCl (2.300 g, 12 mmol) in DCM (40 mL) was stirred at room temperature for 30 min. Compound 3 (2.276 g, 12.53 mmol) and DIPEA (3.102 g, 24 mmol) were added at 0° C. The reaction mixture was stirred for 18 h at room temperature, washed with 5% $NaHCO_3$, 5% HCl, brine. The extract was dried over $Na_2SO_4$ and evaporated. The crude product was purified on a silica gel column (2% AcOH, 2-10% MeOH, DCM), to give 4.26 g (88.6%) of diol 5a as a white solid foam.

NMR $H^1$ (δ, $CDCl_3$): 7.73-7.74 (m, 2H), 7.57-7.59 (m, 2H), 7.36-7.39 (m, 2H), 7.26-7.30 (m, 2H), 5.25 (br. s, J=5 Hz), 4.35 (d, J=7.0 Hz), 4.19 (t, J=7.0 Hz, 1H), 3.59 (s, 4H), 3.53 (br. s, 2H), 3.37 (br. s, 2H), 3.16 (q, J=6.5 Hz, 2H), 2.29 (m, 2H), 1.33-1.60 (m, 10H).

NMR $C^{13}$ (δ, $CDCl_3$): 172.0, 156.8, 144.1 (2C), 141.4 (2C), 127.8 (2C), 127.2 (2C), 125.2 (2C), 120.1 (2C), 68.0, 66.7, 47.4, 41.9, 40.9, 37.9, 37.7, 33.3, 29.8, 29.5, 28.7, 26.6, 24.9.

3

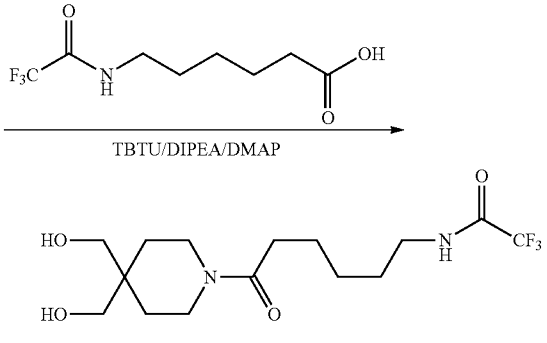

5b

Example 3

N-(6-(4,4-bis(hydroxymethyl)piperidin-1-yl)-6-oxohexyl)-2,2,2-trifluoroacetamide 5b N-Trifluoroacetyl-6-aminohexanoic acid prepared as disclosed in Jagt, R. B. C.; Gomez-Biagi, R. F.; Nitz M. Angew. Chem., Int. Ed. 2009, 48(11), 1995. Compound 3 (4.54 g, 20 mmol), N,N,N',N'-tetramethyl-O-(benzotriazol-1-yl)uronium tetrafluoroborate (TBTU, 7.06 g, 22 mmol), 4-(N,N-dimethylamino)pyridine (DMAP, 0.35 g, 2.86 mmol) were suspended in 30 mL of dry acetonitrile, then diisopropylethylamine (DIPEA, 3.10 g, 24 mmol) was added. The clear reaction mixture was stirred at room temperature for 15 min.

A stirred suspension of hydrochloride 3 (4.00 g, 22 mmol) in acetonitrile (28 mL), dry DCM (50 mL), and N,N-diisopropylethylamine (DIPEA, 3.36 g, 26 mmol) was sonicated in ultrasound bath for 10 min. The suspension was combined with the solution of the reactive ester prepared above under stirring at 0° C. After stirring at room temperature for 18 h, the mixture was concentrated in vacuo, treated with concentrated aqueous solution of sodium bicarbonate (10 mL) plus solid $NaHCO_3$ (5 g) and extracted with ethyl acetate (7×200 mL). The combined organic extracts were dried over sodium sulfate, filtered, and concentrated on rotary evaporator. The crude material obtained was re-crystallized from ethyl acetate/hexanes to give 5.52 g (77.9%) of compound 5b as white needles (m.p. 84-86° C.). The mother liquor was concentrated and purified on flash column (silica gel, 2-20% MeOH in DCM) to give another 1.50 g of compound 5b (total yield of 99.0%).

NMR $H^1$ (δ, $CDCl_3$): 7.03 (br. s, 1H), 3.68 (d, J=5.0 Hz, 4H), 3.57-3.59 (m, 2H), 3.40-3.45 (m, 4H), 2.34 (t, J=5.0 Hz, 2H), 2.28 (br. t, J=5.0 Hz, 2H), 1.57-1.68 (m, 6H), 1.44-1.46 (m, 2H), 1.37-1.40 (m, 2H).

NMR $C^{13}$ (δ, $CDCl_3$): 157.5 (q, $J_{CF}$=36.2 Hz), 116.1 (q, $J_{CF}$=286.2 Hz), 69.1, 41.7, 39.4, 37.8, 32.9, 29.5, 28.8, 28.3, 26.18, 23.8.

Example 3

3

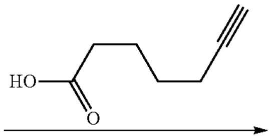

-continued

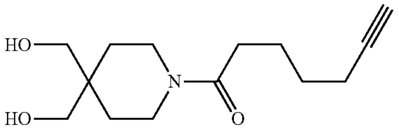

5d 1-(4,4-bis(hydroxymethyl)piperidin-1-yl)hept-6-yn-1-one 5d

A solution of 7-heptynoic acid (Chem Impex International, Inc., 1.26 g, 10 mmol), N-hydroxybenzotriazole (HOBt, 1.837 g, 12 mmol) and EDC-HCl (2.300 g, 12 mmol) in DCM (40 mL) was stirred at room temperature for 30 min. Compound 3 (2.276 g, 12.53 mmol) and DIPEA (3.102 g, 24 mmol) were added at 0° C. The reaction mixture was stirred for 18 h at room temperature, washed with 5% $NaHCO_3$, 5% HCl, brine. The extract was dried over $Na_2SO_4$ and evaporated. The crude product was purified on a silica gel column (2% AcOH, 2-10% MeOH, DCM), to give 2.341 g (92.4%) of diol 5d as a white solid.

Example 4

3 +

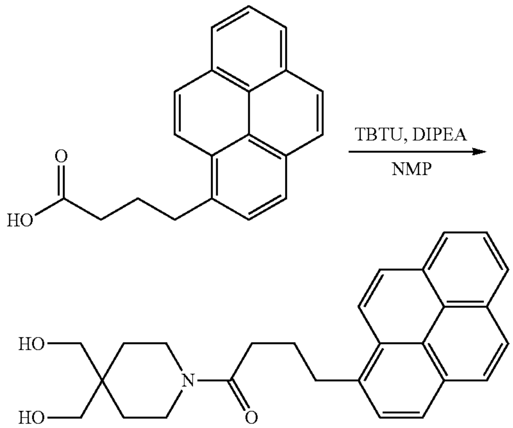

5e 1-(4,4-bis(hydroxymethyl)piperidin-1-yl)-5-(pyren-1-yl)pentan-1-one 5e

Solution of 4-(pyren-1-yl)butanoic acid (0.993 g, 3.44 mmol), TBTU (1.16 g, 3.61 mmol), and DIPEA (1.5 mL, 8.6 mmol) dissolved in NMP (13 g) was stirred for 15 min and added to compound 3 (1.93 g, 3.44 mmol) in NMP (9 g) at 0° C. followed by stirring at this temperature for 1 h. The reaction mixture was diluted with ethyl acetate (200 mL), washed with concentrated $NaHCO_3$ and brine (8 times). The organic phase was dried over $Na_2SO_4$ and evaporated. The product was isolated on a silica gel column (50% hexanes in DCM to 5% MeOH, DCM) to give compound 5e (2.517 g, 88.1%).

Example 5

3

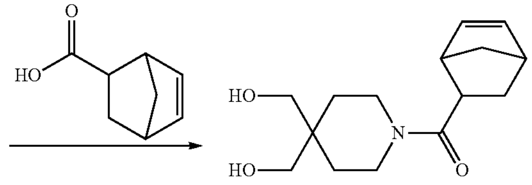

5f

Bicyclo[2.2.1]hept-5-en-2-yl(4,4-bis(hydroxymethyl)piperidin-1-yl)methanone 5f

A solution of bicyclo[2.2.1]hept-5-ene-2-carboxylic acid (Alfa Aesar, 1.38 g, 10 mmol), N-hydroxybenzotriazole (HOBt, 1.837 g, 12 mmol) and EDC-HCl (2.300 g, 12 mmol) in DCM (40 mL) was stirred at room temperature for 30 min. Compound 3 (2.276 g, 12.53 mmol) and DIPEA (3.102 g, 24 mmol) were added at 0° C. The reaction mixture was stirred for 18 h at room temperature, washed with 5% $NaHCO_3$, 5% HCl, brine. The extract was dried over $Na_2SO_4$ and evaporated. The crude product was purified on a silica gel column (2% AcOH, 2-10% MeOH, DCM), to give 2.444 g (92.1%) of diol 5f as a white solid.

Example 6

3

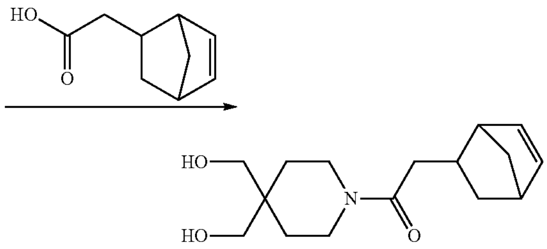

5g 2-(bicyclo[2.2.1]hept-5-en-2-yl)-1-(4,4-bis(hydroxymethyl)piperidin-1-yl)ethan-1-one 5 g A solution of 2-(bicyclo[2.2.1]hept-5-en-2-yl)acetic acid (Alfa Aesar, 1.52 g, 10 mmol), N-hydroxybenzotriazole (HOBt, 1.837 g, 12 mmol) and EDC-HCl (2.300 g, 12 mmol) in DCM (40 mL) was stirred at room temperature for 30 min. Compound 3 (2.276 g, 12.53 mmol) and DIPEA (3.102 g, 24 mmol) were added at 0° C. The reaction mixture was stirred for 18 h at room temperature, washed with 5% $NaHCO_3$, 5% HCl, brine. The extract was dried over $Na_2SO_4$ and evaporated. The crude product was purified on a silica gel column (2% AcOH, 2-10% MeOH, DCM), to give 2.615 g (93.6%) of diol 5 g as a white solid.

Example 7

3

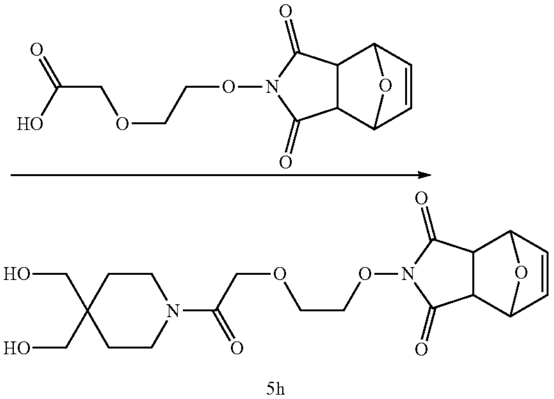

5h 2-(2-(2-(4,4-bis(hydroxymethyl)piperidin-1-yl)-2-oxoethoxy)ethoxy)-3a,4,7,7a-tetrahydro-1H-4,7-epoxyisoindole-1,3(2H)-dione 5h A solution of 2-(2-((1,3-dioxo-1,3,3a,4,7,7a-hexahydro-2H-4,7-epoxyisoindol-2-yl)oxy)ethoxy)acetic acid (2.83 g, 10 mmol), N-hydroxybenzotriazole (HOBt, 1.837 g, 12 mmol) and EDC-HCl (2.300 g, 12 mmol) in DMF (40 mL) was stirred at room temperature for 30 min. Compound 3 (2.276 g, 12.53 mmol) and DIPEA (3.102 g, 24 mmol) were added at 0° C. The reaction mixture was stirred for 18 h at room temperature, diluted with ethyl acetate (200 mL), washed with 5% $NaHCO_3$, 5% HCl, brine. The extract was dried over $Na_2SO_4$ and evaporated. The crude product was purified on a silica gel column (2% AcOH, 2-10% MeOH, DCM), to give 3.439 g (83.8%) of diol 5h as a white solid.

Example 8

3

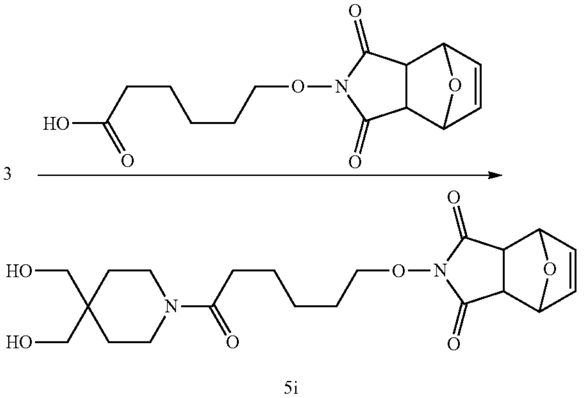

5i 2-((6-(4,4-bis(hydroxymethyl)piperidin-1-yl)-6-oxo-hexyl)oxy)-3a,4,7,7a-tetrahydro-1H-4,7-epoxyisoindole-1,3(2H)-dione 5i A solution of 6-((1,3-dioxo-1,3,3a,4,7,7a-hexahydro-2H-4,7-epoxyisoindol-2-yl)oxy)hexanoic acid (2.95 g, 10 mmol), N-hydroxybenzotriazole (HOBt, 1.837 g, 12 mmol) and EDC-HCl (2.300 g, 12 mmol) in DMF (40 mL) was stirred at room temperature for 30 min. Compound 3 (2.276 g, 12.53 mmol) and DIPEA (3.102 g, 24 mmol) were added at 0° C. The reaction mixture was stirred for 18 h at room temperature, diluted with ethyl acetate (200 mL), washed with 5% $NaHCO_3$, 5% HCl, brine. The extract was dried over $Na_2SO_4$ and evaporated. The crude product was purified on a silica gel column (2% AcOH, 2-10% MeOH, DCM), to give 3.223 g (76.3%) of diol 5i as a white solid.

Example 9

3

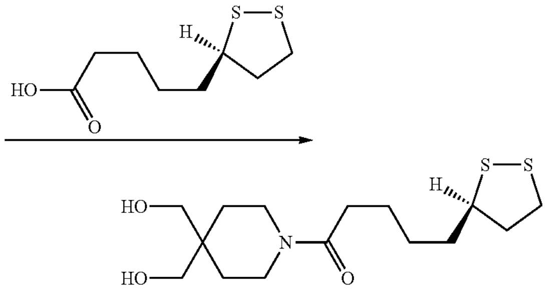

5j (R)-1-(4,4-bis(hydroxymethyl)piperidin-1-yl)-5-(1,2-dithiolan-3-yl)pentan-1-one 5j A solution of (R)-5-(1,2-dithiolan-3-yl)pentanoic acid (2.06 g, 10 mmol), N-hydroxybenzotriazole (HOBt, 1.837 g, 12 mmol) and EDC-HCl (2.300 g, 12 mmol) in DMF (40 mL) was stirred at room temperature for 30 min. Compound 3 (2.276 g, 12.53 mmol) and DIPEA (3.102 g, 24 mmol) were added at 0° C. The reaction mixture was stirred for 18 h at room temperature, diluted with ethyl acetate (200 mL), washed with 5% $NaHCO_3$, 5% HCl, brine. The extract was dried over $Na_2SO_4$ and evaporated. The crude product was purified on a silica gel column (2% AcOH, 2-10% MeOH, DCM), to give 2.271 g (68.1%) of diol 5j as a white solid.

Example 10

3

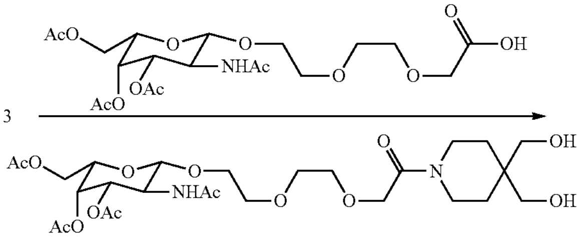

5k

N-(8-((3,4,6-O-triacetyl-2-acetylamino-2-deoxy-β-D-galactopyranosyl)oxy)-3,6-dioxaoctanoyl)-4,4'-bis(hydroxymethyl)piperidine 5k A solution of 8-((3,4,6-O-triacetyl-2-acetylamino-2-deoxy-β-D-galactopyranosyl)oxy)-3,6-dioxaoctanoic acid (4.93 g, 10 mmol), N-hydroxybenzotriazole (HOBt, 1.837 g, 12 mmol) and EDC-HCl (2.300 g, 12 mmol) in DMF (40 mL) was stirred at room temperature for 30 min. Compound 3 (2.276 g, 12.53 mmol) and DIPEA (3.102 g, 24 mmol) were added at 0° C. The reaction mixture was stirred for 18 h at room temperature, diluted with ethyl acetate (200 mL), washed with 5% $NaHCO_3$, 5% HCl, brine. The extract was dried over $Na_2SO_4$ and evaporated. The crude product was purified on a silica gel column (2% AcOH, 2-10% MeOH, DCM), to give 4.522 g (72.9%) of diol 5k as a white solid.

4

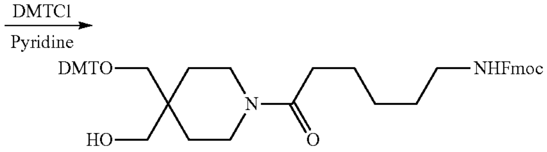

7a

Example 11

(9H-fluoren-9-yl)methyl (6-(4-((bis(4-methoxyphenyl)(phenyl)methoxy)methyl)-4-(hydroxymethyl)piperidin-1-yl)-6-oxohexyl)carbamate 7a DMTrCl (3.24 g, 9.56 mmol) was gradually added to a stirred solution of compound 5a (4.38 g, 9.11 mmol) in pyridine (30 mL) over 4 h at 0° C., and stirring was continued at room temperature for 72 h. The reaction mixture was concentrated, co-evaporated with toluene, and distributed between triethylammonium bicarbonate buffer (pH 7.19) and ethyl acetate. The aqueous layer was additionally extracted with ethyl acetate (2×50 mL). The combined organic phase was dried over $Na_2SO_4$, concentrated, and separated on a silica gel column (0-3% MeOH, DCM) to yield compound 7a (3.515 g, 49.3%).

NMR $H^1$ (δ, $CD_3CN$): 7.81-7.83 (m, 2H), 7.63-7.65 (m, 2H), 7.39-7.45 (m, 4H), 7.28-7.34 (m, 8H), 7.20-7.23 (m, 1H), 6.84-6.87 (m, 4H), 5.69 (br. s, 1H), 4.31 (d, J=7.0 Hz, 2H), 4.21 (t, J=7.0, 1H), 3.75 (s, 6H), 3.54 (d, J=5.0 Hz, 2H), 3.43-3.50 (m, 1H), 3.30-3.36 (m, 1H), 3.00-3.10 (m, 4H), 3.02 (s, 2H), 2.64 (t, J=5.0 Hz, 1H), 2.22 (t, J=7.5 Hz, 2H), 1.23-1.53 (m, 10H).

7a

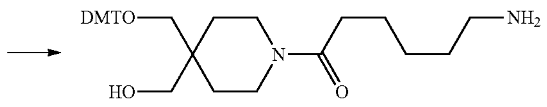

23

Example 12

6-amino-1-(4-((bis(4-methoxyphenyl)(phenyl)methoxy)methyl)-4-(hydroxymethyl)piperidin-1-yl)hexan-1-one 23

Compound 7a (3.515 g, 4.49 mmol) was treated with of 10% piperidine in MeOH (100 mL) overnight. The reaction mixture was evaporated, co-evaporated with xylenes, and separated on a silica gel column (1% $NH_4OH$, 3% MeOH in DCM to 2% $NH_4OH$, 10% MeOH in DCM) to give pure amine 23 (1.966 g, 78.1%) of as a white solid foam.

NMR $H^1$ (δ, DMSO-$d_6$): 7.36-7.40 (m, 2H), 7.28-7.33 (m, 2H), 7.24-7.26 (m, 4H), 7.18-7.23 (m, 1H), 6.87-6.91 (m, 4H), 3.73 (s, 6H), 3.47 (s, 2H), 3.27-3.41 (m, 2H), 2.96-3.05 (m, 2H), 2.93 (s, 2H), 2.20 (t, 7.0 Hz), 1.20-1.46 (m, 10H).

NMR $C^{13}$ (δ, DMSO-$d_6$): 170.2, 157.9 (2C), 145.2, 135.9 (2C), 129.7 (4C), 127.7 (2C), 127.7 (2C), 126.5, 113.0 (4C), 84.9, 64.2, 64.0, 55.0 (2C), 41.5, 40.9, 39.3, 39.2, 39.0, 37.6, 33.1, 32.3, 26.1, 24.7.

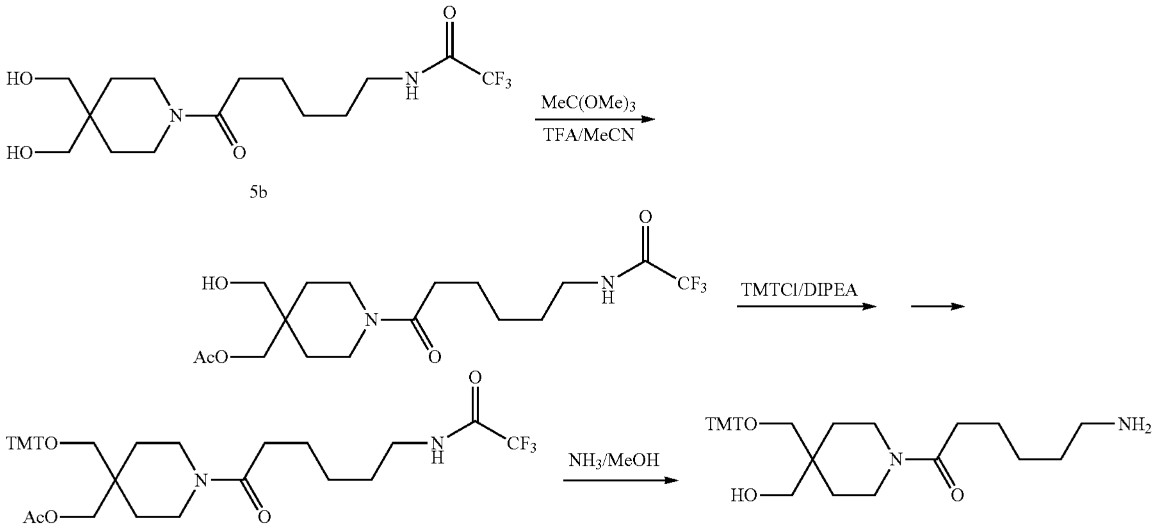

5b

24

Example 13

6-Amino-1-(4-(hydroxymethyl)-4-((tris(4-methoxyphenyl)methoxy)methyl)piperidin-1-yl)hexan-1-one 24

A mixture of compound 5b (5.64 g, 15.9 mmol), 1,1,1-trimethoxyethane (3.82 g, 31.8 mmol), trifluoroacetic acid (0.05 mL), and acetonitrile (17 mL) was briefly heated at 60°

C. and then was stirred at room temperature for 40 min. The reaction mixture was concentrated to ½ of its original volume and water (0.715 g, 39.7 mmol) was added. After heating at 60° C. for 1 h, the mixture was concentrated in vacuo, co-evaporated five times with toluene, dissolved in anhydrous DCM (20 mL), mixed with DIPEA (4.40 g, 34.04 mmol), and dried over freshly flamed molecular sieves 4A (1.0 g) for 1 h at stirring. The reaction mixture was treated with 4, 4', 4"-trimethoxytrityl chloride (7.05 g, 19.11 mmol) at 0° C. and was stirred at room temperature for 18 h. The mixture obtained was diluted with ethyl acetate (200 mL), washed sequentially with concentrated aqueous sodium bicarbonate, dilute aqueous citric acid (pH 6), and brine. The organic phase was dried over $Na_2SO_4$, filtered, and evaporated. Sample (0.1 g) of the crude compound 7 was purified for analytical purposes (flash column, silica gel, 2-5% MeOH in DCM).

NMR $H^1$ (δ, $CDCl_3$): 7.39 (br. s, 1H), 7.26-7.30 (m, 6H), 6.80-6.82 (m, 6H), 4.14, 4.19 (AB, J=10.0 Hz, 2H), 3.77 (s, 9H), 2.58-3.62 (m, 1H), 3.34-3.38 (m, 3H), 2.19-2.23 (m, 1H), 3.04-3.11 (m, 3H), 2.25-2.28 (m, 2H), 1.97 (s, 3H), 1.55-1.62 (m, 4H), 1.46-1.54 (m, 4H), 1.32-1.38 (m, 2H).

NMR $C^{13}$ (δ, $CDCl_3$): 171.1, 171.2, 158.5, 157.5 (q, $J_{CF}$=36.2 Hz), 136.6, 129.9, 116.3 (q, $J_{CF}$=286.1 Hz), 113.2, 85.6, 67.1, 63.7, 55.3, 53.6, 41.4, 39.4, 37.5, 37.0, 32.8, 30.3, 29.5, 28.3, 26.2, 23.9, 20.9.

The remaining crude 7 was dissolved in a mixture of methanol (30 mL) and conc. aqueous ammonia (32%, 30 mL) and heated in a pressure-resistant flask at 55° C. for 5 days. The resulting mixture was evaporated, co-evaporated with toluene, and separated on a silica gel column using a step gradient of conc. aqueous ammonia and MeOH in DCM from 1:3:96 to 2:10:88 to give pure amine 24 (8.98 g, 95.6%) as a white solid foam.

NMR $H^1$ (δ, $CDCl_3$): 7.26-7.30 (m, 6H), 6.81-6.84 (m, 6H), 3.78 (s, 9H), 3.55-3.62 (m, 2H), 3.46-3.54 (m, 1H), 3.30-3.42 (m, 2H), 3.15-3.21 (m, 1H), 3.05-3.14 (m, 2H), 2.29 (br. s, 3H), 2.69 (t, J=7.0 Hz, 2H), 2.26 (t, J=5.5 Hz, 2H), 1.57-1.62 (m, 4H), 1.44-1.50 (m, 4H), 1.33-1.36 (m, 2H).

NMR $C^{13}$ (δ, $CDCl_3$): 171.6, 158.7, 136.3, 129.9, 113.4, 86.2, 67.8, 67.6, 55.4, 42.0, 41.7, 37.9, 37.7, 33.4, 33.2, 30.2, 29.4, 26.8, 25.2.

Example 14

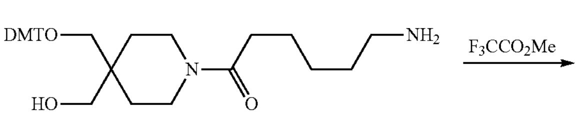

23

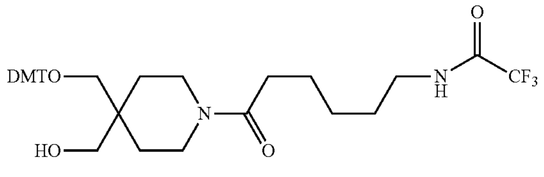

7b

N-(6-(4-((bis(4-methoxyphenyl)(phenyl)methoxy)methyl)-4-(hydroxymethyl)piperidin-1-yl)-6-oxohexyl)-2,2,2-trifluoroacetamide 7b Compound 23 (1.873 g, 3.34 mmol) was dissolved in DCM (10 g), and treated with triethylamine (0.1 mL) and methyltrifluoroacetate (0.855 g, 6.68 mmol) at 30° C. for 4 h. The reaction mixture was evaporated and purified on a silica gel column (50% hexanes/DCM→4% MeOH/DCM) to give compound 7b (1.673 g, 78.6%).

Example 15

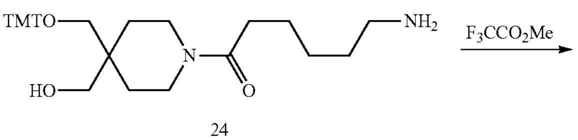

24

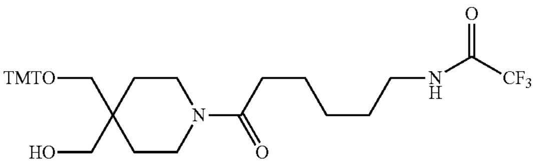

8b

N-(6-(4-((tris(4-methoxyphenyl)methoxy)methyl)-4-(hydroxymethyl)piperidin-1-yl)-6-oxohexyl)-2,2,2-trifluoroacetamide 8b Compound 24 (2.127 g, 3.6 mmol) was dissolved in DCM (10 g), and treated with triethylamine (0.1 mL) and methyltrifluoroacetate (0.922 g, 7.2 mmol) at 30° C. for 4 h. The reaction mixture was evaporated and purified on a silica gel column (50% hexanes/DCM→4% MeOH/DCM) to give compound 8b (1.914 g, 77.4%).

Example 16

5d

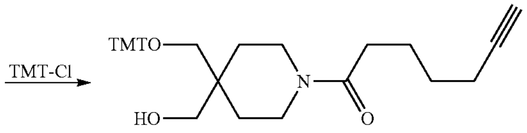

8d 1-(4-(hydroxymethyl)-4-(((4,4',4"-trimethoxytrityl)oxy)methyl)piperidin-1-yl)hept-6-yn-1-one 8d Trimethoxytrityl chloride (3.69 g, 10 mmol) was gradually added to a stirred solution of compound 5d (2.533 g, 10 mmol) in pyridine (30 mL) over 4 h at 0° C., and stirring was continued at room temperature for 72 h. The reaction mixture was concentrated, co-evaporated with toluene, and distributed between triethylammonium bicarbonate buffer (pH 7.19) and ethyl acetate. The aqueous layer was additionally extracted with ethyl acetate (2×50 mL). The combined organic phase was dried over $Na_2SO_4$, concentrated, and separated on a silica gel column (0-3% MeOH, DCM) to yield compound 8d (2.87 g, 49.0%).

Example 17

5e
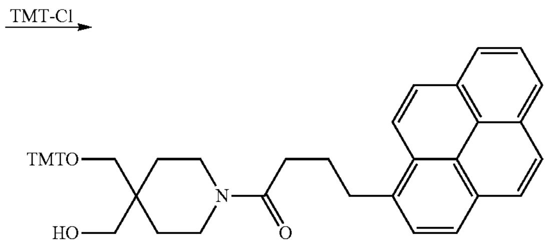

8e 1-(4-(hydroxymethyl)-4-(((4,4',4"-trimethoxytrityl)oxy)methyl)piperidin-1-yl)-4-(pyren-1-yl)butan-1-one 8e Trimethoxytrityl chloride (1.85 g, 5 mmol) was gradually added to a stirred solution of compound 5e (2.078 g, 5 mmol) in pyridine (30 mL) over 4 h at 0° C., and stirring was continued at room temperature for 72 h. The reaction mixture was concentrated, co-evaporated with toluene, and distributed between triethylammonium bicarbonate buffer (pH 7.19) and ethyl acetate. The aqueous layer was additionally extracted with ethyl acetate (2×50 mL). The combined organic phase was dried over $Na_2SO_4$, concentrated, and separated on a silica gel column (0-3% MeOH, DCM) to yield compound 8e (1.960 g, 52.4%).

Example 18

5f
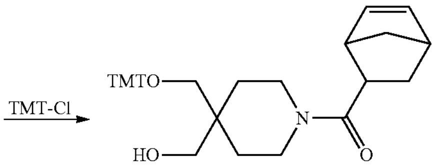

8f

N-(bicyclo[2.2.1]hept-5-en-2-carbonyl)-4-(hydroxymethyl)-4-((4,4',4"-trimethoxytrityl)oxy)methylpiperidine 8f Trimethoxytrityl chloride (1.85 g, 5 mmol) was gradually added to a stirred solution of compound 5f (1.327 g, 5 mmol) in pyridine (30 mL) over 4 h at 0° C., and stirring was continued at room temperature for 72 h. The reaction mixture was concentrated, co-evaporated with toluene, and distributed between triethylammonium bicarbonate buffer (pH 7.19) and ethyl acetate. The aqueous layer was additionally extracted with ethyl acetate (2×50 mL). The combined organic phase was dried over $Na_2SO_4$, concentrated, and separated on a silica gel column (0-3% MeOH, DCM) to yield compound 8f (1.635 g, 54.7%).

Example 19

5g
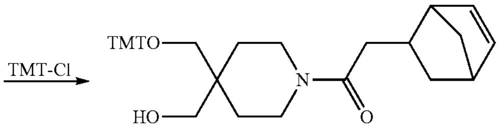

8g

N-(2-(bicyclo[2.2.1]hept-5-en-2-yl)acetyl)-4-(hydroxymethyl)-4-((4,4',4"-trimethoxytrityl)oxy)methylpiperidine 8 g Trimethoxytrityl chloride (2.951 g, 8 mmol) was gradually added to a stirred solution of compound 5g (2.235 g, 8 mmol) in pyridine (30 mL) over 4 h at 0° C., and stirring was continued at room temperature for 72 h. The reaction mixture was concentrated, co-evaporated with toluene, and distributed between triethylammonium bicarbonate buffer (pH 7.19) and ethyl acetate. The aqueous layer was additionally extracted with ethyl acetate (2×50 mL). The combined organic phase was dried over $Na_2SO_4$, concentrated, and separated on a silica gel column (0-3% MeOH, DCM) to yield compound 8g (2.873 g, 58.7%).

Example 20

5h
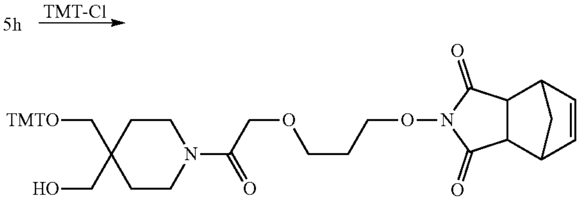

8h 2-(2-(2-(4-(hydroxymethyl)-4-(((4,4',4"-trimethoxytrityl)oxy)methyl)piperidin-1-yl)-2-oxoethoxy)ethoxy)-3a,4,7,7a-tetrahydro-1H-4,7-epoxyisoindole-1,3(2H)-dione 8h Trimethoxytrityl chloride (3.689 g, 10 mmol) was gradually added to a stirred solution of compound 5h (4.104 g, 10 mmol) in pyridine (30 mL) over 4 h at 0° C., and stirring was continued at room temperature for 72 h. The reaction mixture was concentrated, co-evaporated with toluene, and distributed between triethylammonium bicarbonate buffer (pH 7.19) and ethyl acetate. The aqueous layer was additionally extracted with ethyl acetate (2×50 mL). The combined organic phase was dried over $Na_2SO_4$, concentrated, and separated on a silica gel column (0-3% MeOH, DCM) to yield compound 8h (4.013 g, 53.3%).

Example 21

5i

-continued

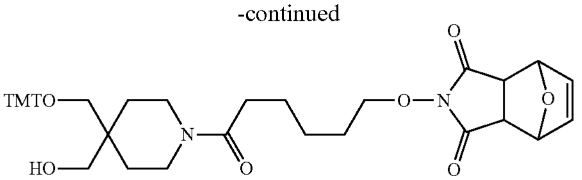

8i 2-((6-(4-(hydroxymethyl)-4-(((4,4',4"-trimethoxytrityl)oxy)methyl)piperidin-1-yl)-6-oxohexyl)oxy)-3a,4,7,7a-tetrahydro-1H-4,7-epoxyisoindole-1,3(2H)-dione 8i Trimethoxytrityl chloride (3.689 g, 10 mmol) was gradually added to a stirred solution of compound 5i (4.225 g, 10 mmol) in pyridine (30 mL) over 4 h at 0° C., and stirring was continued at room temperature for 72 h. The reaction mixture was concentrated, co-evaporated with toluene, and distributed between triethylammonium bicarbonate buffer (pH 7.19) and ethyl acetate. The aqueous layer was additionally extracted with ethyl acetate (2×50 mL). The combined organic phase was dried over $Na_2SO_4$, concentrated, and separated on a silica gel column (0-3% MeOH, DCM) to yield compound 8i (3.918 g, 51.9%).

Example 22

5j 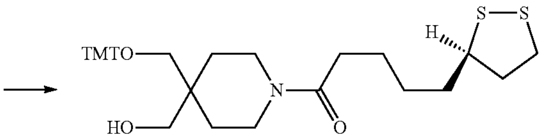

8j (R)-1-(4-(hydroxymethyl)-4-(((4,4',4"-trimethoxytrityl)oxy)methyl)piperidin-1-yl)-5-(1,2-dithiolan-3-yl)pentan-1-one 8j Trimethoxytrityl chloride (3.689 g, 10 mmol) was gradually added to a stirred solution of compound 5j (3.335 g, 10 mmol) in pyridine (30 mL) over 4 h at 0° C., and stirring was continued at room temperature for 72 h. The reaction mixture was concentrated, co-evaporated with toluene, and distributed between triethylammonium bicarbonate buffer (pH 7.19) and ethyl acetate. The aqueous layer was additionally extracted with ethyl acetate (2×50 mL). The combined organic phase was dried over $Na_2SO_4$, concentrated, and separated on a silica gel column (0-3% MeOH, DCM) to yield compound 8j (2.823 g, 42.4%).

Example 23

5k

-continued

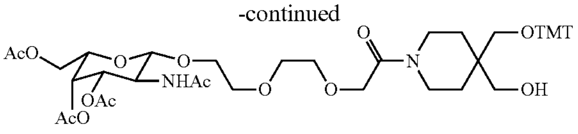

8k

N-(8-((3,4,6-O-triacetyl-2-acetylamino-2-deoxy-j-D-galactopyranosyl)oxy)-3,6-dioxaoctanoyl)-(4-(hydroxymethyl)-4-(((4,4',4"-trimethoxytrityl)oxy)methyl)piperidine 8k Trimethoxytrityl chloride (3.689 g, 10 mmol) was gradually added to a stirred solution of compound 5k (6.207 g, 10 mmol) in pyridine (30 mL) over 4 h at 0° C., and stirring was continued at room temperature for 72 h. The reaction mixture was concentrated, co-evaporated with toluene, and distributed between triethylammonium bicarbonate buffer (pH 7.19) and ethyl acetate. The aqueous layer was additionally extracted with ethyl acetate (2×50 mL). The combined organic phase was dried over $Na_2SO_4$, concentrated, and separated on a silica gel column (0-3% MeOH, DCM) to yield compound 8k (5.042 g, 52.9%).

Example 24

7b 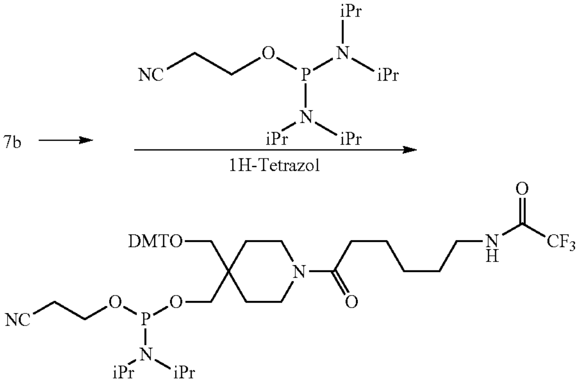

11b (4-((bis(4-methoxyphenyl)(phenyl)methoxy)methyl)-1-(6-(2,2,2-trifluoroacetamido)hexanoyl)piperidin-4-yl)methyl (2-cyanoethyl) diisopropylphosphoramidite 11b Compound 7a (1.580 g, 2.41 mmol) and 2-cyanoethyl N,N,N',N'-tetraisopropylphosphorodiamidite (0.943 g, 3.13 mmol) in anhydrous acetonitrile (25 mL) were shaken with flame-dried molecular sieves 4 Å (1.5 g) for 1 h. This was cooled to −10° C., and 1H-tetrazole (0.45M, 0.96 mmol, 2.14 mL) in acetonitrile was added, and the mixture was stirred overnight. The reaction mixture was quenched with triethylamine (0.5 mL) and diluted with saturated aqueous sodium bicarbonate. The mixture was extracted with DCM, and the organic extract was dried over $Na_2SO_4$ and evaporated to dryness. The crude product was purified on a silica gel column (5% $Et_3N$, 20-80% ethyl acetate in hexanes) to yield 11b (1.58 g, 76.5%) as a white solid foam.

Example 25

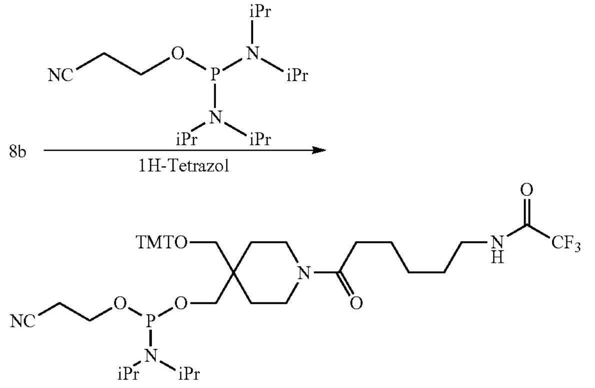

12b (4-((tris(4-methoxyphenyl)methoxy)methyl)-1-(6-(2,2,2-trifluoroacetamido)hexanoyl)piperidin-4-yl) methyl (2-cyanoethyl) diisopropylphosphoramidite 12b Compound 8b (1.374 g, 2.0 mmol) and 2-cyanoethyl N,N,N',N'-tetraisopropylphosphorodiamidite (0.784 g, 2.6 mmol) in anhydrous acetonitrile (25 mL) were shaken with flame-dried molecular sieves 4 Å (1.5 g) for 1 h. This was cooled to −10° C., and 1H-tetrazole (0.45M, 1.0 mmol, 2.22 mL) in acetonitrile was added, and the mixture was stirred overnight. The reaction mixture was quenched with triethylamine (0.5 mL) and diluted with saturated aqueous sodium bicarbonate. The mixture was extracted with DCM, and the organic extract was dried over $Na_2SO_4$ and evaporated to dryness. The crude product was purified on a silica gel column (5% $Et_3N$, 20-80% ethyl acetate in hexanes) to yield 12b (1.38 g, 74.3%) as a white solid foam.

Example 26

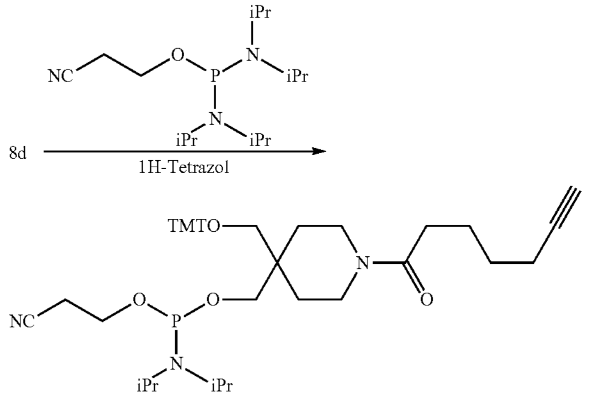

12d (4-((tris(4-methoxyphenyl)methoxy)methyl)-1-(7-heptynoyl)piperidin-4-yl)methyl (2-cyanoethyl) diisopropylphosphoramidite 12d Compound 8d (1.464 g, 2.5 mmol) and 2-cyanoethyl N,N,N',N'-tetraisopropylphosphorodiamidite (0.980 g, 3.2 mmol) in anhydrous acetonitrile (25 mL) were shaken with flame-dried molecular sieves 4 Å (1.5 g) for 1 h. This was cooled to −10° C., and 1H-tetrazole (0.45M, 1.25 mmol, 2.78 mL) in acetonitrile was added, and the mixture was stirred overnight. The reaction mixture was quenched with triethylamine (0.5 mL) and diluted with saturated aqueous sodium bicarbonate. The mixture was extracted with DCM, and the organic extract was dried over $Na_2SO_4$ and evaporated to dryness. The crude product was purified on a silica gel column (5% $Et_3N$, 20-80% ethyl acetate in hexanes) to yield 12d (1.619 g, 82.4%) as a white solid foam.

Example 27

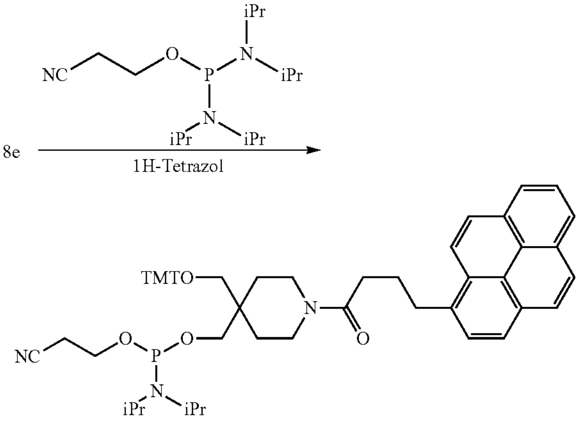

12e (4-((tris(4-methoxyphenyl)methoxy)methyl)-1-(4-(pyren-1-yl)butanoyl)piperidin-4-yl)methyl (2-cyanoethyl) diisopropylphosphoramidite 12e Compound 8e (1.374 g, 2.0 mmol) and 2-cyanoethyl N,N,N',N'-tetraisopropylphosphorodiamidite (0.784 g, 2.6 mmol) in anhydrous acetonitrile (25 mL) were shaken with flame-dried molecular sieves 4 Å (1.5 g) for 1 h. This was cooled to −10° C., and 1H-tetrazole (0.45M, 1.0 mmol, 2.22 mL) in acetonitrile was added, and the mixture was stirred overnight. The reaction mixture was quenched with triethylamine (0.5 mL) and diluted with saturated aqueous sodium bicarbonate. The mixture was extracted with DCM, and the organic extract was dried over $Na_2SO_4$ and evaporated to dryness. The crude product was purified on a silica gel column (5% $Et_3N$, 20-80% ethyl acetate in hexanes) to yield 12e (1.453 g, 76.6%) as a white solid foam.

Example 28

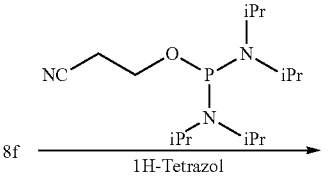

-continued

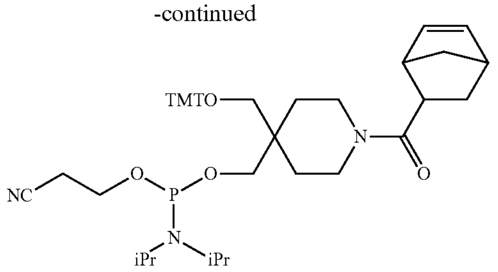

12f (1-(bicyclo[2.2.1]hept-5-ene-2-carbonyl)-4-((tris(4-methoxyphenyl)methoxy)methyl)piperidin-4-yl) methyl (2-cyanoethyl) diisopropylphosphoramidite 12f Compound 8f (0.956 g, 1.6 mmol) and 2-cyanoethyl N,N,N',N'-tetraisopropylphosphorodiamidite (0.627 g, 2.08 mmol) in anhydrous acetonitrile (25 mL) were shaken with flame-dried molecular sieves 4 Å (1.5 g) for 1 h. This was cooled to −10° C., and 1H-tetrazole (0.45M, 0.8 mmol, 1.78 mL) in acetonitrile was added, and the mixture was stirred overnight. The reaction mixture was quenched with triethylamine (0.5 mL) and diluted with saturated aqueous sodium bicarbonate. The mixture was extracted with DCM, and the organic extract was dried over $Na_2SO_4$ and evaporated to dryness. The crude product was purified on a silica gel column (5% $Et_3N$, 20-80% ethyl acetate in hexanes) to yield 12f (1.122 g, 87.9%) as a white solid foam.

Example 29

8g

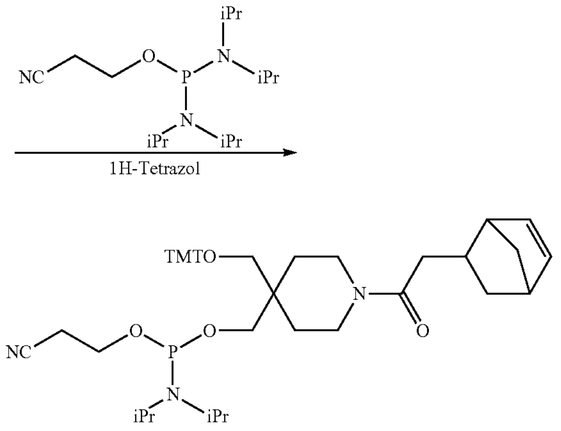

12g (1-(2-(bicyclo[2.2.1]hept-5-en-2-yl)acetyl)-4-((tris (4-methoxyphenyl)methoxy)methyl)piperidin-4-yl) methyl (2-cyanoethyl) diisopropylphosphoramidite 12 g Compound 8g (1.224 g, 2.0 mmol) and 2-cyanoethyl N,N,N',N'-tetraisopropylphosphorodiamidite (0.784 g, 2.6 mmol) in anhydrous acetonitrile (25 mL) were shaken with flame-dried molecular sieves 4 Å (1.5 g) for 1 h. This was cooled to −10° C., and 1H-tetrazole (0.45M, 1.0 mmol, 2.22 mL) in acetonitrile was added, and the mixture was stirred overnight. The reaction mixture was quenched with triethylamine (0.5 mL) and diluted with saturated aqueous sodium bicarbonate. The mixture was extracted with DCM, and the organic extract was dried over $Na_2SO_4$ and evaporated to dryness. The crude product was purified on a silica gel column (5% $Et_3N$, 20-80% ethyl acetate in hexanes) to yield 12 g (1.366 g, 84.1%) as a white solid foam.

Example 30

8h

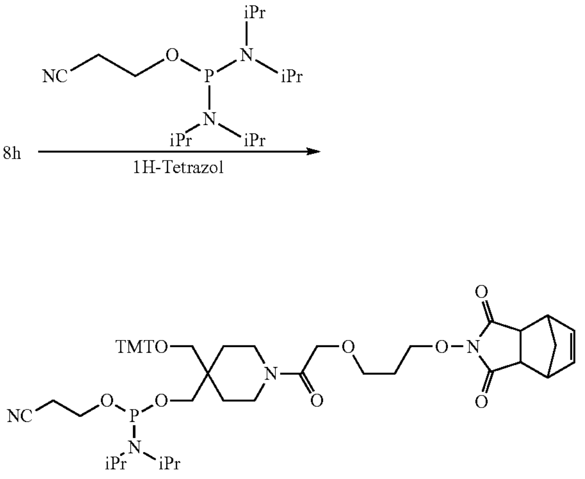

12h (1-(2-(3-((1,3-dioxo-1,3,3a,4,7,7a-hexahydro-2H-4,7-methanoisoindol-2-yl)oxy)propoxy)acetyl)-4-((tris (4-methoxyphenyl)methoxy)methyl)piperidin-4-yl) methyl (2-cyanoethyl) diisopropylphosphoramidite 12h Compound 8h (1.510 g, 2.0 mmol) and 2-cyanoethyl N,N,N',N'-tetraisopropylphosphorodiamidite (0.784 g, 2.6 mmol) in anhydrous acetonitrile (25 mL) were shaken with flame-dried molecular sieves 4 Å (1.5 g) for 1 h. This was cooled to −10° C., and 1H-tetrazole (0.45M, 1.0 mmol, 2.22 mL) in acetonitrile was added, and the mixture was stirred overnight. The reaction mixture was quenched with triethylamine (0.5 mL) and diluted with saturated aqueous sodium bicarbonate. The mixture was extracted with DCM, and the organic extract was dried over $Na_2SO_4$ and evaporated to dryness. The crude product was purified on a silica gel column (5% $Et_3N$, 20-80% ethyl acetate in hexanes) to yield 12h (1.57 g, 82.2%) as a white solid foam.

Example 31

8i

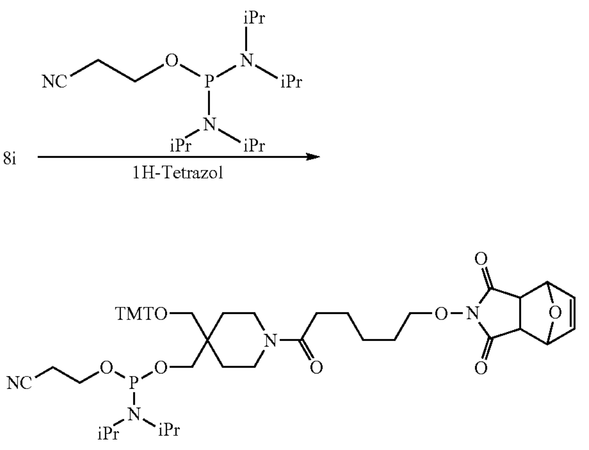

12i (1-(6-((1,3-dioxo-1,3,3a,4,7,7a-hexahydro-2H-4,7-epoxyisoindol-2-yl)oxy)hexanoyl)-4-((tris(4-methoxyphenyl)methoxy)methyl)piperidin-4-yl) methyl (2-cyanoethyl) diisopropylphosphoramidite 12i Compound 8i (1.510 g, 2.0 mmol) and 2-cyanoethyl N,N,N',N'-tetraisopropylphosphorodiamidite (0.784 g, 2.6 mmol) in anhydrous acetonitrile (25 mL) were shaken with flame-dried molecular sieves 4 Å (1.5 g) for 1 h. This was cooled to −10° C., and 1H-tetrazole (0.45M, 1.0 mmol, 2.22 mL) in acetonitrile was added, and the mixture was stirred overnight. The reaction mixture was quenched with triethylamine (0.5 mL) and diluted with saturated aqueous sodium bicarbonate. The mixture was extracted with DCM, and the organic extract was dried over $Na_2SO_4$ and evaporated to dryness. The crude product was purified on a silica gel column (5% $Et_3N$, 20-80% ethyl acetate in hexanes) to yield 12i (1.543 g, 80.8%) as a white solid foam.

Example 32

8j

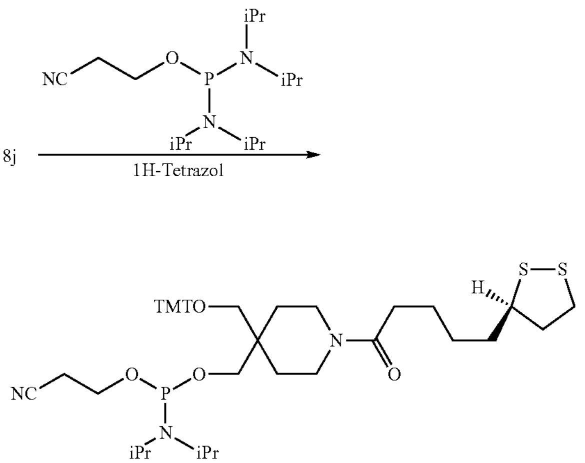

12j (1-(5-((R)-1,2-dithiolan-3-yl)pentanoyl)-4-((tris(4-methoxyphenyl)methoxy)methyl) piperidin-4-yl) methyl (2-cyanoethyl) diisopropylphosphoramidite 12j Compound 8j (1.332 g, 2.0 mmol) and 2-cyanoethyl N,N,N',N'-tetraisopropylphosphorodiamidite (0.784 g, 2.6 mmol) in anhydrous acetonitrile (25 mL) were shaken with flame-dried molecular sieves 4 Å (1.5 g) for 1 h. This was cooled to −10° C., and 1H-tetrazole (0.45M, 1.0 mmol, 2.22 mL) in acetonitrile was added, and the mixture was stirred overnight. The reaction mixture was quenched with triethylamine (0.5 mL) and diluted with saturated aqueous sodium bicarbonate. The mixture was extracted with DCM, and the organic extract was dried over $Na_2SO_4$ and evaporated to dryness. The crude product was purified on a silica gel column (5% $Et_3N$, 20-80% ethyl acetate in hexanes) to yield 12j (1.270 g, 73.3%) as a white solid foam.

8k

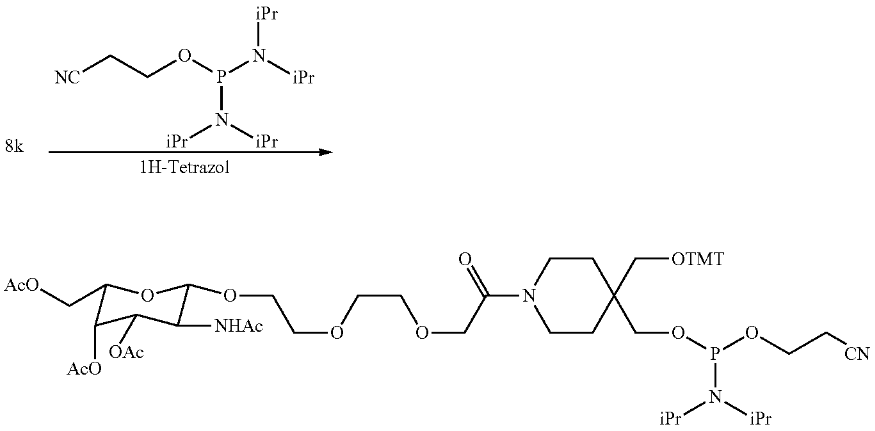

12k

Example 33

(N-(8-((3,4,6-O-triacetyl-2-acetylamino-2-deoxy-j-D-galactopyranosyl)oxy)-3,6-dioxaoctanoyl)-4-(((4,4',4"-trimethoxytrityl)oxy)methyl)piperidin-4-yl) methyl (2-cyanoethyl) diisopropylphosphoramidite 12k Compound 8k (1.906 g, 2.0 mmol) and 2-cyanoethyl N,N,N',N'-tetraisopropylphosphorodiamidite (0.784 g, 2.6 mmol) in anhydrous acetonitrile (25 mL) were shaken with flame-dried molecular sieves 4 Å (1.5 g) for 1 h. This was cooled to −10° C., and 1H-tetrazole (0.45M, 1.0 mmol, 2.22 mL) in acetonitrile was added, and the mixture was stirred overnight. The reaction mixture was quenched with triethylamine (0.5 mL) and diluted with saturated aqueous sodium bicarbonate. The mixture was extracted with DCM, and the organic extract was dried over $Na_2SO_4$ and evaporated to dryness. The crude product was purified on a silica gel column (5% $Et_3N$, 20-80% ethyl acetate in hexanes) to yield 12k (1.541 g, 66.8%) as a white solid foam.

Example 34

7b

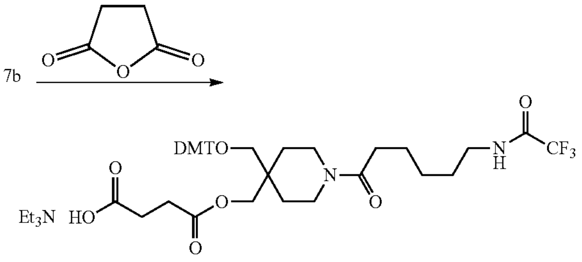

15b

Triethylammonium 4-((4-((bis(4-methoxyphenyl)(phenyl)methoxy)methyl)-1-(6-(2,2,2-trifluoroacetamido)-hexanoyl)piperidin-4-yl)methoxy)-4-oxobutanoate 15b Compound 7b (0.073 g, 0.111 mmol), succinic anhydride (0.434 g, 4.34 mmol) and pyridine (2.0 mL) were stirred at room temperature for 5 days. The reaction mixture was quenched with water and triethylamine (0.4 mL) for 4 h, evaporated to oil, diluted with DCM (100 mL), and washed with 10% aqueous citric acid. Organic phase was basified with triethylamine (0.2 mL), dried over $Na_2SO_4$, and evaporated. The residue was separated on a silica gel column (1% $Et_3N$, 0-5% MeOH, DCM) to yield 15b (0.151 g, 56.7%).

Example 35

8b

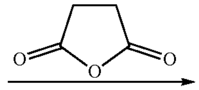

-continued

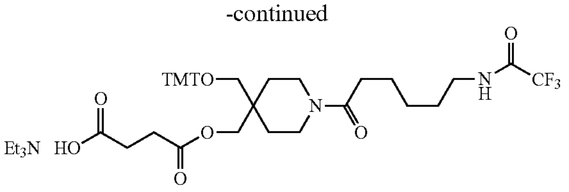

16b

Triethylammonium 4-((4-((tris(4-methoxyphenyl)methoxy)methyl)-1-(6-(2,2,2-trifluoroacetamido)-hexanoyl)piperidin-4-yl)methoxy)-4-oxobutanoate 16b Compound 8b (1.373 g, 2.0 mmol), succinic anhydride (0.600 g, 6.0 mmol) and pyridine (2.0 mL) were stirred at room temperature for 5 days. The reaction mixture was quenched with water and triethylamine (0.4 mL) for 4 h, evaporated to oil, diluted with DCM (100 mL), and washed with 10% aqueous citric acid. Organic phase was basified with triethylamine (0.2 mL), dried over $Na_2SO_4$, and evaporated. The residue was separated on a silica gel column (1% $Et_3N$, 0-5% MeOH, DCM) to yield 16b (1.575 g, 88.7%).

Example 36

8b

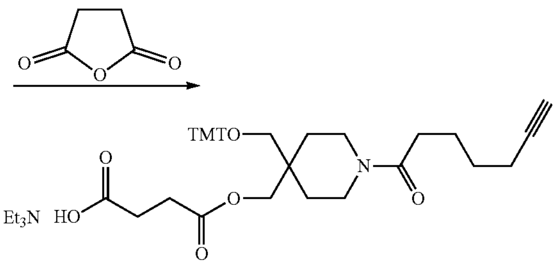

16b

Triethylammonium 4-((1-(hept-6-ynoyl)-4-((tris(4-methoxyphenyl)methoxy) methyl)piperidin-4-yl)methoxy)-4-oxobutanoate 16d Compound 8d (1.171 g, 2.0 mmol), succinic anhydride (0.600 g, 6.0 mmol) and pyridine (2.0 mL) were stirred at room temperature for 5 days. The reaction mixture was quenched with water and triethylamine (0.4 mL) for 4 h, evaporated to oil, diluted with DCM (100 mL), and washed with 10% aqueous citric acid. Organic phase was basified with triethylamine (0.2 mL), dried over $Na_2SO_4$, and evaporated. The residue was separated on a silica gel column (1% $Et_3N$, 0-5% MeOH, DCM) to yield 16d (1.433 g, 91.1%).

Example 37

8e

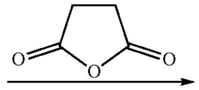

-continued

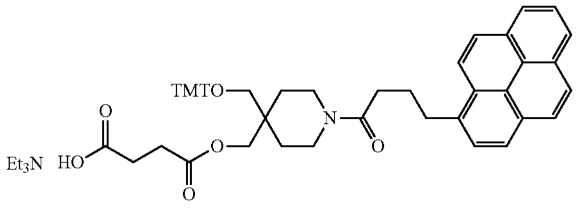

16e

Triethylammonium 4-oxo-4-((1-(4-(pyren-1-yl)butanoyl)-4-((tris(4-methoxyphenyl)methoxy)methyl) piperidin-4-yl)methoxy)butanoate 16e Compound 8e (1.496 g, 2.0 mmol), succinic anhydride (0.600 g, 6.0 mmol) and pyridine (2.0 mL) were stirred at room temperature for 5 days. The reaction mixture was quenched with water and triethylamine (0.4 mL) for 4 h, evaporated to oil, diluted with DCM (100 mL), and washed with 10% aqueous citric acid. Organic phase was basified with triethylamine (0.2 mL), dried over $Na_2SO_4$, and evaporated. The residue was separated on a silica gel column (1% $Et_3N$, 0-5% MeOH, DCM) to yield 16e (1.572 g, 82.8%).

Example 38

8f

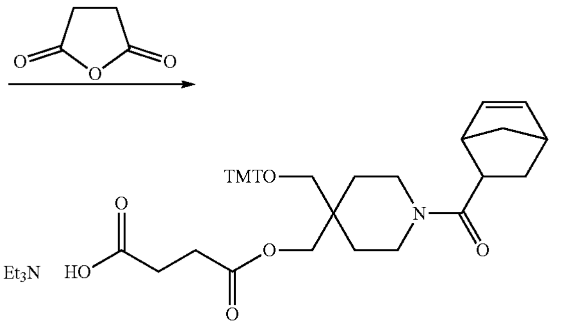

16f

Triethylammonium 4-((1-(bicyclo[2.2.1]hept-5-ene-2-carbonyl)-4-((tris(4-methoxyphenyl)methoxy) methyl)piperidin-4-yl)methoxy)-4-oxobutanoate 16f Compound 8f (1.195 g, 2.0 mmol), succinic anhydride (0.600 g, 6.0 mmol) and pyridine (2.0 mL) were stirred at room temperature for 5 days. The reaction mixture was quenched with water and triethylamine (0.4 mL) for 4 h, evaporated to oil, diluted with DCM (100 mL), and washed with 10% aqueous citric acid. Organic phase was basified with triethylamine (0.2 mL), dried over $Na_2SO_4$, and evaporated. The residue was separated on a silica gel column (1% $Et_3N$, 0-5% MeOH, DCM) to yield 16f (1.346 g, 84.2%).

Example 39

8g

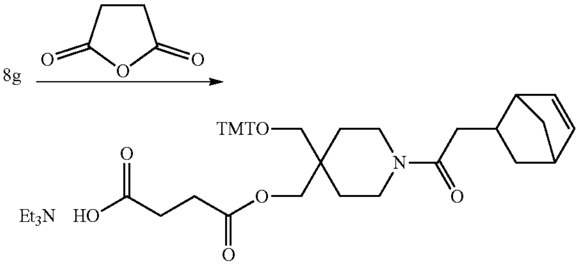

16g

Triethylammonium 4-((1-(2-(bicyclo[2.2.1]hept-5-en-2-yl)acetyl)-4-((tris(4-methoxyphenyl)methoxy) methyl)piperidin-4-yl)methoxy)-4-oxobutanoate 16 g Compound 8g (1.224 g, 1.5 mmol), succinic anhydride (0.450 g, 4.5 mmol) and pyridine (2.0 mL) were stirred at room temperature for 5 days. The reaction mixture was quenched with water and triethylamine (0.4 mL) for 4 h, evaporated to oil, diluted with DCM (100 mL), and washed with 10% aqueous citric acid. Organic phase was basified with triethylamine (0.2 mL), dried over $Na_2SO_4$, and evaporated. The residue was separated on a silica gel column (1% $Et_3N$, 0-5% MeOH, DCM) to yield 16 g (1.357 g, 83.5%).

Example 40

8i

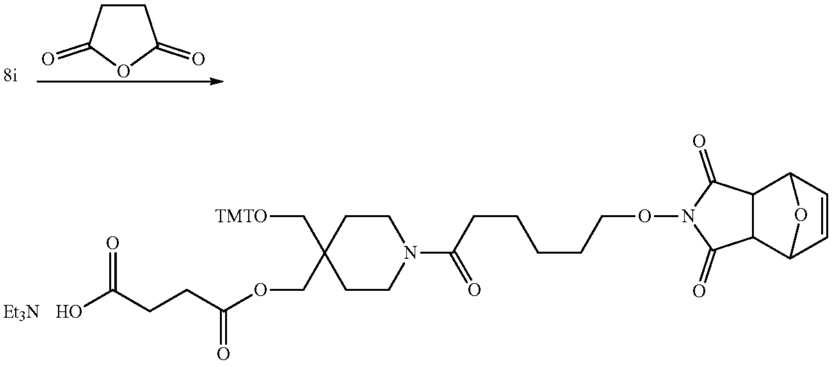

Triethylammonium 4-((1-(6-((1,3-dioxo-1,3,3a,4,7,7a-hexahydro-2H-4,7-epoxyisoindol-2-yl)oxy)hexanoyl)-4-((tris(4-methoxyphenyl)methoxy)methyl)piperidin-4-yl)methoxy)-4-oxobutanoate 16i Compound 8i (1.661 g, 1.5 mmol), succinic anhydride (0.660 g, 6.6 mmol) and pyridine (2.0 mL) were stirred at room temperature for 5 days. The reaction mixture was quenched with water and triethylamine (0.4 mL) for 4 h, evaporated to oil, diluted with DCM (100 mL), and washed with 10% aqueous citric acid. Organic phase was basified with triethylamine (0.2 mL), dried over $Na_2SO_4$, and evaporated. The residue was separated on a silica gel column (1% $Et_3N$, 0-5% MeOH, DCM) to yield 16i (1.487 g, 70.7%).

Example 41

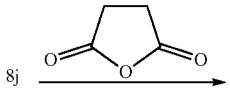

-continued

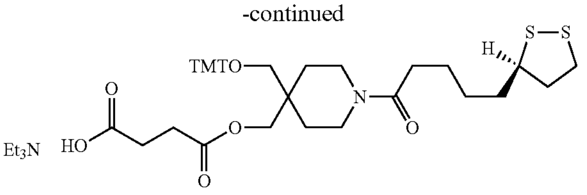

16j

Triethylammonium (R)-4-((1-(5-(1,2-dithiolan-3-yl)pentanoyl)-4-((tris(4-methoxyphenyl)methoxy)methyl)piperidin-4-yl)methoxy)-4-oxobutanoate 16j Compound 8j (1.099 g, 1.65 mmol), succinic anhydride (0.495 g, 4.95 mmol) and pyridine (2.0 mL) were stirred at room temperature for 5 days. The reaction mixture was quenched with water and triethylamine (0.4 mL) for 4 h, evaporated to oil, diluted with DCM (100 mL), and washed with 10% aqueous citric acid. Organic phase was basified with triethylamine (0.2 mL), dried over $Na_2SO_4$, and evaporated. The residue was separated on a silica gel column (1% $Et_3N$, 0-5% MeOH, DCM) to yield 16j (1.057 g, 73.9%).

Example 42

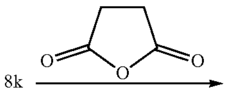

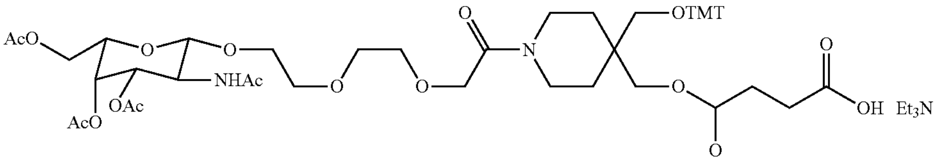

16k

Triethylammonium (N-(8-((3,4,6-O-triacetyl-2-acetylamino-2-deoxy-β-D-galactopyranosyl)oxy)-3,6-dioxaoctanoyl)-4-(((4,4',4''-trimethoxytrityl)oxy)methyl)piperidin-4-yl)methoxy)-4-oxobutanoate 16k Compound 8k (2.954 g, 3.1 mmol), succinic anhydride (0.931 g, 9.3 mmol) and pyridine (2.0 mL) were stirred at room temperature for 5 days. The reaction mixture was quenched with water and triethylamine (0.4 mL) for 4 h, evaporated to oil, diluted with DCM (100 mL), and washed with 10% aqueous citric acid. Organic phase was basified with triethylamine (0.2 mL), dried over $Na_2SO_4$, and evaporated. The residue was separated on a silica gel column (1% $Et_3N$, 0-5% MeOH, DCM) to yield 16k (3.02 g, 84.4%).

Example 43

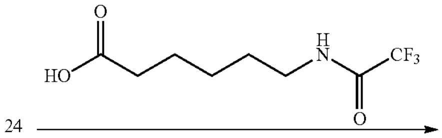

-continued

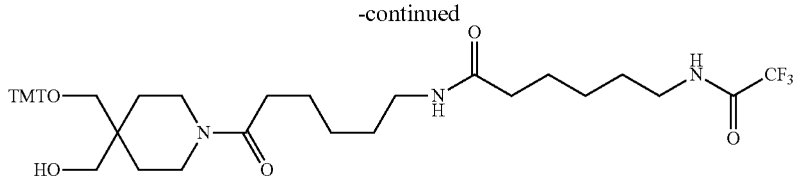

28a

N-(6-(4-(hydroxymethyl)-4-((tris(4-methoxyphenyl) methoxy)methyl)piperidin-1-yl)-6-oxohexyl)-6-(2,2,2-trifluoroacetamido)hexanamide 28a 6-(trifluoroacetamido)hexanoic acid (Chemimpex, 0.631 g, 5.25 mmol), HOBt (0.804 g, 5.25 mmol) and EDC-HCl (1.006 g, 5.25 mmol) were dissolved in DCM (25 mL) and stirred at room temperature for 30 min. At 0° C. amine 24 (2.45 g, 4.37 mmol) and DIPEA (1.358 g, 10.5 mmol) were added. The reaction mixture was stirred 18 h at room temperature, washed with 5% $NaHCO_3$, 5% HCl, brine, dried over $Na_2SO_4$, concentrated and purified on a silica gel column (1-5% MeOH, DCM) to give 2.604 g (74.5%) compound 28a as a white solid foam.

Example 44

23

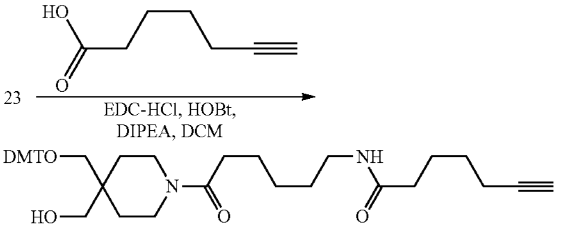

27b

N-(6-(4-((bis(4-methoxyphenyl)(phenyl)methoxy) methyl)-4-(hydroxymethyl)piperidin-1-yl)-6-oxo-hexyl)hept-6-ynamide 27b Hept-6-ynoic acid (TCI America, 0.529 g, 4.20 mmol), HOBt (0.643 g, 4.20 mmol) and EDC-HCl (0.805 g, 4.20 mmol) were dissolved in DCM (20 mL) and stirred at room temperature for 30 min. At 0° C. amine 23 (1.960 g, 3.50 mmol) and DIPEA (1.086 g, 8.4 mmol) were added. The reaction mixture was stirred 18 h at room temperature, washed with 5% $NaHCO_3$, 5% HCl, brine, dried over $Na_2SO_4$, concentrated and purified on a silica gel column (1-5% MeOH, DCM) to give 2.123 g (90.7%) compound 27b as a white dry foam.

Example 45

24

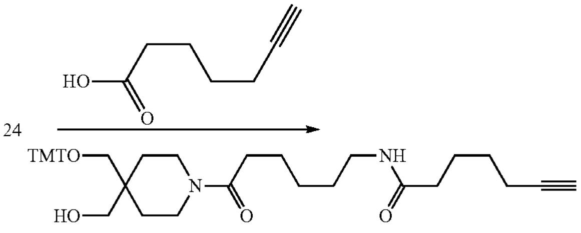

28b

N-(6-(4-((tris(4-methoxyphenyl)methoxy)methyl)-4-(hydroxymethyl)piperidin-1-yl)-6-oxohexyl)hept-6-ynamide 28b Hept-6-ynoic acid (TCI America, 0.303 g, 2.4 mmol), HOBt (0.367 g, 2.40 mmol) and EDC-HCl ((0.46 g, 2.4 mmol) were dissolved in DCM (20 mL) and stirred at room temperature for 30 min. At 0° C. amine 24 (1.960 g, 2.0 mmol) and DIPEA (0.620 g, 4.8 mmol) were added. The reaction mixture was stirred 18 h at room temperature, washed with 5% $NaHCO_3$, 5% HCl, brine, dried over $Na_2SO_4$, concentrated and purified on a silica gel column (1-5% MeOH, DCM) to give 1.320 g (94.4%) compound 28b as a white dry foam.

Example 18

23 +

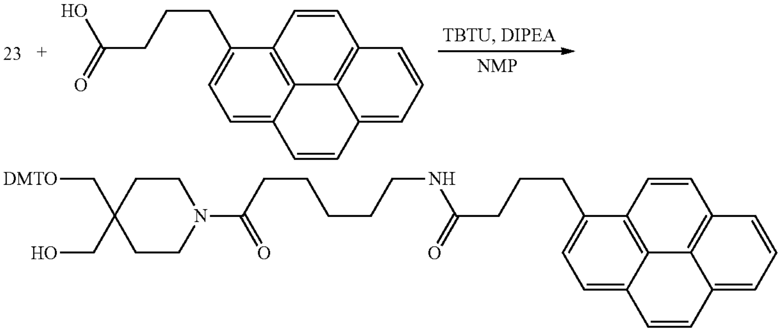

27c

N-(6-(4-((bis(4-methoxyphenyl)(phenyl)methoxy)methyl)-4-(hydroxymethyl)piperidin-1-yl)-6-oxohexyl)-4-(pyren-1-yl)butanamide 27c Solution of 4-(pyren-1-yl)butanoic acid (0.993 g, 3.44 mmol), TBTU (1.16 g, 3.61 mmol), and DIPEA (1.5 mL, 8.6 mmol) dissolved in NMP (13 g) was stirred for 15 min and added to compound 23 (1.93 g, 3.44 mmol) in NMP (9 g) at 0° C. followed by stirring at this temperature for 1 h. The reaction mixture was diluted with ethyl acetate (200 mL), washed with concentrated $NaHCO_3$ and brine (8 times). The organic phase was dried over $Na_2SO_4$ and evaporated. The product was isolated on a silica gel column (50% hexanes in DCM to 5% MeOH, DCM) to give compound 27c (2.517 g, 88.1%).

NMR $H^1$ (δ, DMSO-$d_6$): 8.36 (d, J=9.5 Hz, 1H), 8.23-8.27 (m, 2H), 8.19-8.23 (m, 2H), 8.08-8.13 (m, 2H), 8.03 (t, J=8.0 Hz, 1H), 7.92 (d, J=8.0 Hz, 1H), 7.79 (t, J=5.5 Hz, 1H, NH), 7.35-7.33 (m, 2H), 7.27-7.31 (m, 2H), 7.18-7.26 (m, 5H), 6.84-6.88 (m, 4H), 4.54 (t, J=5.0 Hz, 1H, OH), 3.71 (s, 6H), 3.43 (d, J=5.0 Hz, 2H), 3.20-3.36 (m, 2H), 3.04 (q, J=7.0 Hz, 2H), 2.84-3.0 (m, 2H), 2.90 (s, 2H), 2.20 (t, J=7.0, 2H), 2.17 (t, J=7.5 Hz, 2H), 1.97-2.03 (m, 2H), 1.20-1.45 (m, 10H).

NMR $C^{13}$ (δ, DMSO-$d_6$): 171.6, 170.1, 157.9 (2C), 145.2, 136.5, 135.9 (2C), 130.8, 130.4, 129.7, 129.2, 128.1, 127.7, 127.6, 127.4, 127.4, 127.1, 126.6, 126.4, 126.0, 124.9, 124.7, 124.2, 124.1, 123.4, 113.0, 84.9, 64.2, 64.0, 55.0, 40.0, 39.0, 37.6, 35.0, 32.2, 29.0, 28.5, 27.5, 26.1, 24.5.

Example 46

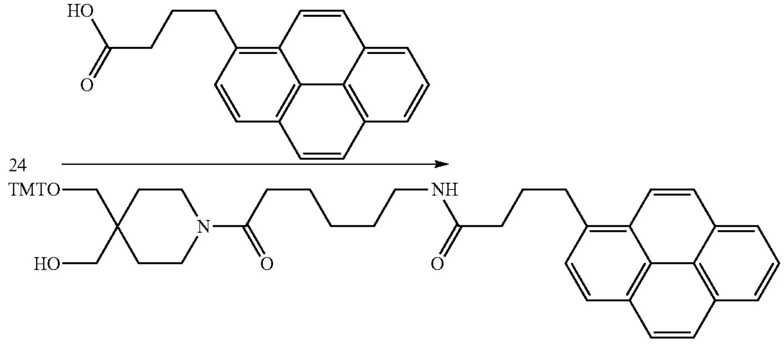

28c

N-(6-(4-(hydroxymethyl)-4-((tris(4-methoxyphenyl)methoxy)methyl)piperidin-1-yl)-6-oxohexyl)-4-(pyren-1-yl)butanamide 28c 4-(pyren-1-yl)butanoic acid (TCI America, 0.623 g, 2.16 mmol), HOBt (0.331 g, 2.16 mmol) and EDC-HCl (0.414 g, 2.16 mmol) were dissolved in DMF (20 mL) and stirred at room temperature for 30 min. At 0° C. amine 24 (1.063 g, 1.80 mmol) and DIPEA (0.558 g, 4.32 mmol) were added. The reaction mixture was stirred 18 h at room temperature, diluted with ethyl acetate (200 mL), washed with 5% $NaHCO_3$, 5% HCl, brine, dried over $Na_2SO_4$, concentrated and purified on a silica gel column (1-5% MeOH, DCM) to give 1.341 g (86.5%) compound 28c as a white dry foam.

Example 47

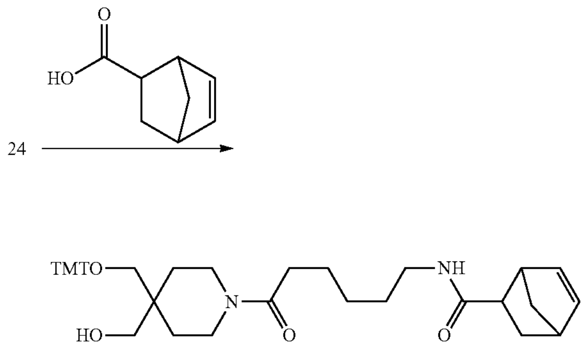

28d

N-(6-(4-(hydroxymethyl)-4-((tris(4-methoxyphenyl)methoxy)methyl)piperidin-1-yl)-6-oxohexyl)bicyclo[2.2.1]hept-5-ene-2-carboxamide 28d bicyclo[2.2.1]hept-5-ene-2-carboxylic acid (TCI America, 0.398 g, 2.88 mmol), HOBt (0.441 g, 2.88 mmol) and EDC-HCl (0.552 g, 2.88 mmol) were dissolved in DCM (20 mL) and stirred at room temperature for 30 min. At 0° C. amine 24 (1.418 g, 2.4 mmol) and DIPEA (0.744 g, 5.76 mmol) were added. The reaction mixture was stirred 18 h at room temperature, washed with 5% $NaHCO_3$, 5% HCl, brine, dried over $Na_2SO_4$, concentrated and purified on a silica gel column (1-5% MeOH, DCM) to give 1.341 g (86.5%) compound 28d as a white dry foam.

Example 48

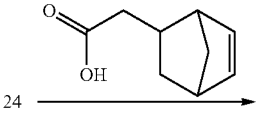

-continued

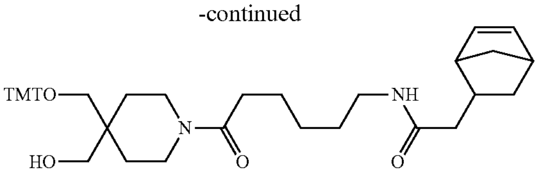

28e 2-(bicyclo[2.2.1]hept-5-en-2-yl)-N-(6-(4-(hydroxymethyl)-4-((tris(4-methoxyphenyl)methoxy)methyl)piperidin-1-yl)-6-oxohexyl)acetamide 28e 2-(bicyclo[2.2.1]hept-5-en-2-yl)acetic acid (TCI America, 0.365 g, 2.4 mmol), HOBt (0.368 g, 2.4 mmol) and EDC-HCl (0.460 g, 2.4 mmol) were dissolved in DCM (20 mL) and stirred at room temperature for 30 min. At 0° C. amine 24 (1.182 g, 2.0 mmol) and DIPEA (0.620 g, 4.8 mmol) were added. The reaction mixture was stirred 18 h at room temperature, washed with 5% $NaHCO_3$, 5% HCl, brine, dried over $Na_2SO_4$, concentrated and purified on a silica gel column (1-5% MeOH, DCM) to give 1.569 g (90.2%) compound 28e as a white dry foam.

Example 49

24

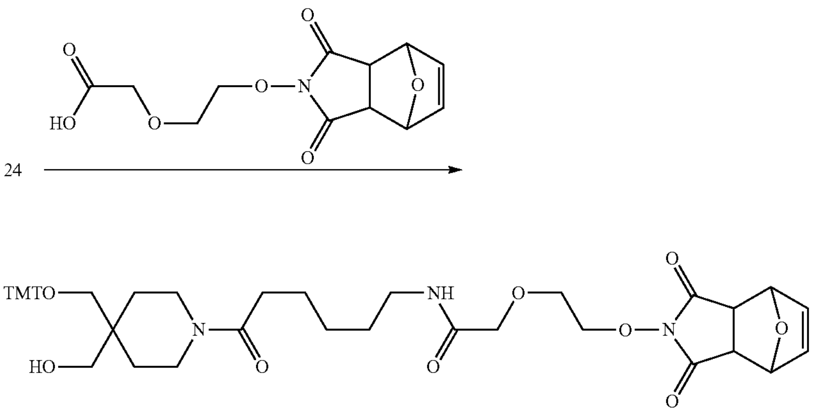

28f 2-(2-((1,3-dioxo-1,3,3a,4,7,7a-hexahydro-2H-4,7-epoxyisoindol-2-yl)-N-(6-(4-(hydroxymethyl)-4-((tris(4-methoxyphenyl)methoxy)methyl)piperidin-1-yl)-6-oxohexyl)acetamide 28f 2-(2-((1,3-dioxo-1,3,3a,4,7,7a-hexahydro-2H-4,7-epoxyisoindol-2-yl)oxy)ethoxy)acetic acid (0.816 g, 2.88 mmol), HOBt (0.441 g, 2.88 mmol) and EDC-HCl (0.552 g, 2.88 mmol) were dissolved in DCM (20 mL) and stirred at room temperature for 30 min. At 0° C. amine 24 (1.417 g, 2.4 mmol) and DIPEA (0.744 g, 5.76 mmol) were added. The reaction mixture was stirred 18 h at room temperature, washed with 5% $NaHCO_3$, 5% HCl, brine, dried over $Na_2SO_4$, concentrated and purified on a silica gel column (1-5% MeOH, DCM) to give compound 28f (1.689 g, 82.2%) as a white dry foam.

Example 50

24

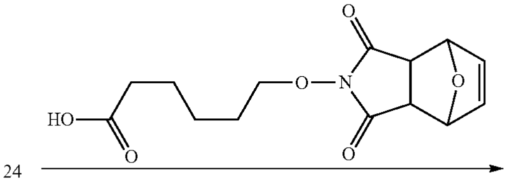

-continued

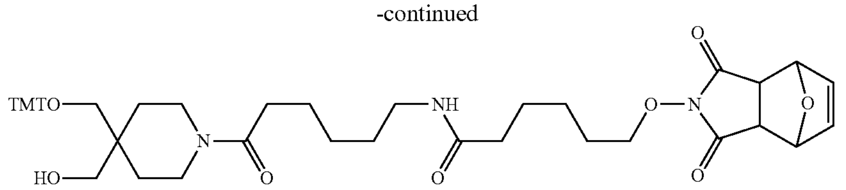

28g 6-((1,3-dioxo-1,3,3a,4,7,7a-hexahydro-2H-4,7-epoxyisoindol-2-yl)oxy)-N-(6-(4-(hydroxymethyl)-4-((tris(4-methoxyphenyl)methoxy)methyl)piperidin-1-yl)-6-oxohexyl)hexanamide 28 g 6-((1,3-dioxo-1,3,3a,4,7,7a-hexahydro-2H-4,7-epoxyisoindol-2-yl)oxy)hexanoic acid (0.709 g, 2.4 mmol), HOBt (0.367 g, 2.4 mmol) and EDC-HCl (0.460 g, 2.4 mmol) were dissolved in DCM (20 mL) and stirred at room temperature for 30 min. At 0° C. amine 24 (1.181 g, 2.0 mmol) and DIPEA (0.620 g, 4.8 mmol) were added. The reaction mixture was stirred 18 h at room temperature, washed with 5% $NaHCO_3$, 5% HCl, brine, dried over $Na_2SO_4$, concentrated and purified on a silica gel column (1-5% MeOH, DCM) to give compound 28g (1.453 g, 83.7%) as a white dry foam.

Example 51

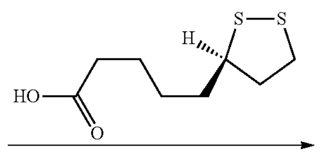

24

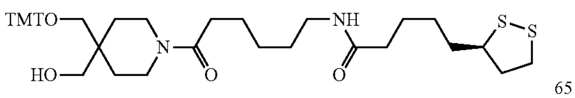

28h (R)-5-(1,2-dithiolan-3-yl)-N-(6-(4-(hydroxymethyl)-4-((tris(4-methoxyphenyl)methoxy)methyl)piperidin-1-yl)-6-oxohexyl)pentanamide 28h Lipoic acid (0.470 g, 2.28 mmol), HOBt (0.349 g, 2.28 mmol) and EDC-HCl (0.437 g, 2.28 mmol) were dissolved in DMF (20 mL) and stirred at room temperature for 30 min. At 0° C. amine 24 (1.122 g, 1.9 mmol) and DIPEA (0.589 g, 4.56 mmol) were added. The reaction mixture was stirred 18 h at room temperature, washed with 5% $NaHCO_3$, 5% HCl, brine, dried over $Na_2SO_4$, concentrated and purified on a silica gel column (1-5% MeOH, DCM) to give compound 28h (0.922 g, 62.3%) as a white dry foam.

Example 52

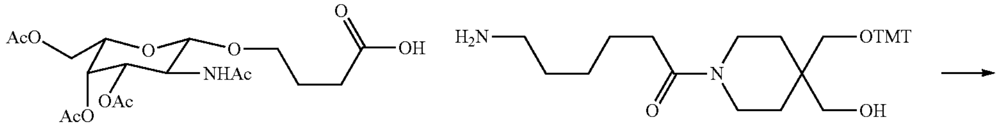

23

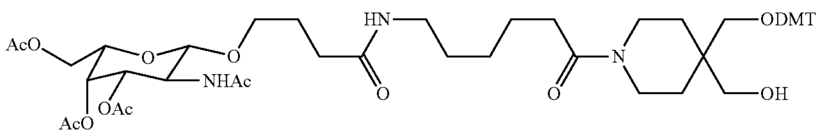

27i

4-Hydroxymethyl-4-(((4,4'-dimethoxytrityl)oxy)methyl)-N-(5-((3,4,6-O-triacetyl-2-acetylamino-2-deoxy-β-D-galactopyranosyl)oxy)pentenoyl)piperidine 27i 1-O-(4-carboxybut-1yl)-3,4,6-O-triacetyl-2-acetylamino-2-deoxy-β-D-galactopyranoside (0.447 g, 1.0 mmol), HOBt (0.184 g, 1.2 mmol) and EDC-HCl (0.230 g, 1.2 mmol) were dissolved in DCM (3 mL) and stirred at room temperature for 30 min. This mixture was added to the solution of amine 23 (0.561 g, 1.0 mmol) and DIPEA (0.310 g, 2.4 mmol) in 10 ml of DCM at 0° C. The reaction mixture was stirred 18 h at room temperature and was diluted with DCM (50 mL). The obtained solution was washed with 5% $NaHCO_3$, 5% HCl, and brine. The organic phase was dried over $Na_2SO_4$ and concentrated. The residue was separated on a silica gel column (1-5% MeOH in DCM) to give compound 27i (0.856 g, 86.5%) as a white solid foam.

Example 53

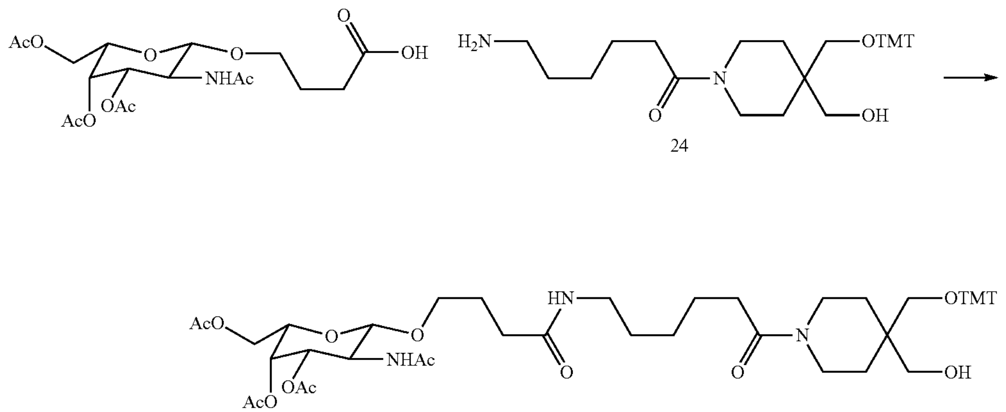
24

28i

4-Hydroxymethyl-4-(((4,4',4"-trimethoxytrityl)oxy) methyl)-N-(5-((3,4,6-O-triacetyl-2-acetylamino-2-deoxy-β-D-galactopyranosyl)oxy)butanoyl)piperidine 28i 1-O-(4-carboxybut-1yl)-3,4,6-O-triacetyl-2-acetylamino-2-deoxy-β-D-galactopyranoside (10.57 g, 19.79 mmol), HOBt (3.21 g, 23.75 mmol), 4-dimethylaminopyridine (DMAP, 0.09 g), and EDC-HCl (4.55 g, 23.75 mmol) were dissolved in DCM (120 mL) and stirred at room temperature for 30 min. The amine 24 (11.69 g, 19.79 mmol) was added at 0° C., and the mixture was stirred at room temperature for 18 h. The resulting solution was washed with saturated aqueous sodium bicarbonate and brine. The organic phase was dried over sodium sulfate, filtered, and evaporated. The crude product was purified on a silica gel column using a step gradient of MeOH (3 to 8%) in DCM to give compound 28i (18.93 g, 95.1%) as a white solid foam.

NMR $H^1$ (δ, $CDCl_3$): 7.26-7.30 (m, 6H), 6.80-6.84 (m, 6H), 6.45 (br. t, J=9.0 Hz, 1H), 6.20 (br. t, J=5.5 Hz, 1H), 5.33 (d, J=3.0 Hz, 1H), 5.16 (dd, J=11.0, 3.0 Hz, 1H), 4.61 (dd, J=8.0, 4.0 Hz, 1H), 4.00-4.20 (m, 3H), 3.85-3.93 (m, 2H), 3.78 (s, 9H), 3.57-3.63 (m, 2H), 3.45-3.55 (m, 2H), 3.30-3.40 (br. m, 2H), 3.15-3.30 (m, 3H), 3.05-3.15 (m, 2H), 2.45-2.53 (m, 1H), 2.15-2.30 (m, 4H), 2.13 (s, 3H), 2.03 (s, 3H), 1.98 (s, 3H), 1.94 (s, 3H), 1.85-1.91 (m, 2H), 1.55-1.64 (m, 3H), 1.40-1.55 (m, 5H), 1.33-1.40 (m, 2H).

NMR $C^{13}$ (δ, $CDCl_3$): 173.1, 171.5, 170.9, 170.7, 170.5, 170.5, 158.7, 136.3, 129.9, 113.4, 101.6, 86.3, 70.8, 70.6, 68.7, 67.8, 67.4, 66.9, 61.7, 55.4, 51.4, 41.8, 39.3, 37.9, 37.8, 33.2, 32.9, 30.2, 29.3, 26.8, 25.9, 24.9, 24.8, 23.6, 21.6, 20.9, 20.9.

Example 54

23 +

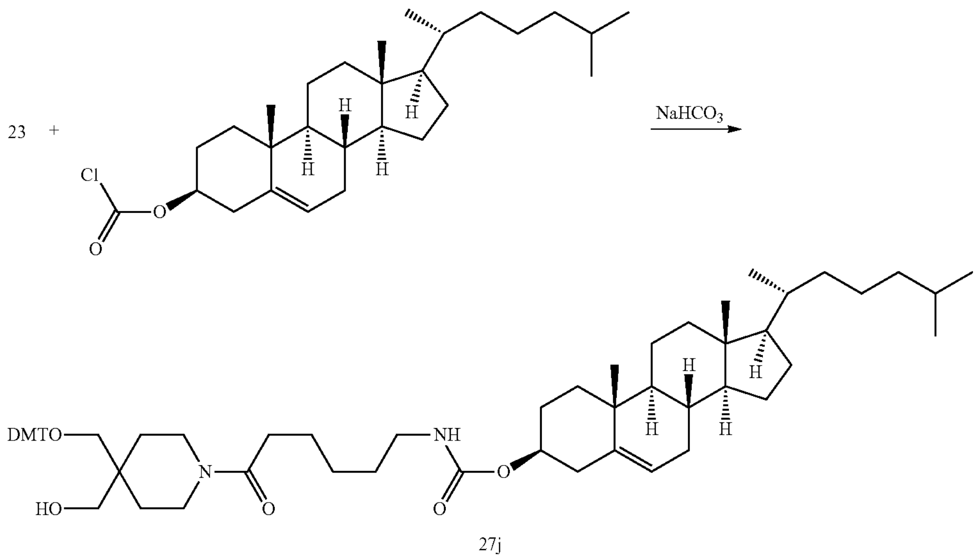

27j

Cholest-5-en-3-yl {6-[4-{[bis(4-methoxyphenyl)(phenyl)methoxy]methyl}-4-(hydroxymethyl)piperidin-1-yl]-6-oxohexyl}carbamate 27j Compound 23 (1.556 g, 2.77 mmol) and sodium bicarbonate (1.11 g, 13.25 mmol) were dissolved in THF (25 ml) and water (12.5 mL) at −5° C., then cholesteryl chloroformate (1.191 g, 2.65 mmol) was added and mixture was stirred at room temperature for 18 h. The reaction mixture was diluted with ethyl acetate and washed with water and brine. The organic phase was dried over $Na_2SO_4$ and evaporated. The residue was purified on a silica gel column (50% hexanes/DCM→5% MeOH/DCM) to give compound 27j (2.11 g, 81.8%).

NMR $H^1$ (δ, DMSO-$d_6$): 7.37-7.39 (m, 2H), 7.27-7.31 (m, 2H), 7.27-7.31 (m, 4H), 7.19-7-25 (m, 1H), 7.00 (t, J=5.5 Hz, 1H, NH), 6.86-6.89 (m, 4H), 5.32 (m, 1H), 4.55 (br. S, 1H, OH), 4.25-4.33 (m, 1H), 3.73 (s, 6H), 3.46 (br.s, 2H), 3.26-3.40 (m, 2H), 2.95-3.03 (br. m, 2H), 2.93 (s, 2H), 2.88-2.93 (m, 2H), 2.14-2.30 (m, 2H), 2.19 (t, J=7.5 Hz, 2H), 1.72-2.00 (m, 5H), 1.45-1.56 (m, 6H), 1.25-1.45 (m, 15H), 1.16-1.25 (m, 6H), 0.85-1.16 (m, 6H), 0.96 (s, 3H), 0.89 (d, J=6.5 Hz, 3H), 0.85 (d, J=7.0 Hz, 3H), 0.84 (d, J=7.0 Hz, 3H), 0.65 (s, 3H).

NMR $C^{13}$ (δ, DMSO-$d_6$): 170.2, 157.9, 145.2, 135.9, 129.7, 127.7, 127.7, 121.7, 113.0, 84.9, 72.7, 64.3, 64.2, 56.1, 55.5, 55.0, 49.4, 41.8, 40.1, 39.8, 39.0, 38.9, 37.9, 37.6, 36.8, 36.5, 36.0, 35.6, 35.1, 32.3, 31.4, 31.3, 29.1, 29.2, 28.3, 27.8, 27.7, 27.3, 25.9, 24.5, 23.8, 23.1, 22.6, 22.3, 20.5, 18.9, 18.5, 11.6.

Example 55

24

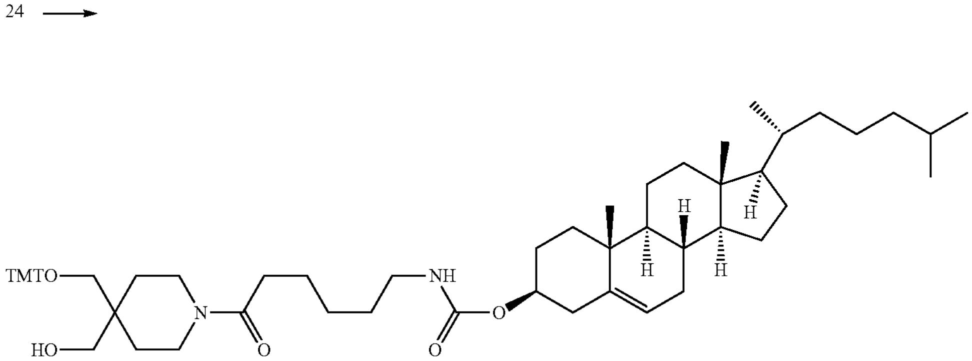

28j

Cholest-5-en-3-yl {6-[4-{[tris(4-methoxyphenyl)methoxy]methyl}-4-(hydroxymethyl)piperidin-1-yl]-6-oxohexyl}carbamate 28j Compound 24 (1.556 g, 3.1 mmol) and sodium bicarbonate (1.11 g, 13.25 mmol) were dissolved in THF (25 ml) and water (12.5 mL) at −5° C., then cholesteryl chloroformate (1.392 g, 3.1 mmol) was added and mixture was stirred at room temperature for 18 h. The reaction mixture was diluted with ethyl acetate and washed with water and brine. The organic phase was dried over $Na_2SO_4$ and evaporated. The residue was purified on a silica gel column (50% hexanes/DCM→5% MeOH/DCM) to give compound 28j (2.417 g, 77.7%).

Example 56

23 +

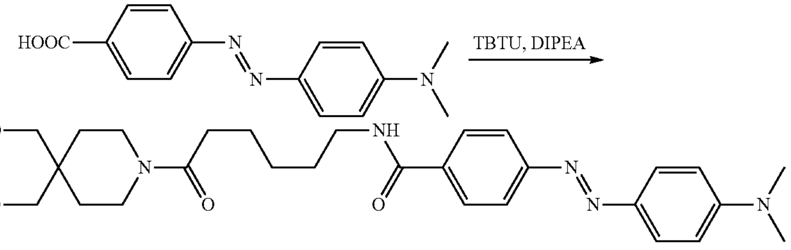

27k (E)-N-(6-(4-((bis(4-methoxyphenyl)(phenyl)methoxy)methyl)-4-(hydroxymethyl)piperidin-1-yl)-6-oxohexyl)-4-((4-(dimethylamino)phenyl)diazenyl)benzamide 27k 4-Dimethylaminoazobenzene-4'-carboxylic acid (TCI America, 0.849 g, 3.15 mmol), TBTU (1.065 g, 3.31 mmol), and DIPEA (1.31 mL, 7.87 mmol), were dissolved in NMP (10 mL) and stirred for 15 min. The obtained solution was added to compound 23 (1.683 g, 3.00 mmol) in NMP (5 g) at 0° C. The mixture was stirred at for 1 h this temperature plus for additional 18 h at room temperature. The reaction mixture was diluted with ethyl acetate (200 mL), washed with conc. aqueous $NaHCO_3$ and brine (8×50 mL). The organic phase was dried over $Na_2SO_4$ and evaporated to dryness. The crude product was purified on a silica gel column (50% hexanes in DCM to 5% MeOH, DCM) to give compound 27k (1.88 g, 88.1%) as an orange solid foam.

Example 57

24

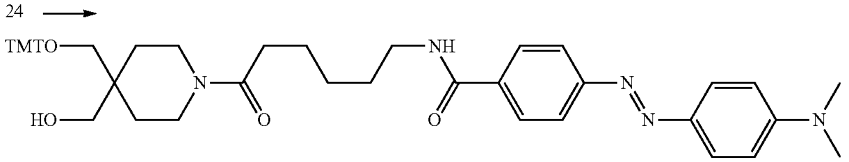

28k (E)-N-(6-(4-((tris(4-methoxyphenyl)methoxy)methyl)-4-(hydroxymethyl)piperidin-1-yl)-6-oxohexyl)-4-((4-(dimethylamino)phenyl)diazenyl)benzamide 28k 4-Dimethylaminoazobenzene-4'-carboxylic acid (TCI America, 0.849 g, 3.15 mmol), TBTU (1.065 g, 3.31 mmol), and DIPEA (1.31 mL, 7.87 mmol), were dissolved in NMP (10 mL) and stirred for 15 min. The obtained solution was added to compound 24 (1.772 g, 3.00 mmol) in NMP (5 g) at 0° C. The mixture was stirred at for 1 h this temperature plus for additional 18 h at room temperature. The reaction mixture was diluted with ethyl acetate (200 mL), washed with conc. aqueous $NaHCO_3$ and brine (8×50 mL). The organic phase was dried over $Na_2SO_4$ and evaporated to dryness. The crude product was purified on a silica gel column (50% hexanes in DCM to 5% MeOH, DCM) to give compound 28k (2.337 g, 92.5%) as an orange solid foam.

Example 58

23 +

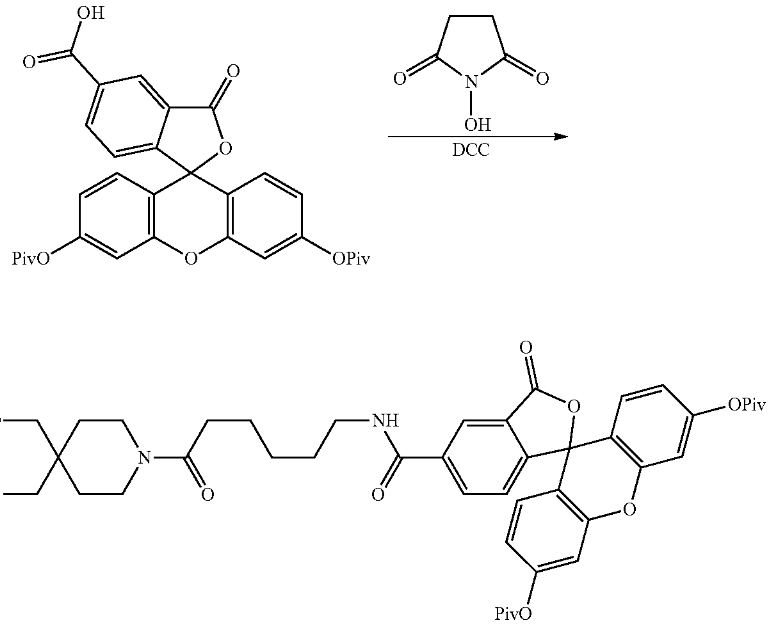

27m 6-((6-(4-((bis(4-methoxyphenyl)(phenyl)methoxy)methyl)-4-(hydroxymethyl)piperidin-1-yl)-6-oxohexyl)carbamoyl)-3-oxo-3H-spiro[isobenzofuran-1,9'-xanthene]-3',6'-diyl bis(2,2-dimethylpropanoate) 27m N,N'-Dicyclohexylcarbodiimide (DCC, 1.171 g, 5.67 mmol) was added to a solution of 6-carboxyfluorescein dipivaloate (3.00 g, 5.51 mmol) and N-hydroxysuccinimide (0.824 g, 7.16 mmol) in DCM (50 mL) at 0° C., and the mixture was stirred at room temperature for 2h. Then amine 23 (3.09 g, 5.51 mmol) was added and stirring was continued for 18 h. The solid was filtered off. The filtrate was diluted with ethyl acetate, washed with 5% NaCl acidified with citric acid to pH 4 followed by triethylammonium bicarbonate buffer (pH 7.19). The organic phase was dried over $Na_2SO_4$ and evaporated. The crude product was purified on a silica gel column (0.02% AcOH, 1-3% MeOH, DCM) to give compound 27m (5.78 g, 96.4%).

NMR $H^1$ (δ, $CD_3CN$): 8.11, 8.05 (AB, J=8.0 Hz, 2H), 7.63 (s, 1H), 7.42-7.46 (m, 2H), 7.26-7.32 (m, 6H), 7.25 (t, J=5.0 Hz, 1H, NH), 7.18-7.23 (m, 1H), 7.09-7.12 (m, 2H), 6.88-6.93 (m, 2H), 6.81-6.87 (m, 6H), 3.75 (s, 6H), 3.52 (d, J=5.0 Hz, 2H), 3.36-3.43 (m, 1H), 3.24-3.33 (m, 3H), 2.96-3.03 (m, 2H), 2.99 (s, 2H), 2.65 (t, J=5.5 Hz, 1H, OH), 2.18 (t, J=7.0 Hz), 1.45-1.52 (m, 2H), 1.37-1.42 (m, 2H), 1.30-1.35 (m, 2H), 1.32 (s, 18H), 1.25-1.30 (m, 2H).

NMR $C^{13}$ (δ, $CD_3CN$): 177.6, 171.9, 169.2, 166.2, 159.7, 154.1, 154.0, 152.6, 146.5, 143.1, 137.4, 131.2 (4C), 130.6, 130.3 (2C), 129.2 (2C), 129.0, 128.9 (2C), 127.8, 126.3, 123.6, 119.3 (2C), 117.2, 114.1 (4C), 111.5 (2C), 86.7, 82.7, 66.5, 65.8, 56.0 (2C), 42.3, 40.5, 39.9, 39.0, 38.2, 33.5, 30.6, 29.9, 29.6, 27.4 (3C), 27.3 (3C), 25.5.

Example 59

24

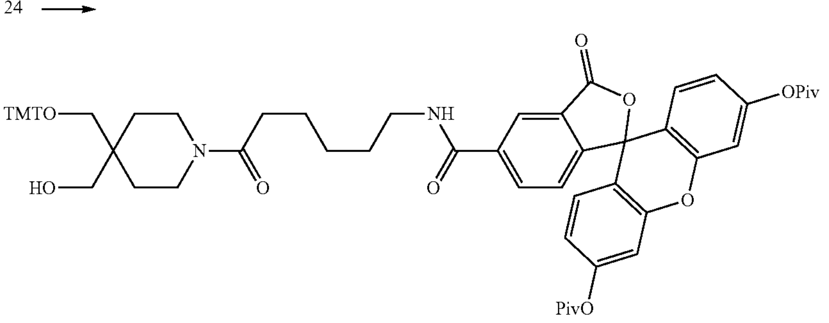

28m 6-((6-(4-((tris(4-methoxyphenyl)methoxy)methyl)-4-(hydroxymethyl)piperidin-1-yl)-6-oxohexyl)carbamoyl)-3-oxo-3H-spiro[isobenzofuran-1,9'-xanthene]-3',6'-diyl bis(2,2-dimethylpropanoate) 28m N,N'-Dicyclohexylcarbodiimide (DCC, 1.171 g, 5.67 mmol) was added to a solution of 6-carboxyfluorescein dipivaloate (3.00 g, 5.51 mmol) and N-hydroxysuccinimide (0.824 g, 7.16 mmol) in DCM (50 mL) at 0° C., and the mixture was stirred at room temperature for 2h. Then amine 24 (3.249 g, 5.5 mmol) was added and stirring was continued for 18 h. The solid was filtered off. The filtrate was diluted with ethyl acetate, washed with 5% NaCl acidified with citric acid to pH 4 followed by triethylammonium bicarbonate buffer (pH 7.19). The organic phase was dried over $Na_2SO_4$ and evaporated. The crude product was purified on a silica gel column (0.02% AcOH, 1-3% MeOH, DCM) to give compound 28m (5.764 g, 93.8%).

Example 60

24

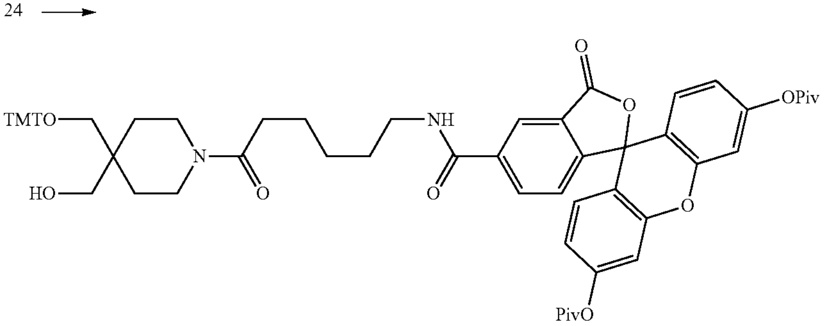

28m

5-((6-(4-((tris(4-methoxyphenyl)methoxy)methyl)-4-(hydroxymethyl)piperidin-1-yl)-6-oxohexyl)carbamoyl)-3-oxo-3H-spiro[isobenzofuran-1,9'-xanthene]-3',6'-diyl bis(2,2-dimethylpropanoate) 28m N,N'-Dicyclohexylcarbodiimide (DCC, 1.171 g, 5.67 mmol) was added to a solution of 5-carboxyfluorescein dipivaloate (3.00 g, 5.51 mmol) and N-hydroxysuccinimide (0.824 g, 7.16 mmol) in DCM (50 mL) at 0° C., and the mixture was stirred at room temperature for 2h. Then amine 24 (3.249 g, 5.5 mmol) was added and stirring was continued for 18 h. The solid was filtered off. The filtrate was diluted with ethyl acetate, washed with 5% NaCl acidified with citric acid to pH 4 followed by triethylammonium bicarbonate buffer (pH 7.19). The organic phase was dried over $Na_2SO_4$ and evaporated. The crude product was purified on a silica gel column (0.02% AcOH, 1-3% MeOH, DCM) to give compound 28m (5.764 g, 93.8%).

Example 61

24

-continued

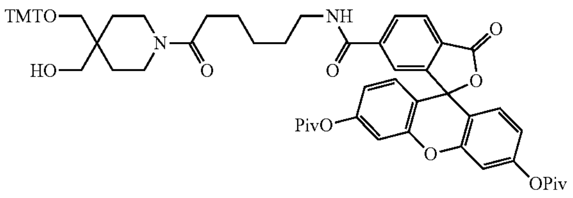

28n

6-((6-(4-((tris(4-methoxyphenyl)methoxy)methyl)-4-(hydroxymethyl)piperidin-1-yl)-6-oxohexyl)carbamoyl)-3-oxo-3H-spiro[isobenzofuran-1,9'-xanthene]-3',6'-diyl bis(2,2-dimethylpropanoate) 28n N,N'-Dicyclohexylcarbodiimide (DCC, 1.171 g, 5.67 mmol) was added to a solution of 6-carboxyfluorescein dipivaloate (3.00 g, 5.51 mmol) and N-hydroxysuccinimide (0.824 g, 7.16 mmol) in DCM (50 mL) at 0° C., and the mixture was stirred at room temperature for 2h. Then amine 24 (3.249 g, 5.5 mmol) was added and stirring was continued for 18 h. The solid was filtered off. The filtrate was diluted with ethyl acetate, washed with 5% NaCl acidified with citric acid to pH 4 followed by triethylammonium bicarbonate buffer (pH 7.19). The organic phase was dried over $Na_2SO_4$ and evaporated. The crude product was purified on a silica gel column (0.02% AcOH, 1-3% MeOH, DCM) to give compound 28n (5.370 g, 87.4%).

Example 62

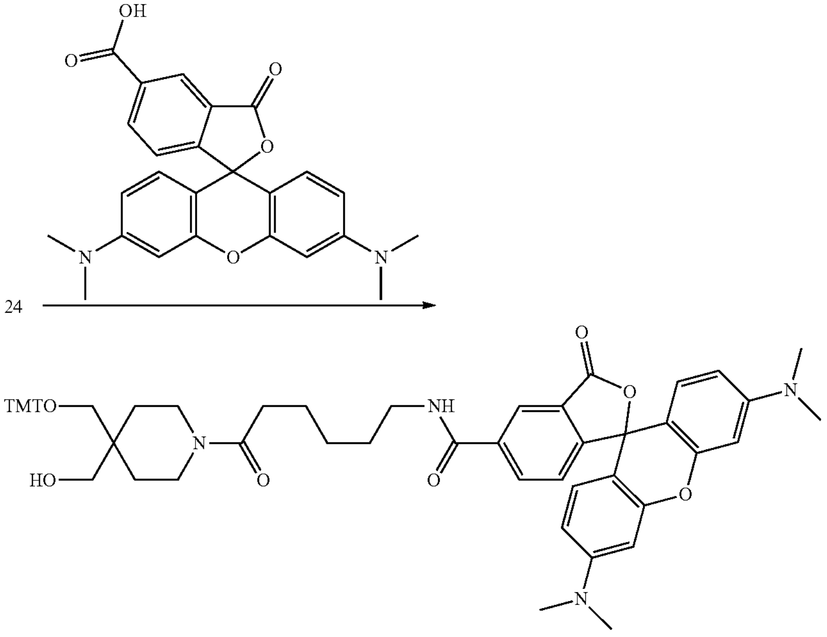

28p

3',6'-bis(dimethylamino)-N-(6-(4-(hydroxymethyl)-4-((tris(4-methoxyphenyl) methoxy)methyl)piperidin-1-yl)-6-oxohexyl)-3-oxo-3H-spiro[isobenzofuran-1,9'-xanthene]-5-carboxamide 28p N,N'-Dicyclohexylcarbodiimide (DCC, 0.681 g, 3.3 mmol) was added to a solution of 3',6'-bis(dimethylamino)-3-oxo-3H-spiro[isobenzofuran-1,9'-xanthene]-5-carboxylic acid (1.382 g, 3.21 mmol) and N-hydroxysuccinimide (0.480 g, 4.17 mmol) in DCM (30 mL) at 0° C., and the mixture was stirred at room temperature for 2h. Then amine 24 (1.891 g, 3.2 mmol) was added and stirring was continued for 18 h. The solid was filtered off. The filtrate was diluted with ethyl acetate, washed with 5% NaCl acidified with citric acid to pH 4 followed by triethylammonium bicarbonate buffer (pH 7.19). The organic phase was dried over $Na_2SO_4$ and evaporated. The crude product was purified on a silica gel column (0.02% AcOH, 1-3% MeOH, DCM) to give compound 28p (2.513 g, 70.3%).

Example 63

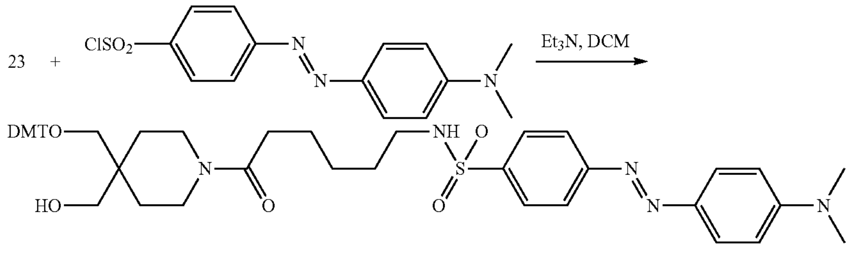

43k (E)-N-(6-(4-((bis(4-methoxyphenyl)(phenyl)methoxy)methyl)-4-(hydroxymethyl)piperidin-1-yl)-6-oxohexyl)-4-((4-(dimethylamino)phenyl)diazenyl)benzenesulfonamide 17

DABSYL chloride (1 g, 3.088 mmol) was added to compound 23 (1.730 g, 3.09 mmol) in triethylamine (0.319 g, 3.15 mmol) and anhydrous DCM (15 mL) at 0° C. The mixture was stirred overnight and diluted with ethyl acetate. The organic phase was washed with conc. aqueous $NaHCO_3$, dried over $Na_2SO_4$, and evaporated. The crude product was purified on silica gel column (50% hexanes/DCM→3% MeOH/DCM) to give compound 43k (2328 g, 90.4%) as an orange solid foam.

Example 64

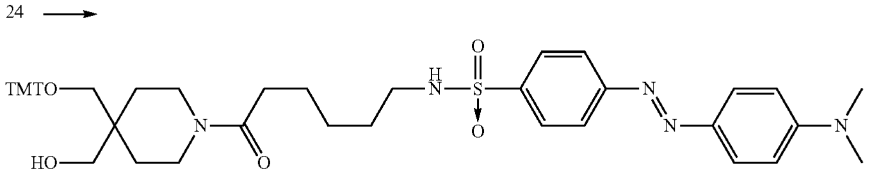

44k (E)-N-(6-(4-((tris(4-methoxyphenyl)methoxy)methyl)-4-(hydroxymethyl)piperidin-1-yl)-6-oxohexyl)-4-((4-(dimethylamino)phenyl)diazenyl)benzenesulfonamide 44k DABSYL chloride (0.950 g, 2.93 mmol) was added to compound 24 (1.644 g, 2.94 mmol) in triethylamine (0.303 g, 2.99 mmol) and anhydrous DCM (15 mL) at 0° C. The mixture was stirred overnight and diluted with ethyl acetate. The organic phase was washed with conc. aqueous $NaHCO_3$, dried over $Na_2SO_4$, and evaporated. The crude product was purified on silica gel column (50% hexanes/DCM→3% MeOH/DCM) to give compound 44k (2.320 g, 89.9%) as an orange solid foam.

Example 65

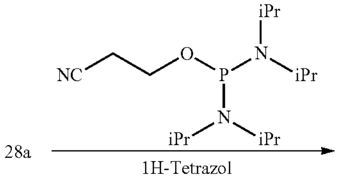

-continued

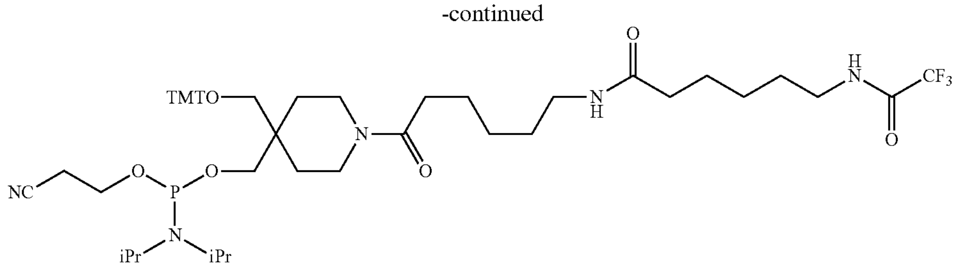

32a ((1-(6-(6-(2,2,2-trifluoroacetamido)hexanamido) hexanoyl)-4-((tris(4-methoxyphenyl)methoxy) methyl)piperidin-4-yl)methyl) (2-cyanoethyl) diisopropylphosphoramidite 32a Compound 28a (1.600 g, 2.0 mmol) and 2-cyanoethyl N,N,N',N'-tetraisopropylphosphorodiamidite (0.783 g, 2.60 mmol) were dissolved in anhydrous acetonitrile (25 mL), and the mixture was shaken with flame-dried molecular sieves 4 Å for 1 h. This was cooled to −10° C., and 1H-tetrazole (0.45M, 1.0 mmol, 2.22 mL) in acetonitrile was added, and the mixture was stirred overnight. The reaction mixture was quenched with triethylamine (0.5 mL) and diluted with saturated aqueous sodium bicarbonate. The product was extracted with DCM, and the organic extract was dried over $Na_2SO_4$ and evaporated to dryness. The crude product was purified on a silica gel column (5% $Et_3N$, 20-80% ethyl acetate in hexanes) to yield 32a (1.548 g, 77.4%) as a white solid foam.

Example 66

27b

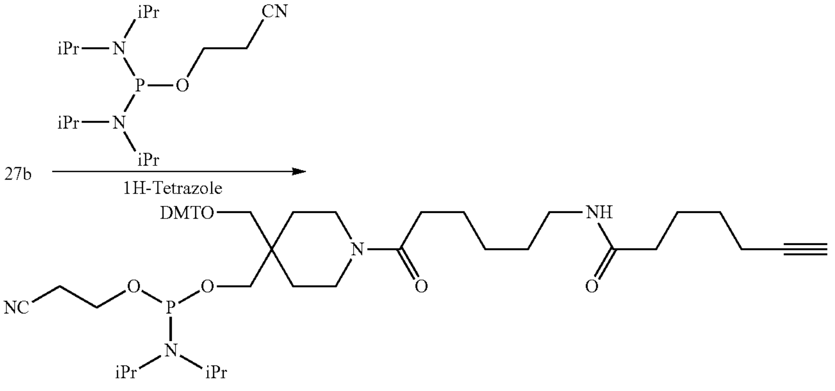

31b (4-((bis(4-methoxyphenyl)(phenyl)methoxy) methyl)-1-(6-(hept-6-ynamido)hexanoyl)piperidin-4-yl)methyl (2-cyanoethyl) diisopropylphosphoramidite 31b Compound 27b (1.821 g, 2.72 mmol) and 2-cyanoethyl N,N,N',N'-tetraisopropylphosphorodiamidite (0.873 g, 2.90 mmol) were dissolved in anhydrous acetonitrile (25 mL), and the mixture was shaken with flame-dried molecular sieves 4 Å for 1 h. This was cooled to −10° C., and 1H-tetrazole (0.45M, 1.09 mmol, 2.42 mL) in acetonitrile was added, and the mixture was stirred overnight. The reaction mixture was quenched with triethylamine (0.5 mL) and diluted with saturated aqueous sodium bicarbonate. The product was extracted with DCM, and the organic extract was dried over $Na_2SO_4$ and evaporated to dryness. The crude product was purified on a silica gel column (5% $Et_3N$, 20-80% ethyl acetate in hexanes) to yield 31b (1.805 g, 76.4%) as a white solid foam.

Example 67

28b

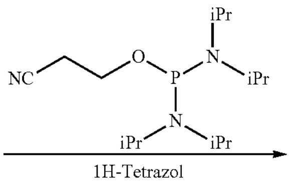

-continued

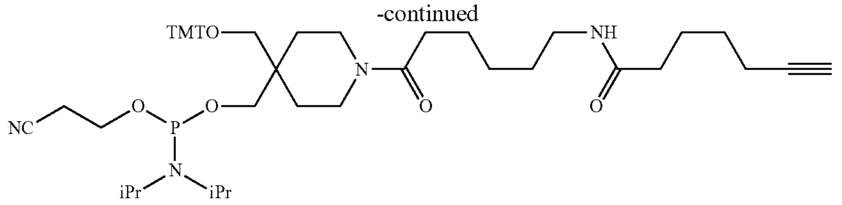

32b (1-(6-(hept-6-ynamido)hexanoyl)-4-((tris(4-methoxyphenyl)methoxy)methyl)piperidin-4-yl) methyl (2-cyanoethyl) diisopropylphosphoramidite 32b Compound 28b (1.468 g, 2.1 mmol) and 2-cyanoethyl N,N,N',N'-tetraisopropylphosphorodiamidite (0.823 g, 2.73 mmol) were dissolved in anhydrous acetonitrile (25 mL), and the mixture was shaken with flame-dried molecular sieves 4 Å for 1 h. This was cooled to −10° C., and 1H-tetrazole (0.45M, 1.05 mmol, 2.33 mL) in acetonitrile was added, and the mixture was stirred overnight. The reaction mixture was quenched with triethylamine (0.5 mL) and diluted with saturated aqueous sodium bicarbonate. The product was extracted with DCM, and the organic extract was dried over $Na_2SO_4$ and evaporated to dryness. The crude product was purified on a silica gel column (5% $Et_3N$, 20-80% ethyl acetate in hexanes) to yield 32b (1.595 g, 84.5%) as a white solid foam.

Example 68

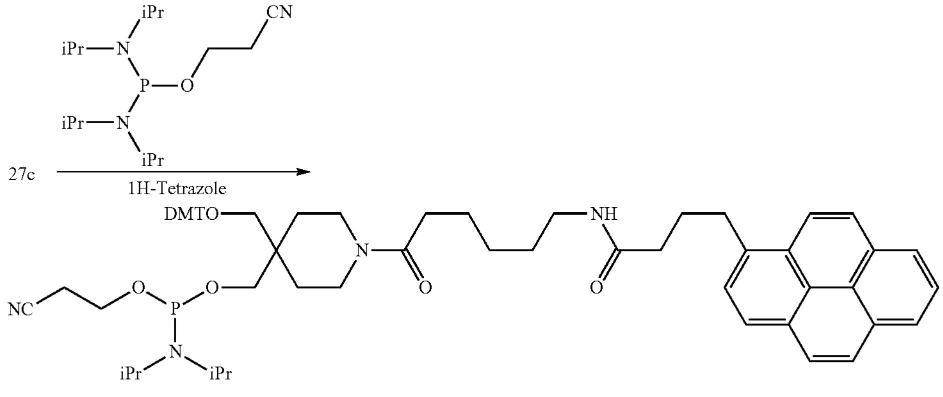

31c (4-((Bis(4-methoxyphenyl)(phenyl)methoxy)methyl)-1-(6-(4-(pyren-1-yl)butanamido)hexanoyl)piperidin-4-yl)methyl (2-cyanoethyl) diisopropylphosphoramidite 31c 1H-tetrazole in acetonitrile (0.45M, 2.45 mL, 1.1 mmol) was added to compound 27c (2.293 g, 2.76 mmol) and 2-cyanoethyl N,N,N',N'-tetraisopropylphosphorodiamidite (0.915 g, 3.04 mmol) dissolved in a mixture of anhydrous DCM and anhydrous acetonitrile (1:1, 10 mL). The reaction mixture was stirred overnight and was quenched with triethylamine (0.5 mL). The mixture was evaporated to mobile oil, which was dissolved in DCM (70 mL). The solution was washed with saturated aqueous sodium bicarbonate solution, dried over $Na_2SO_4$, and evaporated to oil. The product was isolated on a silica gel column (5% $Et_3N$, 30→95% ethyl acetate in hexanes), to give 2.34 g (82.2%) of compound 31c as a white solid foam.

NMR $H^1$ (δ, $CD_3CN$): 8.38 (d, J=9.5 Hz, 1H), 8.18-8.23 (m, 2H), 8.16-8.18 (m, 2H), 8.04-8.08 (m, 2H), 8.03 (t, J=8.0 Hz, 1H), 7.92 (d, J=8.0 Hz, 1H), 7.41-7.44 (m, 2H), 7.28-7.31 (m, 6H), 7.19-7.24 (m, 1H), 6.81-6.85 (m, 4H), 6.43 (t, J=5.5 Hz, 1H, NH), 3.74 (s, 6H), 3.65-3.72 (m, 3H), 3.50-3.60 (m, 3H), 3.31-3.41 (m, 3H), 3.18-3.25 (m, 1H), 3.13-3.18 (m, 2H), 2.85-3.0 (m, 4H), 2.58 (t, J=7.0 Hz, 2H), 2.25 (m, 2H), 2.13-2.19 (m, 2H), 2.07-2.13 (m, 2H), 1.26-1.53 (m, 10H), 1.15 (d, J=7.5 Hz, 6H), 1.09 (dd, J=7.5, 5.0 Hz, 6H).

NMR $C^{13}$ (δ, $CD_3CN$): 173.3, 171.8, 159.7, 146.6, 137.9, 137.3, 132.5, 132.0, 131.2, 130.9, 129.7, 129.2, 128.8, 128.6, 128.6, 128.2, 127.8, 127.6, 127.2, 126.0, 126.0, 125.8, 125.7, 124.7, 119.6, 118.0, 114.0, 86.6, 67.4 (d, ${}^2J_P{}^{31}$=16.0 Hz), 65.1, 59.4 (d, ${}^2J_P{}^{31}$=18.0 Hz), 56.0, 44.0 (d, ${}^2J_P{}^{31}$=12.5 Hz), 42.1, 39.6, 38.9 (d, ${}^3J_P{}^{31}$=8.8 Hz), 38.0, 36.6, 33.6 (d, ${}^3J_P{}^{31}$=10.0 Hz), 30.8 (d, ${}^3J_P{}^{31}$=11.0 Hz), 30.1, 30.1, 28.8, 27.4, 25.6, 25.1 (d, ${}^3J_P{}^{31}$=7.5 Hz), 25.0 (d, ${}^3J_P{}^{31}$=7.5 Hz), 21.2 (d, ${}^3J_P{}^{31}$=6.2 Hz).

Example 69

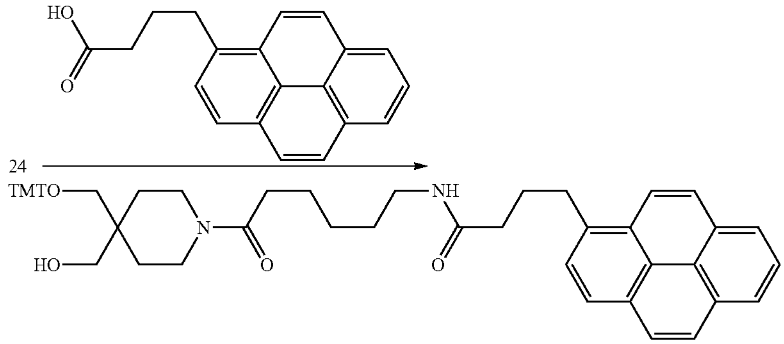

28c (4-((tris(4-methoxyphenyl)methoxy)methyl)-1-(6-(4-(pyren-1-yl)butanamido)hexanoyl)piperidin-4-yl) methyl (2-cyanoethyl) diisopropylphosphoramidite 32c 1H-tetrazole in acetonitrile (0.45M, 3.0 mL, 1.35 mmol) was added to compound 28c (2.325 g, 2.7 mmol) and 2-cyanoethyl N,N,N',N'-tetraisopropylphosphorodiamidite (1.058 g, 3.51 mmol) dissolved in a mixture of anhydrous DCM and anhydrous acetonitrile (1:1, 10 mL). The reaction mixture was stirred overnight and was quenched with triethylamine (0.5 mL). The mixture was evaporated to mobile oil, which was dissolved in DCM (70 mL). The solution was washed with saturated aqueous sodium bicarbonate solution, dried over $Na_2SO_4$, and evaporated to oil. The product was isolated on a silica gel column (5% $Et_3N$, 30→95% ethyl acetate in hexanes), to give 2.525 g (88.1%) of compound 32c as a white solid foam.

Example 70

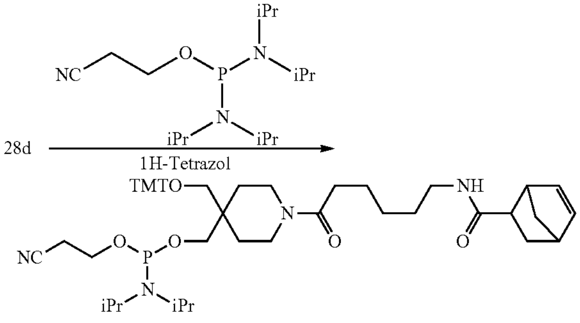

32d (1-(6-(bicyclo[2.2.11]hept-5-ene-2-carboxamido) hexanoyl)-4-((tris(4-methoxyphenyl) methoxy) methyl)piperidin-4-yl)methyl (2-cyanoethyl) diisopropylphosphoramidite 32d 1H-tetrazole in acetonitrile (0.45M, 2.78 mL, 1.25 mmol) was added to compound 28d (1.777 g, 2.5 mmol) and 2-cyanoethyl N,N,N',N'-tetraisopropylphosphorodiamidite (0.980 g, 3.25 mmol) dissolved in a mixture of anhydrous DCM and anhydrous acetonitrile (1:1, 10 mL). The reaction mixture was stirred overnight and was quenched with triethylamine (0.5 mL). The mixture was evaporated to mobile oil, which was dissolved in DCM (70 mL). The solution was washed with saturated aqueous sodium bicarbonate solution, dried over $Na_2SO_4$, and evaporated to oil. The product was isolated on a silica gel column (5% $Et_3N$, 30→95% ethyl acetate in hexanes), to give 1.888 g (82.9%) of compound 32d as a white solid foam.

Example 71

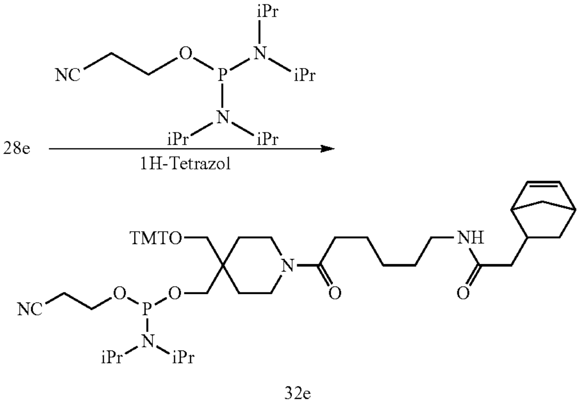

32e (1-(6-(2-(bicyclo[2.2.1]hept-5-en-2-yl)acetamido) hexanoyl)-4-((tris(4-methoxyphenyl) methoxy) methyl)piperidin-4-yl)methyl (2-cyanoethyl) diisopropylphosphoramidite 32e 1H-tetrazole in acetonitrile (0.45M, 2.22 mL, 1.0 mmol) was added to compound 28e (1.450 g, 2.0 mmol) and 2-cyanoethyl N,N,N',N'-tetraisopropylphosphorodiamidite (0.783 g, 2.6 mmol) dissolved in a mixture of anhydrous DCM and anhydrous acetonitrile (1:1, 10 mL). The reaction mixture was stirred overnight and was quenched with triethylamine (0.5 mL). The mixture was evaporated to mobile oil, which was dissolved in DCM (70 mL). The solution was washed with saturated aqueous sodium bicarbonate solution, dried over $Na_2SO_4$, and evaporated to oil. The product was isolated on a silica gel column (5% $Et_3N$, 30→95% ethyl acetate in hexanes), to give 1.562 g (84.4%) of compound 32e as a white solid foam.

Example 72

28f

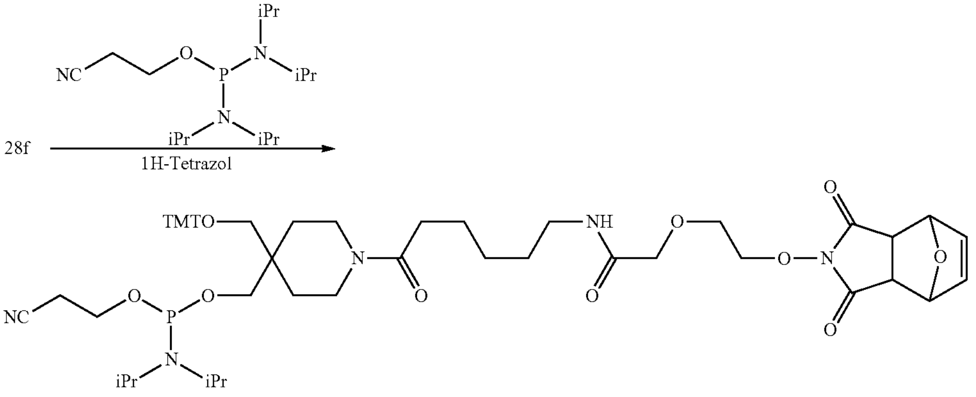

32f (1-(6-(2-(2-((1,3-dioxo-1,3,3a,4,7,7a-hexahydro-2H-4,7-epoxyisoindol-2-yl)oxy)ethoxy)acetamido)hexanoyl)-4-((tris(4-methoxyphenyl)methoxy)methyl)piperidin-4-yl)methyl (2-cyanoethyl) diisopropylphosphoramidite 32f 1H-tetrazole in acetonitrile (0.45M, 2.22 mL, 1.0 mmol) was added to compound 28f (1.711 g, 2.0 mmol) and 2-cyanoethyl N,N,N',N'-tetraisopropylphosphorodiamidite (0.783 g, 2.6 mmol) dissolved in a mixture of anhydrous DCM and anhydrous acetonitrile (1:1, 10 mL). The reaction mixture was stirred overnight and was quenched with triethylamine (0.5 mL). The mixture was evaporated to mobile oil, which was dissolved in DCM (70 mL). The solution was washed with saturated aqueous sodium bicarbonate solution, dried over $Na_2SO_4$, and evaporated to oil. The product was isolated on a silica gel column (5% $Et_3N$, 30→95% ethyl acetate in hexanes), to give 1.616 g (76.5%) of compound 32f as a white solid foam.

Example 73

28g

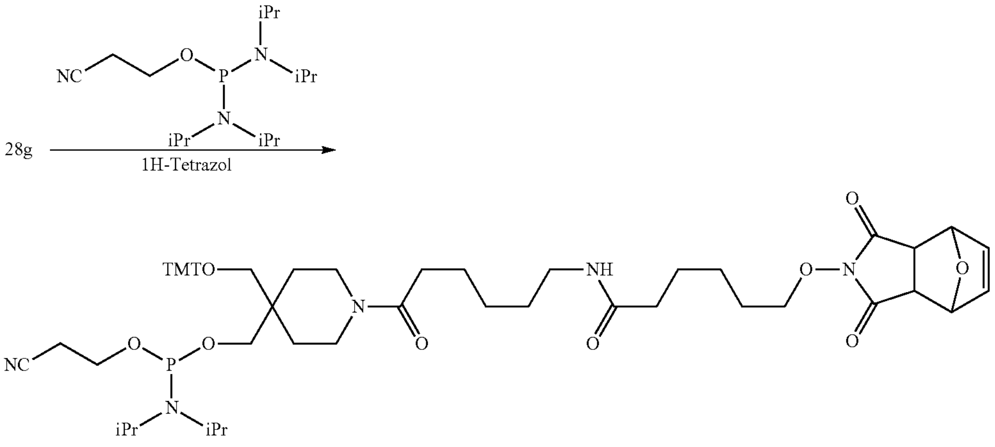

32g (1-(6-(6-((1,3-dioxo-1,3,3a,4,7,7a-hexahydro-2H-4,7-epoxyisoindol-2-yl)oxy)hexanamido)hexanoyl)-4-((tris(4-methoxyphenyl)methoxy)methyl)piperidin-4-yl)methyl (2-cyanoethyl) diisopropylphosphoramidite 32 g 1H-tetrazole in acetonitrile (0.45M, 2.22 mL, 1.0 mmol) was added to compound 28g (1.736 g, 2.0 mmol) and 2-cyanoethyl N,N,N',N'-tetraisopropylphosphorodiamidite (0.783 g, 2.6 mmol) dissolved in a mixture of anhydrous DCM and anhydrous acetonitrile (1:1, 10 mL). The reaction mixture was stirred overnight and was quenched with triethylamine (0.5 mL). The mixture was evaporated to mobile oil, which was dissolved in DCM (70 mL). The solution was washed with saturated aqueous sodium bicarbonate solution, dried over $Na_2SO_4$, and evaporated to oil. The product was isolated on a silica gel column (5% $Et_3N$, 30→95% ethyl acetate in hexanes), to give 1.690 g (79.1%) of compound 32g as a white solid foam.

Example 74

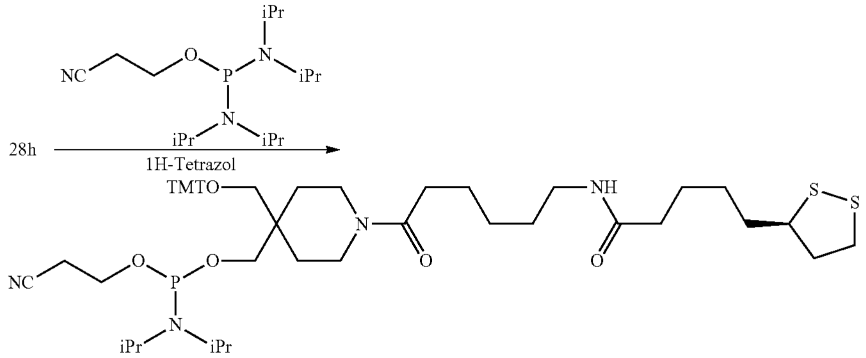

32h (1-(6-(5-((R)-1,2-dithiolan-3-yl)pentanamido)hexanoyl)-4-((tris(4-methoxyphenyl)methoxy)methyl)piperidin-4-yl)methyl (2-cyanoethyl) diisopropylphosphoramidite 32h 1H-tetrazole in acetonitrile (0.45M, 2.13 mL, 1.0 mmol) was added to compound 28h (1.496 g, 1.92 mmol) and 2-cyanoethyl N,N,N',N'-tetraisopropylphosphorodiamidite (0.752 g, 2.5 mmol) dissolved in a mixture of anhydrous DCM and anhydrous acetonitrile (1:1, 10 mL). The reaction mixture was stirred overnight and was quenched with triethylamine (0.5 mL). The mixture was evaporated to mobile oil, which was dissolved in DCM (70 mL). The solution was washed with saturated aqueous sodium bicarbonate solution, dried over $Na_2SO_4$, and evaporated to oil. The product was isolated on a silica gel column (5% $Et_3N$, 30→$_{95}$% ethyl acetate in hexanes), to give 1.386 g (73.7%) of compound 32h as a white solid foam.

Example 75

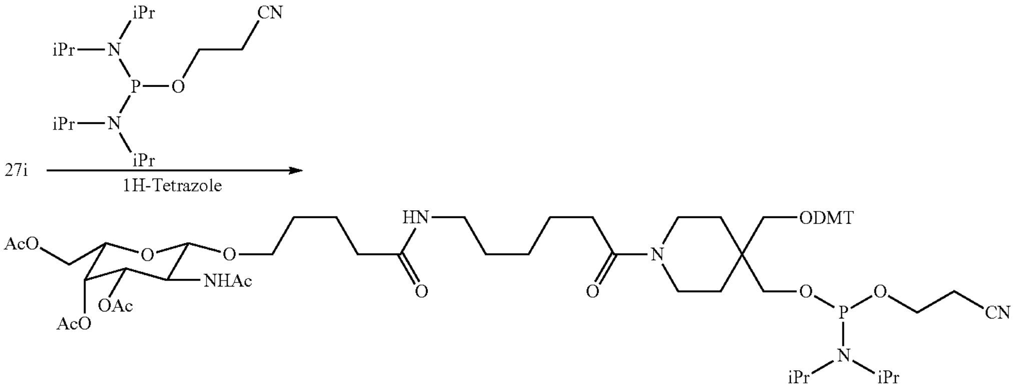

31i

2-Cyanoethyl (N—(O-(5-(3,4,6-O-triacetyl-2-acetylamino-2-deoxy-β-D-galactopyranosyl)oxy)pentanoyl)-4-(((4,4'-dimethoxytrityl)oxy)methyl)piperidin-4-yl)methyl N,N-diisopropylamidophosphite 31i Compound 27i (0.990 g, 1.0 mmol) and 2-cyanoethyl N,N,N',N'-tetraisopropylphosphorodiamidite (0.316 g, 1.05 mmol) were dissolved in anhydrous acetonitrile (20 mL), and the mixture was shaken with flame-dried molecular sieves 4 Å for 1 h. This was cooled to −10° C., 1H-tetrazole (0.45M, 0.40 mmol, 0.889 mL) in acetonitrile was added, and the mixture was stirred overnight. The reaction mixture was quenched with triethylamine (0.5 mL) and diluted with saturated aqueous sodium bicarbonate. The product was extracted with DCM, the organic extract was dried over $Na_2SO_4$ and evaporated to dryness. The crude product was purified on a silica gel column (5% $Et_3N$, 5-45% of ethyl acetate in hexanes) to yield 31i (1.097 g, 92.2%) as a white solid foam.

Example 76

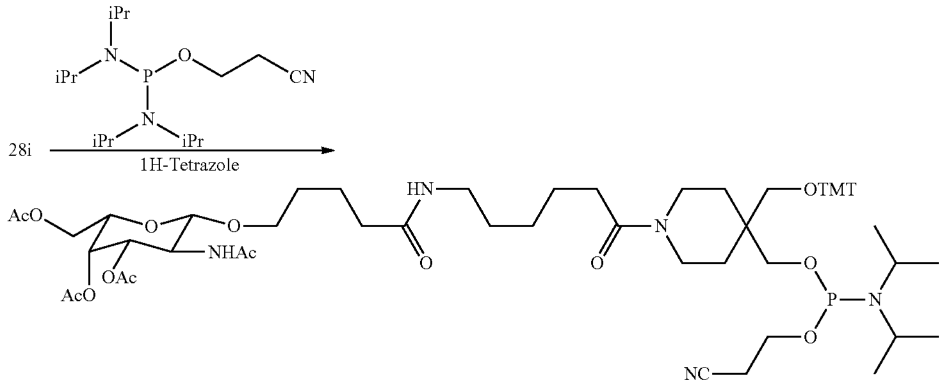

32i

2-Cyanoethyl (N—(O-(5-(3,4,6-O-triacetyl-2-acetylamino-2-deoxy-β-D-galactopyranosyl)oxy)butanoyl)-4-(((4,4'-dimethoxytrityl)oxy)methyl)piperidin-4-yl)methyl N,N-diisopropylamidophosphite 32i Compound 28i (5.00 g, 4.97 mmol) and 2-cyanoethyl N,N,N',N'-tetraisopropylphosphorodiamidite (1.778 g, 5.90 mmol) were dissolved in anhydrous acetonitrile (25 mL). The solution was gently shaken with flame-dried molecular sieves 4 Å (1.5 g) for 1 h, cooled to −10° C., and treated with 1H-tetrazole in acetonitrile (0.45 M, 5.08 mL). Next day, the reaction mixture was quenched with triethylamine (0.5 mL) and diluted with saturated sodium bicarbonate solution. The product was extracted with DCM and purified on a silica gel column (5% $Et_3N$, 0-1% MeOH in ethyl acetate) to give 32i (4.524 g, 75.4%) as a white solid foam.

NMR $H^1$ (δ, $CD_3CN$): 7.30-7.33 (m, 6H), 6.84-6.86 (m, 6H), 6.55 (br. d, J=9.5 Hz, 1H), 6.42 (br. t, J=5.5 Hz, 1H), 5.28 (d, J=3.0 Hz, 1H), 5.02 (dd, J=11.5, 3.5 Hz, 1H), 4.54 (d, J=8.5, 1H), 4.00-4.13 (m, 2H), 3.85-3.93 (m, 2H), 3.76 (s, 9H), 3.40-3.80 (m, 8H), 3.30-3.40 (m, 1H), 3.06-3.15 (m, 3H), 3.00-3.06 (m, 2H), 2.59 (t, J=5.5 Hz, 2H), 2.18-2.27 (m, 4H), 2.13 (t, J=7.0 Hz, 2H), 2.09 (s, 3H), 1.97 (s, 3H), 1.91 (s, 3H), 1.84 (s, 3H), 1.71-1.80 (m, 2H), 1.48-1.55 (m, 3H), 1.36-1.48 (m, 5H), 1.25-1.35 (m, 2H), 1.17 (d, J=7.0 Hz, 6H), 1.11 (d, J=7.0 Hz, 6H).

NMR $C^{13}$ (δ, $CD_3CN$): 173.1, 172.0, 171.3, 171.2, 171.2, 171.1, 159.6, 137.9, 130.9, 119.6, 114.0, 102.4, 86.3, 71.7, 71.6, 69.8, 68.1, 67.0 (d, $J_{CP}$=18.0 Hz), 65.2, 62.6, 59.4 (d, $J_{CP}$=18.7 Hz), 56.0, 51.4, 44.0 (d, $J_{CP}$=11.2 Hz), 42.3, 39.7, 39.0 (d, $J_{CP}$=7.5 Hz), 38.2, 33.8, 33.1, 30.9 (d, $J_{CP}$=13.7 Hz), 30.2, 30.1, 27.5, 26.6, 25.8, 25.1 (d, $J_{CP}$=7.5 Hz), 25.0 (d, $J_{CP}$=7.5 Hz), 23.4, 21.2 (d, $J_{CP}$=7.5 Hz), 21.0, 21.0, 20.9.

Example 77

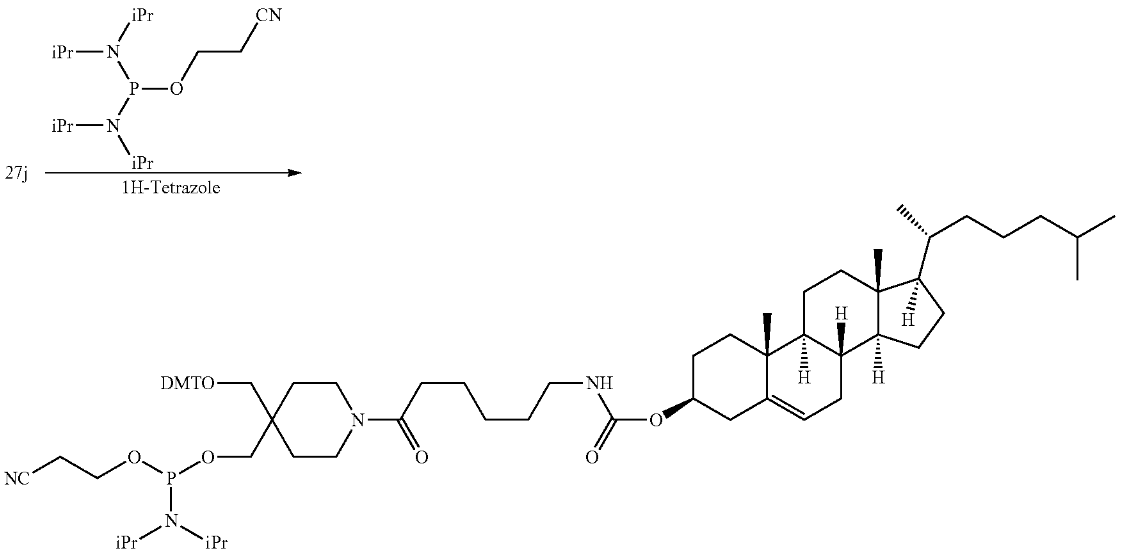

31j

Cholest-5-en-3-yl {6-[4-{[bis(4-methoxyphenyl)(phenyl)methoxy]methyl}-4-({[(2-cyanoethoxy)(diisopropylamino)phosphino]oxy}methyl)piperidin-1-yl]-6-oxohexyl}carbamate 31j Compound 27j (1.925 g, 1.98 mmol) and 2-cyanoethyl N,N,N',N'-tetraisopropylphosphorodiamidite (0.776 g, 2.57 mmol) were dissolved in a mixture of anhydrous DCM (22 mL) and anhydrous acetonitrile (17 mL). The solution was gently shaken with flame-dried molecular sieves 4 Å (1.34 g) for 1 h, cooled to −10° C., and treated with 1H-tetrazole in acetonitrile (0.45 M, 2.28 mL). Next day, the reaction mixture was quenched with triethylamine (0.5 mL) and diluted with saturated sodium bicarbonate solution. The product was extracted with DCM and purified on a silica gel column (5% $Et_3N$, 20→50% ethyl acetate in hexanes), to yield compound 31j (1.90 g, 81.8%) as a white solid foam.

NMR $H^1$ (δ, $CD_3CN$): 7.37-7.39 (m, 2H), 7.27-7.31 (m, 2H), 7.27-7.31 (m, 4H), 7.19-7-25 (m, 1H), 7.00 (t, J=5.5 Hz, 1H, NH), 6.86-6.89 (m, 4H), 5.32 (m, 1H), 4.55 (br. S, 1H, OH), 4.25-4.33 (m, 1H), 3.73 (s, 6H), 3.46 (br. s, 2H), 3.26-3.40 (m, 2H), 2.95-3.03 (br. m, 2H), 2.93 (s, 2H), 2.88-2.93 (m, 2H), 2.14-2.30 (m, 2H), 2.19 (t, J=7.5 Hz, 2H), 1.72-2.00 (m, 5H), 1.45-1.56 (m, 6H), 1.25-1.45 (m, 15H), 1.16-1.25 (m, 6H), 0.85-1.16 (m, 6H), 0.96 (s, 3H), 0.89 (d, J=6.5 Hz, 3H), 0.85 (d, J=7.0 Hz, 3H), 0.84 (d, J=7.0 Hz, 3H), 0.65 (s, 3H).

NMR $P^{31}$ (δ, $CD_3CN$): 147.6 (100%).

Example 78

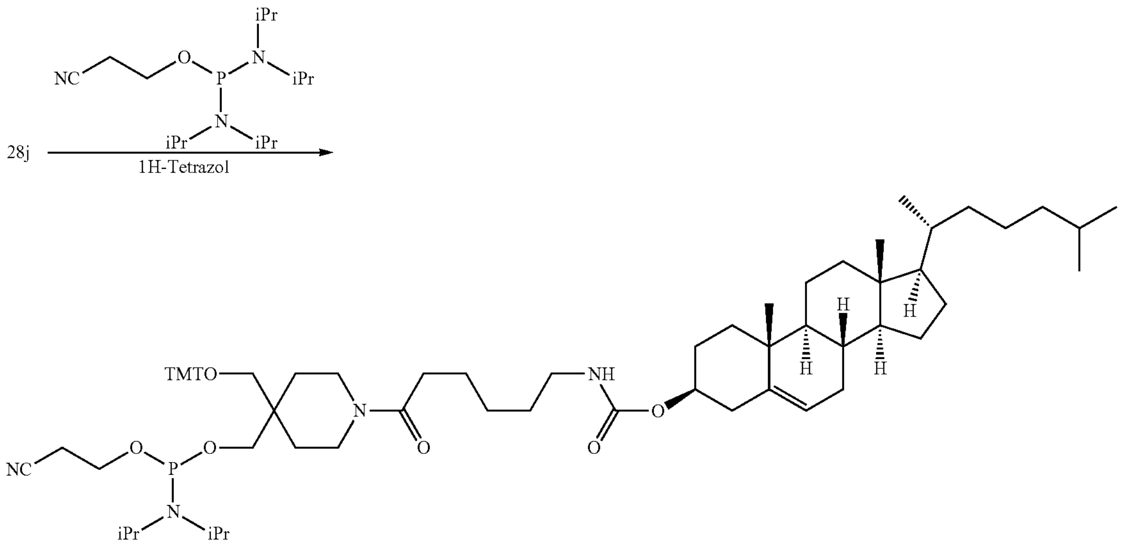

32j

Cholest-5-en-3-yl {6-[4-{[tris(4-methoxyphenyl) methoxy]methyl}-4-({[(2-cyanoethoxy)(diisopropylamino)phosphino]oxy}methyl)piperidin-1-yl]-6-oxohexyl}carbamate 32j Compound 28j (2.689 g, 2.68 mmol) and 2-cyanoethyl N,N,N',N'-tetraisopropylphosphorodiamidite (1.050 g, 3.48 mmol) were dissolved in a mixture of anhydrous DCM (22 mL) and anhydrous acetonitrile (17 mL). The solution was gently shaken with flame-dried molecular sieves 4 Å (1.5 g) for 1 h, cooled to −10° C., and treated with 1H-tetrazole in acetonitrile (0.45 M, 2.98 mL, 1.34 mmol). Next day, the reaction mixture was quenched with triethylamine (0.5 mL) and diluted with saturated sodium bicarbonate solution. The product was extracted with DCM and purified on a silica gel column (5% $Et_3N$, 20→50% ethyl acetate in hexanes), to yield compound 32j (2.864 g, 88.8%) as a white solid foam.

Example 79

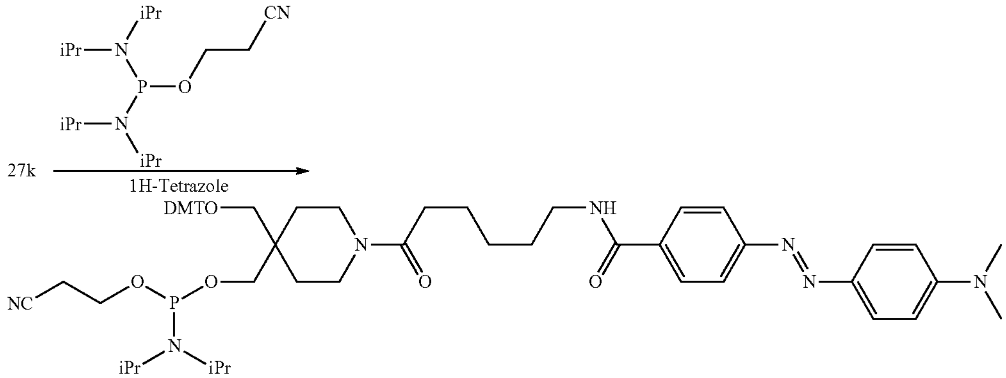

31k (E)-(4-((bis(4-methoxyphenyl)(phenyl)methoxy) methyl)-1-(6-(4-((4-(dimethylamino)phenyl)diazenyl)benzamido)-hexanoyl)piperidin-4-yl)methyl (2-cyanoethyl)diisopropylphosphoramidite 31k Compound 27k (1.710 g, 2.11 mmol) and 2-cyanoethyl-N,N,N',N'-tetraisopropylphosphoramidite (0.825 g, 2.73 mmol) were dissolved in anhydrous acetonitrile (25 mL). The solution was gently shaken with flame-dried molecular sieves 4 Å (1.2 g) for 1 h, cooled to −10° C., and treated with 1H-tetrazole in acetonitrile (0.45 M, 1.872 mL). Next day, the reaction mixture was quenched with triethylamine (0.5 mL) and diluted with saturated sodium bicarbonate solution. The product was extracted with DCM (70 mL), the extract was washed with saturated aqueous sodium bicarbonate solution, dried over $Na_2SO_4$, and evaporated to oil. The crude product was purified on a silica gel column (5% $Et_3N$, 20-80% ethyl acetate in hexanes) to yield 31k (1.936 g, 90.8%) as an orange solid foam.

Example 80

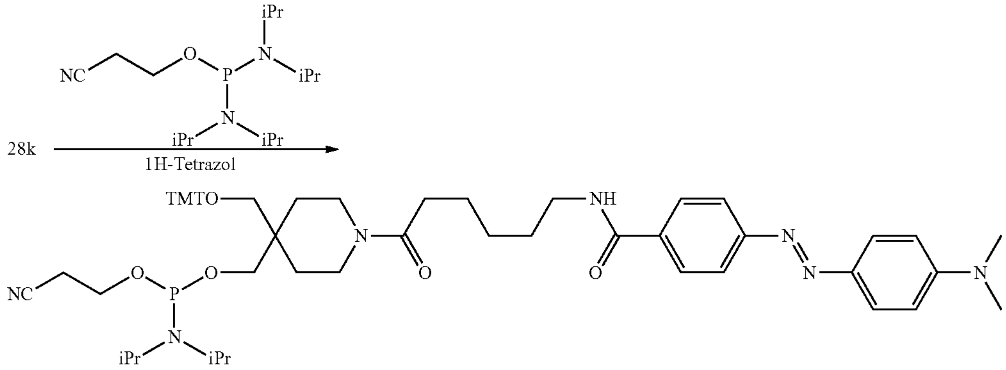

32k (E)-(4-((tris(4-methoxyphenyl)methoxy)methyl)-1-(6-(4-((4-(dimethylamino)phenyl)diazenyl)benzamido)-hexanoyl)piperidin-4-yl)methyl (2-cyanoethyl)diisopropylphosphoramidite 32k Compound 28k (1.474 g, 1.75 mmol) and 2-cyanoethyl-N,N,N',N'-tetraisopropylphosphoramidite (0.686 g, 2.27 mmol) were dissolved in anhydrous acetonitrile (25 mL). The solution was gently shaken with flame-dried molecular sieves 4 Å (1 g) for 1 h, cooled to −10° C., and treated with 1H-tetrazole in acetonitrile (0.45 M, 1.94 mL, 0875 mmol). Next day, the reaction mixture was quenched with triethylamine (0.5 mL) and diluted with saturated sodium bicarbonate solution. The product was extracted with DCM (70 mL), the extract was washed with saturated aqueous sodium bicarbonate solution, dried over $Na_2SO_4$, and evaporated to oil. The crude product was purified on a silica gel column (5% $Et_3N$, 20-80% ethyl acetate in hexanes) to yield 32k (1.536 g, 84.2%) as an orange solid foam.

Example 81

27m

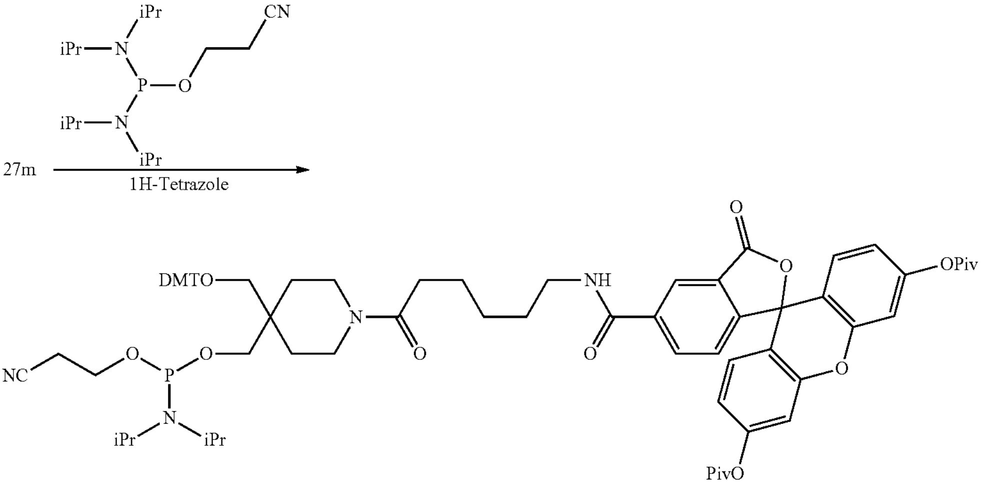

31m 5-((6-(4-((bis(4-methoxyphenyl)(phenyl)methoxy)methyl)-4-((((2-cyanoethoxy)(diisopropylamino)phosphino)-oxy)methyl)piperidin-1-yl)-6-oxohexyl)carbamoyl)-3-oxo-3H-spiro[isobenzofuran-1,9'-xanthene]-3',6'-diyl bis(2,2-dimethylpropanoate) 31m 1H-Tetrazole (0.45 M, 2.4 mL, 1.1 mmol) in acetonitrile was added to a solution of compound 27m (2.400 g, 2.20 mmol) and 2-cyanoethyl N,N,N',N'-tetraisopropylphosphorodiamidite (0.816 g, 2.71 mmol) in anhydrous DCM and anhydrous acetonitrile (1:1, 10 mL), and the mixture was stirred overnight. The reaction mixture was quenched with saturated sodium bicarbonate, the product was extracted with DCM and purified on a silica gel column (3% Py, 70-97% ethyl acetate in hexanes) to give compound 31m (1,748 g, 61.7%) as a white solid foam.

NMR $H^1$ (δ, $CD_3CN$): 8.11, 8.05 (AB, J=8.0 Hz, 2H), 7.63 (s, 1H), 7.42-7.45 (m, 2H), 7.20-7.32 (m, 7H), 7.18-7.22 (m, 1H), 6.90-7.10 (m, 2H), 6.88-6.92 (m, 2H), 6.78-6.86 (m, 6H), 3.74 (s, 6H), 3.66-3.74 (m, 3H), 3.60-3.66 (m, 1H), 3.53-3.58 (m, 2H), 3.35-3.42 (m, 1H), 3.22-3.33 (m, 3H), 2.98-3.08 (m, 4H), 2.58 (t, J=6.0 Hz, 2H), 2.15-2.20 (m, 2H), 1.25-1.52 (m, 10H) 1.32 (s, 18H), 1.16 (d, J=7.0 Hz, 6H), 1.11 (dd, J=7.0 Hz, 1.5 Hz, 6H).

NMR $C^{13}$ (δ, $CD_3CN$): 177.6, 171.9, 169.2, 166.2, 159.7, 154.1, 154.0, 152.6, 146.6, 143.0, 137.3, 131.2, 130.6, 130.3, 129.2, 129.0, 128.8, 127.8, 126.3, 123.6, 119.6, 119.3, 117.2, 114.1, 111.4, 86.6, 82.6, 67.5 (d, $^2J_P{}^{31}$=16.3 Hz), 65.3, 59.4 (d, $^2J_P{}^{31}$=17.6 Hz), 56.0, 44.0 (d, $^2J_P{}^{31}$=12.5 Hz), 42.2, 40.5, 39.9, 39.0 (d, $^3J_P{}^{31}$=8.8 Hz), 38.1, 33.6, 30.8, 30.1, 29.7, 27.4, 25.5, 25.2 (d, $^3J_P{}^{31}$=7.5 Hz), 25.03 (d, $^3J_P{}^{31}$=7.5 Hz), 21.2 (d, $^3J_P{}^{31}$=7.5 Hz).

NMR $P^{31}$ (δ, $CD_3CN$): 147.6 (98.8%).

Example 82

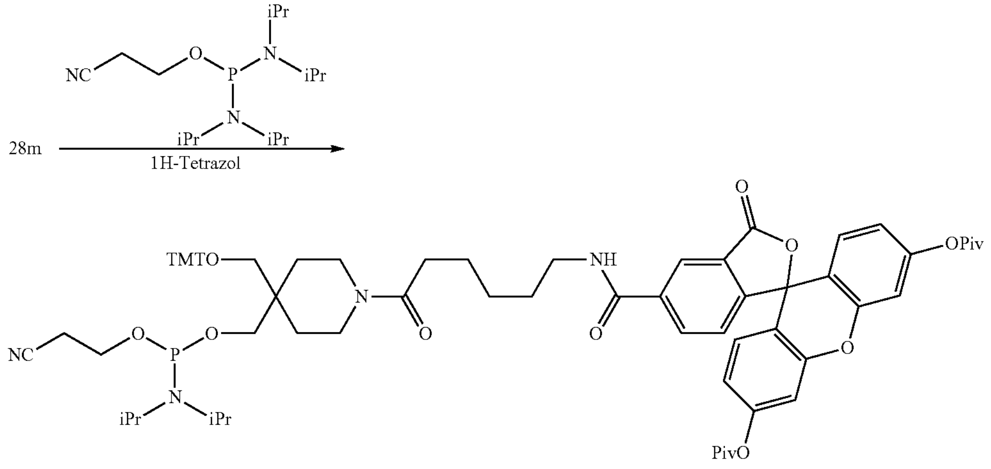

32m 5-((6-(4-((tris(4-methoxyphenyl)methoxy)methyl)-4-((((2-cyanoethoxy)(diisopropylamino)phosphino)-oxy)methyl)piperidin-1-yl)-6-oxohexyl)carbamoyl)-3-oxo-3H-spiro[isobenzofuran-1,9'-xanthene]-3',6'-diyl bis(2,2-dimethylpropanoate) 32m 1H-Tetrazole (0.45 M, 2.7 mL, 1.2 mmol) in acetonitrile was added to a solution of compound 28m (2.681 g, 2.40 mmol) and 2-cyanoethyl N,N,N',N'-tetraisopropylphosphorodiamidite (0.940 g, 3.12 mmol) in anhydrous DCM and anhydrous acetonitrile (1:1, 10 mL), and the mixture was stirred overnight. The reaction mixture was quenched with saturated sodium bicarbonate, the product was extracted with DCM and purified on a silica gel column (3% Py, 70-97% ethyl acetate in hexanes) to give compound 32m (2.105 g, 66.6%) as a white solid foam.

Example 83

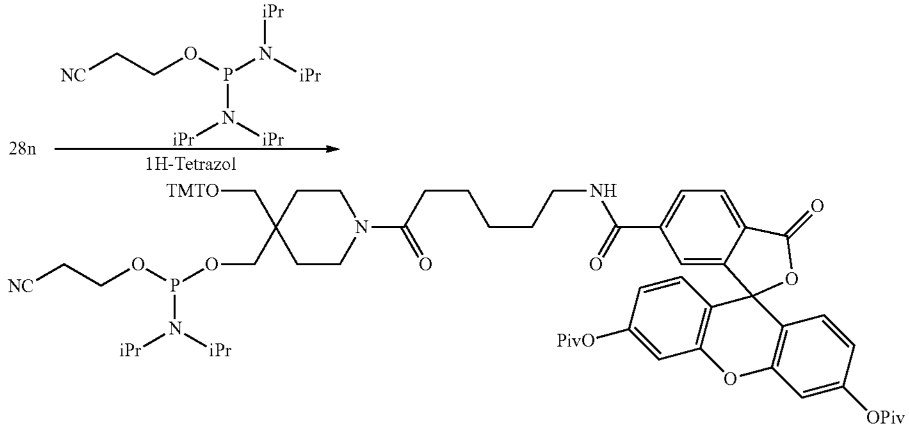

32n 6-((6-(4-((tris(4-methoxyphenyl)methoxy)methyl)-4-((((2-cyanoethoxy)(diisopropylamino)phosphino)-oxy)methyl)piperidin-1-yl)-6-oxohexyl)carbamoyl)-3-oxo-3H-spiro[isobenzofuran-1,9'-xanthene]-3',6'-diyl bis(2,2-dimethylpropanoate) 32n 1H-Tetrazole (0.45 M, 3.9 mL, 1.75 mmol) in acetonitrile was added to a solution of compound 28n (3.911 g, 3.50 mmol) and 2-cyanoethyl N,N,N',N'-tetraisopropylphosphorodiamidite (1.371 g, 4.55 mmol) in anhydrous DCM and anhydrous acetonitrile (1:1, 10 mL), and the mixture was stirred overnight. The reaction mixture was quenched with saturated sodium bicarbonate, the product was extracted with DCM and purified on a silica gel column (3% Py, 70-97% ethyl acetate in hexanes) to give compound 32n (2.896 g, 62.8%) as a white solid foam.

Example 84

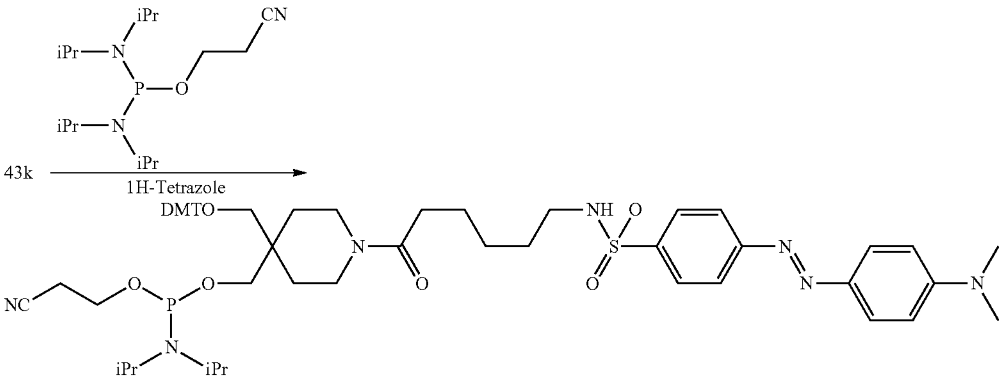

47k (E)-(4-((bis(4-methoxyphenyl)(phenyl)methoxy)methyl)-1-(6-(4-((4-(dimethylamino)phenyl)diazenyl)-phenylsulfonamido)hexanoyl)piperidin-4-yl)methyl (2-cyanoethyl) diisopropylphosphoramidite 47k Compound 43k (1.952 g, 2.30 mmol) and 2-cyanoethyl N,N,N',N'-tetraisopropylphosphorodiamidite (0.902 g, 2.99 mmol) were dissolved in anhydrous acetonitrile (17 mL). The solution was gently shaken with flame-dried molecular sieves 4 Å (1.2 g) for 1 h, cooled to −10° C., and treated with 1H-tetrazole in acetonitrile (0.45 M, 1.81 mL). Next day, the reaction mixture was quenched with triethylamine (0.4 mL) and diluted with saturated sodium bicarbonate solution. The product was extracted with DCM and purified on a silica gel column (5% $Et_3N$, 20-80% ethyl acetate in hexanes) to give 47k (1.888 g, 78.3%) as an orange solid foam.

Example 85

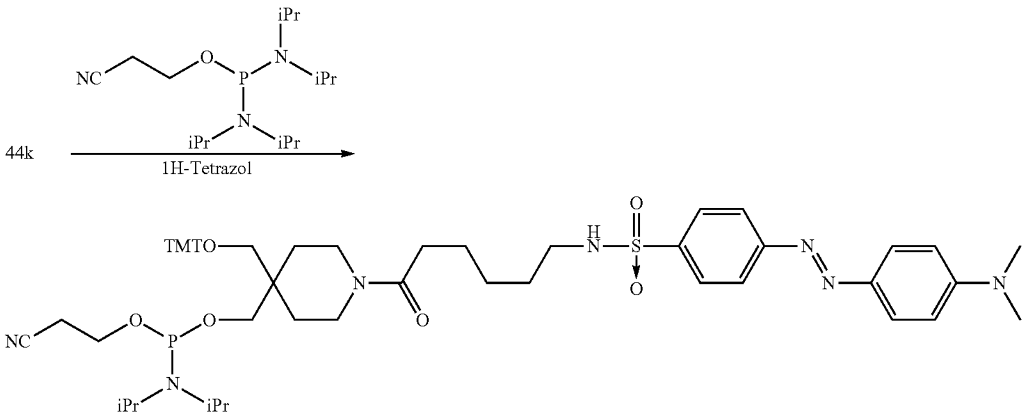

48k (E)-(4-((tris(4-methoxyphenyl)methoxy)methyl)-1-(6-(4-((4-(dimethylamino)phenyl)diazenyl)-phenylsulfonamido)hexanoyl)piperidin-4-yl)methyl (2-cyanoethyl) diisopropylphosphoramidite 48k Compound 44k (2.283 g, 2.6 mmol) and 2-cyanoethyl N,N,N',N'-tetraisopropylphosphorodiamidite (1.019 g, 3.38 mmol) were dissolved in anhydrous acetonitrile (17 mL). The solution was gently shaken with flame-dried molecular sieves 4 Å (1.5 g) for 1 h, cooled to −10° C., and treated with 1H-tetrazole in acetonitrile (0.45 M, 2.9 mL, 1.3). Next day, the reaction mixture was quenched with triethylamine (0.4 mL) and diluted with saturated sodium bicarbonate solution. The product was extracted with DCM and purified on a silica gel column (5% $Et_3N$, 20-80% ethyl acetate in hexanes) to give 48k (2.085 g, 74.4%) as an orange solid foam.

Example 86

27b

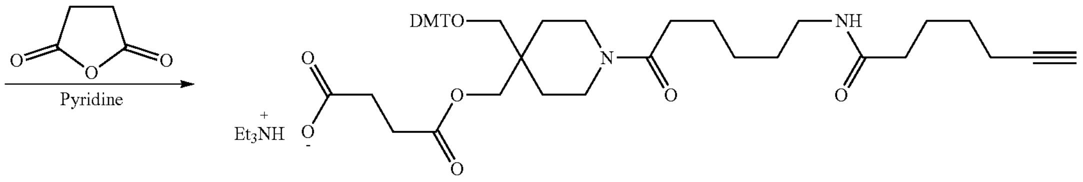

35b

Triethylammonium 4-((4-((bis(4-methoxyphenyl)(phenyl)methoxy)methyl)-1-(6-(hept-6-ynamido)hexanoyl)piperidin-4-yl)methoxy)-4-oxobutanoate 35b Compound 27b (0.223 g, 0.333 mmol), succinic anhydride (0.470 g, 4.70 mmol) and pyridine (2.42 g) were stirred at room temperature for 5 days. The reaction mixture was quenched with water and triethylamine (0.4 mL) for 4 h, evaporated to oil, diluted with DCM (100 mL), and washed with 10% aqueous citric acid. Organic phase was basified with triethylamine (0.4 mL), dried over $Na_2SO_4$, and evaporated. The product was isolated on a silica gel column (1% $Et_3N$, 0-5% MeOH, DCM) to yield 35b (0.246 g, 84.9%).

Example 87

28a

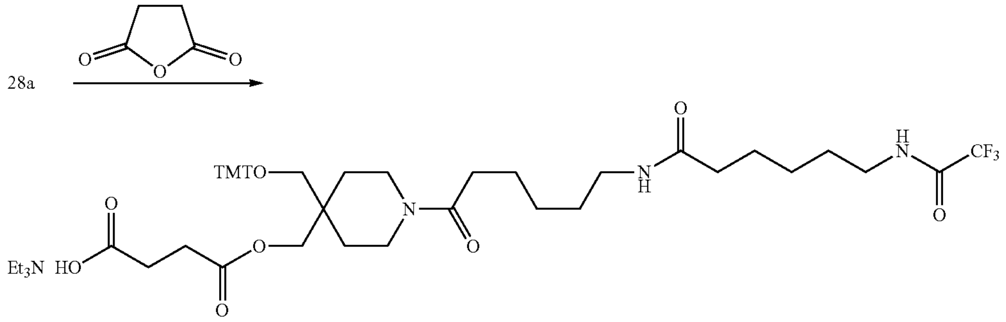

36a

Triethylammonium 4-oxo-4-((1-(6-(6-(2,2,2-trifluoroacetamido)hexanamido)hexanoyl)-4-((tris(4-methoxyphenyl)methoxy)methyl)piperidin-4-yl)methoxy)butanoate 36a Compound 28a (1.360 g, 1.7 mmol), succinic anhydride (0.510 g, 5.1 mmol) and pyridine (4.5 g) were stirred at room temperature for 5 days. The reaction mixture was quenched with water and triethylamine (0.4 mL) for 4 h, evaporated to oil, diluted with DCM (100 mL), and washed with 10% aqueous citric acid. Organic phase was basified with triethylamine (0.4 mL), dried over $Na_2SO_4$, and evaporated. The product was isolated on a silica gel column (1% $Et_3N$, 0-5% MeOH, DCM) to yield 36a (1.530 g, 85.5%).

Example 88

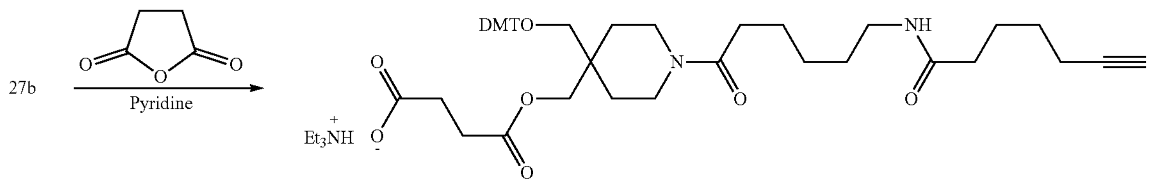

35b

Triethylammonium 4-((4-((bis(4-methoxyphenyl)(phenyl)methoxy)methyl)-1-(6-(hept-6-ynamido)hexanoyl)piperidin-4-yl)methoxy)-4-oxobutanoate 35b Compound 27b (0.223 g, 0.333 mmol), succinic anhydride (0.470 g, 4.70 mmol) and pyridine (2.42 g) were stirred at room temperature for 5 days. The reaction mixture was quenched with water and triethylamine (0.4 mL) for 4 h, evaporated to oil, diluted with DCM (100 mL), and washed with 10% aqueous citric acid. Organic phase was basified with triethylamine (0.4 mL), dried over $Na_2SO_4$, and evaporated. The product was isolated on a silica gel column (1% $Et_3N$, 0-5% MeOH, DCM) to yield 35b (0.246 g, 84.9%).

Example 89

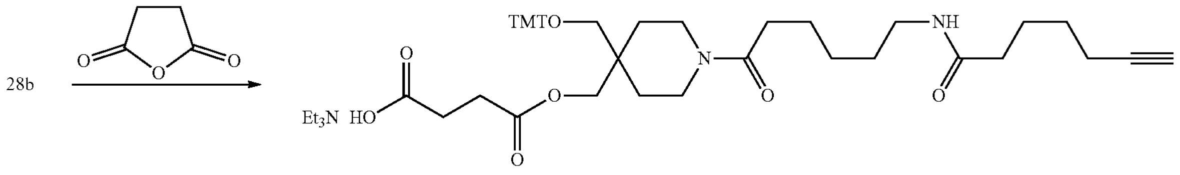

36b

Triethylammonium 4-((4-((tris(4-methoxyphenyl)methoxy)methyl)-1-(6-(hept-6-ynamido)hexanoyl)piperidin-4-yl)methoxy)-4-oxobutanoate 36b Compound 28b (0.908 g, 1.3 mmol), succinic anhydride (0.390 g, 3.90 mmol) and pyridine (2.42 g) were stirred at room temperature for 5 days. The reaction mixture was quenched with water and triethylamine (0.4 mL) for 4 h, evaporated to oil, diluted with DCM (100 mL), and washed with 10% aqueous citric acid. Organic phase was basified with triethylamine (1 mL), dried over $Na_2SO_4$, and evaporated. The product was isolated on a silica gel column (1% $Et_3N$, 0-5% MeOH, DCM) to yield 36b (1.0 g, 85.5%).

Example 90

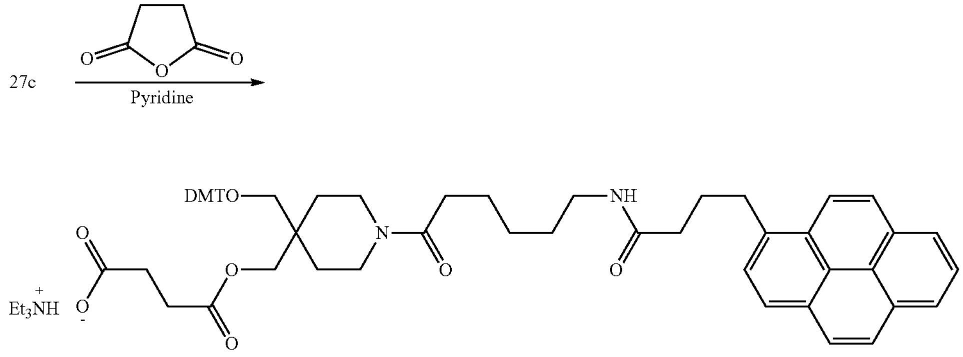

35c

Triethylammonium 4-((4-((bis(4-methoxyphenyl)(phenyl)methoxy)methyl)-1-(6-(4-(pyren-1-yl)butanamido)hexanoyl)piperidin-4-yl)methoxy)-4-oxobutanoate 35c Compound 27c (0.167 g, 0.200 mmol), succinic anhydride (0.200 g, 2 mmol), and pyridine (2 mL) were stirred at room temperature for 10 days. The reaction mixture was quenched with water (0.1 mL, 5.55 mmol) and triethylamine (5 mmol, 0.697 mL) for 4 h, evaporated to oil, diluted with DCM (100 mL), and washed with 10% aqueous citric acid. Organic phase was basified with triethylamine (0.2 mL), dried over $Na_2SO_4$, and evaporated. The product was isolated on a preparative TLC plate (1% $Et_3N$, 2.5% MeOH, DCM) to yield 35c (0.166 g, 80.4%).

NMR $H^1$ (δ, DMSO-$d_6$): 8.36 (d, J=9.5 Hz, 1H), 8.18-8.27 (m, 4H), 8.08-8.13 (m, 2H), 8.03 (t, J=8.0 Hz, 1H), 7.92

(d, J=8.0 Hz, 1H), 7.86 (t, J=5.5 Hz, 1H, NH), 7.27-7.36 (m, 4H), 7.17-7.23 (m, 5H), 6.85-6.89 (m, 4H), 4.06 (s, 2H), 3.71 (s, 6H), 3.19-3.40 (m, 2H), 3.04 (q, J=7.0 Hz, 2H), 2.85-3.0 (m, 2H), 2.89 (s, 2H), 2.42 (q, J=7.5 Hz, 3.39H, non-stoichiometric $Et_3N$ salt), 2.36 (t, J=7.0 Hz), 2.19-2.23 (m, 4H), 2.13-2.18 (m, 2H), 1.97-2.03 (m, 2H), 1.20-1.45 (m, 10H), 0.92 (t, J=7.5 Hz, 5.05H, non-stoichiometric $Et_3N$ salt).

NMR $C^{13}$ (δ, DMSO-$d_6$): 173.8, 172.7, 171.6, 170.2, 158.0 (2C), 144.8, 136.5, 135.5 (2C), 130.8, 130.4, 129.6, 129.2, 128.1, 127.7, 127.6, 127.4, 127.4, 127.1, 126.6, 126.4, 126.0, 124.8, 124.7, 124.2, 124.1, 123.4, 113.1, 85.0, 65.5, 63.4, 55.0, 45.6, 40.5, 36.5, 36.4, 35.0, 32.2, 32.1, 31.2, 30.3, 29.6, 28.9, 27.5, 26.1, 24.4, 11.7.

Example 91

28c

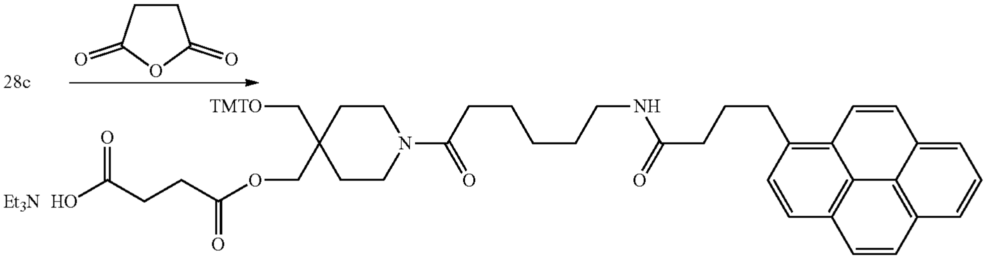

36c

Triethylammonium 4-((4-((bis(4-methoxyphenyl)(phenyl)methoxy)methyl)-1-(6-(4-(pyren-1-yl)butanamido)hexanoyl)piperidin-4-yl)methoxy)-4-oxobutanoate 36c Compound 28c (0.775 g, 0.900 mmol), succinic anhydride (0.80 g, 8 mmol), and pyridine (5 mL) were stirred at room temperature for 10 days. The reaction mixture was quenched with water (0.4 mL) and triethylamine (1 mL) for 4 h, evaporated to oil, diluted with DCM (100 mL), and washed with 10% aqueous citric acid. Organic phase was basified with triethylamine (0.2 mL), dried over $Na_2SO_4$, and evaporated. The product was isolated on a preparative TLC plate (1% $Et_3N$, 2.5% MeOH, DCM) to yield 36c (823 g, 86.1%).

Example 92

28d

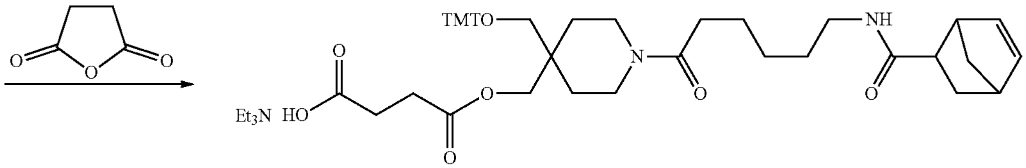

36d

Triethylammonium 4-((1-(6-(bicyclo[2.2.1]hept-5-ene-2-carboxamido)hexanoyl)-4-((tris(4-methoxyphenyl)methoxy)methyl)piperidin-4-yl)methoxy)-4-oxobutanoate 36d Compound 28d (0.355 g, 0.9 mmol), succinic anhydride (0.90 g, 9 mmol) and pyridine (2.42 g) were stirred at room temperature for 5 days. The reaction mixture was quenched with water (1 mL) and triethylamine (1 mL) for 4 h, evaporated to oil, diluted with DCM (100 mL), and washed with 10% aqueous citric acid. Organic phase was basified with triethylamine (1 mL), dried over $Na_2SO_4$, and evaporated. The product was isolated on a silica gel column (1% $Et_3N$, 0-5% MeOH, DCM) to yield 36d (0.421 g, 92.3%).

Example 93

28e

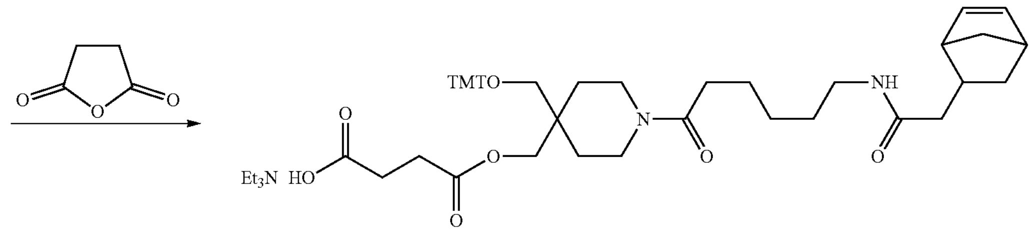

36e

Triethylammonium 4-((1-(6-(2-(bicyclo[2.2.1]hept-5-en-2-yl)acetamido)hexanoyl)-4-((tris(4-methoxyphenyl)methoxy)methyl)piperidin-4-yl)methoxy)-4-oxobutanoate 36e Compound 28e (0.544 g, 0.75 mmol), succinic anhydride (0.750 g, 7.5 mmol) and pyridine (2.42 g) were stirred at room temperature for 5 days. The reaction mixture was quenched with water (1 mL) and triethylamine (1 mL) for 4 h, evaporated to oil, diluted with DCM (100 mL), and washed with 10% aqueous citric acid. Organic phase was basified with triethylamine (1 mL), dried over $Na_2SO_4$, and evaporated. The product was isolated on a silica gel column (1% $Et_3N$, 0-5% MeOH, DCM) to yield 36e (0.579 g, 83.4%).

Example 94

28f

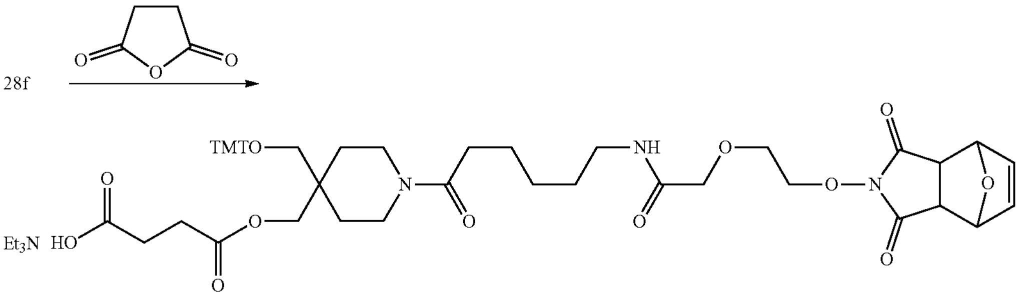

36f

Triethylammonium 4-((1-(6-(2-(2-((1,3-dioxo-1,3,3a,4,7,7a-hexahydro-2H-4,7-epoxyisoindol-2-yl)oxy)ethoxy)acetamido)hexanoyl)-4-((tris(4-methoxyphenyl) methoxy)methyl)piperidin-4-yl)methoxy)-4-oxobutanoate 36f Compound 28f (0.942 g, 1.1 mmol), succinic anhydride (1.10 g, 11 mmol) and pyridine (2.42 g) were stirred at room temperature for 5 days. The reaction mixture was quenched with water (1 mL) and triethylamine (1 mL) for 4 h, evaporated to oil, diluted with DCM (100 mL), and washed with 10% aqueous citric acid. Organic phase was basified with triethylamine (1 mL), dried over $Na_2SO_4$, and evaporated. The product was isolated on a silica gel column (1% $Et_3N$, 0-5% MeOH, DCM) to yield 36f (0.978 g, 84.1%).

Example 95

28g

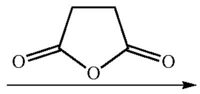

-continued

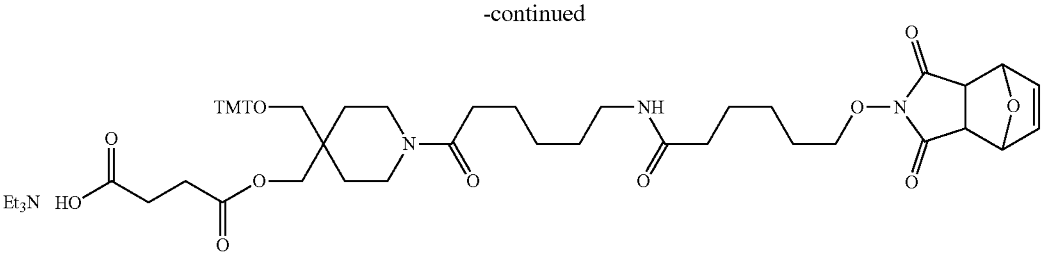

36g

Triethylammonium 4-((1-(6-(6-((1,3-dioxo-1,3,3a,4,7,7a-hexahydro-2H-4,7-epoxyisoindol-2-yl)oxy)hexanamido)hexanoyl)-4-((tris(4-methoxyphenyl)methoxy)methyl)piperidin-4-yl)methoxy)-4-oxobutanoate 36 g Compound 28g (0.868 g, 1.0 mmol), succinic anhydride (1.0 g, 10 mmol) and pyridine (2.42 g) were stirred at room temperature for 5 days. The reaction mixture was quenched with water (1 mL) and triethylamine (1 mL) for 4 h, evaporated to oil, diluted with DCM (100 mL), and washed with 10% aqueous citric acid. Organic phase was basified with triethylamine (1 mL), dried over $Na_2SO_4$, and evaporated. The product was isolated on a silica gel column (1% $Et_3N$, 0-5% MeOH, DCM) to yield 36 g (0.885 g, 82.8%).

Example 96

28h

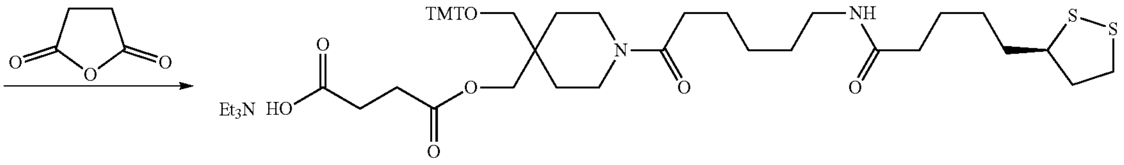

36h

Triethylammonium (R)-4-((1-(6-(5-(1,2-dithiolan-3-yl)pentanamido)hexanoyl)-4-((tris(4-methoxyphenyl)methoxy)methyl)piperidin-4-yl)methoxy)-4-oxobutanoate 36h Compound 28h (0.576 g, 0.74 mmol), succinic anhydride (0.740 g, 7.4 mmol) and pyridine (2.42 g) were stirred at room temperature for 5 days. The reaction mixture was quenched with water (1 mL) and triethylamine (1 mL) for 4 h, evaporated to oil, diluted with DCM (100 mL), and washed with 10% aqueous citric acid. Organic phase was basified with triethylamine (1 mL), dried over $Na_2SO_4$, and evaporated. The product was isolated on a silica gel column (1% $Et_3N$, 0-5% MeOH, DCM) to yield 36h (0.531 g, 73.2%).

Example 97

27i

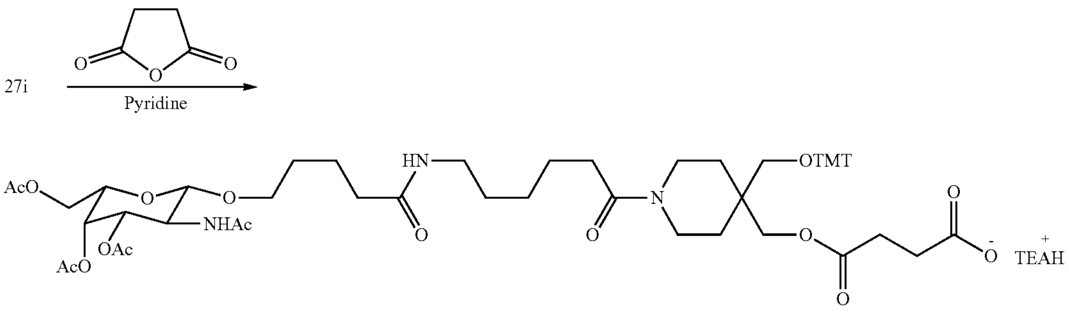

35i

Triethylammonium N—(O-(5-(3,4,6-O-triacetyl-2-acetylamino-2-deoxy-β-D-galactopyranosyl)oxy)pentenoyl)-4-(((4,4'-dimethoxytrityl)oxy)methyl)piperidin-4-yl)methyl hemisuccinate 35i Compound 27i (0.990 g, 1.0 mmol), succinic anhydride (1.00 g, 10 mmol), and pyridine (5.0 mL) were stirred at room temperature for 4 days. The reaction mixture was quenched with water and triethylamine (2 mL) for 4 h, evaporated to an oil, diluted with DCM (50 mL), and washed with 10% aqueous citric acid. The organic phase was basified with triethylamine (4.0 mL), dried over $Na_2SO_4$, and evaporated. The product was isolated on a silica gel column (1% $Et_3N$, 0-4% MeOH in DCM) to yield 35i (1.045 g, 87.7%).

Example 98

28i

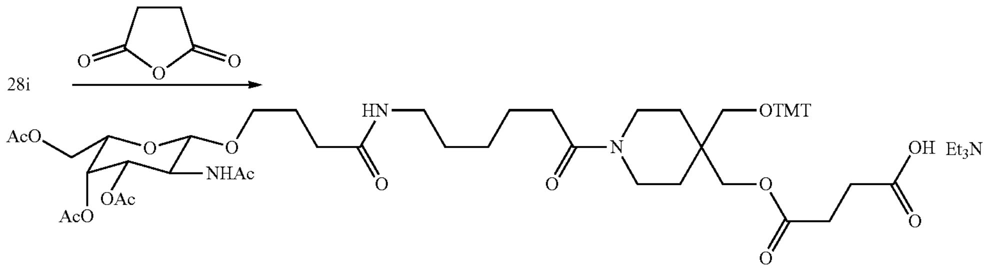

36i (N—(O-(5-(3,4,6-O-triacetyl-2-acetylamino-2-deoxy-β-D-galactopyranosyl)oxy)butanoyl)-4-(((4,4'-dimethoxytrityl)oxy)methyl)piperidin-4-yl)methyl hemisuccinate 36i Compound 28i (0.99 g, 0.984 mmol), succinic anhydride (0.56 g, 5.60 mmol), and pyridine (8.0 mL) were stirred at room temperature for 3 days. The reaction mixture was quenched with water (1 mL, 55.5 mmol) and triethylamine (1.12 g, 11.08 mmol) for 4 h and was co-evaporated with toluene (3×10 mL). The product was isolated on a silica gel column using a step gradient of MeOH (3 to 5%) in a mixture of $Et_3N$ and DCM (1:99) to yield compound 36i (0.874 g, 73.6%).

NMR $H^1$ (δ, $CDCl_3$): 7.26-7.29 (m, 6H), 6.80-6.83 (m, 6H), 6.49 (br. d, J=9.0 Hz, 1H), 6.20 (br. q, J=5.0 Hz, 1H), 5.33 (d, J=3.0 Hz, 1H), 5.14-5.18 (m, 1H), 4.62 (dd, J=8.5, 3.0 Hz, 1H), 4.16-4.22 (m, 2H), 4.02-4.16 (m, 3H), 3.85-3.92 (m, 2H), 3.78 (s, 9H), 3.47-3.68 (m, 3H), 3.45-3.55 (m, 2H), 3.30-3.40 (m, 1H), 3.08-3.15 (m, 1H), 3.00-3.08 (m, 2H), 2.80 (q, J=7.5 Hz, 6H), 2.52-2.57 (m, 2H), 2.45-2.50 (m, 2H), 2.15-2.30 (m, 4H), 2.13 (s, 3H), 2.03 (s, 3H), 1.98 (s, 3H), 1.94 (s, 3H), 1.85-1.91 (m, 2H), 1.54-1.63 (m, 3H), 1.45-1.54 (m, 5H), 1.33-1.40 (m, 2H), 1.14 (t, J=7.5 Hz, 9H).

NMR $C^{13}$ (δ, $CDCl_3$): 177.7, 173.7, 173.2, 171.5, 171.0, 170.7, 170.6, 170.5, 158.6, 136.7, 130.0, 113.3, 101.6, 85.7, 70.9, 70.6, 68.7, 67.0, 66.9, 63.9, 61.7, 55.4, 51.4, 45.5, 41.6, 39.3, 37.6, 37.2, 33.2, 32.9, 31.8, 30.9, 30.2, 29.5, 29.3, 26.7, 26.0, 24.9, 24.7, 23.6, 20.9, 20.9, 9.9.

Example 99

27j

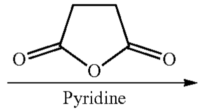

-continued

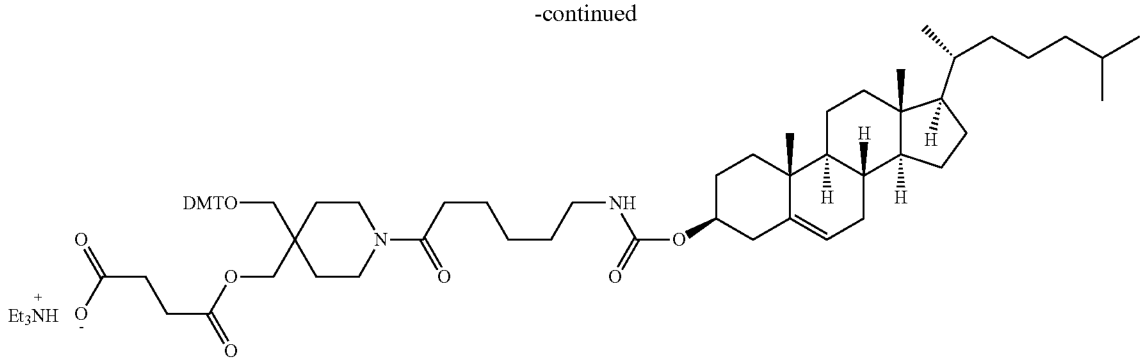

35j

Triethylammonium 4-{[4-{[bis(4-methoxyphenyl)(phenyl)methoxy]methyl}-1-(6-{[(cholest-5-en-3-yloxy)carbonyl]amino}hexanoyl)piperidin-4-yl]methoxy}-4-oxobutanoate 35j Compound 27j (0.157 g, 0.162 mmol), succinic anhydride (0.467 g, 4.66 mmol), and pyridine (2 mL) were stirred at room temperature for 5 days. The reaction mixture was quenched with water (0.2 mL, 11.1 mmol) and triethylamine (1.62 mL, 11.65 mmol) for 4 h, evaporated to oil, diluted with DCM (100 mL), and washed with 10% aqueous citric acid. Organic phase was basified with triethylamine (0.2 mL), dried over $Na_2SO_4$, and evaporated. The product was isolated on a preparative TLC plate (1% $Et_3N$, 3% MeOH, DCM) to yield 35j (0.140 g, 73.7%).

NMR $H^1$ (δ, DMSO-$d_6$): 7.35-7.37 (m, 2H), 7.29-7.33 (m, 2H), 7.20-7.24 (m, 5H), 7.00 (t, J=5.5 Hz, 1H, NH), 6.88-6.90 (m, 4H), 5.32 (m, 1H), 4.26-4.31 (m, 1H), 4.11 (s, 2H), 3.73 (s, 6H), 3.26-3.40 (br. m, 2H), 3.02-3.15 (br. m, 2H), 2.95 (br.s, 2H), 2.90-2.95 (m, 2H), 2.43 (q, J=7.0 Hz, 6H), 2.33-2.38 (m, 2H), 2.14-2.33 (m, 2H), 2.19 (t, J=7.5 Hz, 2H), 1.72-2.00 (m, 5H), 1.45-1.56 (m, 6H), 1.25-1.45 (m, 15H), 1.16-1.25 (m, 4H), 0.85-1.16 (m, 8H), 0.93 (t, J=7.0 Hz, 9H), 0.96 (s, 3H), 0.89 (d, J=6.5 Hz, 3H), 0.85 (d, J=7.0 Hz, 3H), 0.84 (d, J=7.0 Hz, 3H), 0.65 (s, 3H).

Example 100

28j

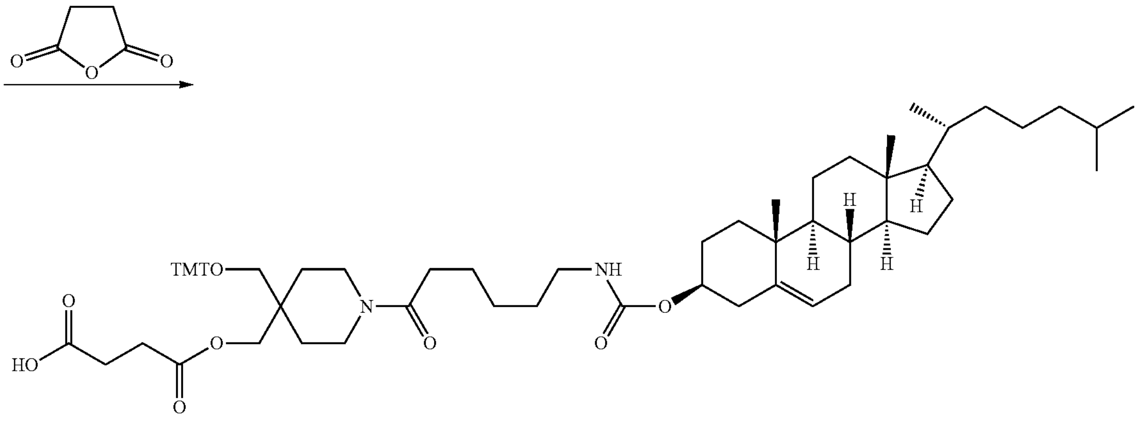

36j

Triethylammonium 4-{[4-{[tris(4-methoxyphenyl)methoxy]methyl}-1-(6-{[(cholest-5-en-3-yloxy)carbonyl]amino}hexanoyl)piperidin-4-yl]methoxy}-4-oxobutanoate 36j Compound 28j (0.903 g, 0.9 mmol), succinic anhydride (0.9 g, 9 mmol), and pyridine (2 mL) were stirred at room temperature for 5 days. The reaction mixture was quenched with water (0.5 mL) and triethylamine (0.5 mL) for 4 h, evaporated to oil, diluted with DCM (100 mL), and washed with 10% aqueous citric acid. Organic phase was basified with triethylamine (0.5 mL), dried over $Na_2SO_4$, and evaporated. The product was isolated on a preparative TLC plate (1% $Et_3N$, 3% MeOH, DCM) to yield 36j (0.842 g, 77.7%).

Example 101

28k

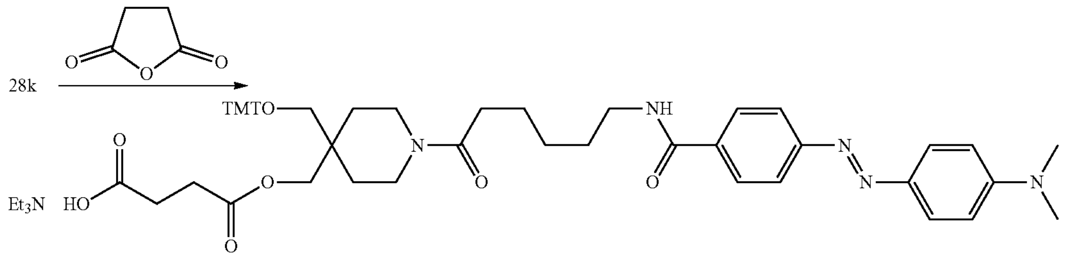

36k

Triethylammonium (E)-4-((4-((tris(4-methoxyphenyl)methoxy)methyl)-1-(6-(4-((4-(dimethylamino)phenyl)diazenyl)benzamido)hexanoyl)piperidin-4-yl)methoxy)-4-oxobutanoate 36k Compound 28k (0.632 g, 0.75 mmol), succinic anhydride (0.588 g, 5.87 mmol) and pyridine (3.0 mL) were stirred at room temperature for 6 days. The reaction mixture was quenched with water and triethylamine (0.5 mL), evaporated to oil, diluted with DCM (100 mL), and washed with 10% aqueous citric acid. Organic phase was basified with triethylamine (0.2 mL), dried over $Na_2SO_4$, and evaporated. The residue was separated on a silica gel column (1% $Et_3N$, 0-5% MeOH, DCM) to yield 36k (0.641 g, 81.9%).

Example 102

27m

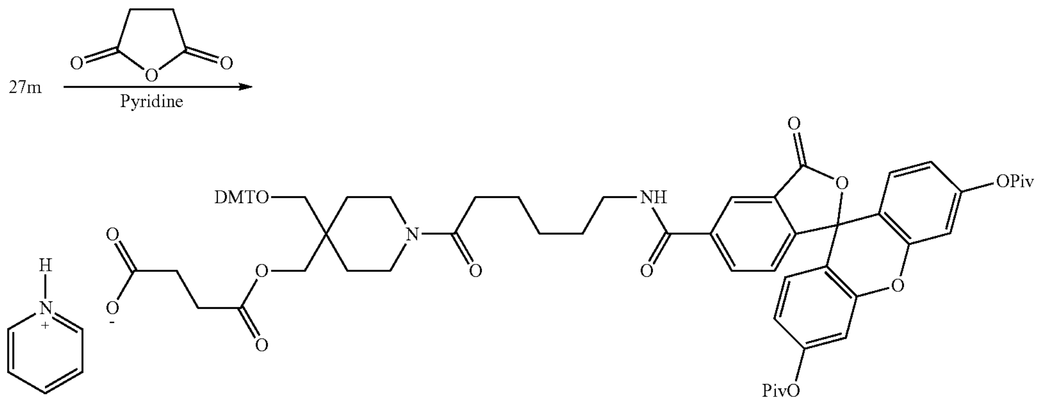

35m

Pyridin-1-ium 4-((4-((bis(4-methoxyphenyl)(phenyl)methoxy)methyl)-1-(6-(3-oxo-3',6'-bis(pivaloyloxy)-3H-spiro[isobenzofuran-1,9'-xanthen]-6-ylcarboxamido)hexanoyl)piperidin-4-yl)methoxy)-4-oxobutanoate 35m Compound 27m (0.221 g, 0.200 mmol), succinic anhydride (0.159 g, 1.59 mmol), and of pyridine (1 mL) were stirred at room temperature for 2 weeks. The reaction mixture was quenched with excess saturated solution of sodium bicarbonate for 4 h, evaporated to oil, diluted with DCM (100 mL), and washed with 10% aqueous citric acid. The organic phase was dried over $Na_2SO_4$, concentrated, and the residue was separated on a silica gel column (0.5% pyridine, 1→5% MeOH, DCM) to yield 35m (0.184 g, 72.6%).

NMR $H^1$ (δ, $CDCl_3$): 8.61 (m, 1.15H, Py), 8.14, 8.15 (AB, J=8.0 Hz, 2H), 7.70 (m, 0.56H, Py), 7.56 (s, 1H), 7.38-7.41 (m, 2H), 7.27-7.33 (m, 7.15H), 7.19-7.21 (m, 1H), 6.98-7.00 (m, 2H), 6.99 (t, J=5.0 Hz, 1H, NH), 6.74-6.83 (m, 8H), 4.16, 4.29 (AB, J=11.0 Hz, 2H), 3.78 (s, 6H), 3.58-3.65 (m, 1H), 3.32-3.48 (m, 3H), 3.00-3.15 (m, 4H), 2.51-2.60 (m, 4H), 2.20-2.35 (m, 2H), 1.36-1.65 (m, 10H) 1.35 (s, 18H).

NMR $C^{13}$ (δ, $CDCl_3$): 176.8, 174.2, 173.0, 172.9, 168.8, 165.7, 158.7, 153.6, 153.0, 151.8, 149.6, 145.0, 142.5, 136.5, 136.1, 130.3, 129.6, 129.1, 128.4, 128.0, 127.1, 125.7, 124.1, 122.9, 118.1, 118.8, 113.3, 110.6, 86.1, 83.0, 67.1, 64.2, 55.4, 41.8, 39.7, 39.4, 37.9, 37.5, 32.9, 30.1, 29.5, 28.9, 28.9, 28.6, 27.3, 26.3, 23.8.

Example 103

28m

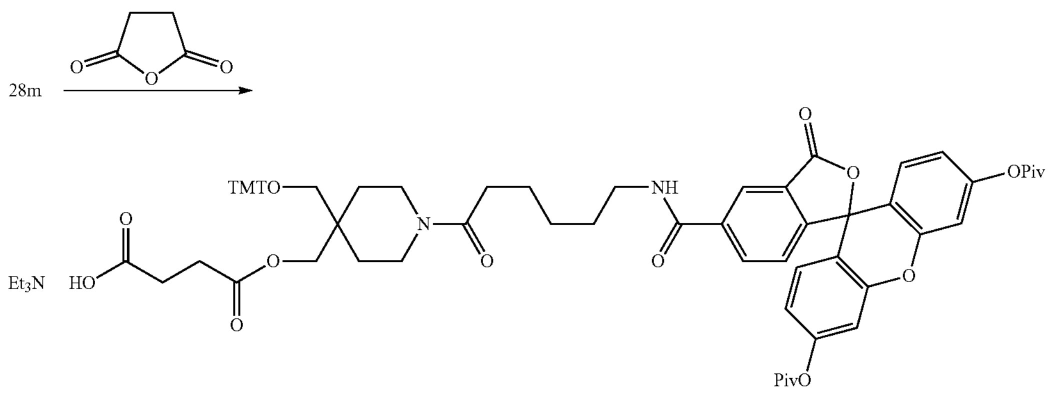

36m

Triethylammonium 4-oxo-4-((1-(6-(3-oxo-3',6'-bis (pivaloyloxy)-3H-spiro[isobenzofuran-1,9'-xanthene]-5-carboxamido)hexanoyl)-4-((tris(4-methoxyphenyl)methoxy)methyl) piperidin-4-yl)methoxy) butanoate 36m Compound 28m (1.676 g, 1.50 mmol), succinic anhydride (1.50 g, 15 mmol), and of pyridine (15 mL) were stirred at room temperature for 1 week. The reaction mixture was quenched with excess saturated solution of sodium bicarbonate for 4 h, evaporated to oil, diluted with DCM (100 mL), and washed with 10% aqueous citric acid. The organic phase was dried over $Na_2SO_4$, concentrated, and the residue was separated on a silica gel column (0.5% pyridine, 1→5% MeOH, DCM) to yield 36m (1.271 g, 64.3%).

Example 104

28n

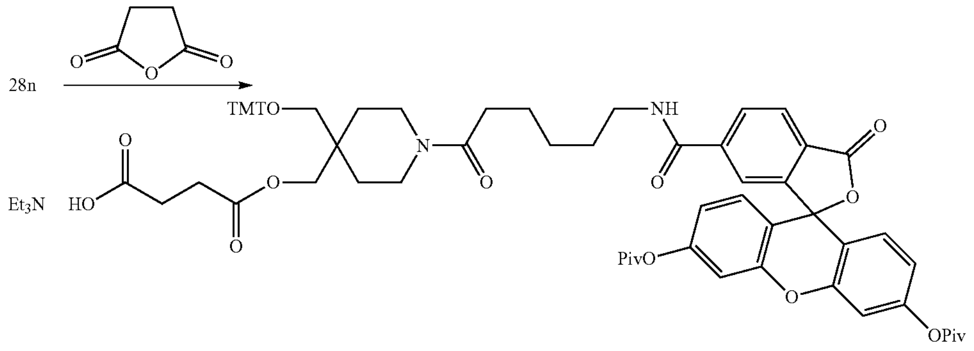

36n

Triethylammonium 4-oxo-4-((1-(6-(3-oxo-3',6'-bis (pivaloyloxy)-3-spiro[isobenzofuran-1,9'-xanthene]-5-carboxamido)hexanoyl)-4-((tris(4-methoxyphenyl) methoxy)methyl) piperidin-4-yl)methoxy)butanoate 36n Compound 28n (1.676 g, 1.50 mmol), succinic anhydride (1.50 g, 15 mmol), and of pyridine (15 mL) were stirred at room temperature for 1 week. The reaction mixture was quenched with excess saturated solution of sodium bicarbonate for 4 h, evaporated to oil, diluted with DCM (100 mL), and washed with 10% aqueous citric acid. The organic phase was dried over $Na_2SO_4$, concentrated, and the residue was separated on a silica gel column (0.5% pyridine, 1→5% MeOH, DCM) to yield 36n (1.323 g, 66.9%).

Example 105

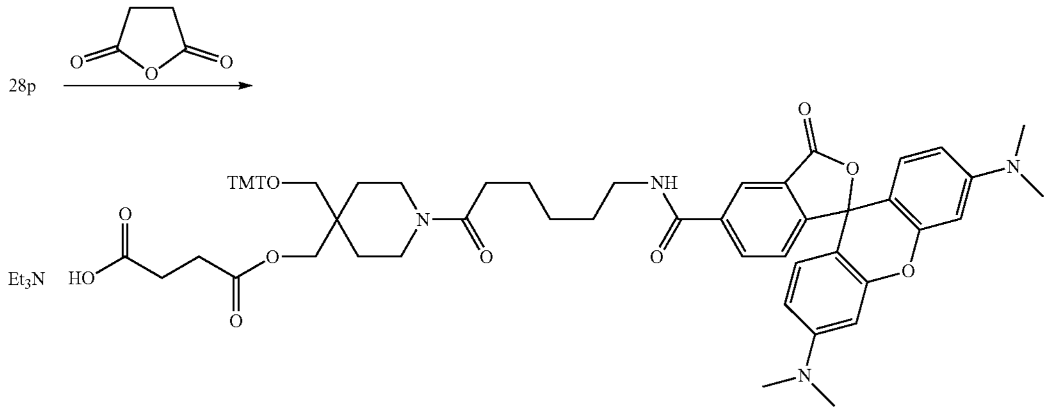

36p

Triethylammonium 4-((1-(6-(3',6'-bis(dimethylamino)-3-oxo-3-spiro[isobenzofuran-1,9'-xanthene]-5-carboxamido)hexanoyl)-4-((tris(4-methoxyphenyl) methoxy)methyl)piperidin-4-yl)methoxy)-4-oxobutanoate 36p Compound 28p (0.662 g, 0.66 mmol), succinic anhydride (0.70 g, 7 mmol), and of pyridine (5 mL) were stirred at room temperature for 1 week. The reaction mixture was quenched with excess saturated solution of sodium bicarbonate for 4 h, evaporated to oil, diluted with DCM (100 mL), and washed with 10% aqueous citric acid. The organic phase was dried over $Na_2SO_4$, concentrated, and the residue was separated on a silica gel column (0.5% pyridine, 1→5% MeOH, DCM) to yield 36p (433 g, 54.5%).

Example 106

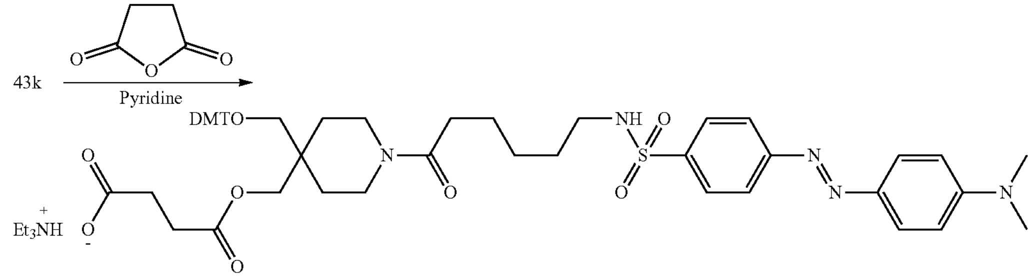

51k

Triethylammonium (E)-4-((4-((bis(4-methoxyphenyl)(phenyl)methoxy)methyl)-1-(6-(4-((4-(dimethylamino)phenyl)diazenyl)phenylsulfonamido) hexanoyl)piperidin-4-yl)methoxy)-4-oxobutanoate 51k Compound 43k (0.277 g, 0.334 mmol), succinic anhydride (0.77 g, 7.69 mmol) and pyridine (3.0 mL) were stirred at room temperature for 4 days. The reaction mixture was quenched with water (0.346 mL, 19.23 mmol), and triethylamine (1.90 g, 19.22 mmol) for 4 h, evaporated to oil, diluted with DCM (100 mL), and washed with 10% aqueous citric acid. The organic phase was basified with triethylamine (0.4 mL), dried over $Na_2SO_4$, and evaporated. The product was isolated on a silica gel column (1% $Et_3N$, 0-5% MeOH, DCM) to yield 51k (0.249 g, 65.7%).

Example 107

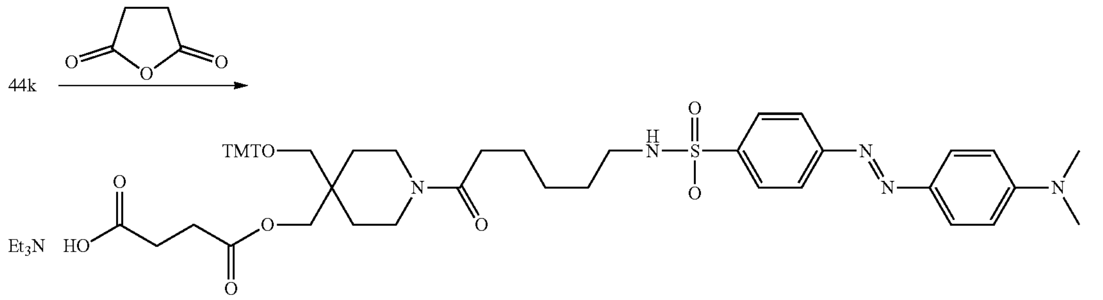

44k

52k

Triethylammonium (E)-4-((4-((bis(4-methoxyphenyl)(phenyl)methoxy)methyl)-1-(6-(4-((4-(dimethylamino)phenyl)diazenyl)phenylsulfonamido)hexanoyl)piperidin-4-yl)methoxy)-4-oxobutanoate 52k Compound 44k (0483 g, 0.55 mmol), succinic anhydride (0.55 g, 5.5 mmol) and pyridine (3.0 mL) were stirred at room temperature for 6 days. The reaction mixture was quenched with water (0.5 mL), and triethylamine (0.5 mL) for 4 h, evaporated to oil, diluted with DCM (100 mL), and washed with 10% aqueous citric acid. The organic phase was basified with triethylamine (0.4 mL), dried over $Na_2SO_4$, and evaporated. The product was isolated on a silica gel column (1% $Et_3N$, 0-5% MeOH, DCM) to yield 52k (0.440 g, 74.1%).

Example 108

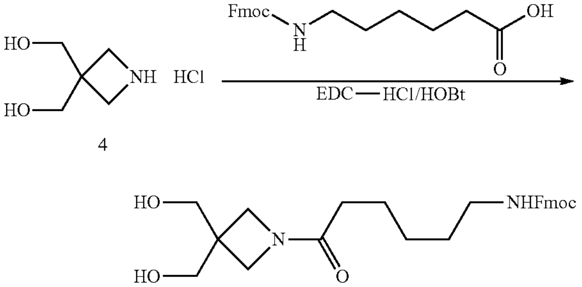

4

6a (9H-fluoren-9-yl)methyl (6-(3,3-bis(hydroxymethyl)azetidin-1-yl)-6-oxohexyl)carbamate 6a A solution of N-Fmoc-6-aminohexanoic acid (Chem Impex International, Inc., 2.208 g, 6.25 mmol), N-hydroxybenzotriazole (HOBt, 1.148 g, 7.5 mmol) and EDC-HCl (1.438 g, 7.5 mmol) in DCM (17 mL) was stirred at room temperature for 30 min. Azetidine-2,2-dimethanol hydrochloride 4 (A2Z Chemicals, Irvine, Calif., 1.00 g, 6.51 mmol) and DIPEA (1.939 g, 15.62 mmol) were added at 0° C. The reaction mixture was stirred for 18 h at room temperature, washed with 5% $NaHCO_3$, 5% HCl, and brine. The extract was dried over $Na_2SO_4$ and evaporated. The crude product was purified on a silica gel column (2% AcOH, 2-10% MeOH, DCM) to give 2.015 g (68.03%) of compound 6a as a white solid foam.

NMR H[1] (δ, $CDCl_3$): 7.76-7.74 (m, 2H), 7.57-7.59 (m, 2H), 7.36-7.40 (m, 2H), 7.25-7.30 (m, 2H), 5.06 (br. t, J=5 Hz, 1H), 4.37 (d, J=7.0 Hz, 2H), 4.20 (t, J=6.5 Hz, 1H), 3.88 (s, 2H), 3.80 (s, 4H), 3.70 (s, 2H), 3.18 (q, J=6.5 Hz, 2H), 2.08 (m, 2H), 1.33-1.60 (m, 6H).

NMR C[13] (δ, $CDCl_3$): 174.0, 156.9, 144.2, 141.5, 127.9, 127.3, 125.3, 120.2, 66.8, 66.0, 54.9, 52.4, 47.5, 41.1, 39.7, 31.2, 26.5, 24.6.

Example 109

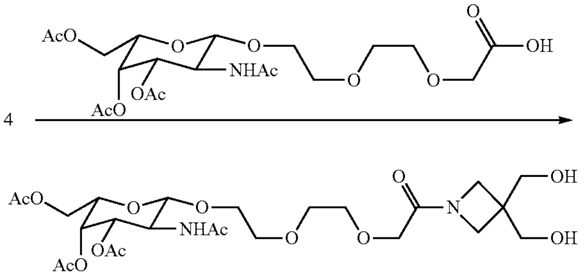

4

6k

N-(8-((3,4,6-O-triacetyl-2-acetylamino-2-deoxy-β-D-galactopyranosyl)oxy)-3,6-dioxaoctanoyl)-3,3-bis(hydroxymethyl)azetidine 6k A solution of 8-((3,4,6-O-triacetyl-2-acetylamino-2-deoxy-β-D-galactopyranosyl)oxy)-3,6-dioxaoctanoic acid (4.93 g, 10 mmol), N-hydroxybenzotriazole (HOBt, 1.837 g, 12 mmol) and EDC-HCl (2.300 g, 12 mmol) in DMF (40 mL) was stirred at room temperature for 30 min. Compound 4 (1.464 g, 12.5 mmol) and DIPEA (3.102 g, 24 mmol) were added at 0° C. The reaction mixture was stirred for 18 h at room temperature, diluted with ethyl acetate (200 mL), washed with 5% $NaHCO_3$, 5% HCl, brine. The extract was dried over $Na_2SO_4$ and evaporated. The crude product was purified on a silica gel column (2% AcOH, 2-10% MeOH, DCM), to give 5.948 g (80.3%) of diol 6k as a white solid.

Example 110

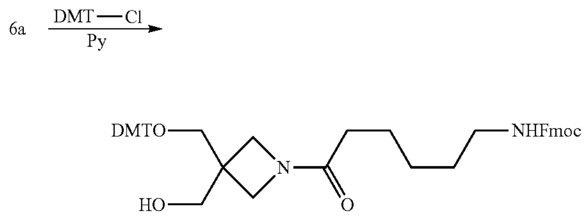

9a (9H-fluoren-9-yl)methyl (6-(3-((bis(4-methoxyphenyl)(phenyl)methoxy)methyl)-3-(hydroxymethyl)azetidin-1-yl)-6-oxohexyl)carbamate 9a DMT-Cl (1.359 g, 4.01 mmol) was gradually added to a stirred solution of compound 6a (1.80 g, 3.98 mmol) in pyridine (15 mL) over 4 h at 0° C., and stirring was continued at room temperature for 72 h. The reaction mixture was concentrated, co-evaporated with toluene, and distributed between triethylammonium bicarbonate buffer (pH 7.19) and ethyl acetate. The aqueous layer was additionally extracted with ethyl acetate (2×50 mL). The combined organic phase was dried over $Na_2SO_4$, concentrated, and separated on a silica gel column (0-3% MeOH, DCM) to yield compound 9a (1.246 g, 41.3%). Fractions containing a bis-DMT side product and the unreacted diol 6a were mixed together, treated with TFA, evaporated, co-evaporated with toluene and pyridine, dissolved in pyridine and treated with an appropriate amount of DMT-C1. Workup and purification as disclosed above gave additional amount compound 9a (0.742 g) in a total yield of 1.951 g (64.9%).

NMR $H^1$ (δ, $CDCl_3$): 7.74-7.76 (m, 2H), 7.58-7.60 (m, 2H), 7.38-7.40 (m, 4H), 7.20-7.37 (m, 9H), 6.80-6.85 (m, 4H), 4.94 (br. s, 1H), 4.39 (d, J=7.0 Hz, 2H), 4.20 (t, J=7.0, 1H), 3.92 (d, J=8.5 Hz, 1H), 3.67-3.82 (m, 11H), 3.31, 3.35 (AB, J=9.5 Hz, 2H), 3.17-3.19 (m, 2H), 2.31 (br. s, 1H), 2.03-2.07 (m, 2H), 1.55-1.65 (m, 2H), 1.46-1.52 (m, 2H), 1.30-1.40 (m, 2H).

NMR $C^{13}$ (δ, $CDCl_3$): 173.6, 158.9, 156.7, 144.7, 144.3, 141.6, 135.8, 130.2, 128.3, 128.2, 127.9, 127.2, 125.3, 120.2, 113.5, 86.6, 66.7, 66.0, 66.0, 55.4, 55.0, 52.6, 47.6, 41.0, 39.1, 31.3, 29.9, 26.6, 24.5.

Example 111

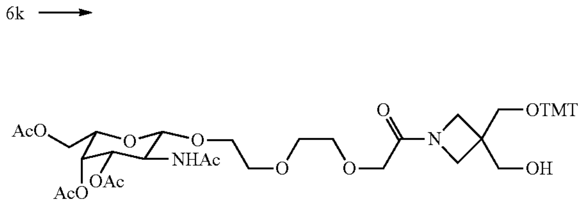

10k

N-(8-((3,4,6-O-triacetyl-2-acetylamino-2-deoxy-j-D-galactopyranosyl)oxy)-3,6-dioxaoctanoyl)-3-(hydroxymethyl)-3-((tris-(4-methoxyphenyl)methoxy)methyl)azetidine 10k Trimethoxytrityl chloride (1.85 g, 5 mmol) was gradually added to a stirred solution of compound 6k (2.963 g, 5 mmol) in pyridine (30 mL) over 4 h at 0° C., and stirring was continued at room temperature for 72 h. The reaction mixture was concentrated, co-evaporated with toluene, and distributed between triethylammonium bicarbonate buffer (pH 7.19) and ethyl acetate. The aqueous layer was additionally extracted with ethyl acetate (2×50 mL). The combined organic phase was dried over $Na_2SO_4$, concentrated, and separated on a silica gel column (0-3% MeOH, DCM) to yield compound 10k (2.567 g, 55.5%).

Example 112

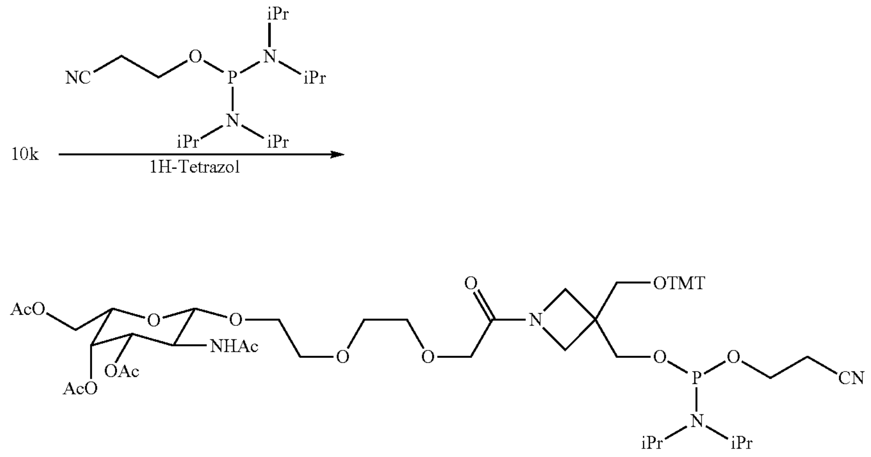

14k (N-(8-((3,4,6-O-triacetyl-2-acetylamino-2-deoxy-β-D-galactopyranosyl)oxy)-3,6-dioxaoctanoyl)-3-(((4,4',4"-trimethoxytrityl)oxy)methyl)azetidin-3-yl) methyl (2-cyanoethyl) diisopropylphosphoramidite 14k Compound 10k (0.675 g, 0.73 mmol) and 2-cyanoethyl N,N,N',N'-tetraisopropylphosphorodiamidite (0.286 g, 0.95 mmol) were dissolved in anhydrous acetonitrile (15 mL), and the mixture was shaken with flame-dried molecular sieves 4 Å for 1 h. This was cooled to −10° C., 1H-tetrazole (0.45M, 0.365 mmol, 0.81 mL) in acetonitrile was added, and the mixture was stirred overnight. The reaction mixture was quenched with triethylamine (0.5 mL) and was diluted with saturated aqueous sodium bicarbonate. The product was extracted with DCM, and the organic extract was dried over $Na_2SO_4$ and was evaporated to dryness. The crude product was purified on a silica gel column (5% $Et_3N$, 20-80% ethyl acetate in hexanes) to yield 14k (0.692 g, 84.2%) as a white solid foam.

Example 113

Example 114

6-amino-1-(3-((bis(4-methoxyphenyl)(phenyl)methoxy)methyl)-3-(hydroxymethyl)azetidin-1-yl)hexan-1-one 25

Compound 9a (1.93 g, 2.56 mmol) was treated with a solution of piperidine in MeOH (10% 100 mL) overnight. The reaction mixture was evaporated, co-evaporated with xylenes, and separated on a silica gel column (1% $NH_4OH$, 0-12% MeOH in DCM) to give pure compound 25 (1.244 g, 91.2%) as a white solid foam.

NMR H1 (δ, $CDCl_3$): 7.37-7.39 (m, 2H), 7.24-7.28 (m, 6H), 7.17-7.21 (m, 1H), 6.79-6.82 (m, 4H), 3.94 (d, J=8.5 Hz, 1H), 3.66-3.80 (m, 11H), 3.25, 3.29 (AB, J=9.5 Hz, 2H), 2.94 (br. s, 3H), 2.67 (t, J=7.0 Hz, 2H), 2.01-2.07 (m, 2H), 1.55-1.61 (m, 2H), 1.42-1.48 (m, 2H), 1.30-1.36 (m, 2H).

NMR $C^{13}$ (δ, $CDCl_3$): 173.7, 158.7, 144.7, 135.8, 130.2, 128.2, 128.0, 127.1, 113.4, 86.3, 65.4, 65.0, 55.3, 54.7, 52.4, 41.7, 39.3, 32.6, 31.3, 26.6, 24.6.

10k

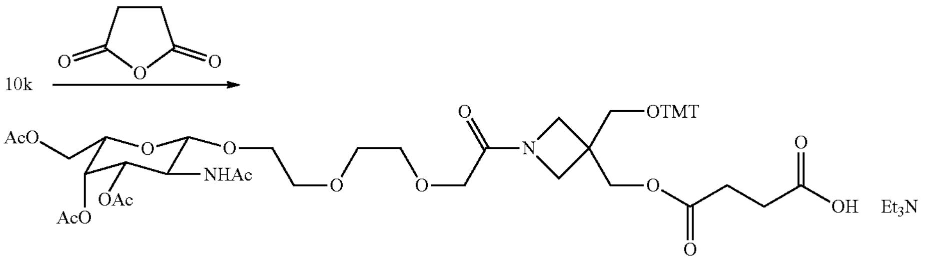

18k

Triethylammonium (N-(8-((3,4,6-O-triacetyl-2-acetylamino-2-deoxy-β-D-galactopyranosyl)oxy)-3,6-dioxaoctanoyl)-3-(((4,4',4"-trimethoxytrityl)oxy)methyl)azetidin-3-yl)methoxy)-4-oxobutanoate 18k Compound 10k (0.499 g, 0.54 mmol), succinic anhydride (0.540 g, 5.4 mmol) and pyridine (2.0 mL) were stirred at room temperature for 5 days. The reaction mixture was quenched with water and triethylamine (0.4 mL) for 4 h, evaporated to oil, diluted with DCM (100 mL), and washed with 10% aqueous citric acid. Organic phase was basified with triethylamine (0.2 mL), dried over $Na_2SO_4$, and evaporated. The residue was separated on a silica gel column (1% $Et_3N$, 0-5% MeOH, DCM) to yield 18k (0.535 g, 88.2%).

Medina, Scott H.; Tekumalla, Venkatesh; Chevliakov, Maxim V.; et al. Biomaterials (2011), 32(17), 4118-4129 • Nishimura, S.; Sato, M.; Furuike, T. From PCT Int. Appl. (2004), WO 2004101619 A1 20041125.

9a

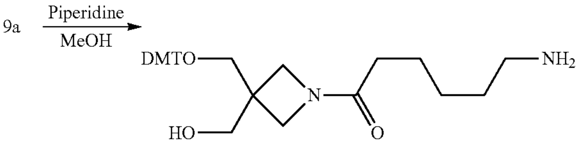

25

Example 115

25

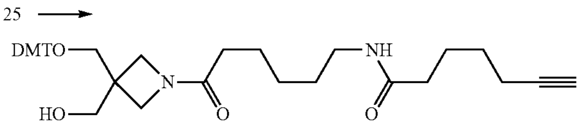

29b

N-(6-(3-((bis(4-methoxyphenyl)(phenyl)methoxy)methyl)-3-(hydroxymethyl)azetidin-1-yl)-6-oxohexyl)hept-6-ynamide 29b Hept-6-ynoic acid (TCI America, 0.242 g, 1.92 mmol), HOBt (0.294 g, 1.92 mmol) and EDC-HCl (0.368 g, 2.304 mmol) were dissolved in DCM (5 mL) and stirred at room temperature for 30 min. This mixture was added to the solution of compound 25 (1.208 g, 1.60 mmol) and DIPEA (0.496 g, 3.84 mmol) in DCM (15 mL) at 0° C. The reaction mixture was stirred for 18 h at room temperature and was diluted with DCM (50 mL). The obtained solution was washed with 5% $NaHCO_3$ and brine and was dried over $Na_2SO_4$. The extract was evaporated, and the residue was separated on a silica gel column (1-5% MeOH, DCM) to give 0.653 g (63.7%) compound 29b as a white solid foam.

NMR $H^1$ (δ, $CDCl_3$): 7.37-7.39 (m, 2H), 7.25-7.29 (m, 6H), 7.18-7.20 (m, 1H), 6.79-6.83 (m, 4H), 5.99 (br. t, J=5.5 Hz, 1H), 3.94 (d, J=8.5 Hz, 1H), 3.66-3.80 (m, 11H), 3.27, 3.31 (AB, J=9.5 Hz, 2H), 3.17-3.23 (m, 2H), 2.13-2.20 (m, 4H), 2.01-2.07 (m, 2H), 1.92 (t, J=3.0 Hz, 1H), 1.70-1.74 (m, 2H), 1.45-1.56 (m, 6H), 1.30-1.35 (m, 2H).

NMR $C^{13}$ (δ, $CDCl_3$): 173.6, 173.0, 158.8, 144.7, 135.8, 130.4, 128.2, 128.1, 127.1, 113.4, 86.4, 84.3, 68.8, 65.6, 65.4, 55.4, 54.8, 53.6, 39.3, 39.3, 36.2, 31.2, 29.4, 28.1, 26.6, 25.0, 24.4, 18.3.

29b

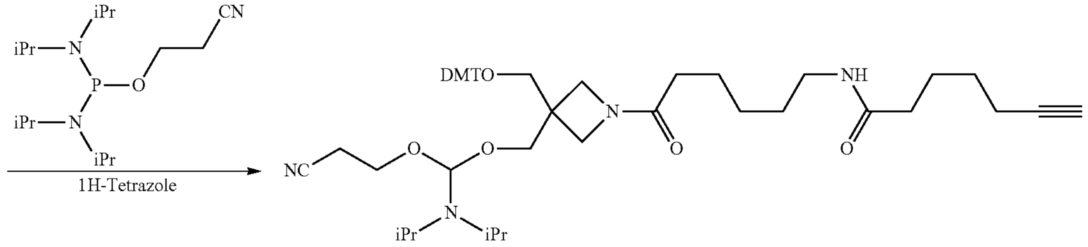

33b

Example 116

2-Cyanoethyl (3-((bis(4-methoxyphenyl)(phenyl)methoxy)methyl)-1-(6-(hept-6-ynamido)hexanoyl)azetidin-3-yl)methyl N,N-diisopropylphosphoramidite 33b Compound 29b (0.513 g, 0.80 mmol) and 2-cyanoethyl N,N,N',N'-tetraisopropylphosphorodiamidite (0.253 g, 0.84 mmol) were dissolved in anhydrous acetonitrile (15 mL), and the mixture was shaken with flame-dried molecular sieves 4 Å for 1 h. This was cooled to −10° C., 1H-tetrazole (0.45M, 0.336 mmol, 0.747 mL) in acetonitrile was added, and the mixture was stirred overnight. The reaction mixture was quenched with triethylamine (0.5 mL) and was diluted with saturated aqueous sodium bicarbonate. The product was extracted with DCM, and the organic extract was dried over $Na_2SO_4$ and was evaporated to dryness. The crude product was purified on a silica gel column (5% $Et_3N$, 20-80% ethyl acetate in hexanes) to yield 33b (0.298 g, 44.3%) as a white solid foam.

Example 117

29b

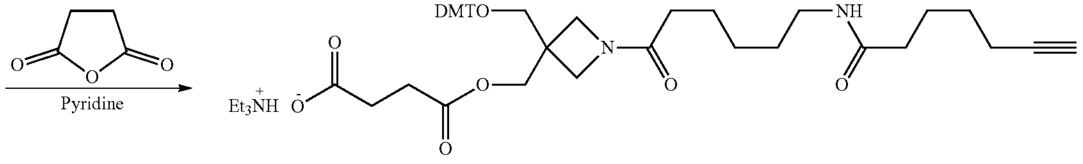

37b

Triethylammonium 4-((4-((bis(4-methoxyphenyl)(phenyl)methoxy)methyl)-1-(6-(hept-6-ynamido)hexanoyl)piperidin-4-yl)methoxy)-4-oxobutanoate 37b Compound 29b (0.096 g, 0.150 mmol), succinic anhydride (0.079 g, 0.79 mmol) and pyridine (0.5 mL) were stirred at room temperature for 4 days. The reaction mixture was quenched with water and triethylamine (0.2 mL) for 4 h, evaporated to an oil, diluted with DCM (50 mL), and washed with 10% aqueous citric acid. The organic phase was treated with triethylamine (0.4 mL), dried over $Na_2SO_4$, and evaporated. The product was isolated on a silica gel column (1% $Et_3N$, 0-6% MeOH, DCM) to yield 37b (0.079 g, 62.6%).

HRESI-MS: calcd for $C_{43}H_{52}N_2O_9Na$, 863.3565 ($MNa^+$); found, 863.3563.

Example 118

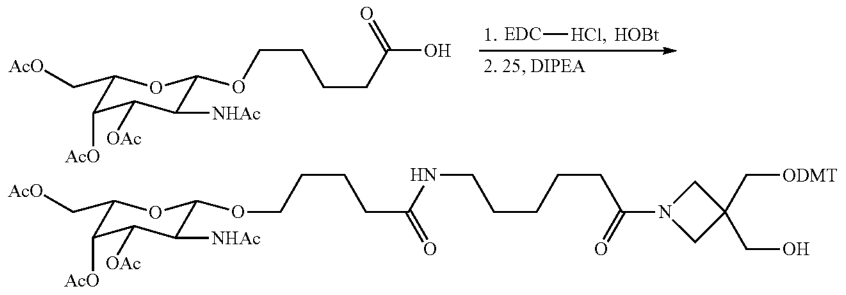

29i

3-Hydroxymethyl-3-(((4,4'-dimethoxytrityl)oxy) methyl)-N-(5-((3,4,6-O-triacetyl-2-acetylamino-2-deoxy-β-D-galactopyranosyl)oxy)butanoyl)azetidine 29i 1-O-(4-carboxybut-1-yl)-3,4,6-O-triacetyl-2-acetylamino-2-deoxy-β-D-galactopyranoside (0.447 g, 1.0 mmol), HOBt (0.184 g, 1.2 mmol) and EDC-HCl (0.230 g, 1.2 mmol) were dissolved in DCM (3 mL) and were stirred at room temperature for 30 min. This mixture was added to the solution of compound 25 (0.533 g, 1.0 mmol) and DIPEA (0.310 g, 2.4 mmol) in 10 ml of DCM at 0° C. The reaction mixture was stirred 18 h at room temperature and was diluted with DCM (50 mL). The obtained solution was washed with 5% $NaHCO_3$ and brine. The organic phase was dried over $Na_2SO_4$ and concentrated. The residue was purified on a silica gel column (1-5% MeOH, DCM) to give 0.725 g (75.4%) compound 29i as a white solid foam.

Example 119

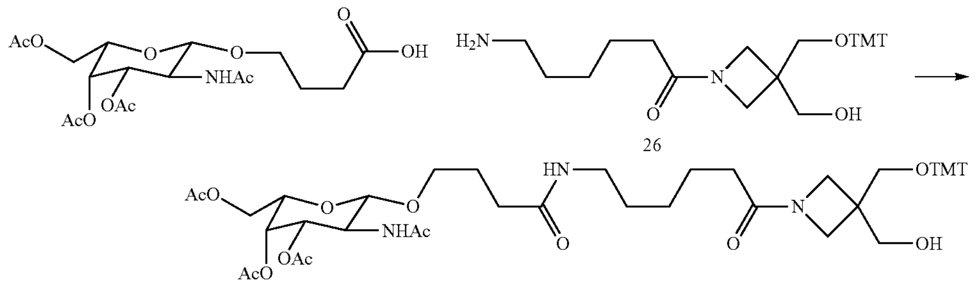

26

30i

3-Hydroxymethyl-3-(((4,4'-dimethoxytrityl)oxy) methyl)-N-(5-((3,4,6-O-triacetyl-2-acetylamino-2-deoxy-β-D-galactopyranosyl)oxy)butanoyl)azetidine 30i 1-O-(4-carboxybut-1-yl)-3,4,6-O-triacetyl-2-acetylamino-2-deoxy-β-D-galactopyranoside (0.447 g, 1.0 mmol), HOBt (0.184 g, 1.2 mmol) and EDC-HCl (0.230 g, 1.2 mmol) were dissolved in DCM (3 mL) and were stirred at room temperature for 30 min. This mixture was added to the solution of compound 26 (0.563 g, 1.0 mmol) and DIPEA (0.310 g, 2.4 mmol) in 10 ml of DCM at 0° C. The reaction mixture was stirred 18 h at room temperature and was diluted with DCM (50 mL). The obtained solution was washed with 5% $NaHCO_3$ and brine. The organic phase was dried over $Na_2SO_4$ and concentrated. The residue was purified on a silica gel column (1-5% MeOH, DCM) to give compound 30i (0.687 g, 70.3%) as a white solid foam.

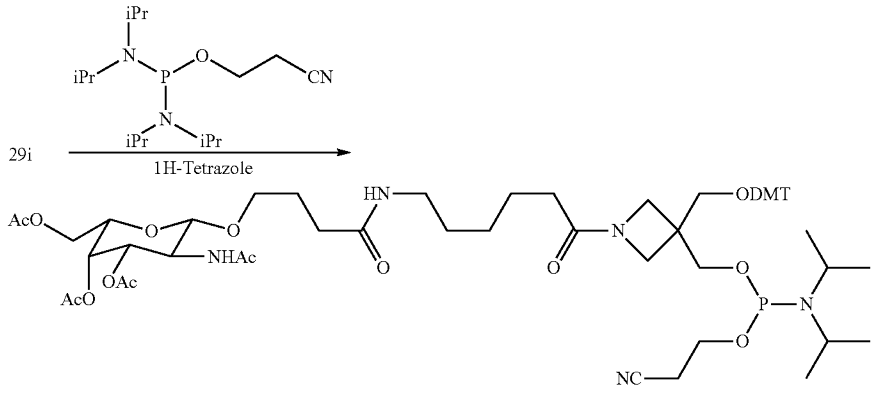

33i

Example 120

2-Cyanoethyl (N—(O-(5-(3,4,6-O-triacetyl-2-acetylamino-2-deoxy-β-D-galactopyranosyl)oxy)pentenoyl)-3-(((4,4'-dimethoxytrityl)oxy)methyl)azetidin-3-yl)methyl N,N-diisopropylamidophosphite 33i Compound 29i (0.962 g, 1.0 mmol) and 2-cyanoethyl N,N,N',N'-tetraisopropylphosphorodiamidite (0.316 g, 1.05 mmol) were dissolved in anhydrous acetonitrile (20 mL), and the mixture was shaken with flame-dried molecular sieves 4 Å for 1 h. Upon cooling to −10° C., 1H-tetrazole (0.45M, 0.40 mmol, 0.889 mL) in acetonitrile was added, and the mixture was stirred overnight. The reaction mixture was quenched with triethylamine (0.5 mL) and diluted with saturated aqueous sodium bicarbonate. The product was extracted with DCM, and the organic extract was dried over $Na_2SO_4$ and evaporated to dryness. The crude product was purified on a silica gel column (5% $Et_3N$, 5-50% ethyl acetate in hexanes) to yield 33i (0.953 g, 83.3%) as a white solid foam.

Example 121

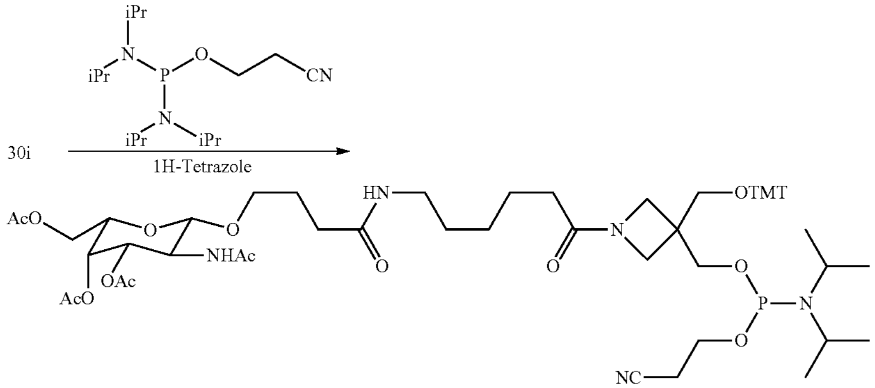

34i

2-Cyanoethyl (N—(O-(5-(3,4,6-O-triacetyl-2-acetylamino-2-deoxy-β-D-galactopyranosyl)oxy)pentenoyl)-3-(((4,4'-dimethoxytrityl)oxy)methyl)azetidin-3-yl)methyl N,N-diisopropylamidophosphite 34i Compound 30i (0.977 g, 1.0 mmol) and 2-cyanoethyl N,N,N',N'-tetraisopropylphosphorodiamidite (0.316 g, 1.05 mmol) were dissolved in anhydrous acetonitrile (20 mL), and the mixture was shaken with flame-dried molecular sieves 4 Å for 1 h. Upon cooling to −10° C., 1H-tetrazole (0.45M, 0.40 mmol, 0.889 mL) in acetonitrile was added, and the mixture was stirred overnight. The reaction mixture was quenched with triethylamine (0.5 mL) and diluted with saturated aqueous sodium bicarbonate. The product was extracted with DCM, and the organic extract was dried over $Na_2SO_4$ and evaporated to dryness. The crude product was purified on a silica gel column (5% $Et_3N$, 5-50% ethyl acetate in hexanes) to yield 34i (1.008 g, 85.6%) as a white solid foam.

Example 122

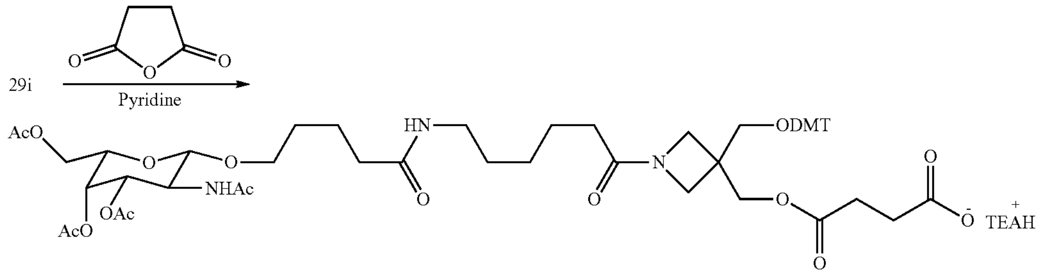

37i (N—(O-(5-(3,4,6-O-triacetyl-2-acetylamino-2-deoxy-β-D-galactopyranosyl)oxy)pentenoyl)-3-(((4,4'-dimethoxytrityl)oxy)methyl)azetidin-3-yl)methyl hemisuccinate 37i Compound 29i (0.962 g, 1.0 mmol), succinic anhydride (1.00 g, 10 mmol), and pyridine (5.0 mL) were stirred at room temperature for 4 days. The reaction mixture was quenched with water and triethylamine (2 mL) for 4 h, evaporated to an oil, diluted with DCM (50 mL), and washed with 10% aqueous citric acid. The organic phase was treated with triethylamine (4.0 mL), dried over $Na_2SO_4$, and evaporated. The product was isolated on a silica gel column (1% $Et_3N$, 0-4% MeOH in DCM) to yield compound 37i (0.985 g, 84.7%).

Example 123

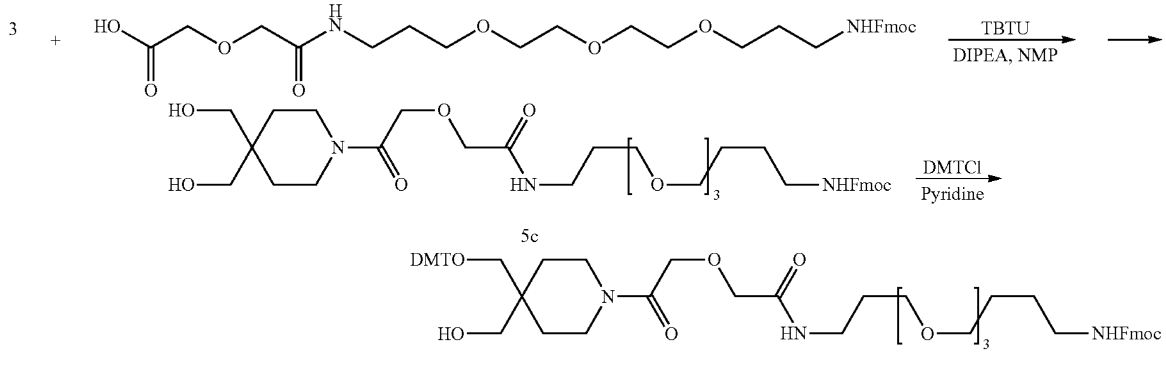

7c

A. (9H-Fluoren-9-yl)methyl (1-(4,4-bis(hydroxymethyl)piperidin-1-yl)-1,5-dioxo-3,10,13,16-tetraoxa-6-azanonadecan-19-yl)carbamate 5c N-[13-((((N-(9H-Fluore-9-yl)methyl)oxy)carbonyl) amino-4,7,10-trioxatridecan-1-yl)malonamic acid (12.00 g, 21.48 mmol, prepared as disclosed in *Eur. J. Med. Chem.* 2007, p. 114), was stirred at room temperature for 0.5 h with DIPEA (9.72 g, 75.2 mmol), TBTU (7.05 g, 21.91 mmol), and NMP (22 g). Compound 3 (4.10 g, 22.57 mmol) was added, and stirring was continued for 18 h. The reaction mixture was diluted with ethyl acetate (300 mL) and extracted with brine (10×50 mL). The organic phase was dried over $Na_2SO_4$ and evaporated. The crude product was purified on a silica gel column (2-15% MeOH in DCM) to give compound 5c (11.87 g, 80.6%).

B. (9H-Fluoren-9-yl)methyl (1-(4-((bis(4-methoxyphenyl)(phenyl)methoxy)methyl)-4-(hydroxymethyl) piperidin-1-yl)-1,5-dioxo-3,10,13,16-tetraoxa-6-azanonadecan-19-yl)carbamate 7c DMT-Cl (3.78 g, 11.17 mmol) was gradually added to a solution of compound 5c (7.295 g, 10.64 mmol) in pyridine (40 mL) over 4 h at 0° C. Next day, the reaction mixture was neutralized with triethylamine (5 mL) and evaporated in vacuo to a thick oil. This was dissolved in ethyl acetate and washed with conc. aqueous sodium bicarbonate and brine. The organic phase was dried over $Na_2SO_4$, evaporated, and co-evaporated with toluene (3×20 mL). The product was isolated on a silica gel column (0-8% MeOH, DCM) to yield compound 7c (7.04 g, 65.4%).

NMR $H^1$ (δ, $CDCl_3$): 7.73-7.76 (m, 2H), 7.57-7.61 (m, 3H), 7.36-7.42 (m, 4H), 7.28-7.32 (m, 8H), 7.20-7.25 (m, 1H), 6.81-6.85 (m, 4H), 5.52 (br. t, 1H, NH), 4.38 (d, 2H), 4.21 (br. t, J=7.0 Hz, 1H), 4.16 (s, 2H), 3.99, 4.03 (AB, J=15.0 Hz, 2H), 3.78 (s, 6H), 3.46-3.64 (m, 15H), 3.33-3.40 (m, 3H), 3.30 (q, J=7.0 Hz, 2H), 3.18-3.26 (m, 1H), 3.17, 3.21 (AB, J=15.0 Hz, 2H), 3.00-3.07 (m, 1H), 2.26 (br. t, 1H, OH), 1.75-1.84 (m, 4H), 1.40-1.65 (m, 4H).

NMR $C^{13}$ (δ, $CDCl_3$): 169.5, 167.1, 158.8, 156.8, 144.7, 144.3, 141.5, 135.7, 130.2, 128.2, 128.2, 127.8, 127.2, 127.2, 125.3, 120.1, 113.4, 86.6, 71.8, 70.8, 70.7, 70.4, 70.4, 69.9, 69.4, 67.6, 67.4, 67.3, 66.6, 55.4, 47.6, 40.6, 39.2, 39.1, 38.05, 38.0, 36.8, 30.0, 29.6, 29.2.

Example 124

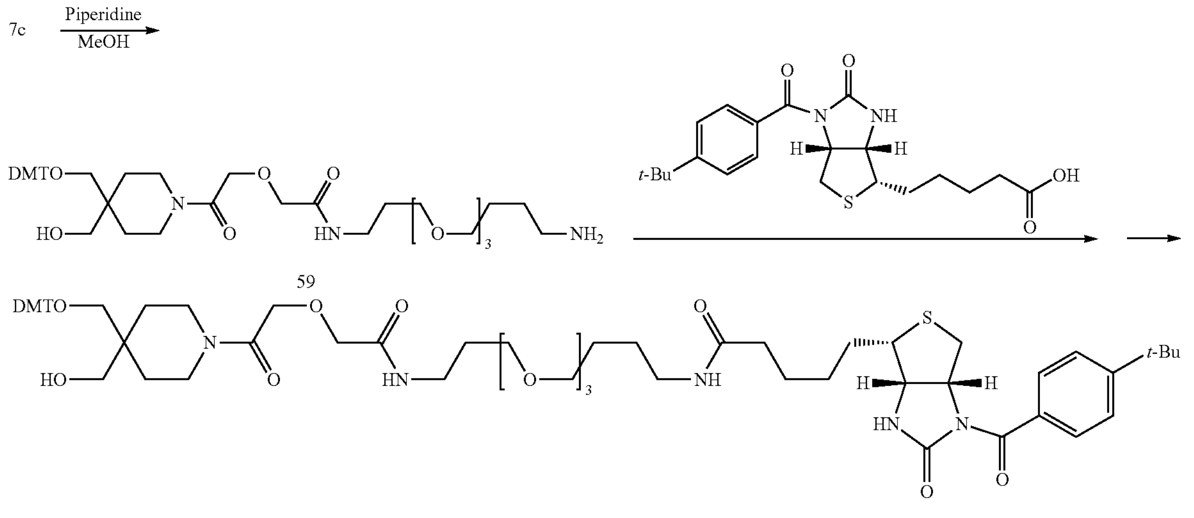

59

61

A. N-(3-(2-(2-(3-aminopropoxy)ethoxy)ethoxy)propyl)-2-(2-(4-((bis(4-methoxyphenyl)(phenyl) methoxy)methyl)-4-(hydroxymethyl)piperidin-1-yl)-2-oxoethoxy)acetamide 59

Compound 7c (6.259 g, 6.33 mmol) was treated with piperidine (25% in methanol, 100 ml) at room temperature for 3 h. The solution was evaporated and co-evaporated with xylenes (3×20 mL). The crude product was purified on a silica gel column (50% hexanes in DCM→3% $NH_4OH$, 25% MeOH in DCM) to yield compound 59 (3.84 g, 79.1%).

NMR $H^1$ (δ, $CDCl_3$): 7.66 (br. t, 1H, NH), 7.35-7.41 (m, 2H), 7.26-7.31 (m, 6H), 7.18-7.23 (m, 1H), 6.80-6.85 (m, 4H), 4.16, 4.20 (AB, J=15.0 Hz, 2H); 3.98, 4.03 (AB, J=15.0 Hz, 2H), 3.78 (s, 6H), 3.50-3.63 (m, 15H), 3.62 (t, J=7.5 Hz, 2H), 3.19-3.35 (m, 2H), 3.00-3.06 (m, 3H), 2.78 (t, J=7.5 Hz, 2H), 1.94 (br.s, 3H, $NH_2$+OH), 1.80 (quin, J=7.5 Hz, 2H), 1.72 (quin, J=7.5 Hz, 2H), 1.43-1.63 (m, 4H).

NMR $C^{13}$ (δ, $CDCl_3$): 169.5, 167.1, 158.8, 144.7, 135.8, 130.2, 128.2, 128.1, 127.2, 113.4, 86.5, 71.8, 70.7, 70.7, 70.4, 70.3, 70.0, 69.7, 69.4, 67.3, 66.9, 55.4, 40.7, 39.8, 38.0, 38.0, 36.8, 33.36, 29.9, 29.5, 29.2.

B. 2-{2-[4-{[bis(4-methoxyphenyl)(phenyl) methoxy]methyl}-4-(hydroxymethyl)piperidin-1-yl]-2-oxoethoxy}-N-(15-oxo-4,7,10-trioxa-14-azahexadec-1-yl)-N-t-butylbenzoylbiotinyl amide 61

Triethylammonium salt of N-[4-(t-butyl)benzoyl]biotin (Chem Impex International, Inc., 1.226 g, 2.43 mmol, prepared as disclosed in *Nucl. Acids Res.* 2003, 31, 2, 709), was stirred at room temperature with DIPEA (0.784 g, 6.06 mmol), TBTU (0.819 g, 2.55 mmol), and NMP (12 g) for 0.5 h. Compound 59 (1.867 g, 2.44 mmol) was added, and the mixture was stirred for 18 h. The mixture was then diluted with ethyl acetate (300 mL) and washed with brine (10×20 mL). The organic phase was dried over $Na_2SO_4$ and evaporated. The crude product was purified on a silica gel column (0-8% MeOH in DCM) to give compound 61 (2.33 g, 83.3%).

Example 125

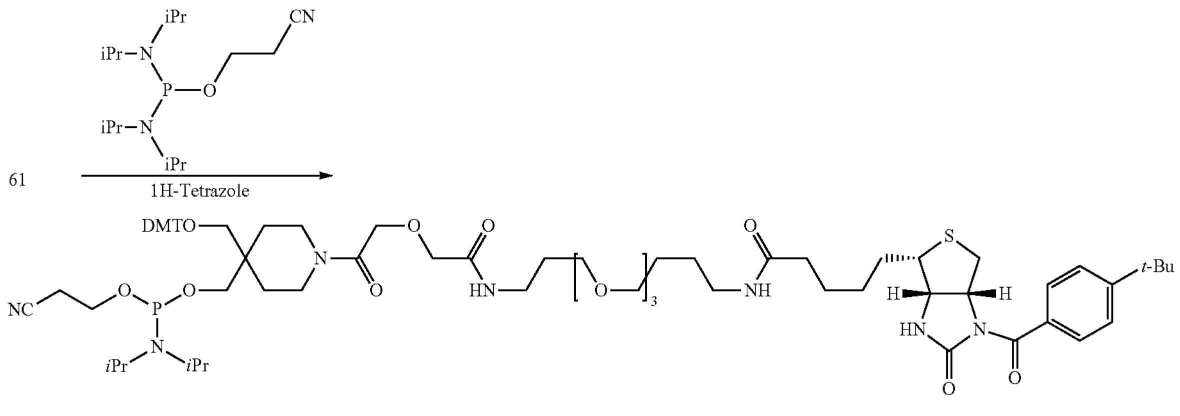

63

(4-((Bis(4-methoxyphenyl)(phenyl)methoxy)methyl)-1-(25-((3aS,4S,6aR)-1-(4-(tert-butyl)benzoyl)-2-oxohexahydro-1H-thieno[3,4-d]imidazol-4-yl)-5,21-dioxo-3,10,13,16-tetraoxa-6,20-diazapentacosan-1-oyl)piperidin-4-yl)methyl (2-cyanoethyl) diisopropylphosphoramidite 63

Compound 61 (1.806 g, 1.57 mmol) and 2-cyanoethyl N,N,N',N'-tetraisopropylphosphorodiamidite (0.614 g, 2.04 mmol) were dissolved in anhydrous acetonitrile (17 mL). The solution was gently shaken with flame-dried molecular sieves 4 Å (1.2 g) for 1 h, cooled to −10° C., and treated with 1H-tetrazole in acetonitrile (0.45 M, 1.81 mL). Next day, the reaction mixture was quenched with triethylamine (0.4 mL) and diluted with saturated sodium bicarbonate solution. The product was extracted with DCM and purified on a silica gel column (5% $Et_3N$, 0→8% methanol in DCM), to yield compound 63 (1.829 g, 86.3%) as a white solid foam.

Example 126

-continued

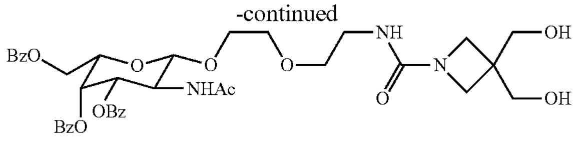

69

N-(5-((3,4,6-O-tribenzoyl-2-acetylamino-2-deoxy-β-D-galactopyranosyl)oxy)-3-oxapentyl)-3,3-bis(hydroxymethyl)azetidine-1-carboxamide 69

A solution of 5-((3,4,6-O-triacetyl-2-acetylamino-2-deoxy-β-D-galactopyranosyl)oxy)-3-oxapentanamine prepared as disclosed in PCT Int. Appl. (2004), WO 2004101619 A1 20041125 (3.055 g, 4 mmol) and carbonyldiimidzole (0.665 g, 4.1 mmol) in DCM (40 mL) was stirred at room temperature for 30 min. Compound 4 (0.48 g, 4.1 mmol) and DIPEA (3.102 g, 24 mmol) were added at 0° C.

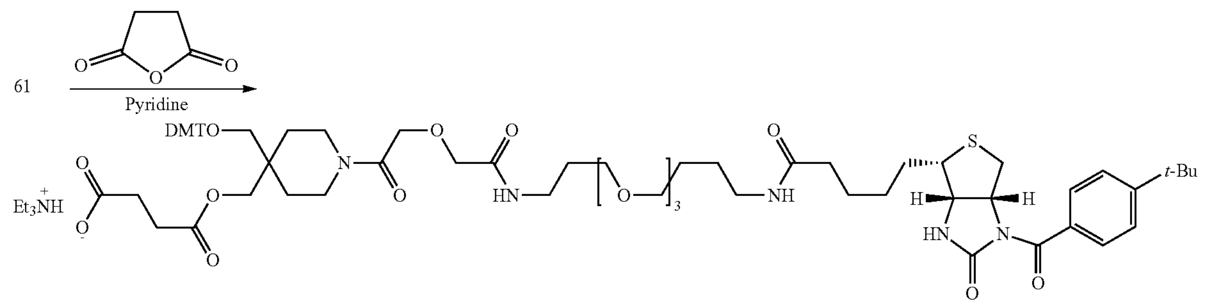

65

Triethylammonium 4-((4-((bis(4-methoxyphenyl)(phenyl)methoxy)methyl)-1-(25-((3aS,4S,6aR)-1-(4-(tert-butyl)benzoyl)-2-oxohexahydro-1H-thieno[3,4-d]imidazol-4-yl)-5,21-dioxo-3,10,13,16-tetraoxa-6,20-diazapentacosan-1-oyl)piperidin-4-yl)methoxy)-4-oxobutanoate 15a Compound 61 (0.385 g, 0.334 mmol), succinic anhydride (0.669 g, 6.68 mmol), and pyridine (3.5 mL) were stirred at room temperature for 7 days. The reaction mixture was quenched with water (0.41 mL, 22.90 mmol) and triethylamine (24.02 mmol, 3.34 mL) for 4 h, evaporated to oil, diluted with DCM (100 mL), and washed with 10% aqueous citric acid. Organic phase was basified with triethylamine (0.4 mL), dried over $Na_2SO_4$, and evaporated. The product was isolated on a silica gel column (1% $Et_3N$, 0-5% MeOH, DCM) to yield compound 65 (0.357 g, 79.0%).

Example 127

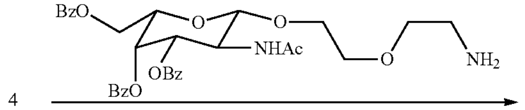

The reaction mixture was stirred for 18 h at room temperature, diluted with ethyl acetate (200 mL), washed with 5% $NaHCO_3$, 5% HCl, brine. The extract was dried over $Na_2SO_4$ and evaporated. The crude product was purified on a silica gel column (2% AcOH, 2-10% MeOH, DCM), to give 2.129 g (69.7%) of diol 69 as a white solid.

Example 128

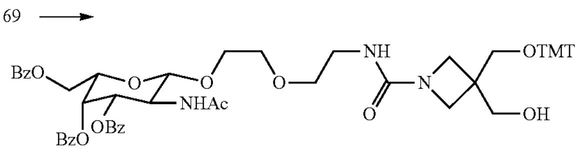

70

N-(5-((3,4,6-O-tribenzoyl-2-acetylamino-2-deoxy-β-D-galactopyranosyl)oxy)-3-oxapentyl)-3-(hydroxymethyl)-3-((tris-(4-methoxyphenyl)methoxy)methyl)azetidine-1-carboxamide 70

Trimethoxytrityl chloride (1.85 g, 5 mmol) was gradually added to a stirred solution of compound 69 (3.819 g, 5 mmol) in pyridine (30 mL) over 4 h at 0° C., and stirring was continued at room temperature for 72 h. The reaction mixture was concentrated, co-evaporated with toluene, and distributed between triethylammonium bicarbonate buffer (pH 7.19) and ethyl acetate. The aqueous layer was additionally extracted with ethyl acetate (2×50 mL). The combined organic phase was dried over $Na_2SO_4$, concentrated, and separated on a silica gel column (0-3% MeOH, DCM) to yield compound 70 (3.283 g, 59.9%).

Example 129

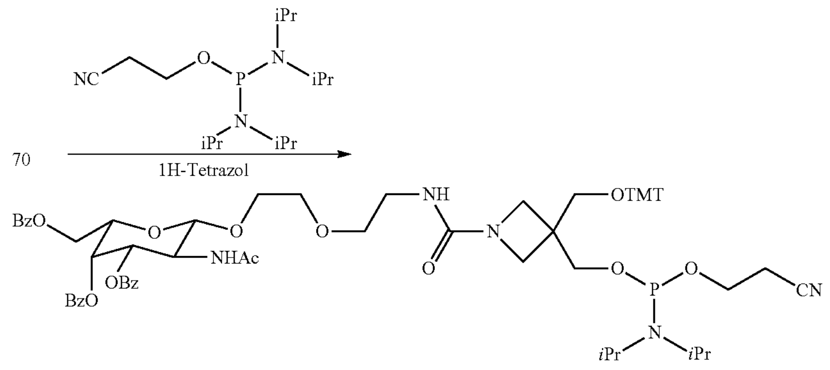

71

(1-(5-((3,4,6-O-tribenzoyl-2-acetylamino-2-deoxy-β-D-galactopyranosyl)oxy)-3-oxapentyl)carbamoyl)-3-(((4,4',4"-trimethoxytrityl)oxy)methyl)azetidin-3-yl) methyl (2-cyanoethyl) diisopropylphosphoramidite 71

Compound 70 (1.315 g, 1.2 mmol) and 2-cyanoethyl N,N,N',N'-tetraisopropylphosphorodiamidite (0.47 g, 1.56 mmol) were dissolved in anhydrous acetonitrile (15 mL), and the mixture was shaken with flame-dried molecular sieves 4 Å for 1 h. This was cooled to −10° C., 1H-tetrazole (0.45M, 0.6 mmol, 1.33 mL) in acetonitrile was added, and the mixture was stirred overnight. The reaction mixture was quenched with triethylamine (0.5 mL) and was diluted with saturated aqueous sodium bicarbonate. The product was extracted with DCM, and the organic extract was dried over $Na_2SO_4$ and was evaporated to dryness. The crude product was purified on a silica gel column (5% $Et_3N$, 20-80% ethyl acetate in hexanes) to yield 71 (1.329 g, 85.4%) as a white solid foam.

Example 130

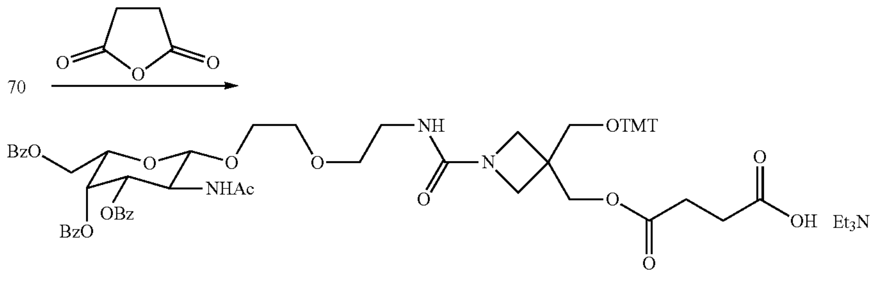

73

Triethylammonium ((1-(5-((3,4,6-O-tribenzoyl-2-acetylamino-2-deoxy-β-D-galactopyranosyl)oxy)-3-oxapentyl)carbamoyl)-3-(((4,4',4"-trimethoxytrityl) oxy)methyl)azetidin-3-yl)methoxy)-4-oxobutanoate 73

Compound 70 (0.691 g, 0.63 mmol), succinic anhydride (0.630 g, 6.3 mmol) and pyridine (2.0 mL) were stirred at room temperature for 5 days. The reaction mixture was quenched with water and triethylamine (0.4 mL) for 4 h, evaporated to oil, diluted with DCM (100 mL), and washed with 10% aqueous citric acid. Organic phase was basified with triethylamine (0.2 mL), dried over $Na_2SO_4$, and evaporated. The residue was separated on a silica gel column (1% $Et_3N$, 0-5% MeOH, DCM) to yield 73 (0.673 g, 82.3%).

Example 131

26

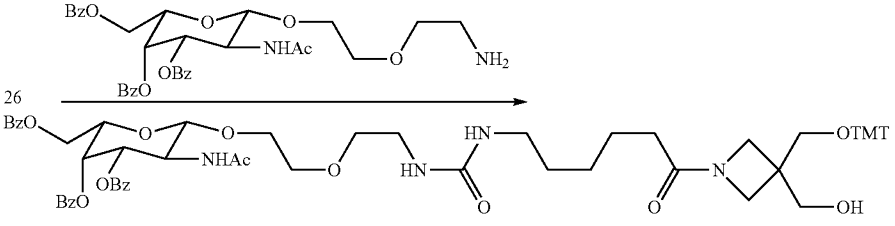

75

1-(5-((3,4,6-O-tribenzoyl-2-acetylamino-2-deoxy-β-D-galactopyranosyl)oxy)-3-oxapenthyl)-3-(6-(3-(hydroxymethyl)-3-((tris(4-methoxyphenyl) methoxy)methyl)azetidin-1-yl)-6-oxohexyl)urea 75

A solution of 5-((3,4,6-O-triacetyl-2-acetylamino-2-deoxy-13-D-galactopyranosyl)oxy)-3-oxapentanamine prepared as disclosed in PCT Int. Appl. (2004), WO 2004101619 A1 20041125 (3.055 g, 4 mmol) and carbonyldiimidzole (0.665 g, 4.1 mmol) in DCM (40 mL) was stirred at room temperature for 30 min. Compound 26 (2.307 g, 4.1 mmol) and DIPEA (3.102 g, 24 mmol) were added at 0° C. The reaction mixture was stirred for 18 h at room temperature, diluted with ethyl acetate (200 mL), washed with 5% $NaHCO_3$, 5% HCl, brine. The extract was dried over $Na_2SO_4$ and evaporated. The crude product was purified on a silica gel column (2% AcOH, 2-10% MeOH, DCM), to give 3.614 g (74.7%) of compound 75 as a white solid.

Example 132

75

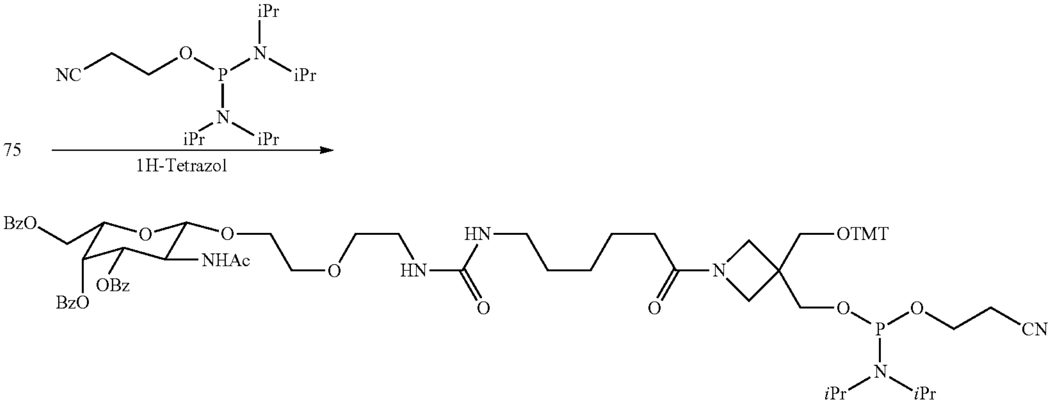

76

((1-(6-(3-(5-((3,4,6-O-tribenzoyl-2-acetylamino-2-deoxy-β-D-galactopyranosyl)oxy)-3-oxapentyl)ureido)hexanoyl)-3-((tris(4-methoxyphenyl)methoxy)methyl)azetidin-3-yl)methyl) (2-cyanoethyl) diisopropylphosphoramidite 76

Compound 75 (1.572 g, 1.3 mmol) and 2-cyanoethyl N,N,N',N'-tetraisopropylphosphorodiamidite (0.51 g, 1.69 mmol) were dissolved in anhydrous acetonitrile (15 mL), and the mixture was shaken with flame-dried molecular sieves 4 Å for 1 h. This was cooled to −10° C., 1H-tetrazole (0.45M, 0.65 mmol, 1.44 mL) in acetonitrile was added, and the mixture was stirred overnight. The reaction mixture was quenched with triethylamine (0.5 mL) and was diluted with saturated aqueous sodium bicarbonate. The product was extracted with DCM, and the organic extract was dried over $Na_2SO_4$ and was evaporated to dryness. The crude product was purified on a silica gel column (5% $Et_3N$, 20-80% ethyl acetate in hexanes) to yield 76 (1.481 g, 80.8%) as a white solid foam.

Example 133

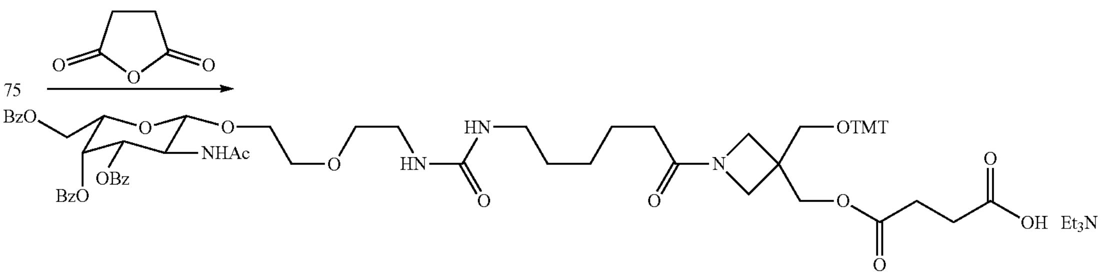

77

Triethylammonium 4-((1-(6-(3-(5-((3,4,6-O-tribenzoyl-2-acetylamino-2-deoxy-β-D-galactopyranosyl)oxy)-3-oxapentyl)ureido)hexanoyl)-3-((tris(4-methoxyphenyl)methoxy)methyl)azetidin-3-yl)methoxy)-4-oxobutanoate 77

Compound 75 (0.81 g, 0.67 mmol), succinic anhydride (0.670 g, 6.7 mmol) and pyridine (5.0 mL) were stirred at room temperature for 5 days. The reaction mixture was quenched with water and triethylamine (0.4 mL) for 4 h, evaporated to oil, diluted with DCM (100 mL), and washed with 10% aqueous citric acid. Organic phase was basified with triethylamine (0.2 mL), dried over $Na_2SO_4$, and evaporated. The residue was separated on a silica gel column (1% $Et_3N$, 0-5% MeOH, DCM) to yield 77 (0.735 g, 77.8%).

Example 134

General Procedure for Synthesis of Solid Supports. Preparation of the Solid Support 39b.

TBTU (155 mg, 0.48 mmol) was added to a solution of compound 35b (400 mg, 0.46 mmol) and N-ethyl-N,N-diisopropylamine (119 mg, 0.92 mmol) in a mixture of anhydrous pyridine (1 mL) and acetonitrile (4 mL). The mixture was stirred for 15 min and transferred to a suspension of aminopropyl CPG1000 (10 g) in anhydrous acetonitrile (45 mL), and the resulting suspension was shaken for 4 h. The suspension was then charged with N-methylimidazole (1 mL) and acetic anhydride (0.5 mL) and was shaken again for 45 min. The solid support was filtered off, washed on the filter with acetonitrile (5×50 mL) and dried in vacuo. The loading of the finished solid support 39b (43 μmol/g) was determined by the standard trityl assay as disclosed in Guzaev, A. P. and Pon, R. T. Attachment of Nucleosides and Other Linkers to Solid-Phase Supports for Oligonucleotide Synthesis. In: *Curr. Protoc. Nucleic Acid Chem.* Ed. Beaucage, S. L., Vol. 52, Unit 3.2, pp. 3.2.1-3.2.23, John Wiley & Sons: 2013.

All other solid supports 19-22, 39-42, 55k-58k, 67, 68, 74 and 78 were synthesized using the procedure disclosed above to give the loading values of 35-45 μmol/g.

Example 135

Oligonucleotide Synthesis, Deprotection, and Analysis.

Oligonucleotides were assembled on an Applied Biosystems DNA/RNA Synthesizer 394 on 1 μmol scale starting with a commercial DMT-T-Succinyl-CPG500 or with non-nucleosidic solid supports disclosed herein, using 0.1 M solutions of commercial protected nucleoside phosphoramidites (Glen Research, Sterling, Va.) and solutions of 1H-tetrazole or 5-benzylthio-1H-tetrazole as activators. Except for cholesterol phosphoramidites 31j-34j that were used as 0.1 M solutions in acetonitrile-dichloromethane (9:1), all other non-nucleosidic phosphoramidites 11-14, 31-34, 47k-50k, 63, 64, 71, and 76 disclosed herein were used as 0.1 M solutions in acetonitrile. For the attachment of phosphoramidites 11e-14e, 31c-34c, 31j-34j, 31k-34k, 31m-34m, 47k-50k, 63, and 64, the coupling protocol was extended to 2×3 min. With all other non-nucleosidic phosphoramidite building blocks, the coupling time was 3 min.

For the attachment of the first nucleoside phosphoramidite to solid supports 19-22, 39-42, 55k-58k, 67, 68, 71, and 76 the coupling time was extended to 2 min. The remaining nucleobases were incorporated by using the standard protocols.

In the synthesis of oligonucleotide phosphorothioates, the sulfurization step was carried out using 0.075 M N,N-dimethyl-N'-(3-thioxo-3H-1,2,4-dithiazol-5-yl)-methanimidamide (DDTT) in pyridine as disclosed in U.S. Pat. No. 7,723,528.

The final cleavage and deprotection of nucleic bases was carried out by treating the solid support-bound, 5'-DMT or 5'-TMT-protected oligonucleotides under the following conditions:

6. Conc. aqueous ammonium hydroxide for 8 h at 65° C.
7. Treatment with a mixture of diethylamine and acetonitrile (5:1) for 3 min followed by acetonitrile wash and final deprotection with conc. aqueous ammonium hydroxide for 8 h at 65° C.

8. A mixture of conc. aqueous ammonium hydroxide with 40% aqueous methylamine (1:1) for 15 min at 65° C.
9. Treatment with a mixture of diethylamine and acetonitrile (5:1) for 3 min followed by acetonitrile wash and final deprotection with a solution of ethylenediamine in toluene (1:1) for 2 h at room temperature, acetonitrile wash, and eltion of the product with water.
10. 50 mM $K_2CO_3$ in methanol at room temperature.

Upon evaporation of deprotection mixtures in vacuo, the crude products were dissolved in water, filtered, and analyzed by reverse-phase HPLC and ES MS.

HPLC analysis was carried out on a Phenomenex Gemini C18 (250×4.6 mm, 5 m) column using 0.05 M aqueous Tris-HCl, pH 7.2 as Buffer A, acetonitrile as Buffer B, and a linear gradient from 0 to 60% B over a period of 40 min at a flow rate of 0.75 mL/min. Oligonucleotides derivatized with cholesterol were analyzed on a Waters Symmetry Shield Tm RP8 5 μm 4.6×150 mm (Part No WAT 2000662) column using buffers disclosed above, a linear gradient of 0 to 80% B in 20 min, and a flow rate of 0.75 mL/min.

Skilled artisans will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A compound of Formula I:

Formula I

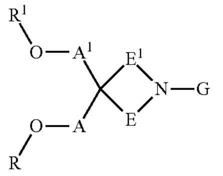

wherein:

A and $A^1$ are the same and are selected from —$CH_2$— or —$(CH_2)_2$—;

E and $E^1$ are the same and are selected from —$CH_2$— or —$(CH_2)_2$—;

G is —C(═O)-L, —C(═O)—OL, and —C(═O)—NHL wherein:

L is a linking moiety —$[[(CH_2)_gX^1(CH_2)_h]$—$X^2$—$[(CH_2)_iX^3(CH_2)_j]]_k$-J, wherein:

each g, h, i, j, and k is, independently, an integer from 0 to 6;

each $X^1$, $X^2$, and $X^3$ is, independently, —O—, —$CH_2$—, —NH—, —C(═O)NH—, —NHC(═O)—, —OC(═O)NH—, NHC(═O)O—, or —NHC(═O)NH—; and J is a hydroxy group alkylated with optionally protected N-acetyl-D-galactosamine;

one of R and $R^1$ is selected from hydrogen or a protecting group of trityl type selected from (4-methoxyphenyl)diphenylmethyl ("MMT"), bis-(4-methoxyphenyl)phenylmethyl ("DMT"), tris-(4-methoxyphenyl)methyl ("TMT"), 9-phenylxanthen-9-yl, or 9-(p-methoxyphenyl)xanthen-9-yl; and the other of R and $R^1$ is selected from hydrogen, acetyl, PA, or $L^1$, wherein:

PA is a phosphoramidite moiety:

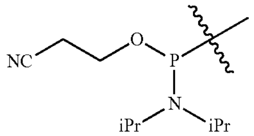 [SMILES: *P(OCCC#N)N(C(C)C)C(C)C]

$L^1$ is $C(═O)CH_2CH_2C(═O)OH$, $C(═O)CH_2CH_2C(═O)O^-$, $C(═O)CH_2CH_2C(═O)$—$W^1$, or $C(═O)CH_2CH_2C(═O)NH$—W, wherein $W^1$ is an aminopropyl controlled pore glass, and W is a solid phase material selected from a magnetic controlled pore glass, polymers of styrene, copolymers of styrene and divinylbenzene, controlled pore glass grafted with polymers of styrene, controlled pore glass grafted with copolymers of styrene and divinylbenzene, copolymers of styrene and divinylbenzene grafted with polyethyleneglycol, or flat glass surface.

2. The compound of claim 1, wherein

A and $A^1$ are —$CH_2$—;

E and $E^1$ are —$(CH_2)_2$—;

each $X^1$, $X^2$, and $X^3$ is, independently, —$CH_2$—, —C(═O)NH—, or —NHC(═O)—;

one of R and $R^1$ is selected from hydrogen, TMT, or DMT; and the other of R and $R^1$ is

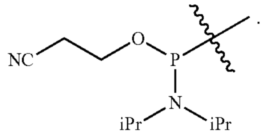 [SMILES: *P(OCCC#N)N(C(C)C)C(C)C]

3. The compound of claim 1, wherein

A and $A^1$ are —$CH_2$—;

E and $E^1$ are —$(CH_2)_2$—;

each $X^1$, $X^2$, and $X^3$ is, independently, —$CH_2$—, —C(═O)NH—, or —NHC(═O)—;

one of R and $R^1$ is selected from hydrogen, TMT, or DMT; and the other of R and $R^1$ is $C(═O)CH_2CH_2C(═O)$—$W^1$ or $(C═O)CH_2CH_2CO$—NH—W, wherein $W^1$ is an aminopropyl controlled pore glass, and W is a solid phase material selected from magnetic controlled pore glass, polymers of styrene, copolymers of styrene and divinylbenzene, controlled pore glass grafted with polymers of styrene, controlled pore glass grafted with copolymers of styrene and divinylbenzene, copolymers of styrene and divinylbenzene grafted with polyethyleneglycol, or flat glass surface.

4. The compound of claim 3, which has the following formula

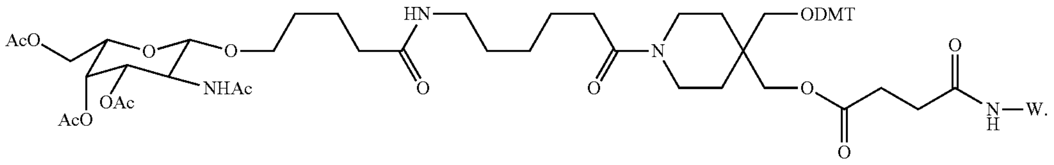

5. The compound of claim 3, which has the following formula

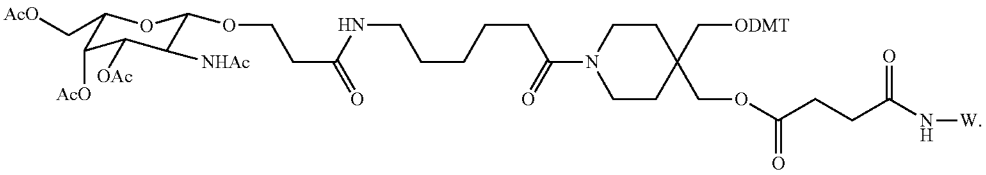

6. The compound of claim 1, wherein at least one of $X^1$, $X^2$, and $X^3$ is —O—.

7. The compound of claim 6, which has the following formula

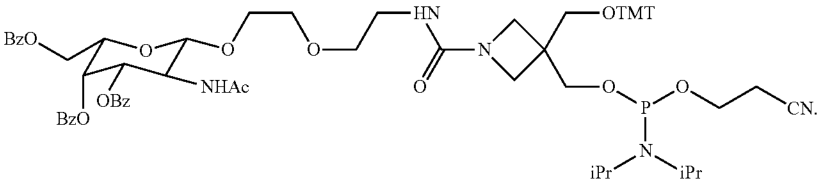

8. The compound of claim 6, wherein at least one of $X^1$, $X^2$, and $X^3$ is —NHC(═O)NH—.

9. The compound of claim 8, which has the following formula

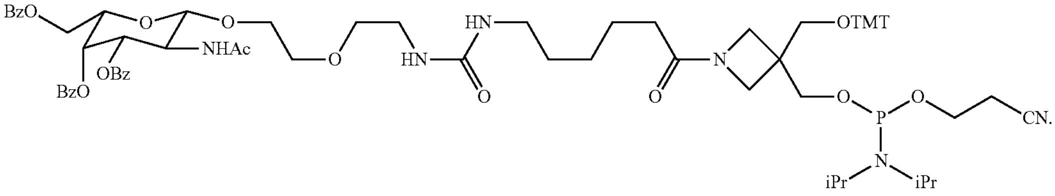

10. The compound of claim 8, which has the following formula

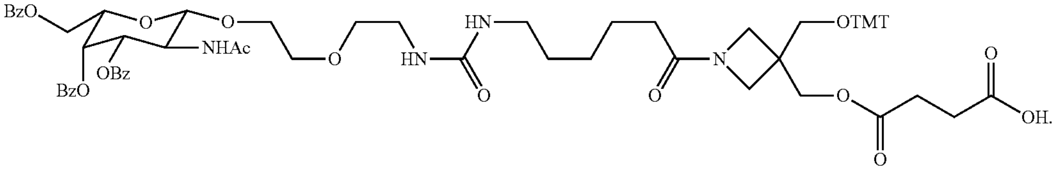

11. The compound of claim 6, wherein at least two of $X^1$, $X^2$, and $X^3$ are —O—.

12. The compound of claim 11, which has the following formula

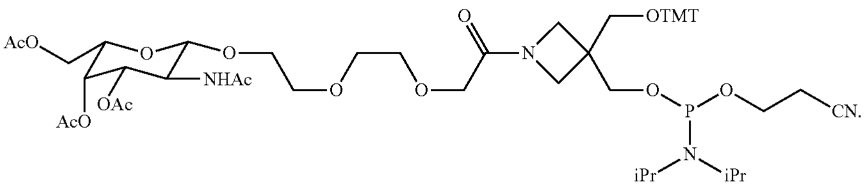

13. The compound of claim 11, which has the following formula

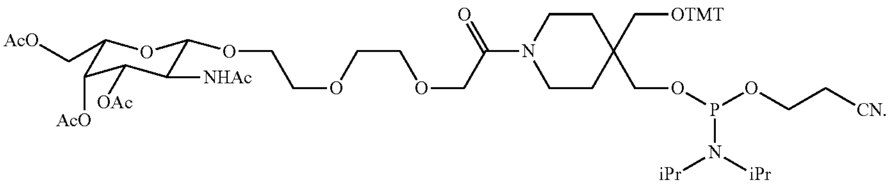

14. The compound of claim 1, wherein at least one of $X^1$, $X^2$, and $X^3$ is —NHC(=O)—.

15. The compound of claim 14, which has the following formula

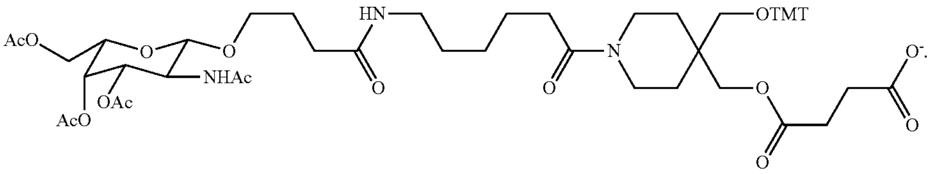

16. The compound of claim 14, which has the following formula

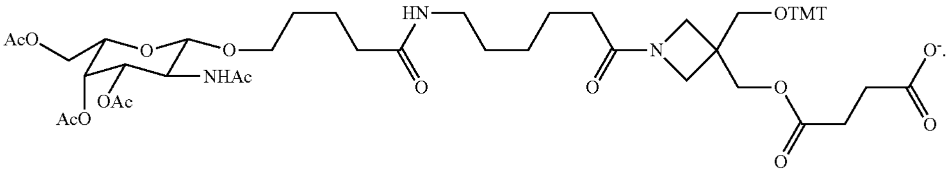

17. The compound of claim 1, which has the Formula 1a wherein

Formula 1a

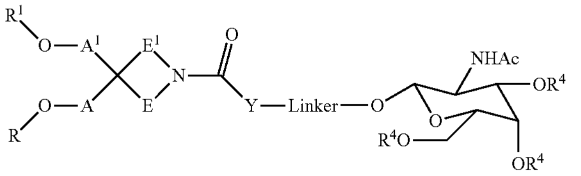

- A and $A^1$ are the same and are selected from $—CH_2—$ or $—(CH_2)_2—$;
- E and $E^1$ are the same and are selected from $—CH_2—$ or $—(CH_2)_2—$;
- Y is —O—, —NH—, or absent;
- Linker is $[[(CH_2)_gX^1(CH_2)_h]—X^2—[(CH_2)iX^3(CH_2)_j]]_k$, wherein:
  - each g, h, i, j, and k is, independently, an integer from 0 to 6; and
  - each $X^1$, $X^2$, and $X^3$ is, independently, —O—, $—CH_2—$, —NH—, —C(=O)NH—, —NHC(=O)—, —OC(=O)NH—, NHC(=O)O—, or —NHC(=O)NH—;
- R is

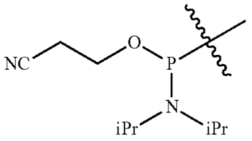 [SMILES: *P(OCCC#N)N(C(C)C)C(C)C]

or $L^1$, wherein
  - $L^1$ is $C(=O)CH_2CH_2C(=O)OH$, $C(=O)CH_2CH_2C(=O)O^-$, $C(=O)CH_2CH_2C(=O)—W^1$, or $C(=O)CH_2CH_2C(=O)NH—W$, wherein
    - $W^1$ is an aminopropyl controlled pore glass, and
    - W is a solid phase material selected from magnetic controlled pore glass, polymers of styrene, copolymers of styrene and divinylbenzene, controlled pore glass grafted with polymers of styrene, controlled pore glass grafted with copolymers of styrene and divinylbenzene, copolymers of styrene and divinylbenzene grafted with polyethyleneglycol, or flat glass surface
- $R^1$ is H, MMT, DMT, TMT, 9-phenylxanthen-9-yl, or 9-(p-methoxyphenyl)xanthen-9-yl; and
- $R^4$ is H or a hydroxyl protecting group.

18. The compound of claim 17, wherein each $X^1$, $X^2$, and $X^3$ is, independently, —O—, —$CH_2$—, —C(=O)NH—, —NHC(=O)—, or —NHC(=O)NH—;

R is

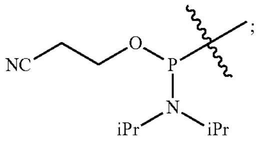 [SMILES: *P(OCCC#N)N(C(C)C)C(C)C]

and $R^4$ is Ac or Bz.

19. The compound of claim 17, wherein each $X^1$, $X^2$, and $X^3$ is, independently, —O—, —$CH_2$—, —C(=O)NH—, —NHC(=O)—, or —NHC(=O)NH—; and R is $L^1$ and $R^4$ is Ac or Bz.

20. The compound of claim 17, which has the following formula

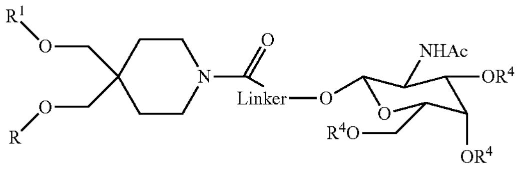

wherein each $X^1$, $X^2$, and $X^3$ is, independently, —O—, —$CH_2$—, —C(=O)NH—, —NHC(=O)—, or —NHC(=O)NH—; and $R^4$ is Ac or Bz.

* * * * *

SEQUENCE LISTING

```
<160> NUMBER OF SEQ ID NOS: 5

<210> SEQ ID NO 1
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1

tttttttttt tt                                                     12


<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2

tttttttttt ttttt                                                  15


<210> SEQ ID NO 3
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3

tagtgctaga tgcct                                                  15


<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4

ccactacctg agcacccagt t                                           21


<210> SEQ ID NO 5
<211> LENGTH: 21
<212> TYPE: DNA
<213> ORGANISM: Artificial Sequence
```

-continued

```
<220> FEATURE:
<223> OTHER INFORMATION: Description of Artificial Sequence: Synthetic
      oligonucleotide

<400> SEQUENCE: 5

ctgggtgctc aggtagtggt t                                               21
```